United States Patent [19]

Kirstgen et al.

[11] Patent Number: 5,633,268
[45] Date of Patent: May 27, 1997

[54] SUBSTITUTED ORTHO-ETHENYLPHENYLACETIC ACID DERIVATIVES

[75] Inventors: Reinhard Kirstgen, Neustadt; Hans Theobald, Limburgerhof; Klaus Oberdorf, Heidelberg; Reinhard Doetzer, Weinheim; Ralf Klintz, Dannstadt-Schauernheim; Bernd Schaefer, Dierbach; Volker Harries, Frankenthal; Uwe Kardorff, Mannheim; Gisela Lorenz, Neustadt; Eberhard Ammermann, Heppenheim, all of Germany

[73] Assignee: BASF Aktiengesellschaft, Ludwigshafen, Germany

[21] Appl. No.: 433,515

[22] PCT Filed: Nov. 12, 1993

[86] PCT No.: PCT/EP93/03067

§ 371 Date: May 12, 1995

§ 102(e) Date: May 12, 1995

[87] PCT Pub. No.: WO94/11334

PCT Pub. Date: May 26, 1994

[30] Foreign Application Priority Data

Nov. 12, 1992 [DE] Germany .................. 42 38 260.2

[51] Int. Cl.⁶ .................. C07D 285/08; A61K 31/41
[52] U.S. Cl. .................. 514/363; 514/364; 514/378; 548/128; 548/131; 548/136; 548/240
[58] Field of Search .................. 548/128, 131, 548/134, 136, 143, 240; 562/435, 440; 560/21, 35; 558/411; 514/363, 364, 378, 522, 539, 567

[56] References Cited

U.S. PATENT DOCUMENTS

| 5,041,618 | 8/1991 | Brand et al. .................. 514/522 |
| 5,112,862 | 5/1992 | Wenderoth et al. .................. 514/522 |

FOREIGN PATENT DOCUMENTS

| 2048983 | 8/1992 | Canada . |
| 407891 | 1/1983 | European Pat. Off. . |
| 348766 | 1/1990 | European Pat. Off. . |
| 378755 | 7/1990 | European Pat. Off. . |
| 474042 | 3/1992 | European Pat. Off. . |
| 513580 | 11/1992 | European Pat. Off. . |
| 544587 | 6/1993 | European Pat. Off. . |

*Primary Examiner*—Mukund J. Shah
*Assistant Examiner*—Anthony Bottino
*Attorney, Agent, or Firm*—Keil & Weinkauf

[57] ABSTRACT

Compounds of the formula I

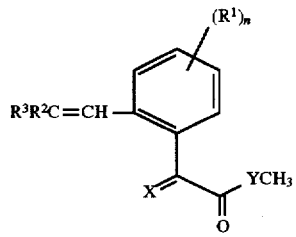

where the index and the substituents have the following meanings as defined in the specification.

19 Claims, No Drawings

SUBSTITUTED ORTHO-ETHENYLPHENYLACETIC ACID DERIVATIVES

This application is a 371 of PCT/EP93/03067 filed Nov. 12, 1993.

The present invention relates to compounds of the general formula I

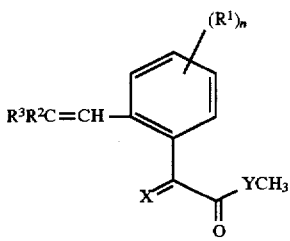

where the index and the substituents have the following meanings:

n is 0, 1, 2, 3 or 4, where the radicals $R^1$ can be different if n>1;

X is $CHOCH_3$, $CHCH_3$ or $NOCH_3$;

Y is O or NH;

$R^1$ is nitro; cyano; halogen;

$C_1-C_4$-alkyl; $C_1-C_4$-haloalkyl; $C_1-C_4$-alkoxy; $C_1-C_4$-haloalkoxy; $C_1-C_4$-alkylthio;

phenyl or phenoxy, where the aromatic rings can carry one to five halogens and/or one to three of the following radicals: $C_1-C_4$-alkyl, $C_1-C_4$-haloalkyl, $C_1-C_4$-alkoxy, $C_1-C_4$-haloalkoxy and $C_1-C_4$-alkylthio;

or, if n>1, is a 1,3-butadiene-1,4-diyl group bonded to two adjacent C atoms of the parent structure, which for its part can carry one to four halogens and/or one or two of the following radicals: nitro, cyano, $C_1-C_4$-alkyl, $C_1-C_4$-haloalkyl, $C_1-C_4$-alkoxy, $C_1-C_4$-haloalkoxy and $C_1-C_4$-alkylthio;

$R^2$ is nitro, cyano, halogen, $C_1-C_4$-alkoxy, $C_1-C_4$-alkylcarbonylamino, $C_1-C_4$-alkoxycarbonylamino or benzyloxycarbonylamino;

$R^3$, if X is $CHOCH_3$ or $NOCH_3$ and $R^2$ is halogen, is an unsubstituted or substituted mono- or binuclear aromatic ring system which apart from carbons can contain one to four nitrogens or one or two nitrogens and an oxygen or sulfur or an oxygen or sulfur as ring members, or is a group $R^4$—T—C(=$Z^1$)— or $R^5$—C(=$Z^2$)—, where =$Z^1$ is =O, =S, =$NR^6$ or =$NOR^4$;

=$Z^2$ is =O, =$NR^6$, =$NOR^4$, =N—$NR^7R^8$, =NO—C(=O)—$R^4$, =NO—C(=O)—$NR^7R^8$ or =N—$NR^7$—C(=O)$R^4$;

—T— is —O—, —S—, —$NR^7$—, —$NR^7NR^8$—, —$ONR^7$— or —$NR^7O$—;

$R^4$ is hydrogen; tri($C_1-C_4$-alkyl)silyl;

unsubstituted or substituted alkyl, alkenyl or alkynyl;

an unsubstituted or substituted saturated or mono- or diunsaturated cyclic system which apart from carbons can contain one to three of the following hetero atoms as ring members: oxygen, sulfur and nitrogen;

or an unsubstituted or substituted mono- or binuclear aromatic ring system which apart from carbons can contain one to four nitrogens or one or two nitrogens and an oxygen or sulfur or an oxygen or sulfur as ring members;

$R^5$ is hydrogen; cyano; halogen;

unsubstituted or substituted alkyl, alkoxy, alkenyl or alkynyl;

an unsubstituted or substituted saturated or mono- or diunsaturated cyclic system which apart from carbons can contain one to three of the following hetero atoms as ring members: oxygen, sulfur and nitrogen;

an unsubstituted or substituted mono- or binuclear aromatic ring system which apart from carbons can contain one to four nitrogens or one or two nitrogens and an oxygen or sulfur or an oxygen or sulfur as ring members;

or, if =$Z^2$ is =O, is a group $R^xR^yC$=NO—, where $R^x$ is hydrogen, cyano, halogen, $C_1-C_4$-alkyl, $C_1-C_4$-haloalkyl, $C_1-C_4$-alkoxy, $C_1-C_4$-alkylthio, $C_3-C_7$-cycloalkyl, phenyl or benzyl and $R^y$ is hydrogen;

unsubstituted or substituted alkyl, cycloalkyl, alkenyl, alkynyl or phenyl;

$R^x$ and $R^y$, together with the C atom to which they are bonded, form an unsubstituted or substituted saturated or mono- or diunsaturated cyclic system which apart from carbons can contain one to three of the following hetero atoms as ring members: oxygen, sulfur and nitrogen;

$R^6$ is hydrogen;

unsubstituted or substituted alkyl;

an unsubstituted or substituted saturated or mono- or diunsaturated cyclic system which apart from carbons can contain one to three of the following hetero atoms as ring members: oxygen, sulfur and nitrogen; or an unsubstituted or substituted mono- or binuclear aromatic ring system which apart from carbons can contain one to four nitrogens or one or two nitrogens and an oxygen or sulfur or an oxygen or sulfur as ring members;

$R^7$ is hydrogen or $C_1-C_4$-alkyl;

$R^8$ is hydrogen, $C_1-C_4$-alkyl or $COR^6$.

In addition, the invention relates to processes for preparing these compounds, compositions containing them and their use for controlling pests and fungi.

alpha-(o-Ethenylphenyl)-beta-alkoxyacrylates (EP-A 178 826, EP-A 203 606, EP-A 378 755, EP-A 474 042, EP-A 475 158), alpha-(o-ethenylphenyl)-alpha-alkoxyiminoacetates (EP-A 253 213, EP-A 254 426, EP-A 393 428, EP-A 398 692) and alpha-(o-ethenylphenyl)-alpha,beta-unsaturated carboxylates (EP-A 280 185, EP-A 348 766) having fungicidal and in some cases having insecticidal (EP-A 178 826, EP-A 378 755) action are known from the literature.

It is an object of the present invention to find novel active compounds which are active against pests and harmful fungi and have improved properties.

We have now found that this object is achieved by the compounds I defined at the beginning. In addition, we have found processes for preparing these compounds, compositions containing them and their use for the control of pests and fungi.

The compounds of the formula I are prepared in a similar manner to various methods known per se from the literature. In the synthesis of the compounds I, the sequence in which the —CH=$CR^2R^3$ groups [sic] and —C(=X)—CO—$YCH_3$ group are synthesized from the corresponding reactive precursors is in general unimportant.

These groups are particularly preferably obtained by the process described below, where, for better clarity, the group which is not involved in the reaction is in each case represented in simplified form in the following reaction schemes:

the —CH=$CR^2R^3$ group and its precursors as R* and the —C(=X)—CO—$YCH_3$ group and its precursors as $R^\#$.

A: Process for the synthesis of the —C(=X)—CO—YCH₃ group A.1:Preparation of the compounds IA (X=CHOCH₃, Y=O, NH)

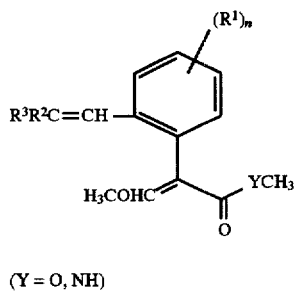

(Y = O, NH)

The compounds IA are obtained in a manner known per se by a method similar to the literature cited at the beginning starting from phenylacetic acid derivatives II by reacting with methyl formate in an inert solvent in the presence of a base and then methylating.

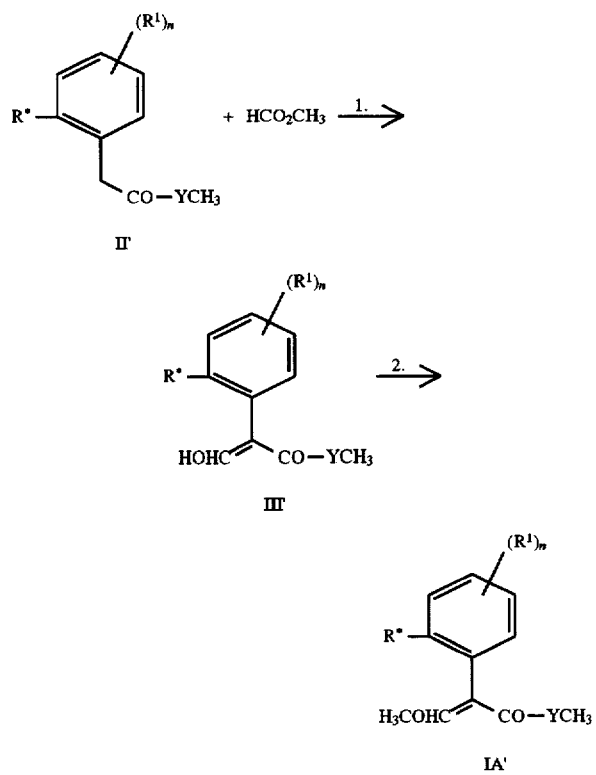

The reaction of the phenylacetic acid derivatives II with methyl formate is customarily carried out at from −20° C. to 60° C., preferably 10° C. to 50° C.

A suitable solvent is methyl formate itself, aliphatic hydrocarbons such as pentane, hexane, cyclohexane and petroleum ether, aromatic hydrocarbons such as toluene, o-, m- and p-xylene, halogenated hydrocarbons such as dichloromethane, chloroform and chlorobenzene, ethers such as diethyl ether, diisopropyl ether, tert-butyl methyl ether, dioxane, anisole and tetrahydrofuran, nitriles such as acetonitrile and propionitrile, alcohols such as methanol, ethanol, n-propanol, isopropanol, n-butanol and tert-butanol and also dimethyl sulfoxide and dimethylformamide, particularly preferably methanol, tetrahydrofuran, dimethyl sulfoxide and dimethylformamide.

Mixtures of the solvents mentioned can also be used.

The bases used are in general inorganic compounds such as alkali metal and alkaline earth metal hydrides such as lithium hydride, sodium hydride, potassium hydride and calcium hydride, alkali metal amides such as lithium diisopropylamide, lithium amide, sodium amide and potassium amide, organometallic compounds, in particular alkali metal alkyls such as methyllithium, n-butyl-lithium and phenyllithium, alkylmagnesium halides such as methylmagnesium chloride and also alkali metal and alkaline earth metal alkoxides such as sodium methoxide, sodium ethoxide, potassium ethoxide, potassium tert-butoxide and dimethoxymagnesium.

Lithium diisopropylamide, sodium hydride, n-butyllithium, sodium methoxide and potassium tert-butoxide are particularly preferred.

The bases are in general used in equimolar amounts or in an excess.

The starting materials are in general reacted with one another in equimolar amounts. It may be advantageous for the yield to employ methyl formate in an excess based on II'.

The preparation of the phenylacetic acid derivatives II' is known from the literature (cf. EP-A 178 824 and EP-A 203 606) or is carried out by a method similar to the literature cited.

The beta-hydroxyacrylates III' are customarily methylated at from 0° C. to 60° C., preferably 0° C. to 30° C.

Suitable reagents for transferring the methyl group are, for example, methyl chloride, methyl bromide, methyl iodide or dimethyl sulfate, in particular methyl iodide and dimethyl sulfate.

The solvents used are aliphatic hydrocarbons such as pentane, hexane, cyclohexane and petroleum ether, aromatic hydrocarbons such as toluene, o-, m- and p-xylene, halogenated hydrocarbons such as dichloromethane, chloroform and chlorobenzene, ethers such as diethyl ether, diisopropyl ether, tert-butyl methyl ether, dioxane, anisole and tetrahydrofuran, nitriles such as acetonitrile and propionitrile, ketones such as acetone, methyl ethyl ketone, diethyl ketone and tert-butyl methyl ketone, and also dimethyl sulfoxide and dimethylformamide.

Mixtures of the solvents mentioned can also be used.

Suitable bases are generally inorganic compounds such as alkali metal and alkaline earth metal hydroxides such as lithium hydroxide, sodium hydroxide, potassium hydroxide, calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal and alkaline earth metal carbonates such as sodium carbonate, potassium carbonate, magnesium carbonate and calcium carbonate and also alkali metal hydrogen carbonates such as sodium hydrogen carbonate, organometallic compounds, in particular alkali metal alkyl such as methyllithium, butyllithium and phenyllithium, alkyl magnesium halides such as methyl magnesium chloride and also alkali metal and alkaline earth metal alkoxides such as sodium methoxide, sodium ethoxide, potassium ethoxide, potassium tert-butoxide and dimethoxymagnesium, and additionally organic bases, e.g. tertiary amines such as trimethylamine, triethylamine, diisopropylethylamine and N-methylpiperidine, pyridine, substituted pyridines such as collidine, lutidine and 4-dimethylaminopyridine and also bicyclic amines.

Sodium carbonate, potassium carbonate, sodium hydrogen carbonate and sodium methoxide are particularly preferred.

The bases are in general used in equimolar amounts, in an excess or if appropriate as a solvent.

The methylating agent is in general employed in equimolar amounts based on III'.

A.2: Preparation of the compounds IB (X=CHCH₃, Y=O, NH)

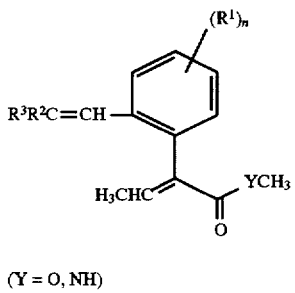

IB (Y = O, NH)

The compounds IB are obtained in a manner known per se by a method similar to the literature cited at the beginning starting from alpha-ketocarboxylic acid derivatives IV' by reacting with ethyltriphenylphosphoniumbromide or chloride in an inert organic solvent in the presence of a base.

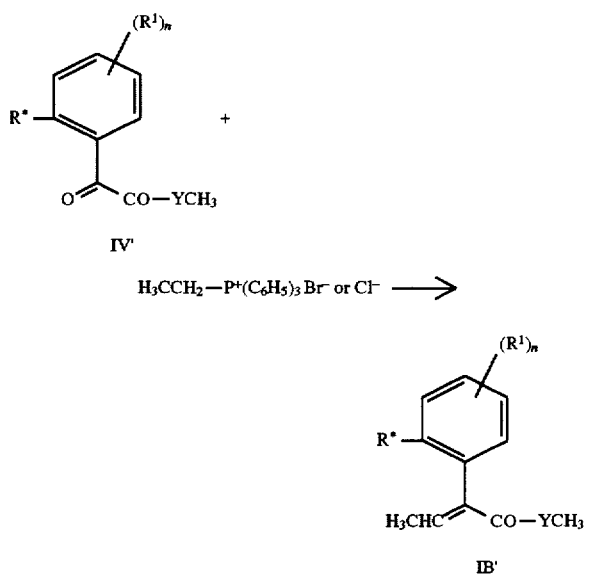

IB'

The reaction is customarily carried out at from -20° C. to 80° C., preferably 0° C. to 60° C.

Suitable solvents are aliphatic hydrocarbons such as pentane, hexane, cyclohexane and petroleum ether, aromatic hydrocarbons such as toluene, o-, m- and p-xylene, halogenated hydrocarbons such as dichloromethane, chloroform and chlorobenzene, ethers such as diethyl ether, diisopropyl ether, tert-butyl methyl ether, dioxane, anisole and tetrahydrofuran, nitriles such as acetonitrile and propionitrile, alcohols such as methanol, ethanol, n-propanol, isopropanol, n-butanol and tert-butanol and also dimethyl sulfoxide and dimethylformamide, particularly preferably toluene, diethyl ether and tetrahydrofuran.

Mixtures of the solvents mentioned can also be used.

Suitable bases are generally inorganic compounds such as alkali metal and alkaline earth metal hydroxides such as lithium hydroxide, sodium hydroxide, potassium hydroxide, calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride, and calcium hydride, alkali metal amides such as lithium amide, sodium amide and potassium amide, alkali metal and also alkali earth metal carbonates such as potassium carbonate and calcium carbonate and also alkali metal hydrogen carbonates such as sodium hydrogen carbonate, organometallic compounds, in particular alkali metal alkyls such as methyllithium, butyllithium and phenyllithium, alkylmagnesium halides such as methylmagnesium chloride and also alkali metal and alkaline earth metal alkoxides such as sodium methoxide, sodium ethoxide, potassium ethoxide, postassiumtert-butoxide and dimethoxymagnesium, and additionally organic bases, e.g. tertiary amines such as trimethylamine, triethylamine, diisopropylethylamine and N-methylpiperidine, pyridine, substituted pyridines such as collidine, lutidine and 4-dimethylaminopyridine and also bicyclic amines.

Sodium amide, n-butyllithium and potassium tert-butoxide are particularly preferred.

The bases are in general used in equimolar amounts, in an excess or if appropriate as a solvent.

The starting materials are in general reacted with one another in equimolar amounts. It may be advantageous for the yield to employ the ethyltriphenylphosphonium salt in an excess based on IV'.

The alpha-ketocarboxylic acid derivatives IV' required for the preparation of the compounds IB are known from the literature (cf. EP-A 280 185 or EP-A 348 766) or can be prepared in accordance with the literature cited.

A.3: Preparation of the compounds IC (X=NHOCH₃, Y=O, NH)

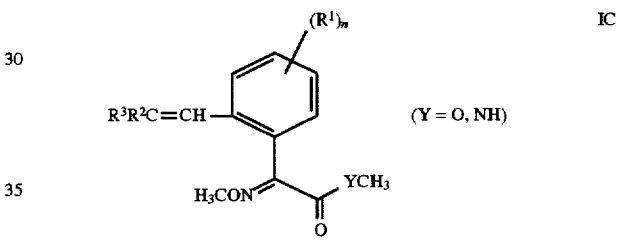

IC (Y = O, NH)

The compounds IC are obtained in a manner known per se (EP-A 253 213, EP-A 254 426, EP-A 363 818, EP-A 398 692) starting from alpha-ketocarboxylic acid derivatives IV' by reacting with O-methylhydroxylamine or its hydrochloride in an inert organic solvent in the presence of a base.

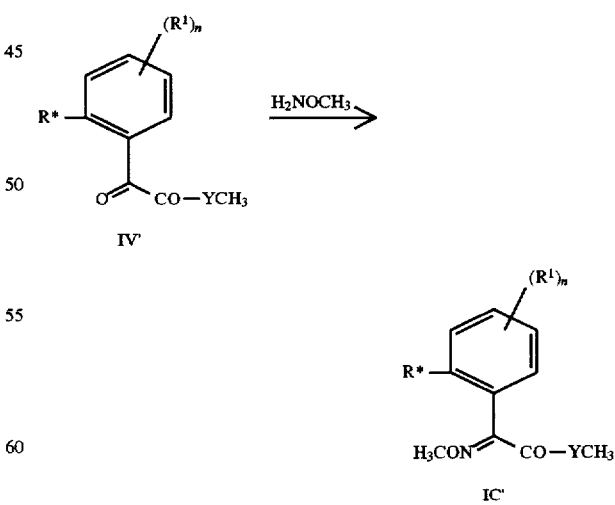

IC'

This reaction is customarily carried out at from 0° C. to 80° C., preferably 20° C. to 60°.

Suitable solvents are aromatic hydrocarbons such as toluene, o-, m- and p-xylene, halogenated hydrocarbons such as dichloromethane, chloroform and chlorobenzene, ethers such as diethyl ether, diisopropyl ether, tert-butyl methyl ether, dioxane, anisole and tetrahydrofuran, nitriles such as acetonitrile and propionitrile, alcohols such as methanol, ethanol, n-propanol, isopropanol, n-butanol and tert-butanol and also dimethyl sulfoxide and dimethylformamide, particularly preferably methanol and toluene.

Mixtures of the solvents mentioned can also be used.

Suitable bases are generally inorganic compounds such as alkali metal and alkaline earth metal hydroxides such as lithium hydroxide, sodium hydroxide, potassium hydroxide, calcium hydroxide, alkali metal and alkaline earth metal oxides such as lithium oxide, sodium oxide, calcium oxide and magnesium oxide, alkali metal and alkaline earth metal carbonates such as lithium carbonate, sodium carbonate, potassium carbonate and calcium carbonate and also alkali metal hydrogen carbonates such as potassium hydrogen carbonate and sodium hydrogen carbonate, and also alkali metal and alkaline earth metal alkoxides such as sodium methoxide, sodium ethoxide, potassium ethoxide, potassium tert-butoxide and dimethoxymagnesium, and additionally organic bases, e.g. tertiary amines such as trimethylamine, triethylamine, diisopropylethylamine and N-methylpiperidine, pyridine, substituted pyridines such as collidine, lutidine and 4-dimethylaminopyridine and also bicyclic amines.

Sodium carbonate and potassium carbonate are particularly preferred.

The bases are in general used in equimolar amounts, in an excess or if appropriate as a solvent.

The starting materials are in general reacted with one another in equimolar amounts. It may be advantageous for the yield to employ O-methylhydroxylamine in an excess based on IV'.

The availability of the alpha-ketocarboxylic acid derivatives required for preparing the compounds IC was already referred to in item A.2.

B: Process for preparing the group —CH=CR²R³

B.1:Preparation of the compounds ID (R²=halogen; R³=aryl, hetaryl)

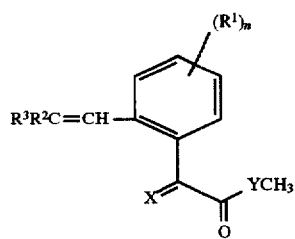

(R² = halogen; R³ = aryl, hetaryl)

The compounds ID.1 are obtained in a manner known per se (lit.: by a method similar to EP-A 378 755) starting from benzaldehydes V by reacting with alpha-halophosphonates VI in an inert organic solvent in the presence of a base.

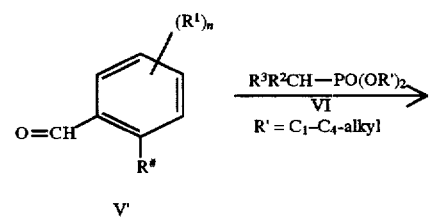

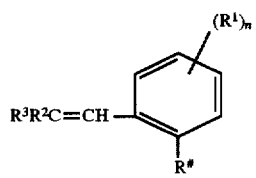

R' in the formula VI is $C_1$–$C_4$-alkyl, in particular methyl or ethyl, Hal in the formula VI and ID' is halogens such as fluorine, chlorine, bromine or iodine, in particular chlorine or bromine.

This reaction is customarily carried out at from −78° C. to 60° C., preferably −30° C. to 40° C.

Suitable solvents are aliphatic hydrocarbons such as pentane, hexane, cyclohexane and petroleum ether, aromatic hydrocarbons such as toluene, o-, m- and p-xylene, halogenated hydrocarbons such as dichloromethane, chloroform and chlorobenzene, ethers such as diethyl ether, diisopropyl ether, tert-butyl methyl ether, dioxane, anisole and tetrahydrofuran, nitriles such as acetonitrile and propionitrile, and also dimethyl sulfoxide and dimethylformamide, particularly preferably tetrahydrofuran and dimethylformamide.

Mixtures of the solvents mentioned can also be used.

Suitable bases are generally inorganic compounds such as alkali metal and alkaline earth metal hydrides such as lithium hydride, sodium hydride, potassium hydride and calcium hydride, alkali metal amides such as lithium amide, sodium amide and potassium amide, lithium diisopropylamide, organometallic compounds, in particular alkali metal alkyls such as methyllithium, butyllithium and phenyllithium, alkylmagnesium halides such as methylmagnesium chloride and also alkali metal and alkaline earth metal alkoxides such as sodium methoxide, sodium ethoxide, potassium ethoxide, potassium tert-butoxide and dimethoxymagnesium.

Sodium hydride, butyllithium and lithium diisopropylamide are particularly preferred.

The bases are in general used in equimolar amounts.

The starting amterials are in general reacted with one another in equimolar amounts. It may be advantageous for the yield to employ the phosphonate VI' in an excess based on the benzaldehyde V.

The starting substances V' and VI required for preparing the compounds ID are known in the literature (Chem. Soc., Chem. Commun. 12 (1987), 907; Heterocycles 28 (1989), 1179) or can be prepared in accordance with the literature cited.

B.2:Preparation of the compounds IE (R²=halogen; R³=R⁴—T—C—(=Z¹)—)

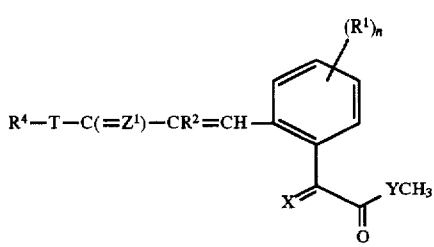

(R² = halogen)

The compounds IE are obtained in a manner known per se (Chem. Ber., 94 (1981), 2996; J. Org. Chem., 27 (1962), 998; J. Organomet. Chem., 332 (1987), 1) starting from Wittig or Wittig-Horner reagents VII, by reacting with the benzaldehyde V' in an inert organic solvent if appropriate in the presence of a base.

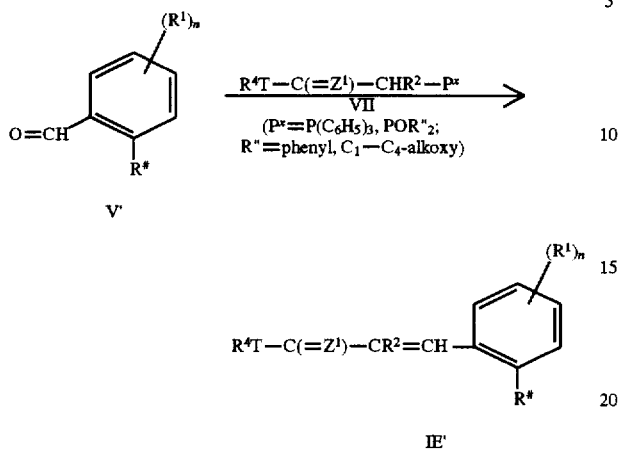

P* in formula VII is $P(C_6H_5)_3$ or a group $POR''_2$, where R'' is phenyl or $C_1$–$C_4$-alkoxy, in particular methoxy or ethoxy. P* in formula VII is preferably $PO(OCH_3)_2$ or $PO(OC_2H_5)$ [sic].

This reaction is customarily carried out at from −78° C. to 80° C., preferably 0° C. to 60° C.

Suitable solvents are aliphatic hydrocarbons such as pentane, hexane, cyclohexane and petroleum ether, aromatic hydrocarbons such as toluene, o-, m- and p-xylene, halogenated hydrocarbons such as dichloromethane, chloroform and chlorobenzene, ethers such as diethyl ether, diisopropyl ether, tert-butyl methyl ether, dioxane, anisole and tetrahydrofuran, nitriles such as acetonitrile and propionitrile, alcohols such as methanol, ethanol, n-propanol, isopropanol, n-butanol and tert-butanol and also ethyl acetate, dimethyl sulfoxide and dimethylformamide, particularly preferably toluene, tetrahydrofuran, methanol, ethyl acetate and dimethylformamide.

Mixtures of the solvents mentioned can also be used.

Suitable bases are generally inorganic compounds such as alkali metal and alkaline earth metal hydroxides such as lithium hydroxide, sodium hydroxide, potassium hydroxide, magnesium hydroxide, calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as sodium carbonate, potassium carbonate and calcium carbonate and also alkali metal hydrogen carbonates such as sodium hydrogen carbonate, organometallic compounds, in particular alkali metal alkyls such as methyllithium, butyllithium and phenyllithium, alkylmagnesium halides such as methylmagnesium chloride and also alkali metal and alkaline earth metal alkoxides such as sodium methoxide, sodium ethoxide, potassium ethoxide, potassium tert-butoxide and dimethoxymagnesium, and additionally organic bases, e.g. tertiary amines such as trimethylamine, tri-ethylamine, diisopropylethylamine and N-methylpiperidine, pyridine, substituted pyridines such as collidine, lutidine and 4-dimethylaminopyridine and also bicyclic amines.

Magnesium hydroxide, potassium carbonate, butyllithium, sodium hydride, potassium tert-butoxide and triethylamine are particularly preferred.

The bases are in general used in equimolar amounts.

The starting materials are in general reacted with one another in equimolar amounts. It may be advantageous for the yield to employ VII in an excess based on V'.

The starting substances VII required for preparing the compounds IE are known from the literature or can be prepared in accordance with the literature cited.

B.3:Preparation of the compounds IF ($R^2$=alkoxy; $R^3$=$R^4$—T—C(=$Z^1$)—)

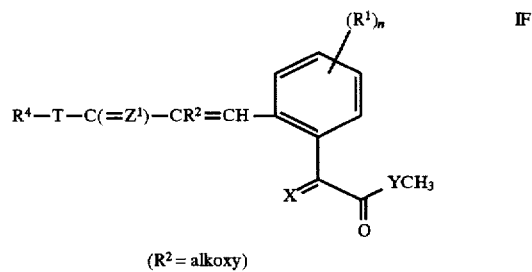

The compounds IF are obtained in a manner known per se (J. Chem. Soc. Rev. 17 (1988), 1; Synthesis 1989, 958) starting from benzyltriphenylphosphonium halide VIII by reacting with oxalic acid esters IX in an inert organic solvent in the presence of a base.

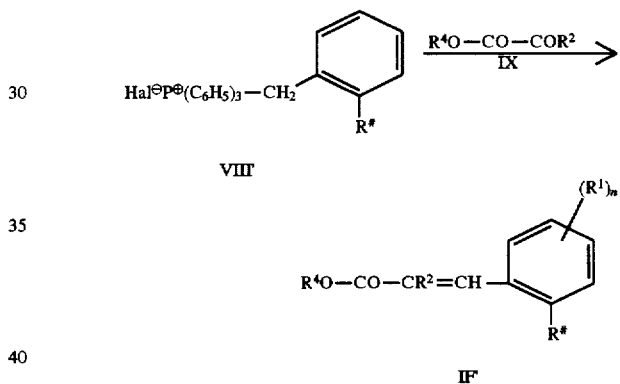

Hal in the formula VIII' is a halogen such as chlorine or bromine.

This reaction is customarily carried out at from −78° C. to 60° C., preferably 0° C. to 30° C.

Suitable solvents are aliphatic hydrocarbons such as pentane, hexane, cyclohexane and petroleum ether, aromatic hydrocarbons such as toluene, o-, m- and p-xylene, halogenated hydrocarbons such as dichloromethane, chloroform and chlorobenzene, ethers such as diethyl ether, diisopropyl ether, tert-butyl methyl ether, dioxane, anisole and tetrahydrofuran, nitriles such as acetonitrile and propionitrile, alcohols such as methanol, ethanol, n-propanol, isopropanol, n-butanol and tert-butanol and also dimethyl sulfoxide and dimethylformamide, particularly preferably tetrahydrofuran.

Mixtures of the solvents mentioned can also be used.

Suitable bases are generally inorganic compounds such as alkali metal and alkaline earth metal hydroxides such as lithium hydroxide, sodium hydroxide, potassium hydroxide, calcium hydroxide, alkali metal and alkaline earth metal oxides such as lithium oxide, sodium oxide, calcium oxide and magnesium oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate and calcium carbonate and also alkali metal hydrogen carbonates such as sodium hydrogen carbonate, organometallic compounds, in particular alkali metal alkyls such as methyllithium, butyllithium and phenyllithium, alkylmagnesium halides such as methylmagnesium chloride and also alkali metal and alkaline earth metal alkoxides such as sodium methoxide, sodium ethoxide, potassium ethoxide, potassium tert-butoxide and dimethoxymagnesium, and additionally organic bases, e.g. tertiary amines such as trimethylamine, triethylamine, diisopropylethylamine and N-methylpiperidine, pyridine, substituted pyridine such as collidine, lutidine and 4-dimethylaminopyridine and also bicyclic amines.

Butyllithium, sodium amide and sodium hydride are particularly preferred.

The bases are in general used in equimolar amounts, in an excess or if appropriate as a solvent.

The starting materials are in general reacted with one another in equimolar amounts. It may be advantageous for the yield to employ IX in an excess based on VIII'.

The starting substances IX required for preparing the compounds IF are known. The phosphonium halides VIII' can be obtained from the halobenzyl compounds (preparation by a method similar to the literature cited at the beginning) by reaction with triphenylphosphine (cf. Angew. Chem., 72 (1960), 572).

B.4:Preparation of the compounds IG [R$^2$=R$^a$—CONH (R$^a$=alkyl, alkoxy, benzyloxy); R$^3$=R$^4$—T—C(=Z$^1$)—]

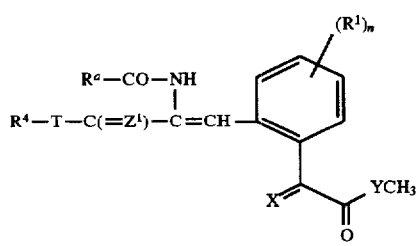

[R$^2$ = R$^a$CONH (R$^a$ = alkyl, alkoxy, benzyloxy)]

The compounds IG are obtained in a manner known per se (Angew. Chem., Int. Ed., 21 (1982), 770; Synthesis 1984, 53) starting from N-acyl-2-(dialkoxyphosphinyl)glycine esters X by reacting with the benzaldehydes V' in an inert organic solvent in the presence of a base.

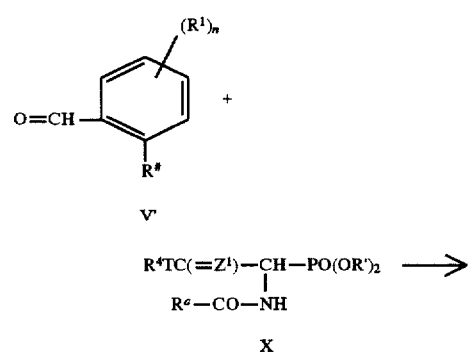

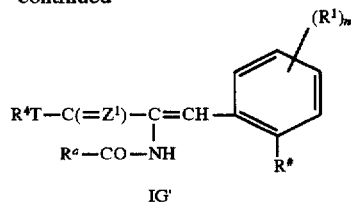

R' in the formula X is $C_1$–$C_4$-alkyl, in particular methyl or ethyl.

R$^a$ in the formulae X and IG' is alkyl or alkoxy having 1 to 4 C atoms or benzyloxy, preferably methyl, benzyl, tert-butoxy or benzyloxy.

This reaction is customarily carried out at from 78° C. [sic] to 40° C., preferably −78° C. to 0° C.

Suitable solvents are aliphatic hydrocarbons such as pentane, hexane, cyclohexane and petroleum ether, aromatic hydrocarbons such as toluene, o-, m- and p-xylene, halogenated hydrocarbons such as dichloromethane, chloroform and chlorobenzene, ethers such as diethyl ether, diisopropyl ether, tert-butyl methyl ether, dioxane and tetrahydrofuran, nitriles such as acetonitrile and propionitrile, alcohols such as methanol, ethanol, n-propanol, isopropanol, n-butanol and tert-butanol and also dimethyl sulfoxide and dimethylformamide, particularly preferably tetrahydrofuran and dichloromethane.

Mixtures of the solvents mentioned can also be used.

Suitable bases are generally inorganic compounds such as alkali metal and alkaline earth metal hydrides such as lithium hydride, sodium hydride, potassium hydride and calcium hydride, alkali metal amides such as lithium diisopropylamide, lithium amide, sodium amide and potassium amide, alkali metal and alkaline earth metal carbonates such as lithium carbonate and calcium carbonate, organometallic compounds, in particular alkali metal alkyls such as methyllithium, butyllithium and phenyllithium, alkylmagnesium halides such as methylmagnesium chloride and also alkali metal and alkaline earth metal alkoxides such as sodium methoxide, sodium ethoxide, potassium ethoxide, potassium tert-butoxide and dimethoxymagnesium.

Sodium hydride, lithium diisopropylamide and potassium tert-butoxide are particularly preferred.

The bases are in general used in equimolar amounts or in an excess.

The starting materials are in general reacted with one another in equimolar amounts.

The starting substances X required for preparing the compounds IG can be prepared in accordance with the literature cited.

B.5:Preparation of compounds IH (R$^2$=NO$_2$, CN; R$^3$=R$^5$—C(=Z$^2$)— or R$^4$—T—C(=Z$^1$)—)

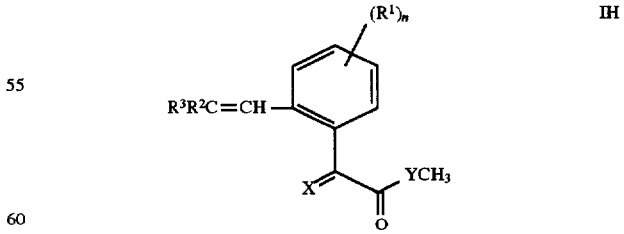

(R$^2$ = NO$_2$, CN; R$^3$ = R$^5$—C(=Z$^2$)— or R$^4$—T—C(=Z$^1$)—)

The compounds IH are obtained in a manner known per se (Tetrahedron 43 (1987), 537; Tetrahedron 28 (1972), 663; Synthesis 1974, 667) starting from the benzaldehydes V' by reacting with beta-carbonyl compounds XIa or XIb (Z$^1$ or $Z^2$=O) in an inert organic solvent in the presence of a base or base/titanium tetrachloride.

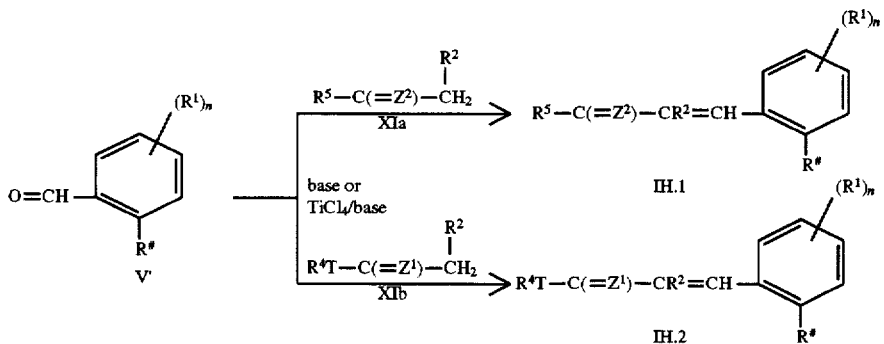

This reaction is customarily carried out at from 0° C. to 60° C., preferably 0° C. to 30° C.

Suitable solvents are aliphatic hydrocarbons such as pentane, hexane, cyclohexane and petroleum ether, aromatic hydrocarbons such as toluene, o-, m- and p-xylene, halogenated hydrocarbons such as dichloromethane, chloroform, carbon tetrachloride and chlorobenzene, ethers such as diethyl ether, diisopropyl ether, tert-butyl methyl ether, dioxane, anisole and tetrahydrofuran, nitriles such as acetonitrile and propionitrile, alcohols such as methanol, ethanol, n-propanol, isopropanol, n-butanol and tert-butanol and also dimethyl sulfoxide and dimethylformamide, particularly preferably carbon tetrachloride, tetrahydrofuran, dimethyl sulfoxide and dimethylformamide.

Mixtures of the solvents mentioned can also be used.

Suitable bases are generally inorganic compounds such as alkali metal and alkaline earth metal hydroxides such as lithium hydroxide, sodium hydroxide, potassium hydroxide, calcium hydroxide, alkali metal and alkaline earth metal oxides such as lithium oxide, sodium oxide, calcium oxide and magnesium oxide, transition metal oxides such as zinc oxide, alkali metal and alkaline earth metal hydrides such as lithium hydride, sodium hydride, potassium hydride and calcium hydride, alkali metal amides such as lithium amide, sodium amide and potassium amide, alkali metal and alkaline earth metal carbonates such as lithium carbonate and calcium carbonate and also alkali metal hydrogen carbonates such as sodium hydrogen carbonate, organometallic compounds, in particular alkali metal alkyls such as methyllithium, butyllithium and phenyllithium, alkylmagnesium halides such as methylmagnesium chloride and also alkali metal and alkaline earth metal alkoxides such as sodium methoxide, sodium ethoxide, potassium ethoxide, potassium tert-butoxide and dimethoxymagnesium, and additionally organic bases, e.g. tertiary amines such as trimethylamine, triethylamine, diisopropylethylamine, N-methylmorpholine and N-methylpiperidine, pyridine, substituted pyridines such as collidine, luridins and 4-dimethylaminopyridine and also bicyclic amines.

Magnesium oxide, zinc oxide, piperidine, N-methylmorpholine and pyridine are particularly preferred.

In general, the addition of a base such as N-methylmorpholine or pyridine is advantageous after activating the aldehyde V with titanium tetrachloride.

The bases are customarily employed in catalytic amounts, but they can also be used in equimolar amounts, in an excess or if appropriate as a solvent.

The starting materials are in general reacted with one another in equimolar amounts. It may be advantageous for the yield to employ XIa or XIb in an excess based on the benzaldehyde V'.

The starting substances XIa or XIb required for preparing the compounds IH are commercially available or known in the literature (Org. Synth. Coll. Vol. VI, 797).

B.6:Preparation of the compounds IK ($R^2$=halogen; $R^3$=$R^5$—C(=$Z^2$)—)

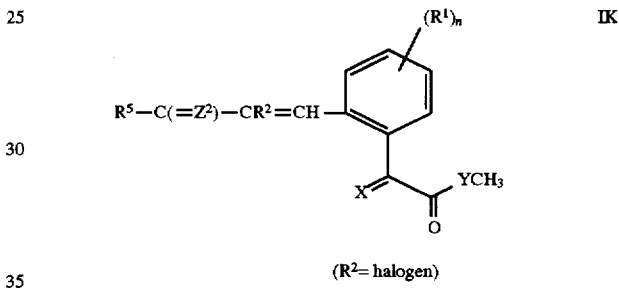

($R^2$= halogen)

The compounds IK are obtained in a manner known per se starting from the benzaldehydes V' by reacting with halophosphoranylidenes XII in an inert organic solvent.

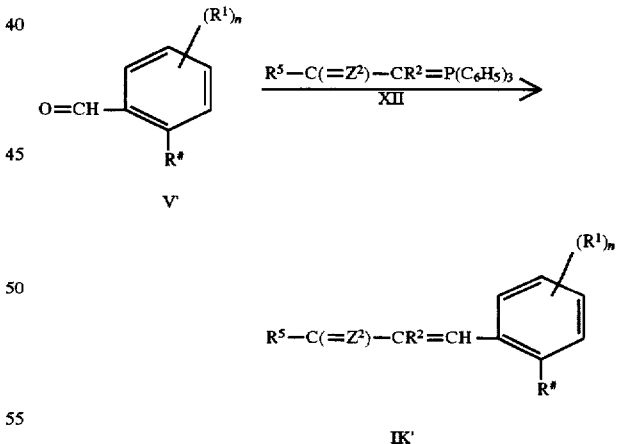

This reaction is customarily carried out at from 0° C. to 80° C., preferably 20° C. to 60° C.

Suitable solvents are aliphatic hydrocarbons such as pentane, hexane, cyclohexane and petroleum ether, aromatic hydrocarbons such as toluene, o-, m- and p-xylene, halogenated hydrocarbons such as dichloromethane, chloroform and chlorobenzene, ethers such as diethyl ether, diisopropyl ether, tert-butyl methyl ether, dioxane, anisole and tetrahydrofuran, nitriles such as acetonitrile and propionitrile, alcohols such as methanol, ethanol, n-propanol, isopropanol, n-butanol and tert-butanol and also dimethyl sulfoxide and dimethylformamide, particularly preferably toluene, tetrahydrofuran and methanol.

Mixtures of the solvents mentioned can also be used.

The starting materials are in general reacted with one another in equimolar amounts. It may be advantageous for the yield to employ XII in an excess based on the benzaldehyde V.

The starting substances XII required for preparing the compounds IK are known in the literature (DE-A 39 41 562) or can be prepared in accordance with the literature cited.

Further compounds, coming under claim 1, in which $R^3$=$R^4T$—C(=$Z^1$)— can be prepared from the alpha-substituted cinnamic acid derivatives IE, IF, IG and IH (collective designations I.1) described in the process for preparation.

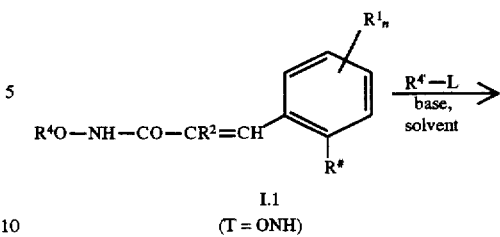

I.1
(T = ONH)

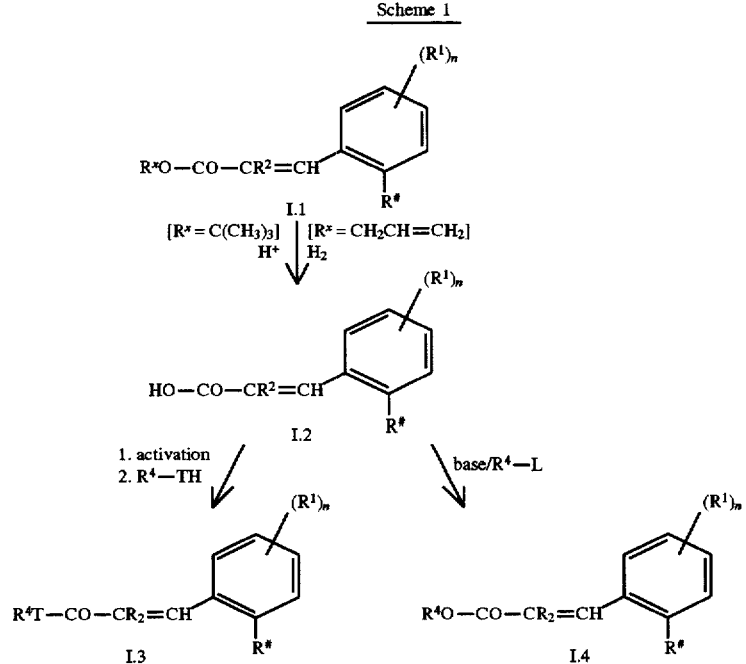

Starting from compounds I.1 in which the group RO(C=O)— can be hydrolyzed under non-basic conditions, a multiplicity of novel compounds of the general formula I in which $R^3$ is a group $R^4T$—C(=O)— can be prepared via the free acids. Of preparative interest are, for example, tert-butyl esters (cleavage in acidic medium, J. Am. Chem. Soc., 99 (1977), 2353) or ally [sic] esters (cleavage with $H_2$ in the presence of Pd compounds, Tetr. Lett. 1979, 613).

The carboxylic acids I.2 are activated and derivatized, for example, by converting into acid chlorides by means of thionyl chloride, oxalyl chloride or phosgene and subsequently derivatizing by nucleophilic replacement of the chlorine atom, by activating by means of e.g. N,N'-dicyclohexylcarbodiimide (J. Am. Chem. Soc., 77 (1955), 1067) or 1,1-carbonyldiimidazole (Chem. Ber. 95 (1962), 1284) or by converting into stable active esters (cf. e.g. Can. J. Chem., 54 (1976), 733; Synthesis 1983, 325; Angew. Chem., Int. Ed., 15 (1976), 444) and subsequently reacting with nucleophiles ($R^4TH$).

Derivatives of the formula I in which $R^3$ is $R^4TC$(=$Z^1$), where $Z^1$=$NOR^4$, can additionally be prepared from the compounds I.1 in which T is —ONH— (cf. Houben-Weyl, Vol. E5, pp. 826–829).

-continued

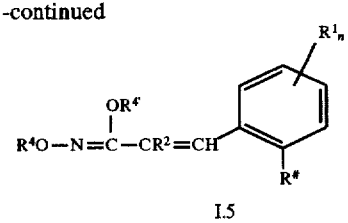

I.5

Suitable alkylating reagents are e.g. halogen compound [sic] (L=Cl, Br, I, cf. J. Med. Chem. 28 (1985), 323) or mesylates and triflates of $R^4$, additionally, if $R^4$ is $CH_3$ or $C_2H_5$, also the Meerwein salts $(H_3C)_3O^{\oplus}BF_4^{\ominus}$ or $(H_5C_2)_3O^{\oplus}BF_4^{\ominus}$ (cf. J. Org. Chem. 36 (1971) 281). Suitable bases are alkaline earth [sic] metal carbonates such as potassium carbonate, metal hydrides such as sodium hydride and potassium hydride or alternatively silver salts such as silver tetrafluoroborate. Suitable solvents are e.g. diethyl ether, tetrahydrofuran, acetone, acetonitrile, dichloromethane, dimethylformamide or 1,3-dimethyltetrahydro-2(1H) pyrimidines or mixtures thereof.

Further compounds coming under claim 1 can be prepared from the keto compounds IH.1 and IK, in which $Z^2$ represents 0, described in the process for preparation.

Scheme III

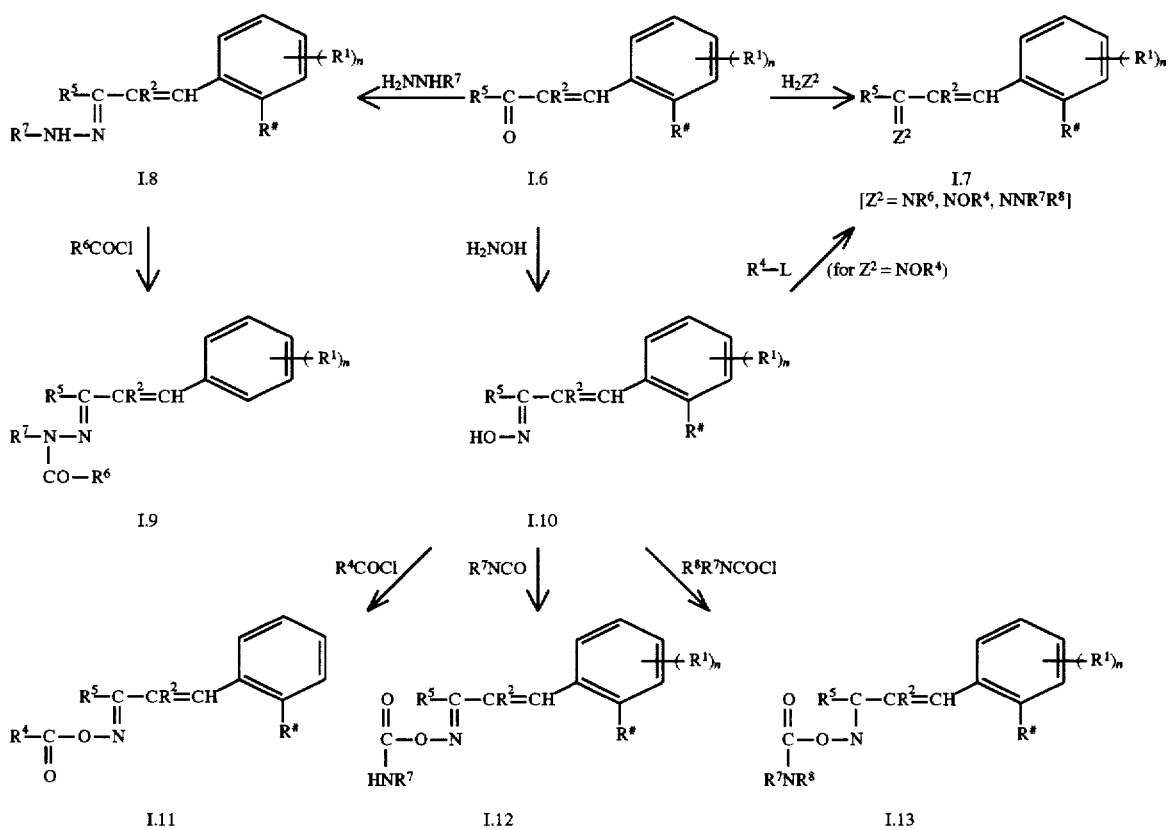

The individual derivatives I.7 to I.13 are prepared from the compounds I.6 by processes known from the literature:

compounds I.7 where $Z^2=NR^6$: Bull. Chem. Chim. Belg., 81 (1972), 643;

compounds I.7 where $Z^2=NOR^4$: J. Org. Chem., 38 (1973), 3749 or in two steps via compounds I.10: Helv. Chim. Acta, 60 (1977), 2294);

compounds I.7 where $Z^2=NNR^7R^8$ and compounds I.8: J. Am. Chem. Soc., 90 (1968), 6821;

compounds I.9: J. Org. Chem., 23 (1958), 1595;

compounds I.10: Helv. Chim. Acta 60 (1977), 2294;

compounds I.11: J. Org. Chem., 33 (1968), 150;

compounds I.12: Chem. Ber., 94 (1961), 67;

compounds I.13: DE-A 31 44 600.

Compounds I in which Y has the meaning NH can advantageously be prepared from the corresponding esters (Y=O).

Scheme IV

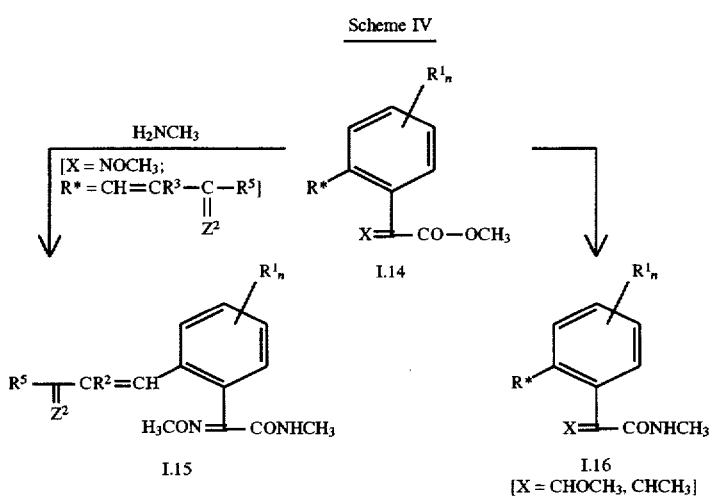

The direct aminolysis of the ester I.14 yields satisfactory yields of methyl amide I.15 only for X=NOCH$_3$ and R*=—CH=CR$^2$—C(=Z$^2$)R$^5$. The hydrolysis of the ester I.14 using alkali metal hydroxides in methanol or, for X=CHOCH$_3$, a variant using LiI/pyridine [Chem. Pharm. Bull. 26 (1988), 3642] and subsequent activation of the free acid and reaction with N-methylamine to give the amides I.16 is generally to be used.

In respect of the biological action against pests such as, in particular, harmful fungi, insects, nematodes and arachnids, those compounds I are suitable in which the index and the substituents have the following meanings:

n is 0, 1, 2, 3, or 4, where the R$^1$ radicals can be different if n>1, in particular 0 or 1;

X is CHOCH$_3$, CHCH$_3$ or NOCH$_3$;

Y is O or NH;

R$^1$ is nitro;

cyano;

halogen such as fluorine, chlorine, bromine or iodine, in particular fluorine or chlorine;

C$_1$-C$_4$-alkyl such as methyl, ethyl, propyl, 1-methylethyl, butyl, 1-methylpropyl, 2-methylpropyl and 1,1-dimethylethyl, preferably methyl and 1-methylethyl, in particular methyl;

C$_1$-C$_4$-haloalkyl, particularly C$_1$-C$_2$-haloalkyl such as trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, preferably difluoromethyl und trifluoromethyl, in particular trifluoromethyl;

C$_1$-C$_4$-alkoxy such as methoxy, ethoxy, propoxy, 1-methylethoxy, butoxy, 1-methylpropoxy, 2-methylpropoxy und 1,1-dimethylethoxy, preferably methoxy and ethoxy, 1-methylethoxy, in particular methoxy;

C$_1$-C$_4$-haloalkoxy, particularly C$_1$-C$_2$-haloalkoxy such as dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, preferably difluoromethoxy and chlorodifluoromethoxy, in particular difluoromethoxyloxy [sic]; C$_1$-C$_4$-alkylthio such as methylthio, ethylthio, propylthio, 1-methylethylthio, butylthio, 1-methylpropylthio, 2-methylpropylthio 2-methylpropylthio and 1,1-dimethylethylthio, preferably methylthio, ethylthio and 1-methylethylthio, in particular methylthio;

phenyl or phenoxy, where the aromatic rings can carry one to five halogens such as fluorine, chlorine, bromine and iodine, in particular fluorine and chlorine and/or one to three of the following radicals:

C$_1$-C$_4$-alkyl as mentioned above, in particular methyl;

C$_1$-C$_4$-haloalkyl, particularly C$_1$-C$_2$-haloalkyl as mentioned above, in particular trifluoromethyl;

C$_1$-C$_4$-alkoxy as mentioned above, in particular methoxy;

or, if n>1, a 1,3-butadiene-1,4-diyl group bonded to two adjacent C atoms of the parent structure, which for its part can carry one to four halogens such as fluorine, chlorine, bromine or iodine, in particular fluorine and chlorine, and/or one or two of the following radicals:

nitro, cyano,

C$_1$-C$_4$-alkyl as mentioned above, in particular methyl;

C$_1$-C$_4$-haloalkyl, particularly C$_1$-C$_2$-haloalkyl as mentioned above, in particular trifluoromethyl;

C$_1$-C$_4$-alkoxy as mentioned above, in particular methoxy;

R$^2$ is nitro, cyano, halogen such as fluorine, chlorine, bromine and iodine, in particular chlorine and bromine;

C$_1$-C$_4$-alkoxy as mentioned above, preferably methoxy and ethoxy, in particular methoxy;

C$_1$-C$_4$-alkylcarbonylamino such as methylcarbonylamino, ethylcarbonylamino, propylcarbonylamino, 1-methylethylcarbonylamino, butylcarbonylamino, 1-methylpropylcarbonylamino, 2-methylpropylcarbonylamino and 1,1-dimethylethylcarbonylamino, preferably methylcarbonylamino, ethylcarbonylamino and 1,1-dimethylethylcarbonylamino, in particular methylcarbonylamino;

C$_1$-C$_4$-alkoxycarbonylamino such as methoxycarbonylamino, ethoxycarbonylamino, propoxycarbonylamino, 1-methylethoxycarbonylamino, butoxycarbonylamino, 1-methylpropoxycarbonylamino, 2-methylpropoxycarbonylamino and 1,1-dimethylethoxycarbonylamino, preferably ethoxycarbonylamino and 1,1-dimethylethoxycarbonylamino, in particular 1,1-dimethylethoxycarbonylamino or benzyloxycarbonylamino;

R$^3$ if X is CHOCH$_3$ or NOCH$_3$ and R$^2$ is halogen, is an unsubstituted or substituted mononuclear or binuclear aromatic ring system which apart from carbons can contain one to four nitrogens or one or two nitrogens and an oxygen or sulfur or an oxygen or sulfur as ring members, ie. aryl radicals such as phenyl and naphthyl, preferably phenyl or 1- or 2-naphthyl, and hetaryl radicals, for example 5-membered ring heteroaromatic systems containing one to three nitrogens is and/or an oxygen or sulfur such as 2-furyl, 3-furyl, 2-thienyl, 3-thienyl, 3-pyrrolyl, 3-isoxazolyl, 5-isoxazolyl, 3-isothiazolyl, 5-isothiazolyl, 3-pyrazolyl, 4-pyrazolyl, 5-pyrazolyl, 2-oxazolyl, 4-oxazolyl, 2-thiazolyl, 4-thiazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-5-yl, 1,3,4-thiadiazol-2-yl, preferably 5-isoxazolyl, 4-oxazolyl, 1,2,4-oxadiazol-5-yl and 1,3,4-thiadiazol-2-yl, in particular 5-isoxazolyl, 1,3,4-thiadiazol-2-yl and 1,2,4-oxadiazol-5-yl or 6-membered ring heteroaromatic systems containing one to three nitrogens as hetero atoms such as 2-pyridinyl, 3-pyridinyl, 4-pyridinyl, 4-pyrimidinyl, 1,3,5-triazin-2-yl, preferably 3-pyridinyl and 4-pyridinyl, in particular 3-pyridinyl, where an unsubstituted or substituted benzene ring can be fused to the above-mentioned 5- or 6-membered heteroaromatic systems, or R$^3$ is an R$^4$—T—C(=Z$^1$)— or R$^5$—C(=Z$^2$)— group, where —T— is —O—, —S—, —NR$^7$—, —NR$^7$NR$^8$—, —ONR$^7$— or —NR$^7$O—;

=Z$^1$ is =O, =S, =NR$^6$ or =NOR$^4$;

=Z$^2$ is =O, =NR$^6$, =NOR$^4$, =N—NR$^7$R$^8$, =NO—C(=O)—R$^4$, =NO—C(=O)—NR$^7$R$^8$ or =N—NR$^7$—C(=O)R$^4$;

R$^4$ is hydrogen;

tri-(C$_1$-C$_4$-alkyl)-silyl, such as in particular trimethylsilyl or dimethyl-(1,1-dimethylethyl)-silyl, unsubstituted or substituted alkyl, particularly C$_1$-C$_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, preferably methyl, ethyl, 1-methylethyl, 1-methylpropyl, 1,1-dimethyl-ethyl, 1,1-dimethylpropyl and 2,3-dimethylbutyl, in particular methyl, 1-methylethyl and 1,1-dimethylethyl;

unsubstituted or substituted alkenyl, particularly $C_3$–$C_6$-alkenyl such as 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dimethyl-2-butenyl, 1,3-dimethyl-3-butenyl, 2,2-dimethylbutenyl, 2,3-dimethyl-2-butenyl, 2,3-dimethyl-3-butenyl, 3,3-dimethyl-2-butenyl, 1-ethyl-2-butenyl, 1-ethyl-3-butenyl, 2-ethyl-2-butenyl, 2-methyl-3-butenyl, 1,1,2-trimethyl-2-propenyl, 1-ethyl-1-methyl-2-propenyl and 1-ethyl-2-methyl-2-propenyl, preferably 1-propenyl, 1-methyl-2-propenyl, 1,1-dimethyl-2-propenyl, 1,1-dimethyl-2-butenyl, in particular 2-propenyl and 1,1-dimethyl-2-propenyl;

or unsubstituted or substituted alkynyl, particularly $C_3$–$C_6$-alkynyl such as 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl, preferably 2-propynyl, 1-methyl-2-propynyl, 1-methyl-2-butynyl, 1,1-dimethyl-2-propynyl and 1,1-dimethyl-2-butynyl, in particular 2-propynyl, 1-methyl-2-propynyl and 1,1-dimethyl-2-propynyl;

an unsubstituted or substituted saturated or mono- or diunsaturated cyclic system, which apart from carbons can contain one to three of the following hetero atoms as ring members: oxygen, sulfur and nitrogen, for example carbocycles such as cyclopropyl, cyclopentyl, cyclohexyl, cyclopent-2-enyl, cyclohex-2-enyl, 5- to 6-membered, saturated or unsaturated heterocycles, containing one to three nitrogens and/or an oxygen or sulfur such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydro-triazin-2-yl and 1,2,4-tetrahydrotriazin-3-yl, preferably 2-tetrahydrofuranyl, 2-tetrahydrothienyl, 2-pyrrolidinyl, 3-isoxazolidinyl, 3-isothiazolidinyl, 1,3,4-oxazolidin-2-yl, 2,3-dihydrothien-2-yl, 4,5-isoxazolin-3-yl, 3-piperidinyl, 1,3-dioxan-5-yl, 4-piperidinyl, 2-tetrahydropyranyl, 4-tetrahydropyranyl;

or an unsubstituted or substituted mononuclear or binuclear aromatic ring system, which apart from carbons can contain one to four nitrogens or one or two nitrogens and an oxygen or sulfur or an oxygen or sulfur as ring members, ie. aryl radicals such as phenyl and naphthyl, preferably phenyl or 1- or 2-naphthyl, and hetaryl radicals, for example 5-ring heteroaromatic systems containing one to three nitrogens and/or an oxygen or sulfur such as preferably 2-imidazolyl, 2-furyl, 3-furyl, 2-thienyl, 3-thienyl, 3-isoxazolyl, 2-oxazolyl, 1,2,4-oxadiazol-3-yl and 1,2,4-triazol-3-yl or 6-membered ring heteroaromatic systems containing one to three nitrogens as heteroatoms, preferably 3-pyridinyl, 2-pyridinyl, 2-pyrimidinyl, 4-pyrimidinyl and 1,3,5-triazin-2-yl, in particular 2-pyridinyl or 3-pyridinyl, where an unsubstituted or substituted benzene ring can be fused to the abovementioned 5- or 6-membered heteroaromatic systems;

$R^5$ is hydrogen;

cyano;

halogen such as fluorine, chlorine, bromine and iodine, in particular chlorine;

unsubstituted or substituted alkyl, particularly $C_1$–$C_6$-alkyl as mentioned above, preferably methyl, ethyl and 1-methylethyl, in particular methyl;

unsubstituted or substituted alkoxy, particularly $C_1$–$C_6$-alkoxy such as methoxy, ethoxy, propoxy, 1-methylethoxy, butoxy, 1-methyl-propoxy, 2-methylpropoxy, 1,1-dimethylethoxy, pentoxy, 1-methylbutoxy, 2-methylbutoxy, 2-methylbutoxy, 2,2-di-methylpropoxy, 1-ethylpropoxy, hexyloxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy, preferably methoxy and ethoxy, in particular methoxy;

unsubstituted or substituted alkenyl, particularly $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-diethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, preferably ethenyl, 1-propenyl, 2-propenyl, 1-methethenyl [sic] and 2-butenyl in particular 2-propenyl and 2-butenyl;

or unsubstituted or substituted alkynyl, particularly $C_2$–$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl, preferably ethynyl, 1-propynyl, 2-propynyl and 1-methyl-2-propionyl, in particular 2-propynyl;

an unsubstituted or substituted saturated or mono- or diunsaturated cyclic system, which apart from carbons can contain one to three of the following hetero atoms as ring members: oxygen, sulfur and nitrogen, in particular cyclopropyl, cyclopentyl and cyclohexyl, and also 2-tetrahydrofuranyl, 3-tetrahydrofuranyl, 2-tetrahydrothienyl, 2-oxazolidinyl and 2-thiazolidinyl;

an unsubstituted or substituted mononuclear or binuclear aromatic ring system, which apart from carbons can contain one to four nitrogens or one or two nitrogens and an oxygen or sulfur or an oxygen or sulfur as ring members, ie. aryl radicals such as phenyl and naphthyl, preferably phenyl or 1- or 2-naphthyl, and hetaryl radicals, for example 5-membered ring heteroaromatic systems containing one to three nitrogens and/or an oxygen or sulfur, preferably 2-furyl, 2-thienyl, 2-oxazolyl, 2-thiazolyl, 1-imidazolyl, 1-pyrrolyl and 1-pyrazolyl, in particular phenyl, 2-thienyl, 2-thiazolyl, 1-imidazolyl or 6-membered ring heteroaromatic systems containing one to three nitrogens as hetero atoms such as preferably 3-pyridinyl and 4-pyrimidinyl, in particular 3-pyridinyl, where an unsubstituted or substituted benzene ring can be fused to the abovementioned 5- or 6-membered heteroaromatic system;

or, if $=Z^2$ is $=O$, a group $R^xR^yC=NO$—, in which $R^x$ is hydrogen;

cyano;

halogen such as fluorine, chlorine, bromine and iodine, in particular bromine and chlorine;

$C_1$–$C_4$-alkyl as mentioned above, preferably methyl, ethyl and 1-methylethyl, in particular methyl;

$C_1$–$C_4$-haloalkyl, particularly $C_1$–$C_2$-haloalkyl as mentioned above, in particular trifluoromethyl;

$C_1$–$C_4$-alkoxy as mentioned above, preferably methoxy, ethoxy, 1-methethoxy [sic] and butoxy, in particular methoxy;

$C_1$–$C_4$-alkylthio as mentioned above, in particular methylthio;

$C_3$–$C_7$-cycloalkyl such as cyclopropyl, cyclobutyl, cyclopentyl, cyclohexyl and cycloheptyl, preferably cyclopropyl and cyclohexyl, in particular cyclopropyl;

phenyl and benzyl and $R^y$ is hydrogen;

unsubstituted or substituted alkyl, particularly $C_1$–$C_6$-alkyl as mentioned above, preferably methyl, ethyl, propyl, 1-methylethyl, butyl, 2-methylpropyl and 1,1-dimethylethyl, in particular methyl, 1-methylethyl and butyl;

unsubstituted or substituted alkenyl, particularly $C_2$–$C_6$-alkenyl as mentioned above: preferably ethenyl, 2-propenyl, 2-butenyl, 1-methylethenyl and 1,1-dimethyl-2-propenyl, in particular 2-propenyl and 2-butenyl;

unsubstituted or substituted alkynyl, particularly $C_2$–$C_6$-alkynyl as mentioned above, preferably ethynyl, 2-propynyl and 2-butynyl, in particular 2-propynyl;

unsubstituted or substituted $C_3$–$C_6$-cycloalkyl, in particular cyclopropyl and cyclohexyl;

or unsubstituted or substituted phenyl, or $R^x$ and $R^y$, together with the C atom to which they are bonded, form an unsubstituted or substituted saturated or mono- or diunsaturated cyclic system, which apart from carbons can contain one to three of the following hetero atoms as ring members: oxygen, sulfur and nitrogen, for example 5- to 6-membered, saturated or unsaturated heterocycles, containing one to three nitrogens and/or an oxygen or sulfur as mentioned above, in particular cyclopentyl, cyclohexyl and 4-piperidinyl;

$R^6$ is hydrogen; unsubstituted or substituted phenyl; unsubstituted or substituted alkyl, particularly $C_1$–$C_6$-alkyl as mentioned above, preferably methyl, ethyl, propyl, 1-methylethyl and 1,1-dimethylethyl, in particular methyl and 1,1-dimethylethyl;

$R^7$ is hydrogen or $C_1$–$C_4$-alkyl as mentioned above, in particular methyl;

$R^8$ is hydrogen, $C_1$–$C_4$-alkyl as mentioned above, in particular methyl, or $COR^7$.

The alkyls mentioned in the radicals $R^4$, $R^5$, $R^6$, $R^x$ and $R^y$ can for their part be partially or completely halogenated, ie. the hydrogens of these groups can be partially or completely replaced by halogens such as fluorine, chlorine, bromine and iodine, preferably fluorine and chlorine. Apart from the designated halogens, the alkyls mentioned can additionally carry one to three of the following substituents:

nitro;

cyano;

$C_1$–$C_4$-alkoxy, preferably methoxy, ethoxy, 1-methylethoxy and 1,1-dimethylethoxy, in particular methoxy;

$C_1$–$C_4$-haloalkoxy, particularly $C_1$–$C_2$-haloalkoxy, preferably difluoromethoxy, trifluoromethoxy and 2,2,2-trifluoroethoxy, in particular difluoromethoxy;

$C_1$–$C_4$-alkylthio, preferably methylthio and 1-methylethylthio, in particular methylthio;

$C_1$–$C_4$-alkylamino such as methylamino, ethylamino, propylamino, 1-methylethylamino, butylamino, 1-methylpropylamino, 2methylpropylamino and 1,1-dimethylethylamino, preferably methylamino and 1,1-dimethylethylamino, in particular methylamino, di-$C_1$–$C_4$-alkylamino such as N,N-dimethylamino, N,N-diethylamino, N,N-dipropylamino, N,N-di(1-methylethyl) amino, N,N-dibutylamino, N,N-di(1-methylpropyl)amino, N,N-di(2-methylpropyl)amino, N,N-di(1,1-dimethylethyl) amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methyl-ethyl)-N-(1-methylpropyl) amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino, preferably N,N-dimethylamino and N,N-diethylamino, in particular N,N-dimethylamino;

$C_3$–$C_6$-alkenyloxy such as 2-propenyloxy, 2-butenyloxy, 3-butenyloxy, 1-methyl-2-propenyloxy, 2-methyl-2-propenyloxy, 2-pentenyloxy, 3-pentenyloxy, 4-pentenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-Dimethyl-2-propenyloxy, 1-Ethyl-2-propenyloxy, 2-hexenyloxy, 3-hexenyloxy, 4-hexenyloxy, 5-hexenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-2-butenyloxy, 1,2-dimethyl-3-butenyloxy, 1,3-dimethyl-2-butenyloxy, 1,3-dimethyl-3-butenyloxy, 2,2-dimethyl-3-butenyloxy, 2,3-dimethyl-2-butenyloxy, 2,3-dimethyl-3-butenyloxy, 3,3-dimethyl-2-butenyloxy, 1-ethyl-2-butenyloxy, 1-ethyl-3-butenyloxy, 2-ethyl-2-butenyloxy, 2-ethyl-3-butenyloxy, 1,1,2-trimethyl-2-propenyloxy, 1-ethyl-1-methyl-2-propenyloxy and 1-ethyl-2-methyl-2-propenyloxy, preferably 2-propenyloxy and 3-methyl-2-butenyloxy, in particular 2-propenyloxy;

$C_3$–$C_6$-alkynyloxy such as 2-propynyloxy, 2-butynyloxy, 3-butynyloxy, 1-methyl-2-propynyloxy, 2-pentynyloxy, 3-pentynyloxy, 4-pentynyloxy, 1-methyl-2-butynyloxy, 1-methyl-3-butynyloxy, 2-methyl-3-butynyloxy, 1,1-dimethyl-2-propynyloxy, 1-ethyl-2-propynyloxy, 2-hexynyloxy, 3-hexynyloxy, 4-hexynyloxy, 5-hexynyloxy, 1-methyl-2-pentynyloxy, 1-methyl-3-pentynyloxy, 1-methyl-4-pentynyloxy, 2-methyl-3-pentynyloxy, 2-methyl-4-pentynyloxy, 3-methyl-4-pentynyloxy, 4-methyl-2-pentynyloxy, 1,1-dimethyl-2-butynyloxy, 1,1-dimethyl-3-butynyloxy, 1,2-dimethyl-3-butynyloxy, 2,2-dimethyl-3-butynyloxy, 1-ethyl-2-butynyloxy, 1-ethyl-3-butynyloxy, 2-ethyl-3-butynyloxy and 1-ethyl-1-methyl-2-propynyloxy, preferably 2-propynyloxy and 2-butynyloxy, in particular 2-propynyloxy;

$C_1$–$C_6$-alkylcarbonyl such as methylcarbonyl, ethylcarbonyl, propylcarbonyl, 1-methylethylcarbonyl, butylcarbonyl, 1-methylpropylcarbonyl, 2-methylpropylcarbonyl, 1,1-dimethylethylcarbonyl, pentylcarbonyl, 1-methylbutylcarbonyl, 2-methylbutylcarbonyl, 3-methylbutylcarbonyl, 1,1-dimethylpropylcarbonyl, 1,2-dimethylpropylcarbonyl, 2,2-dimethylpropylcarbonyl, 1-ethylpropylcarbonyl, hexylcarbonyl, 1-methylpentylcarbonyl, 2-methylpentylcarbonyl, 3-methylpentylcarbonyl, 4-methylpentylcarbonyl, 1,1-dimethylbutylcarbonyl, 1,2-dimethylbutylcarbonyl, 1,3-dimethylbutylcarbonyl, 2,2-dimethylbutylcarbonyl, 2,3-dimethylbutylcarbonyl, 3,3-dimethylbutylcarbonyl, 1-ethylbutylcarbonyl, 2-ethylbutylcarbonyl, 1,1,2-trimethylpropylcarbonyl, 1,2,2-trimethylpropylcarbonyl, 1-ethyl-1-methylpropylcarbonyl and 1-ethyl-2-methylpropylcarbonyl, preferably methylcarbonyl, ethylcarbonyl and 1,1-dimethylcarbonyl, in particular ethylcarbonyl;

$C_1$–$C_6$-alkoxyimino (alk—O—N=) such as methoxyimino, ethoxyimino, propoxyimino, 1-methylethoxyimino, butoxyimino, 1-methylpropoxyimino, 2-methylpropoxyimino, 1,1-dimethylethoxyimino, pentoxyimino, 1-methylbutoxyimino, 2-methylbutoxyimino, 3-methylbutoxyimino, 2,2-dimethylpropoxyimino, 1-ethylpropoxyimino, hexyloxyimino, 1,1-dimethylpropoxyimino, 1,2-dimethylpropoxyimino, 1-methylpentoxyimino, 2-methylpentoxyimino, 3-methylpentoxyimino, 4-methylpentoxyimino, 1,1-dimethylbutoxyimino, 1,2-dimethylbutoxyimino, 1,3-dimethylbutoxyimino, 2,2-dimethylbutoxyimino, 2,3-dimethylbutoxyimino, 3,3-dimethylbutoxyimino, 1-ethylbutoxyimino, 2-ethylbutoxyimino, 1,1,2-trimethylpropoxyimino, 1,2,2-trimethylpropoxyimino, 1-ethyl-1-methylpropoxyimino and 1-ethyl-2-methylpropoxyimino, preferably methoxyimino, ethoxyimino, propoximino, 1,1-dimethylethoximino and 1-methylethoximino, in particular methyloximino and 1,1-dimethylethyloximino;

$C_1$–$C_6$-alkoxycarbonyl such as methoxycarbonyl, ethoxycarbonyl, propoxycarbonyl, 1-methylethoxycarbonyl, butoxycarbonyl, 1-methylpropoxycarbonyl, 2-methylpropoxycarbonyl, 1,1-dimethylethoxycarbonyl, pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, hexyloxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3- dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl and 1-ethyl-2-methylpropoxycarbonyl, preferably methoxycarbonyl, ethoxycarbonyl and 1,1-dimethylethoxycarbonyl, in particular ethoxycarbonyl;

$C_1$–$C_6$-alkylthiocarbonyl such as methylthiocarbonyl, ethylthiocarbonyl, propylthiocarbonyl, 1-methylethylthiocarbonyl, butylthiocarbonyl, 1-methylpropylthiocarbonyl, 2-methylpropylthiocarbonyl, 1,1-dimethylethylthiocarbonyl, pentylthiocarbonyl, 1-methylbutylthiocarbonyl, 2-methylbutylthiocarbonyl, 3-methylbutylthiocarbonyl, 2,2-dimethylpropylthiocarbonyl, 1-ethylpropylthiocarbonyl, hexylthiocarbonyl, 1,1-dimethylpropthiocarbonyl [sic], 1,2-dimethylpropylthiocarbonyl, 1-methylpentylthiocarbonyl, 2-methylpentylthiocarbonyl, 3-methylpentylthiocarbonyl, 4-methylpentylthiocarbonyl, 1,1-dimethylbutylthiocarbonyl, 1,2-dimethylbutylthiocarbonyl, 1,3-dimethylbutylthiocarbonyl, 2,2-dimethylbutylthiocarbonyl, 2,3-dimethylbutylthiocarbonyl, 3,3-dimethylbutylthiocarbonyl, 1-ethylbutylthiocarbonyl, 2-ethylbutylthiocarbonyl, 1,1,2-trimethylpropylthiocarbonyl, 1,2,2-trimethylpropylthiocarbonyl, 1-ethyl-1-methylpropylthiocarbonyl and 1-ethyl-2-methylpropylthiocarbonyl, preferably methylthiocarbonyl and 1-methylethylthiocarbonyl, in particular methylthiocarbonyl;

$C_1$–$C_6$-alkylaminocarbonyl such as methylaminocarbonyl, ethylaminocarbonyl, propylaminocarbonyl, 1-methylethylaminocarbonyl, butylaminocarbonyl, 1-methylpropylaminocarbonyl, 2-methylpropylaminocarbonyl, 1,1-dimethylethylaminocarbonyl, pentylaminocarbonyl, 1-methylbutylaminocarbonyl, 2-methylbutylaminocarbonyl, 3-methylbutylaminocarbonyl, 2,2-dimethylpropylaminocarbonyl, 1-ethylpropylaminocarbonyl, hexylaminocarbonyl, 1,1-dimethylpropylaminocarbonyl, 1,2-dimethylpropylaminocarbonyl, 1-methylpentylaminocarbonyl, 2-methylpentylaminocarbonyl, 3-methylpentylaminocarbonyl, 4-methylpentylaminocarbonyl, 1,1-dimethylbutylaminocarbonyl, 1,2-dimethylbutylaminocarbonyl, 1,3-dimethylbutylaminocarbonyl, 2,2-dimethylbutylaminocarbonyl, 2,3-dimethylbutylaminocarbonyl, 3,3-dimethylbutylaminocarbonyl, 1-ethylbutylaminocarbonyl, 2-ethylbutylaminocarbonyl, 1,1,2-trimethylpropylaminocarbonyl, 1,2,2-trimethylpropylaminocarbonyl, 1-ethyl-1-methylpropylaminocarbonyl and 1-ethyl-2-methylpropylaminocarbonyl, preferably methylamincarbonyl [sic] and ethylamincarbonyl [sic], in particular methylaminocarbonyl;

di-$C_1$–$C_6$-alkylaminocarbonyl, particularly di-$C_1$–$C_4$-alkylaminocarbonyl such as N,N-dimethylaminocarbonyl, N,N-diethylaminocarbonyl, N,N-dipropylaminocarbonyl, N,N-di(1-methylethyl)aminocarbonyl, N,N-dibutylaminocarbonyl, N,N-di(1-methylpropyl)aminocarbonyl, N,N-di(2-methylpropyl)aminocarbonyl, N,N-di(1,1-dimethylethyl)aminocarbonyl, N-Ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-Ethyl-N-(1-methylethyl)aminocarbonyl, N-butyl-N-ethylaminocarbonyl, N-ethyl-N-(1-methylpropyl) aminocarbonyl, N-ethyl-N-(2-methylpropyl) aminocarbonyl, N-ethyl-N-(1,1-dimethylethyl) aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethylethyl)-N-propylaminocarbonyl, N-butyl-N-(1-methylethyl)aminocarbonyl, N-(1-Methylethyl)-N-(1-methylpropyl)aminocarbonyl, N-(1-Methylethyl)-N-(2-methylpropyl)aminocarbonyl, N-(1,1-dimethylethyl)-N-(1-methylethyl)aminocarbonyl, N-butyl-N-(1-methylpropyl) aminocarbonyl, N-butyl-N-(2-methylpropyl) aminocarbonyl, N-butyl-N-(1,1-dimethylethyl) aminocarbonyl, N-(1-methylpropyl)-N-(2-methyl-propyl) aminocarbonyl, N-(1,1-dimethylethyl)-N-(1-methylpropyl) aminocarbonyl and N-(1,1-dimethylethyl)-N-(2-methylpropyl)aminocarbonyl, preferably N,N-dimethylaminocarbonyl and N,N-diethylaminocarbonyl, in particular N,N-dimethylaminocarbonyl;

$C_1$–$C_6$-alkylcarboxyl such as methylcarboxyl, ethylcarboxyl, propylcarboxyl, 1-methylethylcarboxyl, butylcarboxyl, 1-methylpropylcarboxyl, 2-methylpropylcarboxyl, 1,1-dimethylethylcarboxyl, pentylcarboxyl, 1-methylbutylcarboxyl, 2-methylbutylcarboxyl, 3-methylbutylcarboxyl, 1,1-dimethylpropylcarboxyl, 1,2-dimethylpropylcarboxyl, 2,2-dimethylpropylcarboxyl, 1-ethylpropylcarboxyl, hexylcarboxyl, 1-methylpentylcarboxyl, 2-methylpentylcarboxyl, 3-methylpentylcarboxyl, 4-methylpentylcarboxyl, 1,1-dimethylbutylcarboxyl, 1,2-dimethylbutylcarboxyl, 1,3-dimethylbutylcarboxyl, 2,2-dimethylbutylcarboxyl, 2,3-dimethylbutylcarboxyl, 3,3-dimetbylbutylcarboxyl, 1-ethylbutylcarboxyl, 2-ethylbutylcarboxyl, 1,1,2-trimethylpropylcarboxyl, 1,2,2-trimethylpropylcarboxyl, 1-ethyl-1-methylpropylcarboxyl and 1-ethyl-2-methylpropylcarboxyl, preferably methylcarboxyl, ethylcarboxyl and 1,1-dimethylethylcarbonyl, in particular methylcarboxyl and 1,1-dimethylethylcarboxyl;

$C_1$–$C_6$-alkylcarbonylamino such as methylcarbonylamino, ethylcarbonylamino, propylcarbonylamino, 1-methylethylcarbonylamino, butylcarbonylamino, 1-methylpropylcarbonylamino, 2-methylpropylcarbonylamino, 1,1-dimethylethylcarbonylamino, pentylcarbonylamino, 1-methylbutylcarbonylamino, 2-methylbutylcarbonylamino, 3-methylbutylcarbonylamino, 2,2-dimethylpropylcarbonylamino, 1-ethylpropylcarbonylamino, hexylcarbonylamino, 1,1-dimethylpropylcarbonylamino, 1,2-dimethylpropylcarbonylamino, 1-methylpentylcarbonylamino, 2-methylpentylcarbonylamino, 3-methylpentylcarbonylamino, 4-methylpentylcarbonylamino, 1,1-dimethylbutylcarbonylamino, 1,2-dimethylbutylcarbonylamino, 1,3- dimethylbutylcarbonylamino, 2,2-dimethylbutylcarbonylamino, 2,3-dimethylbutylcarbonylamino, 3,3-dimethylbutylcarbonylamino, 1-ethylbutylcarbonylamino, 2-ethylbutylcarbonylamino, 1,1,2-trimethylpropylcarbonylamino, 1,2,2-trimethylpropylcarbonylamino, 1-ethyl-1-methylpropylcarbonylamino and 1-ethyl-2-methylpropylcarbonylamino, preferably methylcarbonylamino and ethylcarbonylamino, in particular ethylcarbonylamino;

$C_3$–$C_7$-cycloalkyl such as cyclopropyl, cyclobutyl, cyclopentyl, cyclohexyl and cycloheptyl, preferably cyclopropyl, cyclopentyl and cyclohexyl, in particular cyclopropyl;

$C_3$–$C_7$-cycloalkoxy such as cyclopropoxy, cyclobutoxy, cyclopentoxy, cyclohexyloxy and cycloheptyloxy, preferably cyclopentoxy and cyclohexyloxy, in particular cyclohexyloxy;

$C_3$–$C_7$-cycloalkylthio such as cyclopropylthio, cyclobutylthie, cyclopentylthio, cyclohexylthio and cycloheptylthio, preferably dyclohexylthio;

$C_3$–$C_7$-cycloalkylamino such as cyclopropylamino, cyclobutylamino, cyclopentylamino, cyclohexylamino and cycloheptylamino, preferably cyclopropylamino and cyclohexylamino, in particular cyclopropylamino;

$C_5$–$C_7$-cycloalkenyl such as cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl and cyclohept-4-enyl, preferably cyclopent-1-enyl, cyclopent-3-enyl and cyclohex-2-enyl, in particular cyclopent-1-enyl;

5- to 6-membered, saturated or unsaturated heterocycles, containing one to three nitrogens and/or an oxygen or sulfur as mentioned above, preferably tetrahydropyrazin-1-yl and 2-tetrahydrofuranyl, tetrahydropyran-4-yl and 1,3-dioxan-2-yl, aromatic systems such as phenyl, 1-naphthyl and 2-naphthyl, 5-membered ring heteroaromatic systems containing one to three nitrogens and/or an oxygen or sulfur as mentioned above, preferably 3-furyl, 3-thienyl, 5-isoxazolyl, 3-isoxazolyl, 4-oxazolyl, 1,3,4-thiadiazol-3-yl and 2-thienyl, where a benzo ring can be fused to the abovementioned 5-membered heteroaromatic systems.

6-membered ring heteroaromatic systems containing one to three nitrogens as hetero atoms, preferably 5-pyrimidyl and 3-pyridinyl, where a benzo ring can be fused to the above-mentioned 6-membered heteroaromatic systems.

The alkenyls and alkynyls mentioned in the case of the radicals $R^4$, $R^5$ and $R^y$ can for their part be partially or completely halogenated, ie. the hydrogens of these groups can be partially or completely replaced by halogens such as fluorine, chlorine, bromine and iodine, preferably fluorine and chlorine. The alkenyls and alkynyls mentioned can additionally carry, apart from the halogens designated, one to three of the following substituents:

nitro; cyano; $C_1$–$C_4$-alkoxy, preferably methoxy, ethoxy and 1-methylethoxy, in particular methoxy;

$C_1$–$C_4$-haloalkoxy, particularly $C_1$–$C_2$-haloalkoxy, in particular difluoromethoxy, $C_1$–$C_4$-alkylthio, preferably methylthio and 1,1-dimethylethylthio, in particular methylthio;

$C_1$–$C_4$-alkylamino, preferably methylamino, ethylamino and 1-methylethylamino, in particular methylamino;

di-$C_1$–$C_4$-alkylamino, preferably N,N-dimethylamino and N,N-diethylamino, in particular N,N-dimethylamino;

$C_3$–$C_6$-alkenyloxy, in particular 2-propenyloxy;

$C_3$–$C_6$-alkynyloxy, in particular 2-propynyloxy;

$C_1$–$C_6$-alkylcarbonyl, preferably methylcarbonyl, ethylenecarbonyl [sic] and 1,1-dimethylcarbonyl, in particular methylcarbonyl;

$C_1$–$C_6$-alkoxyimino (alkyl—O—N=), preferably methoxyimino, propyloximino and 1,1-dimethylethyloximino, in particular methoxyimino and 1,1-dimethylethyloximino;

$C_1$–$C_6$-alkoxycarbonyl, in particular methoxycarbonyl, ethoxycarbonyl and 1,1-dimethylethoxycarbonyl, in particular methoxycarbonyl and 1,1-dimethylethoxycarbonyl;

$C_1$–$C_6$-alkylthiocarbonyl, in particular methylthiocarbonyl;

$C_1$–$C_6$-alkylaminocarbonyl, in particular methyliminocarbonyl [sic];

di-$C_1$–$C_6$-alkylaminocarbonyl, in particular N,N-dimethylaminocarbonyl;

$C_1$–$C_6$-alkylcarboxyl, preferably methylcarboxyl and 1,1-dimethylethylcarboxyl, in particular methylcarboxyl;

$C_1$–$C_6$-alkylcarbonylamino, preferably methylcarbonylamino and 1,1-dimethylethylcarbonylamino, in particular methylcarbonylamino;

$C_3$–$C_7$-cycloalkyl, preferably cyclopropyl, cyclopentyl and cyclohexyl, in particular cyclopropyl;

$C_3$–$C_7$-cycloalkyl, in particular cyclohexyloxy;

$C_3$–$C_7$-cycloalkylthio, in particular cyclohexylthio;

$C_3$–$C_7$-cycloalkylamino, preferably cyclopropylamino and cyclohexylamino, in particular cyclopropylamino;

$C_5$–$C_7$-cycloalkenyl, preferably cyclopent-1-enyl, cyclopent-2-enyl and cyclohex-2-enyl, in particular cyclopent-1-enyl;

5- to 6-membered, saturated or unsaturated heterocycles containing one to three nitrogens and/or an oxygen or sulfur, as mentioned above, preferably tetrahydropyran-4-yl, 2-tetrahydrofuranyl and 1,3-dioxan-2-yl;

aromatic systems such as phenyl, 1-naphthyl and 2-naphthyl;

5-membered ring heteroaromatic systems containing one to three nitrogens and/or an oxygen or sulfur, as mentioned above, preferably 2-furyl, 3-furyl, 2-thienyl, 3-thienyl, 5-isoxazolyl and 4-oxazolyl, in particular 2-furyl and 2-thienyl, where a benzo ring can be fused to the above-mentioned 5-membered heteroaromatic systems.

6-ring heteroaromatic systems containing one to three nitrogens as hetero atoms, such as preferably 2-pyrimidinyl, 5-pyrimidinyl and 3-pyridyl, where a benzo ring can be fused to the above-mentioned 6-membered heteroaromatic systems.

The saturated or mono- or diunsaturated alicyclic or heterocyclic systems mentioned in the case of the radicals $R^4$, $R^5$, $R^6$, $R^x$ and $R^y$, and also the saturated or mono- or diunsaturated alicyclic or heterocyclic systems which [lacuna] as substituents of the alkyls, alkenyls and alkynyls mentioned in the case of the radicals $R^4$, $R^5$, $R^6$, $R^x$ and $R^y$, can for their part be partially or completely halogenated, ie. the hydrogens of these groups can be partially or completely replaced by halogens such as fluorine, chlorine, bromine and iodine, preferably fluorine and chlorine.

These mono- or diunsaturated alicyclic or heterocyclic systems can additonally carry, apart from the halogens designated, one to three of the following substituents:

nitro; cyano; $C_1$–$C_6$-alkyl, preferably methyl and ethyl, in particular methyl;

$C_1$–$C_4$-haloalkyl, particularly $C_1$–$C_2$-haloalkyl, in particular trifluoromethyl;

$C_1$–$C_4$-alkoxy, in particular methoxy;

$C_1$–$C_4$-alkylthio, in particular methylthio;

di-$C_1$–$C_4$-alkylamino, in particular N,N-dimethylamino;

$C_2$–$C_6$-alkenyl, preferably ethenyl, 1-propenyl, 2-propenyl and 1-methylethynyl, in particular ethenyl and 1-methylethenyl, $C_2$–$C_6$-alkynyl, preferably ethynyl, 2-propynyl, 1-butynyl, in particular ethynyl;

$C_1$–$C_6$-alkoxycarbonyl, preferably methoxycarbonyl, ethoxycarbonyl, 1-methylethoxycarbonyl and 1,1-dimethylethoxycarbonyl, in particular ethoxycarbonyl;

$C_1$–$C_6$-alkylaminocarbonyl, in particular methylaminocarbonyl;

di-$C_1$–$C_6$-alkylaminocarbonyl, particularly di-$C_1$–$C_4$-alkylaminocarbonyl, in particular N,N-dimethylaminocarbonyl;

$C_1$–$C_6$-alkylcarboxyl, in particular methylcarboxyl;

$C_1$–$C_6$-alkylcarbonylamino, in particular methylcarbonylamino and 1,1-dimethylcarbonylamino;

$C_3$–$C_7$-cycloalkyl, preferably cyclopropyl and cyclohexyl, in particular cyclopropyl;

aromatic systems such as in particular phenyl;

5-membered ring heteroaromatic systems containing one to three nitrogens and/or an oxygen or sulfur, preferably 2-furyl, 5-isoxazolyl, 1-pyrrolyl and 1-pyrazolyl, in particular 2-furyl and 1-pyrrolyl, where a benzo ring can be fused to the abovementioned 5-membered heteroaromatic systems.

6-membered ring heteroaromatic systems containing one to three nitrogens as hetero atoms such as preferably 2-pyridinyl, 2-pyridinyl [sic] and 2-pyrimidinyl, in particular 3-pyridinyl, where a benzo ring can be fused to the abovementioned 6-membered heteroaromatic systems.

The mono- or binuclear aromatic or heteroaromatic systems mentioned in the case of the radicals $R^3$, $R^4$, $R^5$, $R^6$ and $R^y$, and also the saturated or mono- or diunsaturated aromatic or heteroaromatic systems which have been mentioned as substituents of the alkyls, alkenyls and alkynyls mentioned in the case of the radicals $R^4$, $R^5$, $R^6$, $R^x$ and $R^y$, can for their part be partially or completely halogenated, ie. the hydrogens of these groups can be partially or completely replaced by halogens such as fluorine, chlorine, bromine and iodine, preferably fluorine and chlorine.

These mono- or binuclear aromatic or heteroaromatic systems can additionally contain, apart from the halogens designated one to three of the following substituents:

nitro; cyano; $C_1$–$C_6$-alkyl, preferably methyl, 1-methylethyl and 1,1-dimethylethyl, in particular methyl and 1-methylethyl;

$C_1$–$C_4$-haloalkyl, particularly $C_1$–$C_2$-haloalkyl, preferably trifluoromethyl;

$C_1$–$C_4$-alkoxy, preferably methoxy, ethoxy and 1-methylethoxy, in particular methoxy;

$C_1$–$C_4$-haloalkoxy, particularly $C_1$–$C_2$-haloalkoxy, in particular difluoromethoxy;

$C_1$–$C_4$-alkylthio, preferably methylthio and butylthio, in particular methylthio;

di-$C_1$–$C_4$-alkylamino, preferably N,N-dimethylamino and N,N-diethylamino, in particular N,N-dimethylamino;

$C_3$–$C_6$-alkenyl, preferably ethenyl, 2-propenyl, 2-methyl-2-propenyl and 2-butenyl, in particular 2-propenyl;

$C_3$–$C_6$-alkenyloxy, preferably 2-propenyloxy and 2-butenyloxy, in particular 2-propenyloxy;

$C_2$–$C_6$-alkynyl, preferably ethynyl, 1-propynyl, 2-butynyl and 2-propynyl, in particular ethynyl and 1-propynyl;

$C_1$–$C_6$-alkoxycarbonyl, preferably 1-methoxycarbonyl, ethoxycarbonyl and 1,1-dimethylethoxycarbonyl, in particular 1-methoxycarbonyl;

$C_1$–$C_6$-alkylaminocarbonyl, preferably methylaminocarbonyl and 2-methylethylaminocarbonyl, in particular methyleneaminocarbonyl;

di-$C_1$–$C_6$-alkylaminocarbonyl, particularly di-$C_1$–$C_4$-alkylaminocarbonyl, preferably N,N-dimethylaminocarbonyl and N,N-diethylaminocarbonyl, in particular N,N-dimethylaminocarbonyl;

$C_1$–$C_6$-alkylcarbonylamino, preferably methylcarbonylamino;

$C_3$–$C_7$-cycloalkyl, preferably cyclopropyl, cyclopentyl and cyclohexyl, in particular cyclopropyl and cyclohexyl;

$C_5$–$C_7$-cycloalkenyl, preferably cyclopent-1-enyl, cyclohex-1-enyl and cyclohex-2-enyl, in particular cyclohex-1-enyl;

phenyl;

5- to 6-membered, saturated or unsaturated heterocycles, containing one to three nitrogens and/or an oxygen or sulfur as mentioned above, in particular 2-tetrahydrothienyl and 2-tetrahydrofuranyl;

5-membered ring heteroaromatic systems containing one to three nitrogens and/or an oxygen or sulfur, preferably 5-isoxazolyl, 2-thiozolyl [sic], 2-thienyl and 2-furanyl.

6-membered ring heteroaromatic systems containing one to three nitrogens as hetero atoms, preferably 2-pyridinyl, 3-pyridinyl and 4-pyridinyl, in particular 3-pyridinyl, where the abovementioned aryl and heteroaryl rings can carry one to three of the following groups: fluorine, chlorine, cyano, methyl, methoxy, trifluoromethyl and trifluoromethoxy;

With respect to their use, those compounds I are particularly preferred in which n is 0 or 1.

Compounds I are additionally preferred in which X is $CHOCH_3$, $CHCH_3$ or $NOCH_3$.

In addition, compounds I are preferred in which $R^1$ is halogen, $C_1$–$C_4$-alkyl, $C_1$–$C_2$-haloalkyl, $C_1$–$C_4$-alkoxy, $C_1$–$C_2$-haloalkoxy, $C_1$–$C_2$-alkylthio or phenyl.

Additionally, those compounds I are also preferred in which $R^2$ is halogen.

Those compounds I are additionally preferred in which $R^3$ is a —CO—T—$R^4$ group.

In particular, those compounds I are also preferred in which R [sic] is a —CO—T—$R^4$ group and —T— is —O—, —S— —$NR^7$ [sic] or —$ONR^7$—.

In addition, compounds I are preferred in which $R^3$ is a —CO—$R^5$ group.

In particular, those compounds I are preferred in which $R^3$ is a —CO—$R^5$ group, where $R^5$ is one of the following radicals:

unsubstituted or substituted alkyl, alkenyl or alkynyl;

an unsubstituted or substituted saturated or mono- or diunsaturated cyclic system, which apart from carbons can contain one to three of the following hetero atoms as ring members: oxygen, sulfur and nitrogen;

an unsubstituted or substituted mono- or binuclear aromatic ring system, which apart from carbons can contain one to four nitrogens or one or two nitrogens and an oxygen or sulfur or an oxygen of sulfur as ring members.

Those compounds I are additionally preferred in which $R^3$ is a —C($R^5$)=NO—$R^4$ group.

Those compounds I are particularly preferred in which $R^3$ is a —C($R^5$)=NO—$R^4$ group, where $R^4$ is unsubstituted or substituted alkyl, alkenyl or alkynyl, and $R^5$ is unsubstituted or substituted alkyl, alkoxy, alkenyl or alkynyl; an unsubstituted or substituted saturated or mono- or diunsaturated cyclic system, which apart from carbons can contain one to three of the following hetero atoms as ring members: oxygen, sulfur and nitrogen; or an unsubstituted or substituted mono- or binuclear aromatic ring system, which apart from carbons can contain one to four nitrogens or one or two nitrogens and an oxygen or sulfur or an oxygen or sulfur as ring members, where the compounds in which $R^5$ is unsubstituted or substituted alkoxy are of particular importance.

Additionally, those compounds I are preferred in which $R^3$ is one of the following groups:

unsubstituted or substituted mono- or binuclear aromatic ring system, which apart from carbons can contain one to four nitrogens or one or two nitrogens and an oxygen or sulfur or an oxygen or sulfur as ring members.

In addition, those compounds I are also preferred in which $R^3$ is a group —CO—ON$\alpha$CR$^x$R$^y$.

In particular, those compounds I are preferred in which $R^3$ is a group —CO—ON=CR$^x$R$^y$, in which $R^x$ is cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio or $C_3$–$C_7$-cycloalkyl, and $R^y$ is hydrogen; unsubstituted or substituted alkyl; unsubstituted or substituted $C_3$–$C_6$-cycloalkyl;

or unsubstituted or substituted phenyl; or $R^x$ and $R^y$, together with the C atom to which they are bonded, form an unsubstituted or substituted saturated or mono- or diunsaturated cyclic system, which apart from carbons can contain one to three of the following hetero atoms as ring members: oxygen, sulfur and nitrogen.

Of particular interest are compounds of the general formula I.1

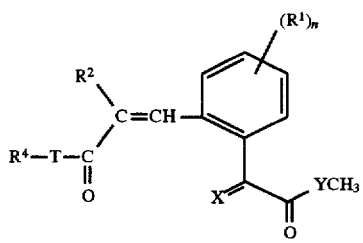

where the index and the substituents have the following meanings:

n is 0 or 1;

X is CHOCH$_3$, CHCH$_3$ or NOCH$_3$;

Y is O or NH;

$R^1$ is halogen, $C_1$–$C_4$-alkyl, $C_1$–$C_2$-haloalkyl, $C_1$–$C_4$-alkoxy, $C_1$–$C_2$-haloalkoxy, $C_1$–$C_2$-alkylthio or phenyl;

$R^2$ is halogen or cyano;

—T— is —O—, —S—, —NR$^7$ [sic] or —ONR$^7$—, $R^4$ is hydrogen; tri($C_1$–$C_4$-alkyl)silyl;

unsubstituted or substituted alkyl, alkenyl or alkynyl;

an unsubstituted or substituted saturated or mono- or diunsaturated cyclic system, which apart from carbons can contain one to three of the following hetero atoms as ring members: oxygen, sulfur and nitrogen;

or an unsubstituted or substituted mono- or binuclear aromatic ring system, which apart from carbons can contain one to four nitrogens or one or two nitrogens and an oxygen or sulfur or an oxygen or sulfur as ring members and $R^7$ is hydrogen or $C_1$–$C_4$-alkyl.

In the formula I.1, in the meaning $R^1$ halogen is to be understood as meaning in particular fluorine or chlorine, $C_1$–$C_4$-alkyl is in particular to be understood as meaning methyl, ethyl, 1-methylethyl or 1,1-dimethylethyl, $C_1$–$C_2$-haloalkyl is in particular to be understood as meaning trifluoromethyl, $C_1$–$C_4$-alkoxy is in particular to be understood as meaning methoxy or ethoxy, $C_1$–$C_2$-haloalkoxy is in particular to be understood as meaning trifluoromethoxy and $C_1$–$C_2$-alkylthio is in particular to be understood as meaning methylthio.

In the formula I.1, in the meaning $R^2$ halogen is to be understood as meaning in particular fluorine, chlorine or bromine.

In the formula I.1, —T— is to be understood as meaning in particular —O— or —S— if $R^4$ has the following meaning:

tri($C_1$–$C_4$-alkyl)silyl, such as in particular trimethylsilyl;

alkyl, particularly straight-chain or branched $C_1$–$C_6$-alkyl as mentioned above in general and in particular and $C_1$–$C_4$-alkyl as mentioned above in general and in particular, which carries one to nine halogens such as in particular fluorine, chlorine and/or bromine and/or one or two of the following radicals:

cyano;

$C_1$–$C_4$-alkoxy as mentioned above, in particular methoxy;

$C_1$–$C_2$-haloalkoxy as mentioned above, in particular trifluoromethoxy;

$C_1$–$C_4$-alkylthio as mentioned above, in particular methylthio;

$C_1$–$C_2$-haloalkylthio as mentioned above, in particular trifluoromethylthio;

$C_1$–$C_4$-alkylamino as mentioned above, in particular methylamino and ethylamino;

di-$C_1$–$C_4$-alkylamino as mentioned above, in particular N,N-dimethylamino and N,N-diethylamino;

$C_1$–$C_6$-alkylcarbonyl as mentioned above, in particular methylcarbonyl and ethylcarbonyl;

$C_1$–$C_6$-alkoxycarbonyl as mentioned above, in particular methoxycarbonyl, ethoxycarbonyl and 1,1-dimethylethoxycarbonyl;

$C_1$–$C_6$-alkyloxyimino (R—ON=) as mentioned above, in particular methoxyimino, ethoxyimino and 1,1-dimethethyloxyimino;

$C_3$–$C_7$-cycloalkyl as mentioned above, in particular such as cyclopropyl, cyclopentyl and cyclohexyl;

5- to 6-membered, saturated or unsaturated heterocycles, as mentioned above, in particular 2-tetrahydrofuranyl, 3-tetrahydrofuranyl, 2-tetrahydrothienyl, 3-tetrahydrothienyl, 1,3-dioxan-2-yl, 1,3-dioxan-4-yl, 1,3-dioxan-5-yl, 1,4-dioxan-2-yl, 2-pyrrolidinyl, 3-pyrrolidinyl, 2-piperidinyl, 3-piperidinyl, 4-piperidinyl, morpholin-2-yl and morpholin-3-yl;

phenyl and 2-naphthyl;

5-ring heteroaromatic systems as mentioned above, in particular furyl, thienyl, isoxazolyl, isothiazolyl, oxazolyl, thiazolyl, imidazolyl, oxadiazolyl and thiadiazolyl;

6-ring heteroaromatic systems as mentioned above, in particular pyridinyl and pyrimidinyl;

where the abovementioned cyclic, aromatic and heteroaromatic radicals can in each case carry one to three of the following groups:

nitro;

cyano;

carbamoyl (H$_2$NC(=O));

thiocarbamoyl (H$_2$NC(=S));

halogen as mentioned above, in particular fluorine, chlorine and bromine;

$C_1$–$C_4$-alkyl as mentioned above, in particular methyl and 1,1-dimethylethyl;

$C_1$–$C_4$-alkoxy as mentioned above, in particular methoxy;

$C_1$–$C_2$-haloalkoxy as mentioned above, in particular trifluoromethoxy;

C$_2$–C$_6$-alkenyl as mentioned above, in particular 2-buten-2-yl;

C$_2$–C$_6$-haloalkenyl as mentioned above, in particular 2,2-dibromovinyl;

C$_1$–C$_6$-alkoxycarbonyl as mentioned above, in particular methoxycarbonyl;

C$_3$–C$_7$-cycloalkyl as mentioned above, in particular cyclopropyl;

5- to 6-membered, saturated or unsaturated heterocycles, as mentioned above, in particular tetrahydrofuranyl, which can carry one to three of the following groups: fluorine, chlorine, methyl or methoxy;

phenyl, phenoxy or benzyl, where the phenyls can carry one to three of the following groups: fluorine, chlorine, bromine, methyl, methoxy, trifluoromethyl and trifluoromethoxy;

5-membered ring heteroaromatic systems as mentioned above, in particular isoxazolyl, which can carry one to three of the following groups: fluorine, chlorine, methyl, 1-methylethyl, methoxy and trifluoromethyl.

Alkenyl, particularly straight-chain or branched C$_3$–C$_6$-alkenyl as mentioned above in general and in particular which carries one to seven halogens, in particular fluorine, chlorine and/or bromine and/or one or two of the following radicals:

C$_1$–C$_6$-alkylcarbonyl as mentioned above, in particular methylcarbonyl and ethylcarbonyl;

C$_1$–C$_6$-alkoxycarbonyl as mentioned above, in particular methoxycarbonyl, ethoxycarbonyl and 1-methylethoxycarbonyl;

C$_1$–C$_6$-alkyloxyimino (R—ON=) as mentioned above, in particular methoxyimino and ethoxyimino;

C$_3$–C$_7$-cycloalkyl as mentioned above, in particular such as cyclopropyl, cyclopentyl and cyclohexyl;

5- to 6-membered saturated or unsaturated heterocycles as mentioned above, in particular 2-tetrahydrofuranyl, 3-tetrahydrofuranyl, 2-tetrahydrothienyl, 3-tetrahydrothienyl, 1,3-dioxan-2-yl, 1,3-dioxan-4-yl, 1,3-dioxan-5-yl, 1,4-dioxan-2-yl, 2- pyrrolidinyl, 3-pyrrolidinyl, 2-piperidinyl, 3-piperidinyl, 4-piperidinyl, morpholin-2-yl and morpholin-3-yl;

phenyl and 2-naphthyl;

5-membered ring heteroaromatic systems as mentioned above, in particular furyl, thienyl, isoxazolyl, isothiazolyl, oxazolyl, thiazolyl, imidazolyl, oxadiazolyl and thiadiazolyl;

6-membered ring heteroaromatic systems as mentioned above, in particular pyridinyl and pyrimidinyl; where the above-mentioned cyclic, aromatic and heteroaromatic radicals can in each case carry one to three of the following groups:

nitro;

cyano;

carbamoyl (H$_2$NC(=O));

thiocarbamoyl (H$_2$NC(=S));

halogen as mentioned above, in particular fluorine, chlorine and bromine;

C$_1$–C$_4$-alkyl as mentioned above, in particular methyl and 1,1-dimethylethyl;

C$_1$–C$_4$-alkoxy as mentioned above, in particular methoxy;

C$_1$–C$_2$-haloalkoxy as mentioned above, in particular trifluoromethoxy;

C$_2$–C$_6$-alkenyl as mentioned above, in particular 2-buten-2-yl;

C$_2$–C$_6$-haloalkenyl as mentioned above, in particular 2,2-dibromovinyl;

C$_1$–C$_6$-alkoxycarbonyl as mentioned above, in particular methoxycarbonyl;

C$_3$–C$_7$-cycloalkyl as mentioned above, in particular cyclopropyl;

5- to 6-membered, saturated or unsaturated heterocycles, as mentioned above, in particular tetrahydrofuranyl, which can carry one to three of the following groups: fluorine, chlorine, methyl or methoxy;

phenyl, phenoxy or benzyl, where the phenyls can carry one to three of the following groups: fluorine, chlorine, methyl, methoxy, trifluoromethyl and trifluoromethoxy;

5-membered ring heteroaromatic systems as mentioned above, in particular isoxazolyl, which can carry one to three of the following groups: fluorine, chlorine, methyl, 1-methylethyl, methoxy and trifluoromethyl.

Alkynyl, particularly straight-chain or branched C$_3$–C$_6$-alkynyl as mentioned above in general and in particular, which carries one to five halogens, in particular fluorine, chlorine and/or bromine and/or one or two of the following radicals:

C$_1$–C$_6$-alkylcarbonyl as mentioned above, in particular methylcarbonyl and ethylcarbonyl;

C$_1$–C$_6$-alkoxycarbonyl as mentioned above, in particular methoxycarbonyl, ethoxycarbonyl and 1-methylethoxycarbonyl;

C$_1$–C$_6$-alkyloxyimino (R—ON=) as mentioned above, in particular methoxyimino and ethoxyimino;

C$_3$–C$_7$-cycloalkyl as mentioned above, in particular cyclopropyl, cyclopentyl and cyclohexyl;

5- to 6-membered saturated or unsaturated heterocycles as mentioned above, in particular 2-tetrahydrofuranyl, 3-tetrahydrofuranyl, 2-tetrahydrothienyl, 3-tetrahydrothienyl, 1,3-dioxan-2-yl, 1,3-dioxan-4-yl, 1,3-dioxan-5-yl, 1,4-dioxan-2-yl, 2- pyrrolidinyl, 3-pyrrolidinyl, 2-piperidinyl, 3-piperidinyl, 4-piperidinyl, morpholin-2-yl and morpholin-3-yl;

phenyl and 2-napthyl;

5-membered ring heteroaromatic systems as mentioned above, in particular furyl, thienyl, isoxazolyl, isothiazolyl and thiadiazolyl;

6-membered ring heteroaromatic systems as mentioned above, in particular pyridinyl and pyrimidinyl;

where the abovementioned cyclic, aromatic and heteroaromatic radicals can in each case carry one to three of the following groups:

nitro;

cyano;

carbamoyl (H$_2$NC(=O));

thiocarbamoyl (H$_2$NC(=S));

halogen as mentioned above, in particular fluorine, chlorine and bromine;

C$_1$–C$_4$-alkyl as mentioned above, in particular methyl and 1,1-dimethylethyl;

C$_1$–C$_4$-alkoxy as mentioned above, in particular methoxy;

C$_1$–C$_2$-haloalkoxy as mentioned above, in particular trifluoromethoxy;

C$_2$–C$_6$-alkenyl as mentioned above, in particular 2-buten-2-yl;

C$_2$–C$_6$-haloalkenyl as mentioned above, in particular 2,2-dibromovinyl;

C$_1$–C$_6$-alkoxycarbonyl as mentioned above, in particular methoxycarbonyl;

C$_3$–C$_7$-cycloalkyl as mentioned above, in particular cyclopropyl;

5- to 6-membered, saturated or unsaturated heterocycles, as mentioned above, in particular tetrahydrofuranyl, which can carry one to three of the following groups: fluorine, chlorine, methyl or methoxy;

phenyl, phenoxy or benzyl, where the phenyls can carry one to three of the following groups: fluorine, chlorine, methyl, methoxy, trifluoromethyl and trifluoromethoxy;

5-membered ring heteroaromatic systems as mentioned above, in particular isoxazolyl, which can carry one to three of the following groups: fluorine, chlorine, methyl, 1-methylethyl, methoxy and trifluoromethyl;

alicyclic or heterocyclic, saturated or mono- or diunsaturated rings as mentioned above, in particular cyclopropyl, cyclopentyl, cyclohexyl, tetrahydrofuryl, tetrahydrofuran-2-one and 1,3-dioxanyl, where these rings can carry one to three of the following radicals:

halogen as mentioned above, in particular fluorine, chlorine and bromine;

$C_1$–$C_4$-alkyl as mentioned above, in particular methyl and 1,1-dimethylethyl;

$C_1$–$C_4$-alkoxy as mentioned above, in particular methoxy;

$C_1$–$C_2$-haloalkoxy as mentioned above, in particular trifluoromethoxy;

$C_2$–$C_6$-alkenyl as mentioned above, in particular 2-buten-2-yl;

$C_2$–$C_6$-haloalkenyl as mentioned above, in particular 2,2-dibromovinyl;

$C_1$–$C_6$-alkoxycarbonyl as mentioned above, in particular methoxycarbonyl.

In the formula I.1, —T— is in particular understood as meaning —$NR^7$—, where $R^4$ and $R^7$ have the following meanings:

$R^4$ is hydrogen; alkyl, particularly straight-chain or branched $C_1$–$C_6$-alkyl as mentioned above in general and in particular and $C_1$–$C_4$-alkyl as mentioned above in general and in particular, which carries one to nine halogens such as in particular fluorine, chlorine and/or bromine and/or one or two of the following radicals:

$C_1$–$C_4$-alkoxy as mentioned above, in particular methoxy;

$C_1$–$C_2$-haloalkoxy as mentioned above, in particular trifluoromethoxy;

$C_1$–$C_4$-alkylthio as mentioned above, in particular methylthio;

$C_1$–$C_2$-haloalkylthio as mentioned above, in particular trifluoromethylthio;

$C_1$–$C_6$-alkylcarbonyl as mentioned above, in particular methylcarbonyl and ethylcarbonyl;

$C_1$–$C_6$-alkoxycarbonyl as mentioned above, in particular methoxycarbonyl, ethoxycarbonyl and 1-methylethoxycarbonyl;

$C_1$–$C_6$-alkyloxyimino (R—ON=) as mentioned above, in particular methoxyimino and ethoxyimino;

$C_3$–$C_7$-cycloalkyl as mentioned above, in particular cyclopropyl, cyclopentyl and cyclohexyl;

$C_3$–$C_7$-cycloalkoxy as mentioned above, in particular cyclohexyloxy;

5- to 6-membered, saturated or unsaturated heterocycles, as mentioned above, in particular tetrahydrofuranyl, tetrahydrothienyl, 1,3-dioxanyl, 1,4-dioxanyl, pyrrolidinyl, piperidinyl and morpholinyl;

phenyl and 2-naphthyl;

5-membered ring heteroaromatic systems as mentioned above, in particular furyl, thienyl, isoxazolyl, isothiazolyl, oxazolyl, thiazolyl, imidazolyl, oxadiazolyl and thiadiazolyl;

6-membered ring heteroaromatic systems as mentioned above, in particular pyridinyl and pyrimidinyl;

where the abovementioned cyclic, aromatic and heteroaromatic radicals can in each case carry one to three of the following groups:

nitro;

cyano;

carbamoyl ($H_2NC(=O)$);

thiocarbamoyl ($H_2NC(=S)$);

halogen as mentioned above, in particular fluorine, chlorine and bromine;

$C_1$–$C_4$-alkyl as mentioned above, in particular methyl and 1,1-dimethylethyl;

$C_1$–$C_4$-alkoxy as mentioned above, in particular methoxy;

$C_1$–$C_2$-haloalkoxy as mentioned above, in particular trifluoromethoxy;

$C_2$–$C_6$-alkenyl as mentioned above, in particular 2-buten-2-yl;

$C_2$–$C_6$-haloalkenyl as mentioned above, in particular 2,2-dibromovinyl;

$C_1$–$C_6$-alkoxycarbonyl as mentioned above, in particular methoxycarbonyl;

$C_3$–$C_7$-cycloalkyl as mentioned above, in particular cyclopropyl;

5- to 6-membered, saturated or unsaturated heterocycles, as mentioned above, in particular tetrahydrofuranyl, which can carry one to three of the following groups: fluorine, chlorine, methyl or methoxy;

phenyl, phenoxy or benzyl, where the phenyls can carry one to three of the following groups: fluorine, chlorine, methyl, methoxy, trifluoromethyl and trifluoromethoxy;

5-membered ring heteroaromatic systems as mentioned above, in particular isoxazolyl, which can carry one to three of the following groups: fluorine, chlorine, methyl, methoxy, trifluoromethyl and trifluoromethoxy.

Alkenyl, particularly straight-chain or branched $C_3$–$C_6$-alkenyl as mentioned above in general and in particular, which carries one to seven halogens, in particular fluorine, chlorine and/or bromine and/or one or two of the following radicals:

$C_1$–$C_6$-alkylcarbonyl as mentioned above, in particular methylcarbonyl and ethylcarbonyl;

$C_1$–$C_6$-alkoxycarbonyl as mentioned above, in particular methoxycarbonyl, ethoxycarbonyl and 1-methylethoxycarbonyl;

$C_1$–$C_6$-alkoxyimino (R—ON=) as mentioned above, in particular methoxyimino and ethoxyimino;

$C_3$–$C_7$-cycloalkyl as mentioned above, in particular such as cyclopropyl, cyclopentyl and cyclohexyl;

5- to 6-membered saturated or unsaturated heterocycles as mentioned above, in particular 2-tetrahydrofuranyl, 3-tetrahydrofuranyl, 2-tetrahydrothienyl, 3-tetrahydrothienyl, 1,3-dioxan-2-yl, 1,3-dioxan-4-yl, 1,3-dioxan-5-yl, 1,4-dioxan-2-yl, 2-pyrrolidinyl, 3-pyrrolidinyl, 2-piperidinyl, 3-piperidinyl, 4-piperidinyl, morpholin-2-yl and morpholin-3-yl;

phenyl and 2-naphthyl;

5-membered ring heteroaromatic systems as mentioned above, in particular furyl, thienyl, isoxazolyl, isothiazolyl, oxazolyl, thiazolyl, imidazolyl, oxadiazolyl and thiadiazolyl;

6-membered ring heteroaromatic systems as mentioned above, in particular pyridinyl and pyrimidinyl;

where the abovementioned cyclic, aromatic and heteroaromatic radicals can in each case carry one to three of the following groups:

nitro;

cyano;

carbamoyl (H$_2$NC(=O));

thiocarbamoyl (H$_2$NC(=S));

halogen as mentioned above, in particular fluorine, chlorine and bromine;

C$_1$–C$_4$-alkyl as mentioned above, in particular methyl and 1,1-dimethylethyl;

C$_1$–C$_4$-alkoxy as mentioned above, in particular methoxy;

C$_1$–C$_2$-haloalkoxy as mentioned above, in particular trifluoromethoxy;

C$_2$–C$_6$-alkenyl as mentioned above, in particular 2-buten-2-yl;

C$_2$–C$_6$-haloalkenyl as mentioned above, in particular 2,2-dibromovinyl;

C$_1$–C$_6$-alkoxycarbonyl as mentioned above, in particular methoxycarbonyl;

C$_3$–C$_7$-cycloalkyl as mentioned above, in particular cyclopropyl;

5- to 6-membered, saturated or unsaturated heterocycles, as mentioned above, in particular tetrahydrofuranyl, which can carry one to three of the following groups: fluorine, chlorine, methyl or methoxy;

phenyl, phenoxy or benzyl, where the phenyls can carry one to three of the following groups: fluorine, chlorine, methyl, methoxy, trifluoromethyl and trifluoromethoxy;

5-membered ring heteroaromatic systems as mentioned above, in particular isoxazolyl, which can carry one to three of the following groups: fluorine, chlorine, methyl, methoxy, trifluoromethyl and trifluoromethoxy.

Alkynyl, particularly straight-chain or branched C$_3$–C$_6$-alkynyl as mentioned above in general and in particular, which carries one to five halogens, in particular fluorine, chlorine and/or bromine and/or one or two of the following radicals:

C$_1$–C$_6$-alkylcarbonyl as mentioned above, in particular methylcarbonyl and ethylcarbonyl;

C$_1$–C$_6$-alkoxycarbonyl as mentioned above, in particular methoxycarbonyl, ethoxycarbonyl and 1-methylethoxycarbonyl;

C$_1$–C$_6$-alkoxyimino (R—ON=) as mentioned above, in particular methoxyimino and ethoxyimino;

C$_3$–C$_7$-cycloalkyl as mentioned above, in particular such as cyclopropyl, cyclopentyl and cyclohexyl;

5- to 6-membered saturated or unsaturated heterocycles as mentioned above, in particular 2-tetrahydrofuranyl, 3-tetrahydrofuranyl, 2-tetrahydrothienyl, 3-tetrahydrothienyl, 1,3-dioxan-2-yl, 1,3-dioxan-4-yl, 1,3-dioxan-5-yl, 1,4-dioxan-2-yl, 2-pyrrolidinyl, 3-pyrrolidinyl, 2-piperidinyl, 3-piperidinyl, 4-piperidinyl, morpholin-2-yl and morpholin-3-yl;

phenyl and 2-naphthyl;

5-membered ring heteroaromatic systems as mentioned above, in particular furyl, thienyl, isoxazolyl, isothiazolyl, oxazolyl, thiazolyl, imidazolyl, oxadiazolyl and thiadiazolyl;

6-membered ring heteroaromatic systems as mentioned above, in particular pyridinyl and pyrimidinyl;

where the abovementioned cyclic, aromatic and heteroaromatic radicals can in each case carry one to three of the following groups:

nitro;

cyano;

carbamoyl (H$_2$NC(=O));

thiocarbamoyl (H$_2$NC(=S));

halogen as mentioned above, in particular fluorine, chlorine and bromine;

C$_1$–C$_4$-alkyl as mentioned above, in particular methyl and 1,1-dimethylethyl;

C$_1$–C$_4$-alkoxy as mentioned above, in particular methoxy;

C$_1$–C$_2$-haloalkoxy as mentioned above, in particular trifluoromethoxy;

C$_2$–C$_6$-alkenyl as mentioned above, in particular 2-buten-2-yl;

C$_2$–C$_6$-haloalkenyl as mentioned above, in particular 2,2-dibromovinyl;

C$_1$–C$_6$-alkoxycarbonyl as mentioned above, in particular methoxycarbonyl;

C$_3$–C$_7$-cycloalkyl as mentioned above, in particular cyclopropyl;

5- to 6-membered, saturated or unsaturated heterocycles, as mentioned above, in particular tetrahydrofuranyl, which can carry one to three of the following groups: fluorine, chlorine, methyl or methoxy;

phenyl, phenoxy or benzyl, where the phenyls can carry one to three of the following groups: fluorine, chlorine, methyl, methoxy, trifluoromethyl and trifluoromethoxy;

5-membered ring heteroaromatic systems as mentioned above, in particular isoxazolyl, which can carry one to three of the following groups: fluorine, chlorine, methyl, methoxy, trifluoromethyl and trifluoromethoxy;

alicyclic or heterocyclic, saturated or mono- or diunsaturated rings as mentioned above, in particular cyclopentyl, cyclohexyl, tetrahydrofuryl, tetrahydrothienyl, tetrahydrothienyl-1,1-dioxide, tetrahydrofuran-2-one and 1,3-dioxanyl, where these rings can carry one to three of the following radicals:

halogen as mentioned above, in particular fluorine, chlorine and bromine;

C$_1$–C$_4$-alkyl as mentioned above, in particular methyl and 1,1-dimethylethyl;

C$_1$–C$_4$-alkoxy as mentioned above, in particular methoxy;

C$_1$–C$_2$-haloalkoxy as mentioned above, in particular trifluoromethoxy;

C$_2$–C$_6$-alkenyl as mentioned above, in particular 2-buten-2-yl;

C$_2$–C$_6$-haloalkenyl as mentioned above, in particular 2,2-dibromovinyl;

C$_1$–C$_6$-alkoxycarbonyl as mentioned above, in particular methoxycarbonyl.

Phenyl, which for its part can carry one to three of the following groups:

nitro;

cyano;

cyanato;

thiocyanato;

carbamoyl (H$_2$NC(=O));

thiocarbamoyl (H$_2$NC(=S));

halogen as mentioned above, in particular fluorine, chlorine and bromine;

C$_1$–C$_4$-alkyl as mentioned above, in particular methyl and ethyl;

C$_1$–C$_4$-haloalkyl as mentioned above, in particular trifluoromethyl;

C$_1$–C$_4$-alkoxy as mentioned above, in particular methoxy and ethoxy;

C$_1$–C$_2$-haloalkoxy as mentioned above, in particular trifluoromethoxy and 1,1,2,2-tetrafluoroethoxy;

$C_1$–$C_4$-alkylthio as mentioned above, in particular methylthio;

$C_2$–$C_6$-alkenyl as mentioned above, in particular 2-buten-2-yl;

$C_2$–$C_6$-haloalkenyl as mentioned above, in particular 2,2-dibromovinyl;

$C_1$–$C_6$-alkoxycarbonyl as mentioned above, in particular methoxycarbonyl and ethoxycarbonyl;

$C_3$–$C_7$-cycloalkyl as mentioned above, in particular cyclopropyl;

5- to 6-membered, saturated or unsaturated heterocycles, as mentioned above, in particular tetrahydrofuranyl, which can carry one to three of the following groups: fluorine, chlorine, methyl or methoxy;

phenyl, phenoxy or benzyl, where the phenyls can carry one to three of the following groups: fluorine, chlorine, methyl, methoxy, trifluoromethyl and trifluoromethoxy;

5-membered ring heteroaromatic systems as mentioned above, in particular isoxazolyl, which can carry one to three of the following groups: fluorine, chlorine, methyl, methoxy, trifluoromethyl and trifluoromethoxy, or propylene ($CH_2CH_2CH_2$) or butylene ($CH_2CH_2CH_2CH_2$) bonded to two adjacent positions of the phenyl ring;

heteroaromatic systems, as mentioned above, in particular isoxazolyl, isothiazolyl, oxazolyl, thiazolyl, oxadiazolyl, thiadiazolyl, imidazolyl, pyridyl and pyrimidyl, where these rings can carry one to three of the following radicals:

halogen as mentioned above, in particular fluorine, chlorine and bromine;

$C_1$–$C_4$-alkyl as mentioned above, in particular methyl and 1,1-dimethylethyl, which for its part can carry one or two of the following radicals: methoxycarbonyl and methoxyimino;

$C_1$–$C_4$-alkoxy as mentioned above, in particular methoxy;

$C_1$–$C_2$-haloalkoxy as mentioned above, in particular trifluoromethoxy;

$C_2$–$C_6$-alkenyl as mentioned above, in particular 2-buten-2-yl;

$C_2$–$C_6$-haloalkenyl as mentioned above, in particular 2,2-dibromovinyl;

$C_1$–$C_6$-alkoxycarbonyl as mentioned above, in particular methoxycarbonyl;

$R^7$ is hydrogen or $C_1$–$C_4$-alkyl as mentioned above, in particular methyl; or $R^4$, together with $R^7$ and the N atom to which they are bonded, [lacuna] a heterocyclic, saturated or aromatic ring as mentioned above, in particular piperidinyl, morpholinyl, thiomorpholinyl, piperazinyl, pyrrolyl, pyrazolyl or imidazolyl, where these rings can carry one to three of the following radicals:

halogen as mentioned above, in particular fluorine, chlorine and bromine;

$C_1$–$C_4$-alkyl as mentioned above, in particular methyl and 1,1-dimethylethyl;

$C_1$–$C_4$-alkoxy as mentioned above, in particular methoxy;

$C_1$–$C_2$-haloalkoxy as mentioned above, in particular trifluoromethoxy;

$C_2$–$C_6$-alkenyl as mentioned above, in particular 2-buten-2-yl;

$C_2$–$C_6$-haloalkenyl as mentioned above, in particular 2,2-dibromovinyl;

$C_1$–$C_6$-alkoxycarbonyl as mentioned above, in particular methoxycarbonyl.

In the formula I.1, —T— is in particular to be understood as meaning —$ONR^7$—, if $R^4$ and $R^7$ have the following meanings:

$R^4$ is hydrogen; alkyl, particularly straight-chain or branched $C_1$–$C_6$-alkyl as mentioned above in general and in particular and $C_1$–$C_4$-alkyl as mentioned above in general and in particular, which carries one to nine halogens such as in particular fluorine, chlorine and/or bromine and/or one or two of the following radicals:

$C_1$–$C_4$-alkoxy as mentioned above, in particular methoxy;

$C_1$–$C_2$-haloalkoxy as mentioned above, in particular trifluoromethoxy;

$C_1$–$C_4$-alkylthio as mentioned above, in particular methylthio;

$C_1$–$C_2$-haloalkylthio as mentioned above, in particular trifluoromethylthio;

$C_1$–$C_6$-alkylcarbonyl as mentioned above, in particular methylcarbonyl and ethylcarbonyl;

$C_1$–$C_6$-alkoxycarbonyl as mentioned above, in particular methoxycarbonyl, ethoxycarbonyl and 1-methylethoxycarbonyl;

$C_1$–$C_6$-alkyloxyimino (R—ON=) as mentioned above, in particular methoxyimino and ethoxyimino;

$C_3$–$C_7$-cycloalkyl as mentioned above, in particular cyclopropyl, cyclopentyl and cyclohexyl;

$C_3$–$C_7$-cycloalkyl as mentioned above, in particular cyclohexyloxy;

5- to 6-membered, saturated or unsaturated heterocycles, as mentioned above, in particular tetrahydrofuranyl, tetrahydrothienyl, 1,3-dioxanyl, 1,4-dioxanyl, pyrrolidinyl, piperidinyl and morpholinyl;

phenyl and 2-naphthyl;

5-membered ring heteroaromatic systems as mentioned above, in particular furyl, thienyl, isoxazolyl, isothiazolyl, oxazolyl, thiazolyl, imidazolyl, oxadiazolyl and thiadiazolyl;

6-membered ring heteroaromatic systems as mentioned above, in particular pyridinyl and pyrimidinyl;

where the abovementioned cyclic, aromatic and heteroaromatic radicals can in each case carry one to three of the following groups:

nitro;

cyano;

carbamoyl ($H_2NC(=O)$);

thiocarbamoyl ($H_2NC(=S)$);

halogen as mentioned above, in particular fluorine, chlorine and bromine;

$C_1$–$C_4$-alkyl as mentioned above, in particular methyl and 1,1-dimethylethyl;

$C_1$–$C_4$-alkoxy as mentioned above, in particular methoxy;

$C_1$–$C_2$-haloalkoxy as mentioned above, in particular trifluoromethoxy;

$C_2$–$C_6$-alkenyl as mentioned above, in particular 2-buten-2-yl;

$C_2$–$C_6$-haloalkenyl as mentioned above, in particular 2,2-dibromovinyl;

$C_1$–$C_6$-alkoxycarbonyl as mentioned above, in particular methoxycarbonyl;

$C_3$–$C_7$-cycloalkyl as mentioned above, in particular cyclopropyl;

5- to 6-membered, saturated or unsaturated heterocycles, as mentioned above, in particular tetrahydrofuranyl, which can carry one to three of the following groups: fluorine, chlorine, methyl or methoxy;

phenyl, phenoxy or benzyl, where the phenyls can carry one to three of the following groups: fluorine, chlorine, methyl, methoxy, trifluoromethyl and trifluoromethoxy;

5-membered ring heteroaromatic systems as mentioned above, in particular isoxazolyl, which can carry one to three of the following groups: fluorine, chlorine, methyl, methoxy, trifluoromethyl and trifluoromethoxy.

Alkenyl, particularly straight-chain or branched $C_3$–$C_6$-alkenyl as mentioned above in general and in particular, which carries one to seven halogens, in particular fluorine, chlorine and/or bromine and/or one or two of the following radicals:

- $C_1$–$C_6$-alkylcarbonyl as mentioned above, in particular methylcarbonyl and ethylcarbonyl;
- $C_1$–$C_6$-alkoxycarbonyl as mentioned above, in particular methoxycarbonyl, ethoxycarbonyl and 1-methylethoxycarbonyl;
- $C_1$–$C_6$-alkoxyimino (R—ON=) as mentioned above, in particular methoxyimino and ethoxyimino;
- $C_3$–$C_7$-cycloalkyl as mentioned above, in particular such as cyclopropyl, cyclopentyl and cyclohexyl;
- 5- to 6-membered saturated or unsaturated heterocycles as mentioned above, in particular 2-tetrahydrofuranyl, 3-tetrahydrofuranyl, 2-tetrahydrothienyl, 3-tetrahydrothienyl, 1,3-dioxan-2-yl, 1,3-dioxan-4-yl, 1,3-dioxan-5-yl, 1,4-dioxan-2-yl, 2- pyrrolidinyl, 3-pyrrolidinyl, 2-piperidinyl, 3-piperidinyl, 4-piperidinyl, morpholin-2-yl and morpholin-3-yl;

phenyl and 2-napthyl;

5-membered ring heteroaromatic systems as mentioned above, in particular furyl, thienyl, isoxazolyl, isothiazolyl, oxazolyl, thiazolyl, imidazolyl, oxadiazolyl and thiadiazolyl;

6-membered ring heteroaromatic systems as mentioned above, in particular pyridinyl and pyrimidinyl;

where the abovementioned cyclic, aromatic and heteroaromatic radicals can in each case carry one to three of the following groups:

nitro;
cyano;
carbamoyl ($H_2NC(=O)$);
thiocarbamoyl ($H_2NC(=S)$);
halogen as mentioned above, in particular fluorine, chlorine and bromine;
$C_1$–$C_4$-alkyl as mentioned above, in particular methyl and 1,1-dimethylethyl;
$C_1$–$C_4$-alkoxy as mentioned above, in particular methoxy;
$C_1$–$C_2$-haloalkoxy as mentioned above, in particular trifluoromethoxy;
$C_2$–$C_6$-alkenyl as mentioned above, in particular 2-buten-2-yl;
$C_2$–$C_6$-haloalkenyl as mentioned above, in particular 2,2-dibromovinyl;
$C_1$–$C_6$-alkoxycarbonyl as mentioned above, in particular methoxycarbonyl;
$C_3$–$C_7$-cycloalkyl as mentioned above, in particular cyclopropyl;
5- to 6-membered, saturated or unsaturated heterocycles, as mentioned above, in particular tetrahydrofuranyl, which can carry one to three of the following groups: fluorine, chlorine, methyl or methoxy;
phenyl, phenoxy or benzyl, where the phenyls can carry one to three of the following groups: fluorine, chlorine, methyl, methoxy, trifluoromethyl and trifluoromethoxy;
5-membered ring heteroaromatic systems as mentioned above, in particular isoxazolyl, which can carry one to three of the following groups: fluorine, chlorine, methyl, methoxy, trifluoromethyl and trifluoromethoxy.

Alkynyl, particularly straight-chain or branched $C_3$–$C_6$-alkynyl as mentioned above in general and in particular, which carries one to five halogens, in particular fluorine, chlorine and/or bromine and/or one or two of the following radicals:

- $C_1$–$C_6$-alkylcarbonyl as mentioned above, in particular methylcarbonyl and ethylcarbonyl;
- $C_1$–$C_6$-alkoxycarbonyl as mentioned above, in particular methoxycarbonyl, ethoxycarbonyl and 1-methylethoxycarbonyl;
- $C_1$–$C_6$-alkoxyimino (R—ON=) as mentioned above, in particular methoxyimino and ethoxyimino;
- $C_3$–$C_7$-cycloalkyl as mentioned above, in particular such as cyclopropyl, cyclopentyl and cyclohexyl;
- 5- to 6-membered saturated or unsaturated heterocycles as mentioned above, in particular 2-tetrahydrofuranyl, 3-tetrahydrofuranyl, 2-tetrahydrothienyl, 3-tetrahydrothienyl, 1,3-dioxan-2-yl, 1,3-dioxan-4-yl, 1,3-dioxan-5-yl, 1,4-dioxan-2-yl, 2- pyrrolidinyl, 3-pyrrolidinyl, 2-piperidinyl, 3-piperidinyl, 4-piperidinyl, morpholin-2-yl and morpholin-3-yl;

phenyl and 2-napthyl;

5-membered ring heteroaromatic systems as mentioned above, in particular furyl, thienyl, isoxazolyl, isothiazolyl, oxazolyl, thiazolyl, imidazolyl, oxadiazolyl and thiadiazolyl;

6-membered zing heteroaromatic systems as mentioned above, in particular pyridinyl and pyrimidinyl;

where the abovementioned cyclic, aromatic and heteroaromatic radicals can in each case carry one to three of the following groups:

nitro;
cyano;
carbamoyl ($H_2NC(=O)$);
thiocarbamoyl ($H_2NC(=S)$);
halogen as mentioned above, in particular fluorine, chlorine and bromine;
$C_1$–$C_4$-alkyl as mentioned above, in particular methyl and 1,1-dimethylethyl;
$C_1$–$C_4$-alkoxy as mentioned above, in particular methoxy;
$C_1$–$C_2$-haloalkoxy as mentioned above, in particular trifluoromethoxy;
$C_2$–$C_6$-alkenyl as mentioned above, in particular 2-buten-2-yl;
$C_2$–$C_6$-haloalkenyl as mentioned above, in particular 2,2-dibromovinyl;
$C_1$–$C_6$-alkoxycarbonyl as mentioned above, in particular methoxycarbonyl;
$C_3$–$C_7$-cycloalkyl as mentioned above, in particular cyclopropyl;
5- to 6-membered, saturated or unsaturated heterocycles, as mentioned above, in particular tetrahydrofuranyl, which can carry one to three of the following groups: fluorine, chlorine, methyl or methoxy;
phenyl, phenoxy or benzyl, where the phenyls can carry one to three of the following groups: fluorine, chlorine, methyl, methoxy, trifluoromethyl and trifluoromethoxy;
5-membered ring heteroaromatic systems as mentioned above, in particular isoxazolyl, which can carry one to three of the following groups: fluorine, chlorine, methyl, methoxy, trifluoromethyl and trifluoromethoxy;

alicyclic or heterocyclic, saturated or mono- or diunsaturated rings as mentioned above, in particular cyclopentyl, cyclohexyl, tetrahydrofuryl, tetrahydrothienyl and 1,3- dioxanyl, where these rings can carry one to three of the following radicals:

halogen as mentioned above, in particular fluorine, chlorine and bromine;

$C_1$–$C_4$-alkyl as mentioned above, in particular methyl and 1,1-dimethylethyl;

$C_1$–$C_4$-alkoxy as mentioned above, in particular methoxy;

$C_1$–$C_2$-haloalkoxy as mentioned above, in particular trifluoromethoxy;

$C_2$–$C_6$-alkenyl as mentioned above, in particular 2-buten-2-yl;

$C_2$–$C_6$-haloalkenyl as mentioned above, in particular 2,2-dibromovinyl;

$C_1$–$C_6$-alkoxycarbonyl as mentioned above, in particular methoxycarbonyl.

$R^7$ is hydrogen or $C_1$–$C_4$-alkyl as mentioned above, in particular methyl.

In the formula I.1, Y is in particular to be understood as meaning NH, if T is a group —$NR^7$— or —$ONR^7$—.

Of particular interest are additionally compounds of the general formula I.2

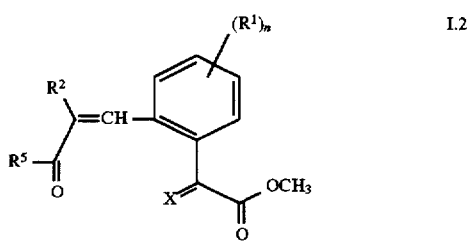

where the index and the substituent have the following meanings:

n is 0 or 1;

X is $CHOCH_3$, $CHCH_3$ or $NOCH_3$;

$R^1$ is halogen, $C_1$–$C_4$-alkyl, $C_1$–$C_2$-haloalkyl, $C_1$–$C_4$-alkoxy, $C_1$–$C_2$-haloalkoxy, $C_1$–$C_2$-alkylthio or phenyl;

$R^2$ is halogen;

$R^5$ is unsubstituted or substituted alkyl, alkenyl or alkynyl;

an unsubstituted or substituted saturated or mono- or diunsaturated cyclic system, which apart from carbons can contain one to three of the following hetero atoms as ring members: oxygen, sulfur and nitrogen;

an unsubstituted or substituted mono- or binuclear aromatic ring system, which apart from carbons can contain one to four nitrogens or one or two nitrogens and an oxygen or sulfur or an oxygen or sulfur as ring members.

In the formula I.2, in the meaning $R^1$ halogen is in particular to be understood as meaning fluorine or chlorine, $C_1$–$C_4$-alkyl is in particular to be understood as meaning methyl, ethyl, 1-methylethyl or 1,1-dimethylethyl, $C_1$–$C_2$-haloalkyl is in particular to be understood as meaning trifluoromethyl, $C_1$–$C_4$-alkoxy is in particular to be understood as meaning methoxy or ethoxy, $C_1$–$C_2$-haloalkoxy is in particular to be understood as meaning trifluoromethoxy, and $C_1$–$C_2$-alkylthio is in particular to be understood as meaning methylthio.

In the formula I.2, in the meaning $R^2$ halogen is in particular to be understood as meaning chlorine or bromine.

In the formula I.2, $R^5$ is in particular the following groups:

alkyl, particularly straight-chain or branched $C_1$–$C_6$-alkyl as mentioned above in general and in particular and $C_1$–$C_4$-alkyl as mentioned above in general and in particular, which carries one to nine halogens such as in particular fluorine, chlorine and/or bromine and/or one or two of the following radicals:

$C_1$–$C_4$-alkoxy as mentioned above, in particular methoxy;

$C_1$–$C_4$-alkylthio as mentioned above, in particular methylthio;

$C_3$–$C_7$-cycloalkyl as mentioned above, in particular such as cyclopropyl and cyclohexyl;

phenyl which can carry one to three of the following radicals:

nitro;

cyano;

halogen as mentioned above, in particular fluorine, chlorine and bromine;

$C_1$–$C_4$-alkyl as mentioned above, in particular methyl and 1,1-dimethylethyl;

$C_1$–$C_4$-alkoxy as mentioned above, in particular methoxy;

Alkenyl, particularly straight-chain or branched $C_2$–$C_6$-alkenyl as mentioned above in general and in particular, which carries one to seven halogens, in particular fluorine, chlorine and/or bromine.

Alkynyl, particularly straight-chain or branched $C_2$–$C_6$-alkynyl as mentioned above in general and in particular.

Alicyclic or heterocyclic, saturated or mono- or diunsaturated rings as mentioned above, in particular cyclopentyl, cyclohexyl, tetrahydrofuryl and 1,3-dioxanyl, where these rings can carry one to three of the following radicals:

halogen as mentioned above, in particular fluorine, chlorine and bromine;

$C_1$–$C_4$-alkyl as mentioned above, in particular methyl and 1,1-dimethylethyl;

$C_1$–$C_4$-alkoxy as mentioned above, in particular methoxy;

$C_1$–$C_2$-haloalkoxy as mentioned above, in particular trifluoromethoxy;

$C_2$–$C_6$-alkenyl as mentioned above, in particular 2-buten-2-yl;

$C_2$–$C_6$-haloalkenyl as mentioned above, in particular 2,2-dibromovinyl;

$C_1$–$C_6$-alkoxycarbonyl as mentioned above, in particular methoxycarbonyl.

Phenyl, which for its part can carry one to three of the following groups:

nitro;

cyano;

carbamoyl ($H_2NC(=O)$);

thiocarbamoyl ($H_2NC(=S)$);

halogen as mentioned above, in particular fluorine, chlorine and bromine;

$C_1$–$C_4$-alkyl as mentioned above, in particular methyl and ethyl;

$C_1$–$C_4$-haloalkyl as mentioned above, in particular trifluoromethyl;

$C_1$–$C_4$-alkoxy as mentioned above, in particular methoxy and ethoxy.

Heteroaromatic systems, as mentioned above, in particular isoxazolyl, isothiazolyl, oxazolyl, thiazolyl, oxadiazolyl, thiadiazolyl, imidazolyl and pyrimidyl, where these rings can carry one to three of the following radicals:

halogen as mentioned above, in particular fluorine, chlorine and bromine;

$C_1$–$C_4$-alkyl as mentioned above, in particular methyl and 1,1-dimethylethyl, which for its part can carry one or two of the following radicals: methoxycarbonyl and methoxyimino;

$C_1$–$C_4$-alkoxy as mentioned above, in particular methoxy;

$C_1$–$C_6$-alkoxycarbonyl as mentioned above, in particular methoxycarbonyl.

47

Of particular interest are additionally compounds of the general formula I.3

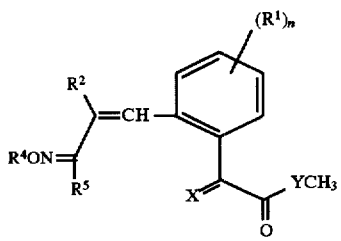

where the index and the substituents have the following meanings:
n is 0 or 1;
X is CHOCH$_3$, CHCH$_3$ or NOCH$_3$;
Y is O or NH;
R$^1$ is halogen, C$_1$–C$_4$-alkyl, C$_1$–C$_2$-haloalkyl, C$_1$–C$_4$-alkoxy, C$_1$–C$_2$-haloalkoxy, C$_1$–C$_2$-alkylthio or phenyl;
R$^3$ is halogen;
R$^4$ is hydrogen; unsubstituted or substituted alkyl, alkenyl or alkynyl;
R$^5$ is unsubstituted or substituted alkyl or alkoxy;
or an unsubstituted or substituted mono- or binuclear aromatic ring system, which apart from carbons can contain one to four nitrogens or one or two nitrogens and an oxygen or sulfur or an oxygen or sulfur as ring members.

In the formula I.3, in the meaning R$^1$ halogen is in particular to be understood as meaning fluorine or chlorine, C$_1$–C$_4$-alkyl is in particular to be understood as meaning methyl, ethyl, 1-methylethyl or 1,1-dimethylethyl, C$_1$–C$_2$-haloalkyl is in particular to be understood as meaning trifluoromethyl, C$_1$–C$_4$-alkoxy is in particular to be understood as meaning methoxy or ethoxy, C$_1$–C$_2$-haloalkoxy is in particular to be understood as meaning trifluoromethoxy, and C$_1$–C$_2$-alkylthio is in particular to be understood as meaning methylthio.

In formula I.3, in the meaning R$^2$ halogen is in particular to be understood as meaning chlorine or bromine.

In the formula I.3, in the meaning R$^4$ alkyl is particularly to be understood as meaning straight-chain or branched C$_1$–C$_6$-alkyl as mentioned above in general and in particular and C$_1$–C$_4$-alkyl as mentioned above in general and in particular, which carries one to nine halogens such as in particular fluorine, chlorine and/or bromine and/or one or two of the following radicals:

cyano;
C$_1$–C$_4$-alkoxy as mentioned above, in particular methoxy;
C$_1$–C$_6$-alkylcarbonyl as mentioned above, in particular methylcarbonyl and ethylcarbonyl;
C$_1$–C$_6$-alkoxycarbonyl as mentioned above, in particular methoxycarbonyl, ethoxycarbonyl and 1,1-dimethylethoxycarbonyl;
C$_3$–C$_7$-cycloalkyl as mentioned above, in particular cyclopropyl;
phenyl and 1-naphthyl;
phenoxy and 1-naphthyloxy;
5-membered ring heteroaromatic systems as mentioned above, in particular furyl, thienyl, isoxazolyl, isothiazolyl, oxazolyl and thiazolyl;
6-membered ring heteroaromatic systems as mentioned above, in particular pyrimidinyl;
hetaryloxy groups such as in particular pyrimidinyloxy;
where the abovementioned aromatic and heteroaromatic radicals can in each case carry one to three of the following groups:

48 cyano;
halogen as mentioned above, in particular fluorine, chlorine and bromine;
C$_1$–C$_4$-alkyl as mentioned above, in particular methyl;
C$_1$–C$_4$-alkoxy as mentioned above, in particular methoxy;
C$_1$–C$_2$-haloalkoxy as mentioned above, in particular trifluoromethoxy;
C$_1$–C$_6$-alkoxycarbonyl as mentioned above, in particular methoxycarbonyl;
phenyl or phenoxy, where the phenyl rings can carry one to three of the following groups: fluorine, chlorine, methyl, methoxy, trifluoromethyl and trifluoromethoxy.

Alkenyl, particularly straight-chain or branched C$_3$–C$_6$-alkenyl as mentioned above in general and in particular, which carries one to seven halogens, in particular fluorine, chlorine and/or bromine and/or one or two of the following radicals:

phenyl and 1-naphthyl;
phenoxy and 1-naphthyloxy;
5-membered ring heteroaromatic systems as mentioned above, in particular furyl, thienyl, isoxazolyl, isothiazolyl, oxazolyl and thiazolyl;
6-membered ring heteroaromatic systems as mentioned above, in particular pyrimidinyl;
hetaryloxy groups such as in particular pyrimidinyloxy;
where the abovementioned aromatic and heteroaromatic radicals can in each case carry one to three of the following groups:

cyano;
halogen as mentioned above, in particular fluorine, chlorine and bromine;
C$_1$–C$_4$-alkyl as mentioned above, in particular methyl;
C$_1$–C$_4$-alkoxy as mentioned above, in particular methoxy;
C$_1$–C$_2$-haloalkoxy as mentioned above, in particular trifluoromethoxy;
C$_1$–C$_6$-alkoxycarbonyl as mentioned above, in particular methoxycarbonyl;
phenyl or phenoxy, where the phenyl rings can carry one to three of the following groups: fluorine, chlorine, methyl, methoxy, trifluoromethyl and trifluoromethoxy.

Alkynyl, particularly straight-chain or branched C$_3$–C$_6$-alkynyl as mentioned above in general and in particular, which carries one to five halogens, in particular fluorine, chlorine and/or bromine and/or one or two of the following radicals:

phenyl and 1-naphthyl;
phenoxy and 1-naphthyloxy;
5-membered ring heteroaromatic systems as mentioned above, in particular furyl, thienyl, isoxazolyl, isothiazolyl, oxazolyl and thiazolyl;
6-membered ring heteroaromatic systems as mentioned above, in particular pyrimidinyl;
hetaryloxy groups such as in particular pyrimidinyloxy;
where the abovementioned aromatic and heteroaromatic radicals can in each case carry one to three of the following groups:

cyano;
halogen as mentioned above, in particular fluorine, chlorine and bromine;
C$_1$–C$_4$-alkyl as mentioned above, in particular methyl;
C$_1$–C$_4$-alkoxy as mentioned above, in particular methoxy;
C$_1$–C$_2$-haloalkoxy as mentioned above, in particular trifluoromethoxy;
C$_1$–C$_6$-alkoxycarbonyl as mentioned above, in particular methoxycarbonyl;

phenyl or phenoxy, where the phenyl rings can carry one to three of the following groups: fluorine, chlorine, methyl, methoxy, trifluoromethyl and trifluoromethoxy.

In the formula I.3, in the meaning $R^5$ alkyl is particularly to be understood as meaning straight-chain or branched $C_1$–$C_6$-alkyl as mentioned above in general and in particular and $C_1$–$C_4$-alkyl as mentioned above in general and in particular, which carries one to nine halogens such as in particular fluorine, chlorine and/or bromine and/or one or two of the following radicals:

$C_1$–$C_4$-alkoxy as mentioned above, in particular methoxy;

phenyl or phenoxy where the phenyl rings can carry one to three of the following groups: fluorine, chlorine, methyl, methoxy, trifluoromethyl and trifluoromethoxy;

alkoxy, particularly straight-chain or branched $C_1$–$C_6$-alkoxy as mentioned above in general and in particular and $C_1$–$C_4$-alkoxy, which carries one to nine halogens such as in particular fluorine, chlorine and/or bromine and/or one or two of the following radicals:

cyano;

$C_1$–$C_4$-alkoxy as mentioned above, in particular methoxy;

$C_1$–$C_6$-alkoxycarbonyl as mentioned above, in particular methoxycarbonyl;

phenyl;

naphthyl;

5-membered ring heteroaromatic systems as mentioned above, in particular furyl, thienyl, isoxazolyl, oxazolyl, thiazolyl, thiadiazolyl and oxadiazolyl, 6-membered ring heteroaromatic systems as mentioned above, in particular pyrimidinyl and pyridyl where the abovementioned cyclic radicals can in each case carry one to three of the following groups:

cyano;

halogen, in particular fluorine and chlorine;

$C_1$–$C_4$-alkyl, in particular methyl;

$C_1$–$C_4$-alkoxy, in particular methoxy;

$C_1$–$C_4$-haloalkyl, in particular trifluoromethyl;

phenyl or phenoxy.

Aryl is particularly to be understood as meaning phenyl and hetaryl is particularly to be understood as meaning furyl, 1,3-thiazolyl and 1,3,4-thiadiazolyl, which can carry one to five halogens such as in particular fluorine and chlorine and/or one to three of the following radicals:

cyano;

$C_1$–$C_4$-alkyl as mentioned above, in particular methyl and ethyl;

$C_1$–$C_4$-haloalkyl as mentioned above, in particular trifluoromethyl;

$C_1$–$C_4$-alkoxy as mentioned above, in particular methoxy and ethoxy;

$C_1$–$C_2$-haloalkoxy as mentioned above, in particular trifluoromethoxy and 1,1,2,2-tetrafluoroethoxy;

$C_1$–$C_4$-alkylthio as mentioned above, in particular methylthio;

$C_1$–$C_6$-alkoxycarbonyl as mentioned above, in particular methoxycarbonyl and ethoxycarbonyl.

Of particular interest are additionally compounds of the general formula I.4

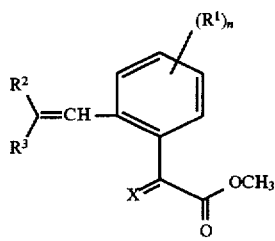

where the index and the substituents have the following meanings:

n is 0 or 1;

X is $CHOCH_3$, $CHCH_3$ or $NOCH_3$;

$R^1$ is halogen, $C_1$–$C_4$-alkyl, $C_1$–$C_2$-haloalkyl, $C_1$–$C_4$-alkoxy, $C_1$–$C_2$-haloalkoxy, $C_1$–$C_2$-alkylthio or phenyl;

$R^2$ is halogen;

$R^3$ is an unsubstituted or substituted mono- or binuclear aromatic ring system, which apart from carbons can contain one to four nitrogens or one or two nitrogens and an oxygen or sulfur or an oxygen or sulfur as ring members.

In the formula I.4, in the meaning $R^1$ halogen is in particular to be understood as meaning fluorine or chlorine, $C_1$–$C_4$-alkyl is in particular to be understood as meaning methyl, ethyl, 1-methylethyl or 1,1-dimethylethyl, $C_1$–$C_2$-haloalkyl is in particular to be understood as meaning trifluoromethyl, $C_1$–$C_4$-alkoxy is in particular to be understood as meaning methoxy or ethoxy, $C_1$–$C_2$-haloalkoxy is in particular to be understood as meaning trifluoromethoxy, and $C_1$–$C_2$-alkylthio is in particular to be understood as meaning methylthio.

In the formula I.4, in the meaning $R^2$ halogen is in particular to be understood as meaning chlorine or bromine.

In the formula I.4, in the meaning $R^3$ aryl or heteroaryl is in particular to be understood as meaning phenyl, furyl, thienyl, oxazolyl, thiazolyl, isoxazolyl, isothiazolyl, oxadiazolyl and thiadiazolyl, where these rings can carry one to three of the following substituents:

nitro;

cyano;

halogen as mentioned above, in particular fluorine, chlorine and bromine;

$C_1$–$C_4$-alkyl as mentioned above, in particular methyl and ethyl;

$C_1$–$C_4$-haloalkyl as mentioned above, in particular trifluoromethyl;

$C_1$–$C_4$-alkoxy as mentioned above, in particular methoxy and ethoxy;

$C_1$–$C_2$-haloalkoxy as mentioned above, in particular trifluoromethoxy and 1,1,2,2-tetrafluoroethoxy;

$C_1$–$C_4$-alkylthio as mentioned above, in particular methylthio;

$C_1$–$C_6$-alkoxycarbonyl as mentioned above, in particular methoxycarbonyl and ethoxycarbonyl;

$C_3$–$C_7$-cycloalkyl as mentioned above, in particular cyclopropyl;

5- to 6-membered, saturated or unsaturated heterocycles, as mentioned above, in particular tetrahydrofuranyl, which can carry one to three of the following groups: fluorine, chlorine, methyl, or methoxy;

phenyl or phenoxy, where the phenyls can carry one to three of the following groups: fluorine, chlorine, cyano, methyl, methoxy, trifluoromethyl and trifluoromethoxy;

5-membered ring heteroaromatic systems as mentioned above, in particular isoxazolyl, which can carry one to three of the following groups: chlorine, methyl, 1-methylethyl, methoxy and trifluoromethyl, or propylene ($CH_2CH_2CH_2$) or butylene ($CH_2CH_2CH_2CH_2$) bonded to two adjacent positions of the phenyl ring.

Of particular interest are additionally compounds of the general formula I.5

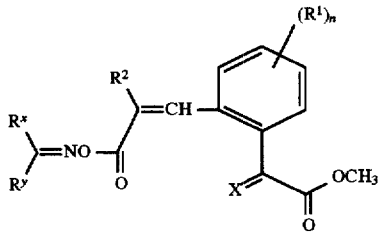

I.5 where the index and the substituents have the following meanings:

n is 0 or 1;

X is $CHOCH_3$, $CHCH_3$ or $NOCH_3$;

$R^1$ is halogen, $C_1$–$C_4$-alkyl, $C_1$–$C_2$-haloalkyl, $C_1$–$C_4$-alkoxy, $C_1$–$C_2$-haloalkoxy, $C_1$–$C_2$-alkylthio or phenyl;

$R^2$ is halogen;

$R^x$ is cyano, halogen, $C_1$–$C_4$-alkyl, $C_1$–$C_4$-haloalkyl, $C_1$–$C_4$-alkoxy, $C_1$–$C_4$-alkylthio, $C_3$–$C_7$-cycloalkyl, phenyl or benzyl and $R^y$ is hydrogen, cyano;

unsubstituted or substituted alkyl, alkenyl or alkynyl; an unsubstituted or substituted cycloalkyl;

or unsubstituted or substituted phenyl; or $R^x$ and $R^y$, together with the C atom to which they are bonded, form an unsubstituted or substituted saturated or mono- or diunsaturated cyclic system, which apart from carbons can contain one to three of the following hetero atoms as ring members: oxygen, sulfur and nitrogen.

In the formula I.5, in the meaning of $R^1$ halogen is in particular to be understood as meaning fluorine or chlorine, $C_1$–$C_4$-alkyl is in particular to be understood as meaning methyl, ethyl, 1-methylethyl or 1,1-dimethylethyl, $C_1$–$C_2$-haloalkyl is in particular to be understood as meaning trifluoromethyl, $C_1$–$C_4$-alkoxy is in particular to be understood as meaning methoxy or ethoxy, $C_1$–$C_2$-haloalkoxy is in particular to be understood as meaning trifluoromethoxy and $C_1$–$C_2$-alkylthio is in particular to be understood as meaning methylthio.

In the formula I.5, in the meaning $R^2$ halogen is in particular to be understood as meaning chlorine or bromine.

In the formula I.5, in the meaning $R^x$ halogen is in particular to be understood as meaning chlorine, $C_1$–$C_4$-alkyl is in particular to be understood as meaning methyl, ethyl and 1-methylethyl, $C_1$–$C_4$-haloalkyl is in particular to be understood as meaning trifluoromethyl and chloromethyl, $C_1$–$C_4$-alkoxy is in particular to be understood as meaning methoxy or ethoxy, $C_1$–$C_2$-alkylthio is in particular to be understood as meaning methylthio, $C_3$–$C_7$-cycloalkyl is in particular to be understood as meaning cyclopropyl.

In the formula I.5, in the meaning $R^y$ alkyl is particularly to be understood as meaning straight-chain or branched $C_1$–$C_6$-alkyl as mentioned above in general and in particular and $C_1$–$C_4$-alkyl as mentioned above in general and in particular, which carries one to nine halogens such as in particular fluorine and/or one or two of the following radicals:

$C_1$–$C_4$-alkoxy as mentioned above, in particular methoxy, 1-methylethoxy and 1,1-dimethylethoxy;

$C_1$–$C_2$-haloalkoxy as mentioned above, in particular trifluoromethoxy;

$C_1$–$C_4$-alkylthio as mentioned above, in particular methylthio;

$C_3$–$C_7$-cycloalkyl as mentioned above, in particular cyclopropyl;

phenyl and naphthyl;

6-membered ring heteroaromatic systems as mentioned above, in particular pyridinyl and pyrimidinyl;

where the abovementioned cyclic, aromatic and heteroaromatic radicals can in each case carry one to three of the following groups:

cyano;

halogen as mentioned above, in particular fluorine, chlorine and bromine;

$C_1$–$C_4$-alkyl as mentioned above, in particular methyl, and 1,1-dimethylethyl;

$C_1$–$C_4$-alkoxy as mentioned above, in particular methoxy;

$C_1$–$C_2$-haloalkoxy as mentioned above, in particular trifluoromethoxy.

In the formula I.5, in the meaning $R^y$ alkenyl is particularly to be understood as meaning straight-chain or branched $C_2$–$C_6$-alkenyl as mentioned above in general and in particular and $C_2$–$C_4$-alkenyl as mentioned above in general and in particular, which carries one to seven halogens, in particular fluorine, chlorine and/or bromine;

In the formula I.5, in the meaning $R^y$ alkynyl is particularly to be understood as meaning straight-chain or branched $C_2$–$C_6$-alkynyl as mentioned above in general and in particular and $C_2$–$C_4$-alkynyl as mentioned above in general and in particular, which carries one to five halogens, in particular fluorine, chlorine and/or bromine;

In the formula I.5, in the meaning $R^y$ alicyclic or heterocyclic [lacuna] to be understood as meaning saturated or mono- or diunsaturated rings as mentioned above, in particular cyclopropyl, cyclopentyl, cyclohexyl, tetrahydropyranyl and morpholinyl, where these rings can carry one to three of the following radicals:

halogen as mentioned above, in particular fluorine, chlorine and bromine;

$C_1$–$C_4$-alkyl as mentioned above, in particular methyl and 1,1-dimethylethyl;

$C_1$–$C_4$-alkoxy as mentioned above, in particular methoxy;

$C_1$–$C_2$-haloalkoxy as mentioned above, in particular trifluoromethoxy.

In the formula I.5, in the meaning $R^y$ aromatic is to be understood as meaning systems as mentioned above, in particular phenyl, where these radicals can be partially or completely halogenated and/or can carry one to three of the following substituents:

nitro;

cyano;

$C_1$–$C_4$-alkyl as mentioned above, in particular methyl and ethyl;

$C_1$–$C_4$-haloalkyl as mentioned above, in particular trifluoromethyl;

$C_1$–$C_4$-alkoxy as mentioned above, in particular methoxy, ethoxy and 1-methylethoxy;

$C_1$–$C_2$-haloalkoxy as mentioned above, in particular trifluoromethoxy and 1,1,2,2-tetrafluoroethoxy;

$C_1$–$C_4$-alkylthio as mentioned above, in particular methylthio;

$C_1$–$C_4$-alkylcarbonylamino as mentioned above, in particular methylcarbonylamino and ethylcarbonylamino;

$C_1$–$C_4$-alkoxycarbonylamino as mentioned above, in particular methoxycarbonylamino and ethoxycarbonylamino;

$C_1-C_4$-alkoxyiminomethyl as mentioned above, in particular methoxyiminomethyl and ethoxyiminomethyl;

phenyl or phenoxy, where the phenyls can carry one to three of the following groups: fluorine, chlorine, methyl, methoxy, trifluoromethyl and trifluoromethoxy.

In the formula I.5, the radicals $R^x$ and $R^y$ can also together form an alicyclic or heterocyclic ring as mentioned above in general and in particular, in particular cyclopentyl, cyclohexyl, cyclooctyl, 2-cyclohexenyl, 2,4-cyclohexanedienyl, tetrahydropyranyl, tetrahydrofuranyl, fluorenyl or indanyl, where these radicals can be partially or completely halogenated and/or can carry one to three of the following substituents:

$C_1-C_4$-alkyl as mentioned above, in particular methyl and ethyl;

$C_1-C_4$-haloalkyl as mentioned above, in particular trifluoromethyl;

$C_1-C_4$-alkoxy as mentioned above, in particular methoxy, ethoxy and 1-methylethoxy;

$C_1-C_2$-haloalkoxy as mentioned above, in particular trifluoromethoxy and 1,1,2,2-tetrafluoroethoxy;

$C_1-C_4$-alkylthio as mentioned above, in particular methylthio.

Of particular interest are additionally compounds of the general formula I.6

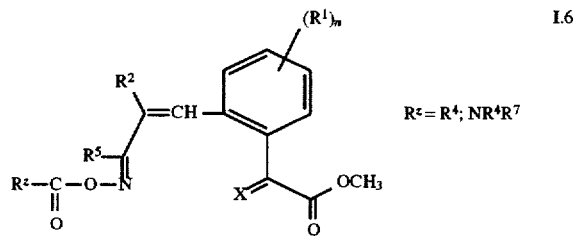

I.6 where the index and the substituents have the following meanings:

n is 0 or 1;

X is $CHOCH_3$, $CHCH_3$ or $NOCH_3$;

$R^1$ is halogen, $C_1-C_4$-alkyl, $C_1-C_2$-haloalkyl, $C_1-C_4$-alkoxy, $C_1-C_2$-haloalkoxy, $C_1-C_2$-alkylthio or phenyl;

$R^2$ is halogen;

$R^5$ is unsubstituted or substituted alkyl;

or an unsubstituted or substituted mono- or binuclear aromatic ring system, which apart from carbons can contain one to four nitrogens or one or two nitrogens and an oxygen or sulfur or an oxygen or sulfur as ring members and $R^z$ is $R^4$ or $NR^4R^7$;

$R^4$ is unsubstituted or substituted alkyl; unsubstituted or substituted alkenyl, unsubstituted or substituted alkynyl;

$R^7$ is hydrogen or $C_1-C_4$-alkyl;

or an unsubstituted or substituted mono- or binuclear aromatic ring system, which apart from carbons can contain one to four nitrogens or one or two nitrogens and an oxygen or sulfur or an oxygen or sulfur as ring members.

In the formula I.6, in the meaning $R^1$ halogen is in particular to be understood as meaning fluorine or chlorine. $C_1-C_4$-alkyl is in particular to be understood as meaning methyl, ethyl, 1-methylethyl or 1,1-dimethylethyl, $C_1-C_2$-haloalkyl is in particular to be understood as meaning trifluoromethyl, $C_1-C_4$-alkoxy is in particular to be understood as meaning methoxy or ethoxy, $C_1-C_2$-haloalkoxy is in particular to be understood as meaning trifluoromethoxy, and $C_1-C_2$-alkylthio is in particular to be understood as meaning methylthio.

In the formula I.6, in the meaning $R^2$ halogen is in particular to be understood as meaning chlorine or bromine.

In the formula I.6, in the meaning $R^5$ alkyl is particularly to be understood as meaning straight-chain or branched $C_1-C_6$-alkyl as mentioned above in general and in particular and $C_1-C_4$-alkyl as mentioned above in general and in particular, which carries one to nine halogens such as in particular fluorine, chlorine and/or bromine and/or one or two of the following radicals:

$C_1-C_4$-alkoxy as mentioned above, in particular methoxy;

phenyl or phenoxy, where the phenyl rings can carry one to three of the following groups: fluorine, chlorine, methyl, methoxy, trifluoromethyl and trifluoromethoxy.

Aryl [lacuna] particularly to be understood as meaning phenyl, which can carry one to five halogens such as in particular fluorine and chlorine and/or one to three of the following radicals:

cyano;

$C_1-C_4$-alkyl as mentioned above, in particular methyl and ethyl;

$C_1-C_4$-haloalkyl as mentioned above, in particular trifluoromethyl;

$C_1-C_4$-alkoxy as mentioned above, in particular methoxy and ethoxy;

$C_1-C_2$-haloalkoxy as mentioned above, in particular trifluoromethoxy and 1,1,2,2-tetrafluoroethoxy;

$C_1-C_4$-alkylthio as mentioned above, in particular methylthio;

$C_1-C_6$-alkoxycarbonyl as mentioned above, in particular methoxycarbonyl and ethoxycarbonyl.

In the formula I.6, in the meaning $R^4$ alkyl is particularly to be understood as meaning straight-chain or branched $C_1-C_6$-alkyl as mentioned above in general and in particular and $C_1-C_4$-alkyl as mentioned above in general and in particular, which carries one to nine halogens such as in particular fluorine, chlorine and/or bromine and/or one or two of the following radicals:

$C_1-C_4$-alkoxy as mentioned above, in particular methoxy;

phenyl or phenoxy, where the phenyl rings can carry one to three of the following groups: fluorine, chlorine, methyl, methoxy, trifluoromethyl and trifluoromethoxy.

Aryl [lacuna] particularly to be understood as meaning phenyl, which can carry one to five halogens such as in particular fluorine and chlorine and/or one to three of the following radicals:

cyano;

$C_1-C_4$-alkyl as mentioned above, in particular methyl and ethyl;

$C_1-C_4$-haloalkyl as mentioned above, in particular trifluoromethyl;

$C_1-C_4$-alkoxy as mentioned above, in particular methoxy and ethoxy;

$C_1-C_2$-haloalkoxy as mentioned above, in particular trifluoromethoxy and 1,1,2,2-tetrafluoroethoxy;

$C_1-C_4$-alkylthio as mentioned above, in particular methylthio;

$C_1-C_6$-alkoxycarbonyl as mentioned above, in particular methoxycarbonyl and ethoxycarbonyl.

In the formula I.6, in the meaning $R^x$ $C_1-C_4$-alkyl is in particular to be understood as meaning methyl, ethyl and 1-methylethyl, $C_1-C_4$-alkoxy is in particular to be understood as meaning methoxy or ethoxy, $C_3-C_7$-cycloalkyl is in particular to be understood as meaning cyclopropyl, $C_2-C_6$-alkenyl is in particular to be understood as meaning 2-propen-1-yl, $C_2-C_6$-alkynyl is in particular to be understood as meaning 2-propyn-1-yl.

The compounds I according to the invention can exist in different isomers (Z- or E-isomers) with respect to the double bonds, it being possible for the different isomers to show differing actions. In particular, those compounds I are preferred whose double bond in the radical R# (C(=X)—COYCH₃) has the E-configuration.

Additionally, those compounds I are preferred in which the double bond in the radical R* has the Z-configuration with respect to the radical R² and the phenyl ring.

In the compounds of the general formula I, identically designated radicals, if they are bonded in different positions, can have different meanings (e.g. the radical R⁴, if R³ is R⁴TC(=Z¹) and Z¹ is an NOR⁴ group).

Particularly preferred compounds of the formulae I.1, I.2, I.3, I.4, I.5 and I.6 are compiled in Tables A.1.1, A.1.2, A.1.3, A.1.4, A.2, A.3.1, A.3.2, A.4, A.5 and A.6 below.

TABLE A.1.1

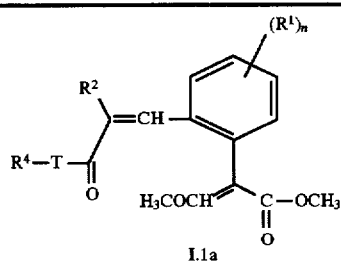

I.1a

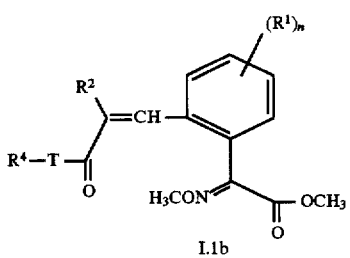

I.1b

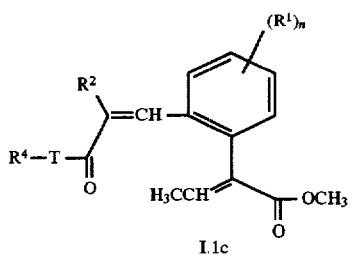

I.1c

| R¹ₙ | R² | R⁴ | T |
|---|---|---|---|
| H | Cl | H₃C— | O |
| H | Cl | H₅C₂— | O |
| H | CN | H₅C₂— | O |
| H | NO₂ | H₅C₂— | O |
| 3-Cl | Cl | H₅C₂— | O |
| 4-Cl | Cl | H₅C₂— | O |
| 5-Cl | Cl | H₅C₂— | O |
| 6-Cl | Cl | H₅C₂— | O |
| 4-OCH₃ | Cl | H₅C₂— | O |
| 4-OCH₃ | CN | H₅C₂— | O |
| 4-OCH₃ | NO₂ | H₅C₂— | O |
| 6-CH₃ | Cl | H₅C₂— | O |
| 6-C₆H₅ | Cl | H₅C₂— | O |
| H | Br | H₅C₂— | O |
| 4-Cl | Br | H₅C₂— | O |
| 6-Cl | Br | H₅C₂— | O |
| 4-OCH₃ | Br | H₅C₂— | O |
| 6-CH₃ | Br | H₅C₂— | O |
| 6-C₆H₅ | Br | H₅C₂— | O |

TABLE A.1.1-continued

| R¹ₙ | R² | R⁴ | T |
|---|---|---|---|
| H | Cl | (H₃C)₂CH— | O |
| H | CN | (H₃C)₂CH— | O |
| H | NO₂ | (H₃C)₂CH— | O |
| 4-OCH₃ | Cl | (H₃C)₂CH— | O |
| H | Br | (H₃C)₂CH— | O |
| 4-OCH₃ | Br | (H₃C)₂CH— | O |
| 6-Cl | Br | (H₃C)₂CH— | O |
| H | Cl | (H₃C)₃C— | O |
| H | CN | (H₃C)₃C— | O |
| H | NO₂ | (H₃C)₃C— | O |
| 3-Cl | Cl | (H₃C)₃C— | O |
| 4-Cl | Cl | (H₃C)₃C— | O |
| 5-Cl | Cl | (H₃C)₃C— | O |
| 6-Cl | Cl | (H₃C)₃C— | O |
| 4-OCH₃ | Cl | (H₃C)₃C— | O |
| 6-CH₃ | Cl | (H₃C)₃C— | O |
| 6-C₆H₅ | Cl | (H₃C)₃C— | O |
| H | Br | (H₃C)₃C— | O |
| 4-OCH₃ | Br | (H₃C)₃C— | O |
| H | Cl | H₃CCH₂HC(CH₃)— | O |
| H | Cl | (H₅C₂)(H₃C)₂C— | O |
| H | Br | (H₅C₂)(H₃C)₂C— | O |
| H | Cl | (H₅C₂)₂H₃CC— | O |
| H | Cl | (H₇C₃)H₃CCH— | O |
| H | Cl | (H₇C₃)(H₃C)₂C— | O |
| H | Br | (H₅C₂)₂H₃CC— | O |
| H | Cl | n-H₇C₃— | O |
| 4-OCH₃ | Cl | n-H₇C₃— | O |
| 6-Cl | Cl | n-H₇C₃— | O |
| H | Br | n-H₇C₃— | O |
| H | Cl | n-H₉C₄— | O |
| H | Br | n-H₉C₄— | O |
| H | Cl | (H₃C)₂HCCH₂— | O |
| H | Cl | (H₃C)₃CCH₂— | O |
| H | Cl | [(H₃C)₃C]H₃CCH— | O |
| H | Cl | [(H₃C)₂C]CH₂(H₃C)CH— | O |
| H | Cl | [(H₃C)₂HC](H₃C)₂C— | O |
| H | Cl | [(H₃C)₂HCCH₂CH₂](CH₃)₂C— | O |
| H | Cl | H₂C:CHCH₂— | O |
| H | CN | H₂C:CHCH₂— | O |
| H | Cl | H₂C:CHCH₂— | O |
| H | CN | H₂C:CHCH₂— | O |
| H | NO₂ | H₂C:CHCH₂— | O |
| 4-Cl | Cl | H₂C:CHCH₂— | O |
| 6-Cl | Cl | H₂C:CHCH₂ | O |
| 4-OCH₃ | Cl | H₂C:CHCH₂— | O |
| 6-CH₃ | Cl | H₂C:CHCH₂— | O |
| H | Br | H₂C:CHCH₂— | O |
| 4-OCH₃ | Br | H₂C:CHCH₂— | O |
| H | Cl | HC≡CCH₂— | O |
| H | Br | HC≡CCH₂— | O |
| H | Cl | IC≡CCH₂— | O |
| H | Br | IC≡CCH₂— | O |
| H | Cl | (H₃CSCH₂)H₃CCH— | O |
| H | Cl | (H₃CSCH₂)(CH₃)₂C— | O |
| H | Cl | (H₃COCH₂)H₃CCH— | O |
| H | Cl | (H₃COCH₂)(CH₃)₂C— | O |
| H | Cl | 2-Ethyl-1,3-dioxan-5-yl | O |
| H | Br | 2-Ethyl-1,3-dixoan-5-yl [sic] | O |
| H | Cl | 2-Isopropyl-1,3-dioxan-5-yl | O |
| H | Br | 2-Isopropyl-1,3-dioxan-5-yl | O |
| H | Cl | ClH₂C(CH₃)₂C— | O |
| H | Cl | Cl₃C(CH₃)₂C— | O |
| H | Cl | F₃C(CH₃)₂C— | O |
| H | Cl | Cl₃C(CH₃)CH— | O |
| H | Cl | (H₂C:CHCH₂)(CH₃)₂C— | O |
| H | Cl | (H₂C:CCH₃)(CH₃)₂C— | O |
| H | Cl | [(H₃C)₂C:CH]CH₂— | O |
| H | Cl | [(H₃CO)₂H₃CC]H₃CCH— | O |
| H | Cl | {[(H₃CO)₂HC]C≡C}(CH₃)₂C— | O |
| H | Cl | 2-Methoxycarbonylpropan-2-yl | O |
| H | Cl | 1-tert-Butoxypropan-2-yl | O |
| H | Cl | 1-Methoxybutan-2-yl | O |
| H | Cl | 3-Methylpentan-3-yl | O |

TABLE A.1.1-continued

| | | | |
|---|---|---|---|
| H | Cl | 3-Methyl-1-pentyn-3-yl | O |
| H | Cl | (HC≡C)H₃CCH— | O |
| H | CN | (HC≡C)H₃CCH— | O |
| H | NO₂ | (HC≡C)H₃CCH— | O |
| H | Cl | (HC≡C)(CH₃)₂C— | O |
| H | Cl | (H₂C:C)(CH₃)₂C— | O |
| H | Cl | 2-Isopropoxycarbonylpropan-2-yl | O |
| H | Cl | 1-Ethoxycarbonylethyl | O |
| H | Cl | 2-Methylcarbonylpropen-2-yl | O |
| H | Cl | 3-Methoxyimino-2-methylbutan-2-yl | O |
| H | Cl | F₃CCH₂— | O |
| 6-CH₃ | Cl | F₃C(H₃C)CH— | O |
| H | Cl | F₃C(H₃C)₂C— | O |
| H | Cl | [(H₃C)₂NCH₂]H₃CCH— | O |
| H | Cl | (H₃C)₃Si— | O |
| H | CN | (H₃C)₃Si | O |
| H | NO₂ | (H₃C)₃Si— | O |
| 4-Cl | Cl | (H₃C)₃Si— | O |
| 4-OCH₃ | Cl | (H₃C)₃Si— | O |
| 6-CH₃ | Cl | (H₃C)₃Si— | O |
| H | Br | (H₃C)₃Si— | O |
| H | Cl | Benzyl- | O |
| 6-Cl | Cl | Benzyl- | O |
| H | Br | Benzyl- | O |
| 3-Cl | Br | Benzyl- | O |
| H | Cl | 4-Cl-Benzyl- | O |
| H | CN | 4-Cl-Benzyl- | O |
| H | NO₂ | 4-Cl-Benzyl- | O |
| H | Cl | 3-Cl-Benzyl- | O |
| H | Cl | 2-Cl-Benzyl- | O |
| H | Cl | 2,6-Di-Cl-benzyl- | O |
| H | Cl | 2,6-Di-F-benzyl | O |
| 4-OCH₃ | Cl | 2,6-Di-F-benzyl | O |
| H | Cl | 4-F-Benzyl | O |
| H | Cl | 3-F-Benzyl | O |
| H | Cl | 2-Br-Benzyl | O |
| H | Cl | 4-CH₃-Benzyl | O |
| H | Cl | 4-C(CH₃)₃-Benzyl | O |
| H | Cl | 4-CH₃-Benzyl | O |
| H | Cl | 3-NO₂-Benzyl | O |
| H | Cl | 4-CN-Benzyl | O |
| H | Br | 2-CN-Benzyl | O |
| H | Cl | 4-CO₂CH₃-Benzyl | O |
| H | Cl | 3-CF₃-Benzyl | O |
| H | Cl | 4-CF₃-Benzyl | O |
| H | Br | 3-CF₃-Benzyl | O |
| H | Cl | 4-F₃CO-Benzyl | O |
| H | Cl | 3-H₂NC(=S)-Benzyl | O |
| H | Cl | 2-Naphthylmethyl | O |
| H | Cl | 1-Phenylethyl | O |
| H | CN | 1-Phenylethyl | O |
| H | NO₂ | 1-Phenylethyl | O |
| H | Cl | 2-Methyl-4-phenylpent-2-yl | O |
| H | Cl | 2-Phenylprop-2-yl | O |
| H | Cl | 2-(4-Chlorophenyl)prop-2-yl | O |
| H | Cl | 2-(3-Methyl-5-isoxizolyl)prop-2-yl | O |
| H | Cl | 3-Phenyl-5-isoxazolylmethyl | O |
| H | Cl | 3-(4-Chlorophenyl)-5-isoxazolmethyl | O |
| H | Cl | 5-Phenyl-1,3,4-oxadiazolylmethyl | |
| H | Cl | 5-Phenyl-1,3,4-thiadiazolylmethyl | O |
| H | Cl | 2-(4-Chlorophenyl)-4-oxazolymethyl | O |
| H | C | 3-(Tetrahydrofuran-2-yl)-5-isoxazolyl-methyl | O |
| H | Cl | 3-(Tetrahydrofuran-2-yl)-5-isoxazolyl-methyl | O |
| H | CN | 3-(Tetrahydrofuran-2-yl)-5-isoxazolyl-methyl | O |
| H | NO₂ | 3-(Tetrahydrofuran-2-yl)-5-isoxazolyl-methyl | O |
| H | Cl | 4-Chloro-3-(chlorophenyl)-5-isoxazo-lylmethyl | O |
| 4-OCH₃ | Cl | 4-Chloro-3-isopropyl-5-isoxazolyl-methyl | O |
| 6-Cl | Cl | 4-Chloro-3-isopropyl-5-isoxazolyl-methyl | O |

TABLE A.1.1-continued

| | | | |
|---|---|---|---|
| H | Br | 3-Isopropyl-5-isoxazolylmethyl | O |
| H | Cl | (4-Chlorophenyl)cyclopropylmethyl | O |
| H | Cl | Cyclopropyl(1-methyl-2-imidazolyl)methyl [sic] | O |
| H | Cl | Cyclopropylmethyl | O |
| H | Cl | 1-Cyclopropylethyl | O |
| H | CN | 1-Cyclopropylethyl | O |
| H | NO₂ | 1-Cyclopropylethyl | O |
| H | Cl | 2-Cyclopropylpropan-2-yl | O |
| H | Br | 1-Cyclopropylethyl | O |
| H | Cl | Cyclopropyl(1-methyl-2-imidazolyl)-methyl | O |
| H | Cl | Cyclopentyl | O |
| H | Cl | 1-Methylcyclopentyl | O |
| H | CN | 1-Methylcyclopentyl | O |
| H | NO₂ | 1-Methylcyclopentyl | O |
| H | Br | 1-Methylcyclopentyl | O |
| H | Cl | Cyclohexyl | O |
| H | Cl | 2-Methylcyclohexyl | O |
| H | Cl | 1-Methylcyclohexyl | O |
| H | Cl | 1-Ethynylcyclohexyl | O |
| H | Cl | 1-Vinylcyclohexyl | O |
| H | Cl | 1-Methylcyclohexyl | O |
| H | Cl | 3-Methyltetrahydrofuran-2-on-3-yl | O |
| H | Cl | 1-Methylcyclohexyl | O |
| H | Cl | 2-Cyanopropan-2-yl | O |
| H | Br | 2-Cyanopropan-2-yl | O |
| 4-OCH₃ [sic] | Cl | 2-Cyanopropan-2-yl | O |
| 6-Cl | Cl | 2-Cyanopropan-2-yl | O |
| H | CN | 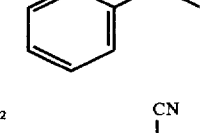 | O |
| H | NO₂ | 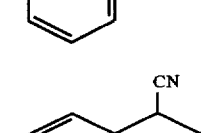 | O |
| H | Br | 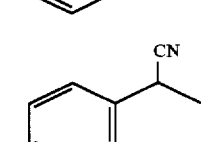 | O |
| 4-OCH₃ [sic] | Cl | 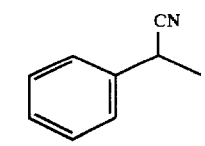 | O |
| H | Cl | 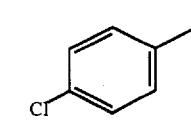 | O |
| H | Cl |  | O |

TABLE A.1.1-continued

| | | | |
|---|---|---|---|
| H | Cl | 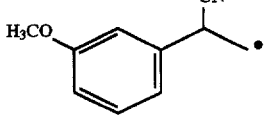 | O |
| H | Cl | 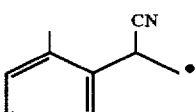 | O |
| H | Cl | 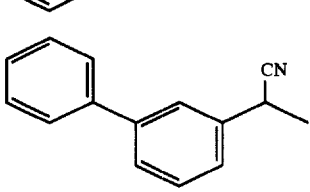 | O |
| H | Br | 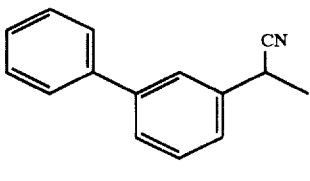 | O |
| H | Cl | 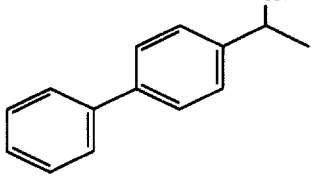 | O |
| H | Cl | 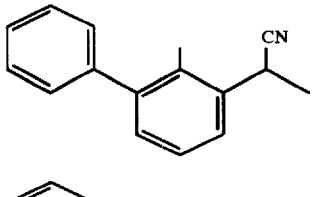 | O |
| H | Cl | 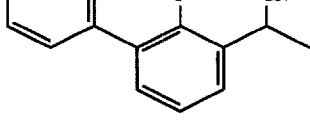 | O |
| H | Cl | 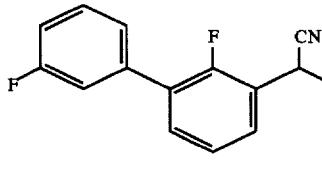 | O |
| H | Cl | 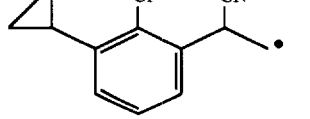 | O |
| H | Cl | 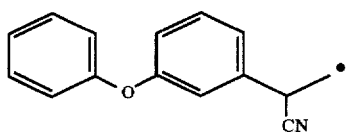 | O |

TABLE A.1.1-continued

| | | | |
|---|---|---|---|
| H | Br | 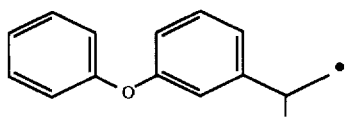 | O |
| H | Cl | 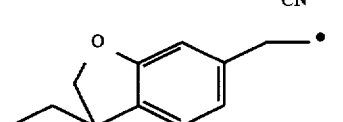 | O |
| H | Cl | 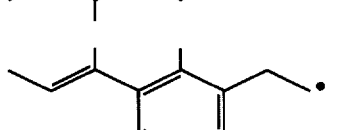 | O |
| H | Cl | 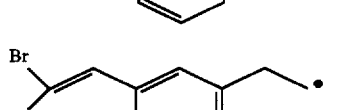 | O |
| H | Cl | 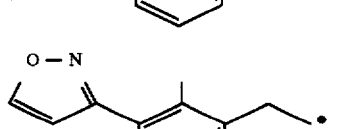 | O |
| H | Cl | 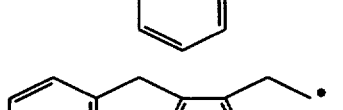 | O |
| H | Cl | 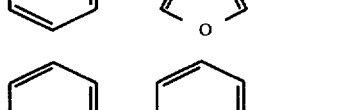 | O |
| H | Cl | 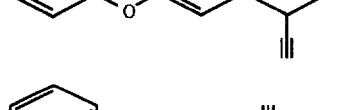 | O |
| H | Cl | 1-(3-Trifluoromethylphenyl)-2-propynyl | O |
| H | Cl | 1-(5,5-Dimethyl-1,3-dioxan-2-yl)-2-propynyl | O |
| H | Cl | 4-Methyl-2-ethyltetrahydropyran-4-yl | S |
| H | Cl | $CH_3$ | S |
| H | Br | $CH_3$ | S |
| H | Cl | $CH_2CH_3$ | S |
| H | Br | $CH_2CH_3$ | S |
| H | Cl | $CH_2CH_2CH_3$ | S |
| H | Br | $CH_2CH_2CH_3$ | S |
| H | Cl | $CH(CH_3)_2$ | S |
| H | CN | $CH(CH_3)_2$ | S |
| H | $NO_2$ | $CH(CH_3)_2$ | S |
| H | Br | $CH(CH_3)_2$ | S |
| H | Cl | $C(CH_3)_3$ | S |
| 4-$OCH_3$ | Cl | $C(CH_3)_3$ | S |
| 4-$OCH_3$ | CN | $C(CH_3)_3$ | S |
| 4-$OCH_3$ | $NO_2$ | $C(CH_3)_3$ | S |
| H | Br | $C(CH_3)_3$ | S |
| 4-$OCH_3$ | Cl | $CH(CH_3)_2$ | S |
| 6-Cl | Cl | $CH(CH_3)_2$ | S |
| 5-$C(CH_3)_3$ | Cl | $CH(CH_3)_2$ | S |
| H | Cl | $CH_2-(3-Cl-C_6H_5)$ | S |

TABLE A.1.1-continued

| | | | |
|---|---|---|---|
| H | CN | $CH_2-(3-Cl-C_6H_5)$ | S |
| H | $NO_2$ | $CH_2-(3-Cl-C_6H_5)$ | S |
| H | Cl | $CH_2-(4-CH_3-C_6H_5)$ | S |
| H | Cl | $CH_2-(4-CO_2CH_3-C_6H_5)$ | S |
| H | Cl | $CH_2-(2-CN-C_6H_5)$ | S |
| H | Br | $CH_2-C_6H_5$ | S |

TABLE A.1.2

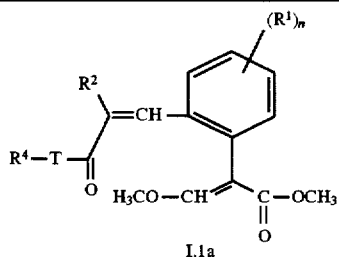
I.1a

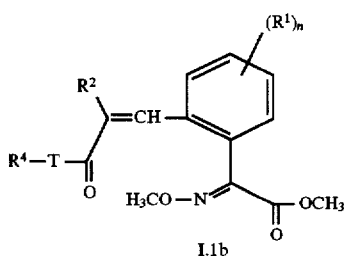
I.1b

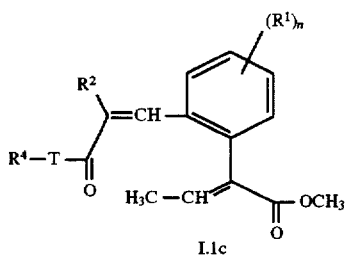
I.1c

| $R^1_a$ | $R^2$ | T | $R^7$ | $R^4$ |
|---|---|---|---|---|
| H | Cl | $ONR^7$ | $CH_3$ | $CH_3$ |
| H | Br | $ONR^7$ | $CH_3$ | $CH_3$ |
| 4-$OCH_3$ | Cl | $ONR^7$ | $CH_3$ | $CH_3$ |
| 4-Cl | Cl | $ONR^7$ | $CH_3$ | $CH_3$ |
| 6-Cl | Cl | $ONR^7$ | $CH_3$ | $CH_3$ |
| H | Cl | $ONR^7$ | $C_2H_5$ | $C_2H_5$ |
| H | Br | $ONR^7$ | $CH_2CH_2CH_3$ | $CH_2CH_2CH_3$ |
| H | Cl | $ONR^7$ | $CH_2C_6H_5$ | $CH_2C_6H_5$ |
| H | Cl | $ONR^7$ | $CH_2(4-Cl-C_6H_4)$ | $CH_2(4-Cl-C_6H_4)$ |
| H | Br | $ONR^7$ | $CH_2(4-Cl-C_6H_4)$ | $CH_2(4-Cl-C_6H_4)$ |
| H | Cl | $ONR^7$ | $CF_3$ | |
| H | Cl | $ONR^7$ | | $-CH_2CH_2CH_2CH_2CH_2-$ |
| H | Br | $ONR^7$ | | $-CH_2CH_2CH_2CH_2CH_2-$ |
| H | Cl | $ONR^7$ | | $-\underset{O}{\overset{\|}{C}}-CH=CH-\underset{O}{\overset{\|}{C}}-$ |
| H | Br | $ONR^7$ | | $-\underset{O}{\overset{\|}{C}}-CH=CH-\underset{O}{\overset{\|}{C}}-$ |
| H | Cl | $-ONR^7-$ | H | Methyl |
| H | Cl | $-ONR^7-$ | H | Ethyl |
| H | Cl | $-ONR^7-$ | H | n-Propyl |
| H | Cl | $-ONR^7-$ | H | i-Propyl |
| H | Cl | $-ONR^7-$ | H | n-Butyl |

TABLE A.1.2-continued

| | | | | |
|---|---|---|---|---|
| H | Cl | —ONR$^7$— | H | s-Butyl |
| H | Cl | —ONR$^7$— | H | i-Butyl |
| H | Cl | —ONR$^7$— | H | t-Butyl |
| H | Cl | —ONR$^7$— | H | Allyl |
| H | Cl | —ONR$^7$— | H | (E)-3-Chloro-2-propenyl |
| H | Cl | —ONR$^7$— | H | 2-Chloro 2-propenyl |
| H | Cl | —ONR$^7$— | H | (E)-2-Butenyl |
| H | Cl | —ONR$^7$— | H | 2-Methyl-2-propenyl |
| H | Cl | —ONR$^7$— | H | 2-Propynyl |
| H | Cl | —ONR$^7$— | H | 2-Butynyl |
| H | Cl | —ONR$^7$— | H | Cyanomethyl |
| H | Cl | —ONR$^7$— | H | tert-Butoxycarbonylmethyl |
| H | Cl | —ONR$^7$— | H | 1-Methoxypropan-2-yl |
| H | Cl | —ONR$^7$— | H | Benzyl |
| H | Cl | —ONR$^7$— | H | 3-Methylbenzyl |
| H | Cl | —ONR$^7$— | H | 4-Methoxycarbonylbenzyl |
| H | Cl | —ONR$^7$— | H | 3-Fluorobenzyl |
| H | Cl | —ONR$^7$— | H | 3-Bromobenzyl |
| H | Cl | —ONR$^7$— | H | 2-Chlorobenzyl |
| H | Cl | —ONR$^7$— | H | 3,4-Dichlorobenzyl |
| H | Cl | —ONR$^7$— | H | 3-Fluorobenzyl |
| H | Cl | —ONR$^7$— | H | 2,6-Difluorobenzyl |
| H | Cl | —ONR$^7$— | H | 3-Phenylbenzyl |
| H | Cl | —ONR$^7$— | H | 3-Phenylbenzyl |
| H | Cl | —ONR$^7$— | H | 3-Cyanobenzyl |
| H | Cl | —ONR$^7$— | H | 2-Phenylethyl |
| H | Cl | —ONR$^7$— | H | 3-Phenylpropan-1-yl |
| H | Cl | —ONR$^7$— | H | 4-Phenylbutan-1-yl |
| H | Cl | —ONR$^7$— | H | 4-(4-Chlorophenyl)-2-buten-1-yl |
| H | Cl | —ONR$^7$— | H | 2-(1-Naphthyl)ethyl |
| H | Cl | —ONR$^7$— | H | 4-(5-Chloro-2-thienyl)-3-buten-1-yl |
| H | Cl | —ONR$^7$— | H | 2-(4-Methylphenyl)-4-oxazolylmethyl |
| H | Cl | —ONR$^7$— | H | 2-(4-Chlorophenoxy)propan-1-yl |
| H | Cl | —ONR$^7$— | H | 6-Methoxy-2-methyl-4-pyrimidoxymethyl |
| H | Cl | —ONR$^7$— | RH | 1-Phenylethyl |
| H | Cl | —ONR$^7$— | CH$_3$ | Ethyl |
| H | Cl | —ONR$^7$— | CH$_3$ | n-Propyl |
| H | Cl | —ONR$^7$— | CH$_3$ | i-Propyl |
| H | Cl | —ONR$^7$— | CH$_3$ | n-Butyl |
| H | Cl | —ONR$^7$— | CH$_3$ | s-Butyl |
| H | Cl | —ONR$^7$— | CH$_3$ | i-Butyl |
| H | Cl | —ONR$^7$— | CH$_3$ | t-Butyl |
| H | Cl | —ONR$^7$— | CH$_3$ | Allyl |
| H | Cl | —ONR$^7$— | CH$_3$ | (E)-3-Chloro-2-propenyl |
| H | Cl | —ONR$^7$— | CH$_3$ | 2-Chloro-2-propenyl |
| H | Cl | —ONR$^7$— | CH$_3$ | (E)-2-Butenyl |
| H | Cl | —ONR$^7$— | CH$_3$ | 2-Methyl-2-propenyl |
| H | Cl | —ONR$^7$— | CH$_3$ | 2-Propynyl |
| H | Cl | —ONR$^7$— | CH$_3$ | 2-Butynyl |
| H | Cl | —ONR$^7$— | CH$_3$ | Cyanomethyl |
| H | Cl | —ONR$^7$— | CH$_3$ | tert-Butoxycarbonylmethyl |
| H | Cl | —ONR$^7$— | CH$_3$ | 1-Methoxypropan-2-yl |
| H | Cl | —ONR$^7$— | CH$_3$ | Benzyl |
| H | Cl | —ONR$^7$— | CH$_3$ | 3-Methylbenzyl |
| H | Cl | —ONR$^7$— | CH$_3$ | 4-Methoxycarbonylbenzyl |
| H | Cl | —ONR$^7$— | CH$_3$ | 3-Fluorobenzyl |
| H | Cl | —ONR$^7$— | CH$_3$ | 3-Bromobenzyl |
| H | Cl | —ONR$^7$— | CH$_3$ | 2-Chlorobenzyl |
| H | Cl | —ONR$^7$— | CH$_3$ | 3,4-Dichlorobenzyl |
| H | Cl | —ONR$^7$— | CH$_3$ | 3-Fluorobenzyl |
| H | Cl | —ONR$^7$— | CH$_3$ | 2,6-Difluorobenzyl |
| H | Cl | —ONR$^7$— | CH$_3$ | 3-Phenylbenzyl |
| H | Cl | —ONR$^7$— | CH$_3$ | 3-Phenylbenzyl |
| H | Cl | —ONR$^7$— | CH$_3$ | 3-Cyanobenzyl |
| H | Cl | —ONR$^7$— | CH$_3$ | 2-Phenylethyl |
| H | Cl | —ONR$^7$— | CH$_3$ | 3-Phenylpropan-1-yl |
| H | Cl | —ONR$^7$— | CH$_3$ | 4-Phenylbutan-1-yl |
| H | Cl | —ONR$^7$— | CH$_3$ | 4-(4-Chlorophenyl)-2-buten-1-yl |
| H | Cl | —ONR$^7$— | CH$_3$ | 2-(1-Naphthyl)ethyl |
| H | Cl | —ONR$^7$— | CH$_3$ | 4-(5-Chloro-2-thienyl)-3-buten-1-yl |
| H | Cl | —ONR$^7$— | CH$_3$ | 2-(4-Methylphenyl)-4-oxazolylmethyl |
| H | Cl | —ONR$^7$— | CH$_3$ | 2-(4-Chlorophenoxy)propan-1-yl |

TABLE A.1.2-continued

| | | | | |
|---|---|---|---|---|
| H | Cl | $-ONR^7-$ | $CH_3$ | 6-Methoxy-2-methyl-4-pyrimid-oxymethyl |
| H | Cl | $-ONR^7-$ | $CH_3$ | 1-Phenylethyl |
| H | Br | $-ONR^7-$ | H | Methyl |
| H | Br | $-ONR^7-$ | H | Ethyl |
| H | Br | $-ONR^7-$ | H | n-Propyl |
| H | Br | $-ONR^7-$ | H | i-Propyl |
| H | Br | $-ONR^7-$ | H | n-Butyl |
| H | Br | $-ONR^7-$ | H | s-Butyl |
| H | Br | $-ONR^7-$ | H | i-Butyl |
| H | Br | $-ONR^7-$ | H | t-Butyl |
| H | Br | $-ONR^7-$ | H | Allyl |
| H | Br | $-ONR^7-$ | H | (E)-3-Chloro-2-propenyl |
| H | Br | $-ONR^7-$ | H | 2-Chloro-2-propenyl |
| H | Br | $-ONR^7-$ | H | (E)-2-Butenyl |
| H | Br | $-ONR^7-$ | H | 2-Methyl-2-propenyl |
| H | Br | $-ONR^7-$ | H | 2-Propynyl |
| H | Br | $-ONR^7-$ | H | 2-Butynyl |
| H | Br | $-ONR^7-$ | H | Cyanomethyl |
| H | Br | $-ONR^7-$ | H | tert-Butoxycarbonylmethyl |
| H | Br | $-ONR^7-$ | H | 1-Methoxypropan-2-yl |
| H | Br | $-ONR^7-$ | H | Benzyl |
| H | Br | $-ONR^7-$ | H | 3-Methylbenzyl |
| H | Br | $-ONR^7-$ | H | 4-Methoxycarbonylbenzyl |
| H | Br | $-ONR^7-$ | H | 3-Fluorobenzyl |
| H | Br | $-ONR^7-$ | H | 3-Bromobenzyl |
| H | Br | $-ONR^7-$ | H | 2-Chlorobenzyl |
| H | Br | $-ONR^7-$ | H | 3,4-Dichlorobenzyl |
| H | Br | $-ONR^7-$ | H | 3-Fluorobenzyl |
| H | Br | $-ONR^7-$ | H | 2,6-Difluorobenzyl |
| H | Br | $-ONR^7-$ | H | 3-Phenylbenzyl |
| H | Br | $-ONR^7-$ | H | 3-Phenylbenzyl |
| H | Br | $-ONR^7-$ | H | 3-Cyanobenzyl |
| H | Br | $-ONR^7-$ | H | 2-Phenylethyl |
| H | Br | $-ONR^7-$ | H | 3-Phenylpropan-1-yl |
| H | Br | $-ONR^7-$ | H | 4-Phenylbutan-1-yl |
| H | Br | $-ONR^7-$ | H | 4-(4-Chlorophenyl)-2-buten-1-yl |
| H | Br | $-ONR^7-$ | H | 2-(1-Naphthyl)ethyl |
| H | Br | $-ONR^7-$ | H | 4-(5-Chloro-2-thienyl)-3-buten-1-yl |
| H | Br | $-ONR^7-$ | H | 2-(4-Methylphenyl)-4-oxazolyl-methyl |
| H | Br | $ONR^7-$ | H | 2-(4-Chlorophenoxy)propan-1-yl |
| H | Br | $-ONR^7-$ | H | 6-Methoxy-2-methyl-4-primid-oxymethyl |
| H | Br | $-ONR^7-$ | H | 1-Phenylethyl |
| H | Br | $-ONR^7-$ | $CH_3$ | Ethyl |
| H | Br | $-ONR^7-$ | $CH_3$ | n-Propyl |
| H | Br | $-ONR^7-$ | $CH_3$ | i-Propyl |
| H | Br | $-ONR^7-$ | $CH_3$ | n-Butyl |
| H | Br | $-ONR^7-$ | $CH_3$ | s-Butyl |
| H | Br | $-ONR^7-$ | $CH_3$ | i-Butyl |
| H | Br | $ONR^7-$ | $CH_3$ | t-Butyl |
| H | Br | $-ONR^7-$ | $CH_3$ | Allyl |
| H | Br | $-ONR^7-$ | $CH_3$ | (E)-3-Chloro-2-propenyl |
| H | Br | $-ONR^7-$ | $CH_3$ | 2-Chloro-2-propenyl |
| H | Br | $-ONR^7-$ | $CH_3$ | (E)-2-Butenyl |
| H | Br | $-ONR^7-$ | $CH_3$ | 2-Methyl-2-propenyl |
| H | Br | $-ONR^7-$ | $CH_3$ | 2-Propynyl |
| H | Br | $-ONR^7-$ | $CH_3$ | 2-Butynyl |
| H | Br | $-ONR^7-$ | $CH_3$ | Cyanomethyl |
| H | Br | $-ONR^7-$ | $CH_3$ | tert-Butoxycarbonylmethyl |
| H | Br | $-ONR^7-$ | $CH_3$ | 1-Methoxypropan-2-yl |
| H | Br | $-ONR^7-$ | $CH_3$ | Benzyl |
| H | Br | $-ONR^7-$ | $CH_3$ | 3-Methylbenzyl |
| H | Br | $-ONR^7-$ | $CH_3$ | 4-Methoxycarbonylbenzyl |
| H | Br | $-ONR^7-$ | $CH_3$ | 3-Fluorobenzyl |
| H | Br | $-ONR^7-$ | $CH_3$ | 3-Bromobenzyl |
| H | Br | $-ONR^7-$ | $CH_3$ | 2-Chlorobenzyl |
| H | Br | $-ONR^7-$ | $CH_3$ | 3,4-Dichlorobenzyl |
| H | Br | $-ONR^7-$ | $CH_3$ | 3-Fluorobenzyl |
| H | Br | $-ONR^7-$ | $CH_3$ | 2,6-Difluorobenzyl |
| H | Br | $-ONR^7-$ | $CH_3$ | 3-Phenylbenzyl |
| H | Br | $-ONR^7-$ | $CH_3$ | 3-Phenylbenzyl |
| H | Br | $-ONR^7-$ | $CH_3$ | 3-Cyanobenzyl |
| H | Br | $-ONR^7-$ | $CH_3$ | 2-Phenylethyl |
| H | Br | $-ONR^7-$ | $CH_3$ | 3-Phenylpropan-1-yl |

TABLE A.1.2-continued

| | | | | |
|---|---|---|---|---|
| H | Br | $-ONR^7-$ | CH₃ | 4-Phenylbutan-1-yl |
| H | Br | $-ONR^7-$ | CH₃ | 4-(4-Chlorophenyl)-2-buten-1-yl |
| H | Br | $-ONR^7-$ | CH₃ | 2-(1-Naphthyl)ethyl |
| H | Br | $-ONR^7-$ | CH₃ | 4-(5-chloro-2-thienyl)-3-buten-1-yl |
| H | Br | $-ONR^7-$ | CH₃ | 2-(4-Methylphenyl)-4-oxazolylmethyl |
| H | Br | $-ONR^7-$ | CH₃ | 2-(4-Chlorophenoxy)propan-1-yl |
| H | Br | $-ONR^7-$ | CH₃ | 6-Methoxy-2-methyl-4-pyrimidoxymethyl |
| H | Br | $-ONR^7-$ | CH₃ | 1-Phenylethyl |
| H | CN | $-ONR^7-$ | H | Methyl |
| H | CN | $-ONR^7-$ | H | Ethyl |
| H | CN | $-ONR^7-$ | H | n-Propyl |
| H | CN | $-ONR^7-$ | H | i-Propyl |
| H | CN | $-ONR^7-$ | H | n-Butyl |
| H | CN | $-ONR^7-$ | H | s-Butyl |
| H | CN | $-ONR^7-$ | H | i-Butyl |
| H | CN | $-ONR^7-$ | H | t-Butyl |
| H | CN | $-ONR^7-$ | H | Allyl |
| H | CN | $-ONR^7-$ | H | (E)-3-Chloro-2-propenyl |
| H | CN | $-ONR^7-$ | H | 2-Chloro-2-propenyl |
| H | CN | $-ONR^7-$ | H | (E)-2-Butenyl |
| H | CN | $-ONR^7-$ | H | 2-Methyl-2-propenyl |
| H | CN | $-ONR^7-$ | H | 2-Propynyl |
| H | CN | $-ONR^7-$ | H | 2-Butynyl |
| H | CN | $-ONR^7-$ | H | Cyanomethyl |
| H | CN | $-ONR^7-$ | H | tert-Butoxycarbonylmethyl |
| H | CN | $-ONR^7-$ | H | 1-Methoxypropan-2-yl |
| H | CN | $-ONR^7-$ | H | Benzyl |
| H | CN | $-ONR^7-$ | H | 3-Methylbenzyl |
| H | CN | $-ONR^7-$ | H | 4-Methoxycarbonylbenzyl |
| H | CN | $-ONR^7-$ | H | 3-Fluorobenzyl |
| H | CN | $-ONR^7-$ | H | 3-Bromobenzyl |
| H | CN | $-ONR^7-$ | H | 2-Chlorobenzyl |
| H | CN | $-ONR^7-$ | H | 3,4-Dichlorobenzyl |
| H | CN | $-ONR^7-$ | H | 3-Fluorobenzyl |
| H | CN | $-ONR^7-$ | H | 2,6-Difluorobenzyl |
| H | CN | $-ONR^7-$ | H | 3-Phenylbenzyl |
| H | CN | $-ONR^7-$ | H | 3-Phenylbenzyl |
| H | CN | $-ONR^7-$ | H | 3-Cyanobenzyl |
| H | CN | $-ONR^7-$ | H | 2-Phenylethyl |
| H | CN | $-ONR^7-$ | H | 3-Phenylpropan-1-yl |
| H | CN | $-ONR^7-$ | H | 4-Phenylbutan-1-yl |
| H | CN | $-ONR^7-$ | H | 4-(4-Chlorophenyl)-2-buten-1-yl |
| H | CN | $-ONR^7-$ | H | 2-(1-Naphthyl)ethyl |
| H | CN | $-ONR^7-$ | H | 4-(5-Chloro-2-thienyl)-3-buten-1-yl |
| H | CN | $-ONR^7-$ | H | 2-(4-Methylphenyl)-4-oxazolylmethyl |
| H | CN | $-ONR^7-$ | H | 2-(4-Chlorophenoxy)propan-1-yl |
| H | CN | $-ONR^7-$ | H | 6-Methoxy-2-methyl-4-pyrimidoxymethyl |
| H | CN | $-ONR^7-$ | H | 1-Phenylethyl |
| H | NO₂ | $-ONR^7-$ | H | Methyl |
| H | NO₂ | $-ONR^7-$ | H | Ethyl |
| H | NO₂ | $-ONR^7-$ | H | n-Propyl |
| H | NO₂ | $-ONR^7-$ | H | i-Propyl |
| H | NO₂ | $-ONR^7-$ | H | n-Butyl |
| H | NO₂ | $-ONR^7-$ | H | s-Butyl |
| H | NO₂ | $-ONR^7-$ | H | i-Butyl |
| H | NO₂ | $-ONR^7-$ | H | t-Butyl |
| H | NO₂ | $-ONR^7-$ | H | Allyl |
| H | NO₂ | $-ONR^7-$ | H | (E)-3-Chloro-2-propenyl |
| H | NO₂ | $-ONR^7-$ | H | 2-Chloro-2-propenyl |
| H | NO₂ | $-ONR^7-$ | H | (E)-2-Butenyl |
| H | NO₂ | $-ONR^7-$ | H | 2-Methyl-2-propenyl |
| H | NO₂ | $-ONR^7-$ | H | 2-Propynyl |
| H | NO₂ | $-ONR^7-$ | H | 2-Butynyl |
| H | NO₂ | $-ONR^7-$ | H | Cyanomethyl |
| H | NO₂ | $-ONR^7-$ | H | tert-Butoxycarbonylmethyl |
| H | NO₂ | $-ONR^7-$ | H | 1-Methoxypropan-2-yl |
| H | NO₂ | $-ONR^7-$ | H | Benzyl |
| H | NO₂ | $-ONR^7-$ | H | 3-Methylbenzyl |
| H | NO₂ | $-ONR^7-$ | H | 4-Methoxycarbonylbenzyl |

TABLE A.1.2-continued

| | | | | |
|---|---|---|---|---|
| H | NO$_2$ | —ONR$^7$— | H | 3-Fluorobenzyl |
| H | NO$_2$ | —ONR$^7$— | H | 3-Bromobenzyl |
| H | NO$_2$ | —ONR$^7$— | H | 2-Chlorobenzyl |
| H | NO$_2$ | —ONR$^7$— | H | 3,4-Dichlorobenzyl |
| H | NO$_2$ | —ONR$^7$— | H | 3-Fluorobenzyl |
| H | NO$_2$ | —ONR$^7$— | H | 2,6-Difluorobenzyl |
| H | NO$_2$ | —ONR$^7$— | H | 3-Phenylbenzyl |
| H | NO$_2$ | —ONR$^7$— | H | 3-Phenylbenzyl |
| H | NO$_2$ | —ONR$^7$— | H | 3-Cyanobenzyl |
| H | NO$_2$ | —ONR$^7$— | H | 2-Phenylethyl |
| H | NO$_2$ | —ONR$^7$— | H | 3-Phenylpropan-1-yl |
| H | NO$_2$ | ONR$^7$— | H | 4-Phenylbutan-1-yl |
| H | NO$_2$ | —ONR$^7$— | H | 4-(4-Chlorophenyl)-2-buten-1-yl |
| H | NO$_2$ | —ONR$^7$— | H | 2-(1-Naphthyl)ethyl |
| H | NO$_2$ | —ONR$^7$— | H | 4-(5-Chloro-2-thienyl)-3-buten-1-yl |
| H | NO$_2$ | —ONR$^7$— | H | 2-(4-Methylphenyl)-4-oxazolyl-methyl |
| H | NO$_2$ | —ONR$^7$— | H | 2-(4-Chlorophenoxy)propan-1-yl |
| H | NO$_2$ | —ONR$^7$— | H | 6-Methoxy-2-methyl-4-pyrimid-oxymethyl |
| H | NO$_2$ | —ONR$^7$— | H | 1-Phenylethyl |
| H | Cl | NR$^7$ | H | H |
| H | Br | NR$^7$ | H | H |
| H | Cl | NR$^7$ | H | CH$_3$ |
| H | Br | NR$^7$ | H | CH$_3$ |
| H | Cl | NR$^7$ | CH$_3$ | CH$_3$ |
| H | Br | NR$^7$ | CH$_3$ | CH$_3$ |
| H | Cl | NR$^7$ | H | CH$_2$CH$_3$ |
| H | Br | NR$^7$ | H | CH$_2$CH$_3$ |
| H | Cl | NR$^7$ | H | CH$_2$CH$_2$CH$_3$ |
| H | Cl | NR$^7$ | H | CH$_2$(CH$_3$)$_2$ |
| H | Cl | NR$^7$ | H | CH(CH$_3$)CH$_2$CH$_3$ |
| H | Cl | NR$^7$ | H | CH$_2$CH(CH$_3$)$_2$ |
| H | Cl | NR$^7$ | H | C(CH$_3$)$_3$ |
| 4-OCH$_3$ | Cl | NR$^7$ | H | C(CH$_3$)$_3$ |
| 4-Cl | Cl | NR$^7$ | H | C(CH$_3$)$_3$ |
| 6-Cl | Cl | NR$^7$ | H | C(CH$_3$)$_3$ |
| 6-C$_6$H$_5$ | Cl | NR$^7$ | H | C(CH$_3$)$_3$ |
| H | Cl | NR$^7$ | H | C(CH$_3$)$_2$C$_2$H$_5$ |
| H | Cl | NR$^7$ | H | C(CH$_3$)$_2$i-C$_3$H$_7$ |
| H | Cl | NR$^7$ | H | C(CH$_3$)$_2$C≡CH |
| H | Cl | NR$^7$ | H | C(CH$_3$)$_2$CH≡CH$_2$ |
| H | Cl | NR$^7$ | H | C(CH$_3$)$_2$CN |
| H | Cl | NR$^7$ | H | C(CH$_3$)$_2$CH$_2$CN |
| H | Cl | NR$^7$ | H | C(CH$_3$)$_2$CH$_2$SCH$_3$ |
| H | Cl | NR$^7$ | H | CH(C$_2$H$_5$)i-C$_3$H$_7$ |
| H | Cl | NR$^7$ | H | CH(CH$_3$)cyclo-C$_3$H$_5$ |
| H | Cl | NR$^7$ | H | CH(H$_3$COCH$_2$)i-C$_3$H$_7$ |
| H | Cl | NR$^7$ | H | Cyclopropyl |
| H | Cl | NR$^7$ | H | Cyclopentyl |
| H | Cl | NR$^7$ | H | Cyclohexyl |
| H | Cl | NR$^7$ | H | 1-Methylcyclopentyl |
| B | Cl | NR$^7$ | H | 1-Methylcyclohexyl |
| H | Cl | NR$^7$ | H | 4-Methyltetrahydropyran-4-yl |
| H | Br | NR$^7$ | H | CH(CH$_3$)$_2$ |
| H | Br | NR$^7$ | H | C(CH$_3$)$_3$ |
| H | Br | NR$^7$ | H | C(CH$_3$)$_2$C≡CH |
| H | Br | NR$^7$ | H | C(CH$_3$)$_2$CH≡CH$_2$ |
| H | Br | NR$^7$ | H | CH(CH$_3$)cyclo-C$_3$H$_5$ |
| H | Br | NR$^7$ | H | Cyclopropyl |
| H | Br | NR$^7$ | H | Cyclopentyl |
| H | Br | NR$^7$ | H | Cyclohexyl |
| H | Br | NR$^7$ | H | 1-Methylcyclopentyl |
| H | Br | NR$^7$ | H | 1-Methylcyclohexyl |
| H | CN | NR$^7$ | H | C(CH$_3$)$_3$ |
| H | CN | NR$^7$ | H | C(CH$_3$)$_2$C≡CH |
| H | CN | NR$^7$ | H | C(CH$_3$)$_2$CH≡CH$_2$ |
| H | CN | NR$^7$ | H | CH(CH$_3$)cyclo-C$_3$H$_5$ |
| H | CN | NR$^7$ | H | Cyclopropyl |
| H | CN | NR$^7$ | H | Cyclopentyl |

TABLE A.1.2-continued

| | | | | |
|---|---|---|---|---|
| H | CN | NR$^7$ | H | Cyclohexyl |
| H | CN | NR$^7$ | H | 1-Methylcyclopentyl |
| H | CN | NR$^7$ | H | 1-Methylcyclohexyl |
| H | NO$_2$ | NR$^7$ | H | C(CH$_3$)$_3$ |
| H | NO$_2$ | NR$^7$ | H | C(CH$_3$)$_2$C≡CH |
| H | NO$_2$ | NR$^7$ | H | C(CH$_3$)$_2$CH=CH$_2$ |
| H | NO$_2$ | NR$^7$ | H | CH(CH$_3$)cyclo-C$_3$H$_5$ |
| H | NO$_2$ | NR$^7$ | H | Cyclopropyl |
| H | NO$_2$ | NR$^7$ | H | Cyclopentyl |
| H | NO$_2$ | NR$^7$ | H | Cyclohexyl |
| H | NO$_2$ | NR$^7$ | H | 1-Methylcyclopentyl |
| H | NO$_2$ | NR$^7$ | H | 1-Methylcyclohexyl |
| H | Cl | NR$^7$ | H | CH$_2$C$_6$H$_5$ |
| H | Cl | NR$^7$ | CH$_3$ | CH$_2$C$_6$H$_5$ |
| H | Br | NR$^7$ | H | CH$_2$C$_6$H$_5$ |
| H | Br | NR$^7$ | CH$_3$ | CH$_2$C$_6$H$_5$ |
| H | Cl | NR$^7$ | CH$_3$ | CH$_2$(2-CH$_3$—C$_6$H$_4$) |
| H | Cl | NR$^7$ | H | CH(CH$_3$)C$_6$H$_5$ |
| H | Cl | NR$^7$ | H | CH(CH$_3$)(4-F—C$_6$H$_4$) |
| H | Cl | NR$^7$ | H | CH(CH$_3$)(4-CH$_3$—C$_6$H$_4$) |
| H | Cl | NR$^7$ | H | CH(CH$_3$)(3-Cl—C$_6$H$_4$) |
| H | Cl | NR$^7$ | H | CH(CH$_3$)(4-CH$_3$O—C$_6$H$_4$) |
| H | Cl | NR$^7$ | H | CH(CH$_3$)(3-CF$_3$—C$_6$H$_4$) |
| H | Cl | NR$^7$ | H | CH$_2$CH$_2$C$_6$H$_5$ |
| H | Cl | NR$^7$ | | —CH$_2$CH$_2$OCH$_2$CH$_2$— |
| H | Br | NR$^7$ | | —CH$_2$CH$_2$OCH$_2$CH$_2$— |
| H | Cl | NR$^7$ | | —CH$_2$CH$_2$CH$_2$CH$_2$CH$_2$— |
| H | Br | NR$^7$ | | —CH$_2$CH$_2$CH$_2$CH$_2$CH$_2$— |
| H | Cl | NR$^7$ | | —CH$_2$CH$_2$—N(C$_2$H$_5$)—CH$_2$CH$_2$— |
| H | Br | NR$^7$ | | —CH$_2$CH$_2$—N(C$_2$H$_5$)—CH$_2$CH$_2$— |
| 4-Cl | Cl | NR$^7$ | | —CH$_2$CH$_2$—O—CH$_2$CH$_2$— |
| 4-OCH$_3$ | Cl | NR$^7$ | | —CH$_2$CH$_2$—O—CH$_2$CH$_2$— |
| 6-Cl | Cl | NR$^7$ | | —CH$_2$CH$_2$—O—CH$_2$CH$_2$— |
| 6-C$_6$H$_5$ | Cl | NR$^7$ | | —CH$_2$CH$_2$—O—CH$_2$CH$_2$— |
| H | Cl | NR$^7$ | | —CH=N—CH=CH— |
| H | Br | NR$^7$ | | —CH=N—CH=CH— |
| H | Cl | NR$^7$ | H | 2-Pyrimidinyl |
| H | Cl | NR$^7$ | H | 5-C$_6$H$_5$-Thiazol-2-yl |
| H | Cl | NR$^7$ | H | 4-[C(=NOCH$_3$)—CO$_2$CH$_3$]-Thiazol-2-yl |
| H | Cl | NR$^7$ | H | Thiazol-2-yl |
| H | Cl | NR$^7$ | H | Tetrahydrothiophen-3-yl-1,1-dioxide |
| H | Cl | NR$^7$ | H | Isoxazol-5-yl |
| H | Cl | NR$^7$ | H | 2-CF$_3$-1,3,5-Thiadiazol-5-yl |
| H | Cl | NR$^7$ | H | CH(CH$_3$)—CO$_2$CH$_3$ |
| H | Cl | NR$^7$ | H | CH[CH(CH$_3$)$_2$]—CO$_2$C(CH$_3$)$_3$ |
| H | Br | NR$^7$ | H | CH[CH(CH$_3$)$_2$]—CO$_2$CH$_3$ |
| H | Cl | NR$^7$ | H | CH[CH(CH$_3$)$_2$]—CO$_2$CH$_3$ |
| H | Cl | NR$^7$ | H | CH(CH$_3$)—CO$_2$C(CH$_3$)$_3$ |
| H | Cl | NR$^7$ | H | CH(C$_6$H$_5$)—CO$_2$CH$_3$ |
| H | Cl | NR$^7$ | H | CH(CO$_2$CH$_3$)—CH$_2$CO$_2$CH$_3$ |
| H | Cl | —NR$^7$O— | H | CH$_3$ |
| H | Cl | —NR$^7$O— | H | CH$_2$CH$_3$ |
| H | Cl | —NR$^7$O— | H | CH$_2$CH$_2$CH$_3$ |
| H | Cl | —NR$^7$O— | H | CH(CH$_3$)$_2$ |
| H | Cl | —NR$^7$O— | H | C(CH$_3$)$_3$ |
| H | Br | —NR$^7$O— | H | C(CH$_3$)$_3$ |
| H | Cl | —NR$^7$O— | H | CH$_2$CH=CH$_2$ |
| H | Cl | —NR$^7$O— | H | CH$_2$CH=CH—Cl (trans) |
| H | Cl | —NR$^7$O— | H | CH$_2$—(3-Cl—C$_6$H$_5$) |
| H | Cl | —NR$^7$O— | H | CH$_2$—(4-CO$_2$CH$_3$—C$_6$H$_4$) |
| H | Cl | —NR$^7$O— | H | CH$_2$—C$_6$H$_5$ |
| H | Cl | —NR$^7$O— | H | CH$_2$—(3-thienyl) |
| H | Cl | —NR$^7$O— | H | CH$_2$—C(Cl)=CH$_2$ |
| H | Cl | —NR$^7$O— | H | CH$_2$—CH=CHCH$_3$ (trans) |
| H | Cl | —NR$^7$O— | H | C(CH$_3$)-Cyclopropyl |
| H | Cl | —NR$^7$O— | H | Cyclopentyl |
| H | Cl | —NR$^7$O— | H | Cyclohexyl |
| H | Cl | —NR$^7$O— | CH$_3$ | CH$_3$ |
| H | Cl | —NR$^7$O— | CH$_3$ | CH$_2$CH$_3$ |
| H | Cl | —NR$^7$O— | CH$_3$CH$_3$ | CH$_3$ |
| H | Cl | —NR$^7$O— | CH$_3$ | CH(CH$_3$)$_2$ |
| H | Cl | —NR$^7$O— | CH$_3$ | CH$_2$—CH=CH$_2$ |
| H | Br | —NR$^7$O— | H | CH$_2$CH$_3$ |
| H | Br | —NR$^7$O— | H | CH$_2$C$_6$H$_5$ |
| H | Br | —NR$^7$O— | CH$_3$ | CH(CH$_3$)$_2$ |
| H | Br | —NR$^7$O— | H | Cyclohexyl |

TABLE A.1.2-continued

| | | | | |
|---|---|---|---|---|
| H | Cl | $-NR^7-$ | H | $C_6H_5$ |
| H | Cl | $-NR^7-$ | H | $2\text{-}CH_3-C_6H_4$ |
| H | Cl | $-NR^7-$ | H | $4\text{-}CH_2CH_3-C_6H_4$ |
| H | Cl | $-NR^7-$ | H | $3,4\text{-}(CH_3)_2-C_6H_3$ |
| H | Cl | $-NR^7-$ | H | $3,4\text{-}(CH_3)_2-C_6H_3$ |
| H | Cl | $-NR^7-$ | H | $4\text{-}Cl-C_6H_4$ |
| H | Cl | $-NR^7-$ | H | $3\text{-}F-C_6H_4$ |
| H | Cl | $-NR^7-$ | H | $2,6\text{-}Cl_2-C_6H_3$ |
| H | Cl | $-NR^7-$ | H | $2\text{-}Br-C_6H_4$ |
| H | Cl | $-NR^7-$ | H | $4\text{-}OCH_3-C_6H_4$ |
| H | Cl | $-NR^7-$ | H | $3\text{-}OCH_2CH_3-C_6H_4$ |
| H | Cl | $-NR^7-$ | H | $3,4\text{-}(OCH_3)_2-C_6H_3$ |
| H | Cl | $-NR^7-$ | H | $4\text{-}CN-C_6H_4$ |
| H | Cl | $-NR^7-$ | E | $3\text{-}NO_2-C_6H_4$ |
| H | Cl | $-NR^7-$ | H | $3\text{-}CO_2CH_3-C_6H_4$ |
| H | Cl | $-NR^7-$ | H | $3\text{-}CS-NH_2-C_6H_4$ |
| H | Cl | $-NR^7-$ | H | $3,4\text{-}(OCH_3)_2-C_6H_3$ |
| H | Cl | $-NR^7-$ | H | $4\text{-}CO_2CH_2CH_3-C_6H_4$ |
| H | Cl | $-NR^7-$ | H | $4\text{-}SCN-C_6H_4$ |
| H | Cl | $-NR^7-$ | H | $4\text{-}SCH_3-C_6H_4$ |
| H | Cl | $-NR^7-$ | H | $3\text{-}NO_2-C_6H_4$ |
| H | Cl | $-NR^7-$ | H | $3\text{-}CF_3-C_6H_4$ |
| H | Cl | $-NR^7-$ | $CH_3$ | $C_6H_5$ |
| H | Cl | $-NR^7-$ | $CH_3$ | $2\text{-}CH_3-C_6H_4$ |
| H | Cl | $-NR^7-$ | $CH_3$ | $4\text{-}CH_2CH_3-C_6H_4$ |
| H | Cl | $-NR^7-$ | $CH_3$ | $3,4\text{-}(CH_3)_2-C_6H_3$ |
| H | Cl | $-NR^7-$ | $CH_3$ | $3,4\text{-}(CH_3)_2-C_6H_3$ |
| H | Cl | $-NR^7-$ | $CH_3$ | $4\text{-}Cl-C_6H_4$ |
| H | Cl | $-NR^7-$ | $CH_3$ | $3\text{-}F-C_6H_4$ |
| H | Cl | $-NR^7-$ | $CH_3$ | $2,6\text{-}Cl_2-C_6H_3$ |
| H | Cl | $-NR^7-$ | $CH_3$ | $2\text{-}Br-C_6H_4$ |
| H | Cl | $-NR^7-$ | $CH_3$ | $4\text{-}OCH_3-C_6H_4$ |
| H | Cl | $-NR^7-$ | $CH_3$ | $3\text{-}OCH_2CH_3-C_6H_4$ |
| H | Cl | $-NR^7-$ | $CH_3$ | $3,4\text{-}(OCH_3)_2-C_6H_3$ |
| H | Cl | $-NR^7-$ | $CH_3$ | $4\text{-}CN-C_6H_4$ |
| H | Cl | $-NR^7-$ | $CH_3$ | $3\text{-}NO_2-C_6H_4$ |
| H | Cl | $-NR^7-$ | $CH_3$ | $3\text{-}CO_2CH_3-C_6H_4$ |
| H | Cl | $-NR^7-$ | $CH_3$ | $3\text{-}CS-NH_2-C_6H_4$ |
| H | Cl | $-NR^7-$ | $CH_3$ | $4\text{-}CO_2CH_2CH_3-C_6H_4$ |
| H | Cl | $-NR^7-$ | $CH_3$ | $4\text{-}SCN-C_6H_4$ |
| H | Cl | $-NR^7-$ | $CH_3$ | $4\text{-}SCH_3-C_6H_4$ |
| H | Cl | $-NR^7-$ | $CH_3$ | $3\text{-}NO_2-C_6H_4$ |
| H | Cl | $-NR^7-$ | $CH_3$ | $3\text{-}CF_3-C_6H_4$ |
| H | Br | $-NR^7-$ | H | $C_6H_5$ |
| H | Br | $-NR^7-$ | H | $2\text{-}CH_3-C_6H_4$ |
| H | Br | $-NR^7-$ | H | $4\text{-}CH_2CH_3-C_6H_4$ |
| H | Br | $-NR^7-$ | H | $3,4\text{-}(CH_3)_2-C_6H_3$ |
| H | Br | $-NR^7-$ | H | $3,4\text{-}(CH_3)_2-C_6H_3$ |
| H | Br | $-NR^7-$ | H | $4\text{-}Cl-C_6H_4$ |
| H | Br | $-NR^7-$ | H | $3\text{-}F-C_6H_4$ |
| H | Br | $-NR^7-$ | H | $2,6\text{-}Cl_2-C_6H_3$ |
| H | Br | $-NR^7-$ | H | $2\text{-}Br-C_6H_4$ |
| H | Br | $-NR^7-$ | H | $4\text{-}OCH_3\text{-}C_6H_4$ |
| H | Br | $-NR^7-$ | H | $3\text{-}OCH_2CH_3-C_6H_4$ |
| H | Br | $-NR^7-$ | H | $3,4\text{-}(OCH_3)_2-C_6H_3$ |
| H | Br | $-NR^7-$ | H | $4\text{-}CN-C_6H_4$ |
| H | Br | $-NR^7-$ | H | $3\text{-}NO_2-C_6H_4$ |
| H | Br | $-NR^7-$ | H | $3\text{-}CO_2CH_3-C_6H_4$ |
| H | Br | $-NR^7-$ | H | $3\text{-}CS-NH_2-C_6H_4$ |
| H | Br | $-NR^7-$ | H | $3,4\text{-}(OCH_3)_2-C_6H_3$ |
| H | Br | $-NR^7-$ | H | $4\text{-}CO_2CH_2CH_3-C_6H_4$ |
| H | Br | $-NR^7-$ | H | $4\text{-}SCN-C_6H_4$ |
| H | Br | $-NR^7-$ | H | $4\text{-}SCH_3-C_6H_4$ |
| H | Br | $-NR^7-$ | H | $3\text{-}NO_2-C_6H_4$ |
| H | Br | $-NR^7-$ | H | $3\text{-}CF_3-C_6H_4$ |
| H | Br | $NR^7$ | $CH_3$ | $C_6H_5$ |
| H | CN | $-NR^7-$ | H | $C_6H_5$ |
| H | CN | $-NR^7-$ | H | $2\text{-}CH_3-C_6H_4$ |
| H | CN | $-NR^7-$ | H | $4\text{-}CH_2CH_3-C_6H_4$ |
| H | CN | $-NR^7-$ | H | $3,4\text{-}(CH_3)_2-C_6H_3$ |
| H | CN | $-NR^7-$ | H | $3,4\text{-}(CH_3)_2-C_6H_3$ |
| H | CN | $-NR^7-$ | H | $4\text{-}Cl-C_6H_4$ |
| H | CN | $-NR^7-$ | H | $3\text{-}F-C_6H_4$ |
| H | CN | $-NR^7-$ | H | $2,6\text{-}Cl_2-C_6H_3$ |
| H | CN | $-NR^7-$ | H | $2\text{-}Br-C_6H_4$ |
| H | CN | $-NR^7-$ | H | $4\text{-}OCH_3-C_6H_4$ |
| H | CN | $-NR^7-$ | H | $3\text{-}OCH_2CH_3-C_6H_4$ |
| H | CN | $-NR^7-$ | H | $3,4\text{-}(OCH_3)_2-C_6H_3$ |
| H | CN | $-NR^7-$ | H | $4\text{-}CN-C_6H_4$ |

TABLE A.1.2-continued

| | | | | |
|---|---|---|---|---|
| H | CN | —NR⁷— | H | 3-NO₂—C₆H₄ |
| H | CN | —NR⁷— | H | 3-CO₂CH₃—C₆H₄ |
| H | CN | —NR⁷— | H | 3-CS—NH₂—C₆H₄ |
| H | CN | —NR⁷— | H | 3,4-(OCH₃)₂—C₆H₃ |
| H | CN | —NR⁷— | H | 4-CO₂CH₂CH₃—C₆H₄ |
| H | CN | —NR⁷— | H | 4-SCN—C₆H₄ |
| H | CN | —NR⁷— | H | 4-SCH₃—C₆H₄ |
| H | CN | —NR⁷— | H | 3-NO₂—C₆H₄ |
| H | CN | —NR⁷— | H | 3-CF₃—C₆H₄ |
| H | Br | NR⁷ | CH₃ | C₆H₅ |
| H | Br | NR⁷ | CH₃ | 4-CH₂CH₃—C₆H₄ |
| H | Br | NR⁷ | CH₃ | 4-Cl—C₆H₄ |
| H | Br | NR⁷ | CH₃ | 3-F—C₆H₄ |
| H | Br | NR⁷ | CH₃ | 4-OCH₃—C₆H₄ |
| H | Br | NR⁷ | CH₃ | 3-OCF₃—C₆H₄ |
| H | Br | NR⁷ | CH₃ | 4-CN—C₆H₄ |
| H | Br | NR⁷ | CH₃ | 3-CO₂CH₃—C₆H₄ |
| H | Br | NR⁷ | CH₃ | 3-CF₃—C₆H₄ |
| H | Br | NR⁷ | CH₃ | 4-NO₂—C₆H₄ |
| 4-OCH₃ | Cl | NR⁷ | H | C₆H₅ |
| 4-Cl | Cl | NR⁷ | H | C₆H₅ |
| 6-Cl | Cl | NR⁷ | H | C₆H₅ |
| 6-CH₃ | Cl | NR⁷ | H | C₆H₅ |
| 4-OCH₃ | Cl | NR⁷ | CH₃ | C₆H₅ |
| 4-OCH₃ | Cl | NR⁷ | H | 2-CH₃—C₆H₄ |
| 6-Cl | Cl | NR⁷ | H | 4-OCH₃—C₆H₄ |
| 3-Cl | Cl | NR⁷ | H | 3-CO₂CH₃—C₆H₄ |
| 4-OCH₃ | Cl | NR⁷ | H | 4-CF₃—C₆H₄ |
| H | Cl | NR⁷ | H | 3-C₆H₅—C₆H₄ |

TABLE A.1.3

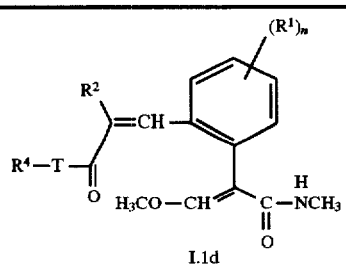

I.1d

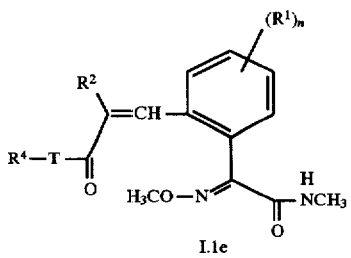

I.1e

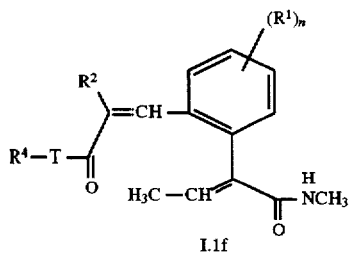

I.1f

| R¹ₙ | R² | T | R⁷ | R⁴ |
|---|---|---|---|---|
| H | Cl | ONR⁷ | CH₃ | |
| H | Br | ONR⁷ | CH₃ | CH₃ |
| 4-OCH₃ | Cl | ONR⁷ | CH₃ | CH₃ |
| 4-Cl | Cl | ONR⁷ | CH₃ | CH₃ |

TABLE A.1.3-continued

| | | | | |
|---|---|---|---|---|
| 6-Cl | Cl | ONR$^7$ | CH$_3$ | CH$_3$ |
| H | Cl | ONR$^7$ | C$_2$H$_5$ | C$_2$H$_5$ |
| H | Br | ONR$^7$ | CH$_2$CH$_2$CH$_3$ | CH$_2$CH$_2$CH$_3$ |
| H | Cl | ONR$^7$ | CH$_2$C$_6$H$_5$ | CH$_2$C$_6$H$_5$ |
| H | Cl | ONR$^7$ | CH$_2$(4-Cl—C$_6$H$_4$) | CH$_2$(4-Cl—C$_6$H$_4$) |
| H | Br | ONR$^7$ | CH$_2$(4-Cl—C$_6$H$_4$) | CH$_2$(4-Cl—C$_6$H$_4$) |
| H | Cl | ONR$^7$ | CF$_3$ | CF$_3$ |
| H | Cl | ONR$^7$ | | —CH$_2$CH$_2$CH$_2$CH$_2$CH$_2$— |
| H | Br | ONR$^7$ | | —CH$_2$CH$_2$CH$_2$CH$_2$CH$_2$— |
| H | Cl | ONR$^7$ | | —C(=O)—CH=CH—C(=O)— |
| H | Br | ONR$^7$ | | —C(=O)—CH=CH—C(=O)— |
| H | Cl | —ONR$^7$— | H | Methyl |
| H | Cl | —ONR$^7$— | H | Ethyl |
| H | Cl | —ONR$^7$— | H | n-Propyl |
| H | Cl | —ONR$^7$— | H | i-Propyl |
| H | Cl | —ONR$^7$— | H | n-Butyl |
| H | Cl | —ONR$^7$— | H | s-Butyl |
| H | Cl | —ONR$^7$— | H | i-Butyl |
| H | Cl | —ONR$^7$— | H | t-Butyl |
| H | Cl | —ONR$^7$— | H | Allyl |
| H | Cl | —ONR$^7$— | H | (E)-3-Chloro-2-propenyl |
| H | Cl | —ONR$^7$— | H | 2-Chloro-2-propenyl |
| H | Cl | —ONR$^7$— | H | (E)-2-Butenyl |
| H | Cl | —ONR$^7$— | H | 2-Methyl-2-propenyl |
| H | Cl | —ONR$^7$— | H | 2-Propynyl |
| H | Cl | —ONR$^7$— | H | 2-Butynyl |
| H | Cl | —ONR$^7$— | H | Cyanomethyl |
| H | Cl | —ONR$^7$— | H | tert-Butoxycarbonylmethyl |
| H | Cl | —ONR$^7$— | H | 1-Methoxypropan-2-yl |
| H | Cl | —ONR$^7$— | H | Benzyl |
| H | Cl | —ONR$^7$— | H | 3-Methylbenzyl |
| H | Cl | —ONR$^7$— | H | 4-Methoxycarbonylbenzyl |
| H | Cl | —ONR$^7$— | H | 3-Fluorobenzyl |
| H | Cl | —ONR$^7$— | H | 3-Bromobenzyl |
| H | Cl | —ONR$^7$— | H | 2-Chlorobenzyl |
| H | Cl | —ONR$^7$— | H | 3,4-Dichlorobenzyl |
| H | Cl | —ONR$^7$— | H | 3-Fluorobenzyl |
| H | Cl | —ONR$^7$— | H | 2,6-Difluorobenzyl |
| H | Cl | —ONR$^7$— | H | 3-Phenylbenzyl |
| H | Cl | —ONR$^7$— | H | 3-Phenylbenzyl |
| H | Cl | —ONR$^7$— | H | 3-Cyanobenzyl |
| H | Cl | —ONR$^7$— | H | 2-Phenylethyl |
| H | Cl | —ONR$^7$— | H | 3-Phenylpropan-1-yl |
| H | Cl | —ONR$^7$— | H | 4-Phenylbutan-1-yl |
| H | Cl | —ONR$^7$— | H | 4-(4-Chlorophenyl)-2-buten-1-yl |
| H | Cl | —ONR$^7$— | H | 2-(1-Naphthyl)ethyl |
| H | Cl | —ONR$^7$— | H | 4-(5-Chloro-2-thienyl)-3-buten-1-yl |
| H | Cl | —ONR$^7$— | H | 2-(4-Methylphenyl)-4-oxazolyl-methyl |
| H | Cl | —ONR$^7$— | H | 2-(4-Chlorophenoxy)propan-1-yl |
| H | Cl | —ONR$^7$— | H | 6-Methoxy-2-methyl-4-pyrimid-oxymethyl |
| H | Cl | —ONR$^7$— | H | 1-Phenylethyl |
| H | Cl | —ONR$^7$— | CH$_3$ | Ethyl |
| H | Cl | —ONR$^7$— | CH$_3$ | n-Propyl |
| H | Cl | —ONR$^7$— | CH$_3$ | i-Propyl |
| H | Cl | —ONR$^7$— | CH$_3$ | n-Butyl |
| H | Cl | —ONR$^7$— | CH$_3$ | s-Butyl |
| H | Cl | —ONR$^7$— | CH$_3$ | i-Butyl |
| H | Cl | —ONR$^7$— | CH$_3$ | t-Butyl |
| H | Cl | —ONR$^7$— | CH$_3$ | Allyl |
| H | Cl | —ONR$^7$— | CH$_3$ | (E)-3-Chloro-2-propenyl |
| H | Cl | —ONR$^7$— | CH$_3$ | 2-Chloro-2-propenyl |
| H | Cl | —ONR$^7$— | CH$_3$ | (E)-2-Butenyl |
| H | Cl | —ONR$^7$— | CH$_3$ | 2-Methyl-2-propenyl |
| H | Cl | —ONR$^7$— | CH$_3$ | 2-Propynyl |
| H | Cl | —ONR$^7$— | CH$_3$ | 2-Butynyl |
| H | Cl | —ONR$^7$— | CH$_3$ | Cyanomethyl |
| H | Cl | —ONR$^7$— | CH$_3$ | tert-Butoxycarbonylmethyl |

TABLE A.1.3-continued

| | | | | |
|---|---|---|---|---|
| H | Cl | —ONR$^7$— | CH$_3$ | 1-Methoxypropan-2-yl |
| H | Cl | —ONR$^7$— | CH$_3$ | Benzyl |
| H | Cl | —ONR$^7$— | CH$_3$ | 3-Methylbenzyl |
| H | Cl | —ONR$^7$— | CH$_3$ | 4-Methoxycarbonylbenzyl |
| H | Cl | —ONR$^7$— | CH$_3$ | 3-Fluorobenzyl |
| H | Cl | —ONR$^7$— | CH$_3$ | 3-Bromobenzyl |
| H | Cl | —ONR$^7$— | CH$_3$ | 2-Chlorobenzyl |
| H | Cl | —ONR$^7$— | CH$_3$ | 3,4-Dichlorobenzyl |
| H | Cl | —ONR$^7$— | CH$_3$ | 3-Fluorobenzyl |
| H | Cl | —ONR$^7$— | CH$_3$ | 2,6-Difluorobenzyl |
| H | Cl | —ONR$^7$— | CH$_3$ | 3-Phenylbenzyl |
| H | Cl | —ONR$^7$— | CH$_3$ | 3-Phenylbenzyl |
| H | Cl | —ONR$^7$— | CH$_3$ | 3-Cyanobenzyl |
| H | Cl | —ONR$^7$— | CH$_3$ | 2-Phenylethyl |
| H | Cl | —ONR$^7$— | CH$_3$ | 3-Phenylpropan-1-yl |
| H | Cl | —ONR$^7$— | CH$_3$ | 4-Phenylbutan-1-yl |
| H | Cl | —ONR$^7$— | CH$_3$ | 4-(4-Chlorophenyl)-2-buten-1-yl |
| H | Cl | —ONR$^7$— | CH$_3$ | 2-(1-Naphthyl)ethyl |
| H | Cl | —ONR$^7$— | CH$_3$ | 4-(5-Chloro-2-thienyl)-3-buten-1-yl |
| H | Cl | —ONR$^7$— | CH$_3$ | 2-(4-Methylphenyl)-4-oxazolyl-methyl |
| H | Cl | —ONR$^7$— | CH$_3$ | 2-(4-Chlorophenoxy)propan-1-yl |
| H | Cl | —ONR$^7$— | CH$_3$ | 6-Methoxy-2-methyl-4-pyrimid-oxymethyl |
| H | Cl | —ONR$^7$— | CH$_3$ | 1-Phenylethyl |
| H | Br | —ONR$^7$— | H | Methyl |
| H | Br | —ONR$^7$— | H | Ethyl |
| H | Br | —ONR$^7$— | H | n-Propyl |
| H | Br | —ONR$^7$— | H | i-Propyl |
| H | Br | —ONR$^7$— | H | n-Butyl |
| H | Br | —ONR$^7$— | H | s-Butyl |
| H | Br | —ONR$^7$— | H | i-Butyl |
| H | Br | —ONR$^7$— | H | t-Butyl |
| H | Br | —ONR$^7$— | H | Allyl |
| H | Br | —ONR$^7$— | H | (E)-3-Chloro-2-propenyl |
| H | Br | —ONR$^7$— | H | 2-Chloro-2-propenyl |
| H | Br | —ONR$^7$— | H | (E)-2-Butenyl |
| H | Br | —ONR$^7$— | H | 2-Methyl--2-propenyl |
| H | Br | —ONR$^7$— | H | 2-Propynyl |
| H | Br | —ONR$^7$— | H | 2-Butynyl |
| H | Br | —ONR$^7$— | H | Cyanomethyl |
| H | Br | —ONR$^7$— | H | tert-Butoxycarbonylmethyl |
| H | Br | —ONR$^7$— | H | 1-Methoxypropan-2-yl |
| H | Br | —ONR$^7$— | H | Benzyl |
| H | Br | —ONR$^7$— | H | 3-Methylbenzyl |
| H | Br | —ONR$^7$— | H | 4-Methoxycarbonylbenzyl |
| H | Br | —ONR$^7$— | H | 3-Fluorobenzyl |
| H | Br | —ONR$^7$— | H | 3-Bromobenzyl |
| H | Br | —ONR$^7$— | H | 2-Chlorobenzyl |
| H | Br | —ONR$^7$— | H | 3,4-Dichlorobenzyl |
| H | Br | —ONR$^7$— | H | 3-Fluorobenzyl |
| H | Br | —ONR$^7$— | H | 2,6-Difluorobenzyl |
| H | Br | —ONR$^7$— | H | 3-Phenylbenzyl |
| H | Br | —ONR$^7$— | H | 3-Phenylbenzyl |
| H | Br | —ONR$^7$— | H | 3-Cyanobenzyl |
| H | Br | —ONR$^7$— | H | 2-Phenylethyl |
| H | Br | —ONR$^7$— | H | 3-Phenylpropan-1-yl |
| H | Br | —ONR$^7$— | H | 4-Phenylbutan-1-yl |
| H | Br | —ONR$^7$— | H | 4-(4-Chlorophenyl)-2-buten-1-yl |
| H | Br | —ONR$^7$— | H | 2-(1-Naphthyl)ethyl |
| H | Br | —ONR$^7$— | H | 4-(5-Chloro-2-thienyl)-3-buten-1-yl |
| H | Br | —ONR$^7$— | H | 2-(4-Methylphenyl)-4-oxazolyl-methyl |
| H | Br | —ONR$^7$— | H | 2-(4-Chlorophenoxy)propan-1-yl |
| H | Br | —ONR$^7$— | H | 6-Methoxy-2-methyl-oxymethyl |
| H | Br | —ONR$^7$— | H | 1-Phenylethyl |
| H | Br | —ONR$^7$— | CH$_3$ | Ethyl |
| H | Br | —ONR$^7$— | CH$_3$ | n-Propyl |
| H | Br | —ONR$^7$— | CH$_3$ | i-Propyl |
| H | Br | —ONR$^7$— | CH$_3$ | n-Butyl |
| H | Br | —ONR$^7$— | CH$_3$ | s-Butyl |
| H | Br | —ONR$^7$— | CH$_3$ | i-Butyl |

TABLE A.1.3-continued

| | | | | |
|---|---|---|---|---|
| H | Br | —ONR$^7$— | CH$_3$ | t-Butyl |
| H | Br | —ONR$^7$— | CH$_3$ | Allyl |
| H | Br | —ONR$^7$— | CH$_3$ | (E)-3-Chloro-2-propenyl |
| H | Br | —ONR$^7$— | CH$_3$ | 2-Chloro-2-propenyl |
| H | Br | —ONR$^7$— | CH$_3$ | (E)-2-Butenyl |
| H | Br | —ONR$^7$— | CH$_3$ | 2-Methyl-2-propenyl |
| H | Br | —ONR$^7$— | CH$_3$ | 2-Propynyl |
| H | Br | —ONR$^7$— | CH$_3$ | 2-Butynyl |
| H | Br | —ONR$^7$— | CH$_3$ | Cyanomethyl |
| H | Br | —ONR$^7$— | CH$_3$ | tert-Butoxycarbonylmethyl |
| H | Br | —ONR$^7$— | CH$_3$ | 1-Methoxypropan-2-yl |
| H | Br | —ONR$^7$— | CH$_3$ | Benzyl |
| H | Br | —ONR$^7$— | CH$_3$ | 3-Methylbenzyl |
| H | Br | —ONR$^7$— | CH$_3$ | 4-Methoxycarbonylbenzyl |
| H | Br | —ONR$^7$— | CH$_3$ | 3-Fluorobenzyl |
| H | Br | —ONR$^7$— | CH$_3$ | 3-Bromobenzyl |
| H | Br | —ONR$^7$— | CH$_3$ | 2-Chlorobenzyl |
| H | Br | —ONR$^7$— | CH$_3$ | 3,4-Dichlorobenzyl |
| H | Br | —ONR$^7$— | CH$_3$ | 3-Fluorobenzyl |
| H | Br | —ONR$^7$— | CH$_3$ | 2,6-Difluorobenzyl |
| H | Br | —ONR$^7$— | CH$_3$ | 3-Phenylbenzyl |
| H | Br | —ONR$^7$— | CH$_3$ | 3-Phenylbenzyl |
| H | Br | —ONR$^7$— | CH$_3$ | 3-Cyanobenzyl |
| H | Br | —ONR$^7$— | CH$_3$ | 2-Phenylethyl |
| H | Br | —ONR$^7$— | CH$_3$ | 3-Phenylpropan-1-yl |
| H | Br | —ONR$^7$— | CH$_3$ | 14-Phenylbutan-1-yl |
| H | Br | —ONR$^7$— | CH$_3$ | 4-(4-Chlorophenyl)-2-buten-1-yl |
| H | Br | —ONR$^7$— | CH$_3$ | 2-(1-Naphthyl)ethyl |
| H | Br | —ONR$^7$— | CH$_3$ | 4-(5-Chloro-2-thienyl)-3-buten-1-yl |
| H | Br | —ONR$^7$— | CH$_3$ | 2-(4-Methylphenyl-4-oxazolyl-methyl |
| H | Br | —ONR$^7$— | CH$_3$ | 2-(4-Chlorophenoxy)propan-1-yl |
| H | Br | —ONR$^7$— | CH$_3$ | 6-Methoxy-2-methyl-4-pyrimid-oxymethyl |
| H | Br | —ONR$^7$— | CH$_3$ | 1-Phenylethyl |
| H | CN | —ONR$^7$— | H | Methyl |
| H | CN | —ONR$^7$— | H | Ethyl |
| H | CN | —ONR$^7$— | H | n-Propyl |
| H | CN | —ONR$^7$— | H | i-Propyl |
| H | CN | —ONR$^7$— | H | n-Butyl |
| H | CN | —ONR$^7$— | H | s-Butyl |
| H | CN | —ONR$^7$— | H | i-Butyl |
| H | CN | —ONR$^7$— | H | t-Butyl |
| H | CN | —ONR$^7$— | H | Allyl |
| H | CN | —ONR$^7$— | H | (E)-3-Chloro-2-propenyl |
| H | CN | —ONR$^7$— | H | 2-Chloro-2-propenyl |
| H | CN | —ONR$^7$— | H | (E)-2-Butenyl |
| H | CN | —ONR$^7$— | H | 2-Methyl-2-propenyl |
| H | CN | —ONR$^7$— | H | 2-Propynyl |
| H | CN | —ONR$^7$— | H | 2-Butynyl |
| H | CN | —ONR$^7$— | H | Cyanomethyl |
| H | CN | —ONR$^7$— | H | tert-Butoxycarbonylmethyl |
| H | CN | —ONR$^7$— | H | 1-Methoxypropan-2-yl |
| H | CN | —ONR$^7$— | H | Benzyl |
| H | CN | —ONR$^7$— | H | 3-Methylbenzyl |
| H | CN | —ONR$^7$— | H | 4-Methoxycarbonylbenzyl |
| H | CN | —ONR$^7$— | H | 3-Fluorobenzyl |
| H | CN | —ONR$^7$— | H | 3-Bromobenzyl |
| H | CN | —ONR$^7$— | H | 2-Chlorobenzyl |
| H | CN | —ONR$^7$— | H | 3,4-Dichlorobenzyl |
| H | CN | —ONR$^7$— | H | 3-Fluorobenzyl |
| H | CN | —ONR$^7$— | H | 2,6-Difluorobenzyl |
| H | CN | —ONR$^7$— | H | 3-Phenylbenzyl |
| H | CN | —ONR$^7$— | H | 3-Phenylbenzyl |
| H | CN | —ONR$^7$— | H | 3-Cyanobenzyl |
| H | CN | —ONR$^7$— | H | 2-Phenylethyl |
| H | CN | —ONR$^7$— | H | 3-Phenylpropan-1-yl |
| H | CN | —ONR$^7$— | H | 4-Phenylbutan-1-yl |
| H | CN | —ONR$^7$— | H | 4-(4-Chlorophenyl)-2-buten-1-yl |
| H | CN | —ONR$^7$— | H | 2-(1-Naphthyl)ethyl |
| H | CN | —ONR$^7$— | H | 4-(5-Chloro-2-thienyl)-3-buten-1-yl |
| H | CN | —ONR$^7$— | H | 2-(4-Methylphenyl)-4-oxazolyl-methyl |
| H | CN | —ONR$^7$— | H | 2-(4-Chlorophenoxy)propan- |

TABLE A.1.3-continued

| | | | | |
|---|---|---|---|---|
| H | CN | $-ONR^7-$ | H | 6-Methoxy-2-methyl-4-pyrimid-oxymethyl |
| H | CN | $-ONR^7-$ | H | 1-Phenylethyl |
| H | $NO_2$ | $-ONR^7-$ | H | Methyl |
| H | $NO_2$ | $-ONR^7-$ | H | Ethyl |
| H | $NO_2$ | $-ONR^7-$ | H | n-Propyl |
| H | $NO_2$ | $-ONR^7-$ | H | i-Propyl |
| H | $NO_2$ | $-ONR^7-$ | H | n-Butyl |
| H | $NO_2$ | $-ONR^7-$ | H | s-Butyl |
| H | $NO_2$ | $-ONR^7-$ | H | i-Butyl |
| H | $NO_2$ | $-ONR^7-$ | H | t-Butyl |
| H | $NO_2$ | $-ONR^7-$ | H | Allyl |
| H | $NO_2$ | $-ONR^7-$ | H | (E)-3-Chloro-2-propenyl |
| H | $NO_2$ | $-ONR^7-$ | H | 2-Chloro-2-propenyl |
| H | $NO_2$ | $-ONR^7-$ | H | (E)-2-Butenyl |
| H | $NO_2$ | $-ONR^7-$ | H | 2-Methyl-2-propenyl |
| H | $NO_2$ | $-ONR^7-$ | H | 2-Propynyl |
| H | $NO_2$ | $-ONR^7-$ | H | 2-Butynyl |
| H | $NO_2$ | $-ONR^7-$ | H | Cyanomethyl |
| H | $NO_2$ | $-ONR^7-$ | H | tert-Butoxycarbonylmethyl |
| H | $NO_2$ | $-ONR^7-$ | H | 1-Methoxypropan-2-yl |
| H | $NO_2$ | $-ONR^7-$ | H | Benzyl |
| H | $NO_2$ | $-ONR^7-$ | H | 3-Methylbenzyl |
| H | $NO_2$ | $-ONR^7-$ | H | 4-Methoxycarbonylbenzyl |
| H | $NO_2$ | $-ONR^7-$ | H | 3-Fluorobenzyl |
| H | $NO_2$ | $-ONR^7-$ | H | 3-Bromobenzyl |
| H | $NO_2$ | $-ONR^7-$ | H | 2-Chlorobenzyl |
| H | $NO_2$ | $-ONR^7-$ | H | 3,4-Dichlorobenzyl |
| H | $NO_2$ | $-ONR^7-$ | H | 3-Fluorobenzyl |
| H | $NO_2$ | $-ONR^7-$ | H | 2,6-Difluorobenzyl |
| H | $NO_2$ | $-ONR^7-$ | H | 3-Phenylbenzyl |
| H | $NO_2$ | $-ONR^7-$ | H | 3-Phenylbenzyl |
| H | $NO_2$ | $-ONR^7-$ | H | 3-Cyanobenzyl |
| H | $NO_2$ | $-ONR^7-$ | H | 2-Phenylethyl |
| H | $NO_2$ | $-ONR^7-$ | H | 3-Phenylpropan-1-yl |
| H | $NO_2$ | $-ONR^7-$ | H | 4-Phenylbutan-1-yl |
| H | $NO_2$ | $-ONR^7-$ | H | 4-(4-Chlorophenyl)-2-buten-1-yl |
| H | $NO_2$ | $-ONR^7-$ | H | 2-(1-Naphthyl)ethyl |
| H | $NO_2$ | $-ONR^7-$ | H | 4-(5-Chloro-2-thienyl)-3-buten-1-yl |
| H | $NO_2$ | $-ONR^7-$ | H | 2-(4-Methylphenyl)-4-oxazolyl-methyl |
| H | $NO_2$ | $-ONR^7-$ | H | 2-(4-Chlorophenoxy)propan-1-yl |
| H | $NO_2$ | $-ONR^7-$ | H | 6-Methoxy-2-methyl-4-pyrimid-oxymethyl |
| H | $NO_2$ | $-ONR^7-$ | H | 1-Phenylethyl |
| H | Cl | $NR^7$ | H | H |
| H | Br | $NR^7$ | H | H |
| H | Cl | $NR^7$ | H | $CH_3$ |
| H | Br | $NR^7$ | H | $CH_3$ |
| H | Cl | $NR^7$ | $CH_3$ | $CH_3$ |
| H | Br | $NR^7$ | $CH_3$ | $CH_3$ |
| H | Cl | $NR^7$ | H | $CH_2CH_3$ |
| H | Br | $NR^7$ | H | $CH_2CH_3$ |
| H | Cl | $NR^7$ | H | $CH_2CH_2CH_3$ |
| H | Cl | $NR^7$ | H | $CH_2(CH_3)_2$ |
| H | Cl | $NR^7$ | H | $CH(CH_3)CH_2CH_3$ |
| H | Cl | $NR^7$ | H | $CH_2CH(CH_3)_2$ |
| H | Cl | $NR^7$ | H | $C(CH_3)_3$ |
| 4-$OCH_3$ | Cl | $NR^7$ | H | $C(CH_3)_3$ |
| 4-Cl | Cl | $NR^7$ | H | $C(CH_3)_3$ |
| 6-Cl | Cl | $NR^7$ | H | $C(CH_3)_3$ |
| 6-$C_6H_5$ | Cl | $NR^7$ | H | $C(CH_3)_3$ |
| H | Cl | $NR^7$ | H | $C(CH_3)_2C_2H_5$ |
| H | Cl | $NR^7$ | H | $C(CH_3)_2$i-$C_3H_7$ |
| H | Cl | $NR^7$ | H | $C(CH_3)_2C\equiv CH$ |
| H | Cl | $NR^7$ | H | $C(CH_3)_2CH=CH_2$ |
| H | Cl | $NR^7$ | H | $C(CH_3)_2CN$ |
| H | Cl | $NR^7$ | H | $C(CH_3)_2CH_2CN$ |
| H | Cl | $NR^7$ | H | $C(CH_3)_2CH_2SCH_3$ |
| H | Cl | $NR^7$ | H | $CH(C_2H_5)$i-$C_3H_7$ |
| H | Cl | $NR^7$ | H | $CH(CH_3)$cyclo-$C_3H_5$ |
| H | Cl | $NR^7$ | H | $CH(H_3COCH_2)$i-$C_3H_7$ |
| H | Cl | $NR^7$ | H | Cyclopropyl |
| H | Cl | $NR^7$ | H | Cyclopentyl |

TABLE A.1.3-continued

| | | | | |
|---|---|---|---|---|
| H | Cl | NR$^7$ | H | Cyclohexyl |
| H | Cl | NR$^7$ | H | 1-Methylcyclopentyl |
| H | Cl | NR$^7$ | H | 1-Methylcyclohexyl |
| H | Cl | NR$^7$ | H | 4-Methyltetrahydropyran-4-yl |
| H | Br | NR$^7$ | H | CH(CH$_3$)$_2$ |
| H | Br | NR$^7$ | H | C(CH$_3$)$_3$ |
| H | Br | NR$^7$ | H | C(CH$_3$)$_2$C≡CH |
| H | Br | NR$^7$ | H | C(CH$_3$)$_2$CH=CH$_2$ |
| H | Br | NR$^7$ | H | CH(CH$_3$)cyclo-C$_3$H$_5$ |
| H | Br | NR$^7$ | H | Cyclopropyl |
| H | Br | NR$^7$ | H | Cyclopentyl |
| H | Br | NR$^7$ | H | Cyclohexyl |
| H | Br | NR$^7$ | H | 1-Methylcyclopentyl |
| H | Br | NR$^7$ | H | 1-Methylcyclohexyl |
| H | CN | NR$^7$ | H | C(CH$_3$)$_3$ |
| H | CN | NR$^7$ | H | C(CH$_3$)$_2$C≡CH |
| H | CN | NR$^7$ | H | CH$_3$)$_2$CH=CH$_2$ |
| H | CN | NR$^7$ | H | CH(CH$_3$)cyclo-C$_3$H$_5$ |
| H | CN | NR$^7$ | H | Cyclopropyl |
| H | CN | NR$^7$ | H | Cyclopentyl |
| H | CN | NR$^7$ | H | Cyclohexyl |
| H | CN | NR$^7$ | H | 1-Methylcyclopentyl |
| H | CN | NR$^7$ | H | 1-Methylcyclohexyl |
| H | NO$_2$ | NR$^7$ | H | C(CH$_3$)$_3$ |
| H | NO$_2$ | NR$^7$ | H | C(CH$_3$)$_2$C≡CH |
| H | NO$_2$ | NR$^7$ | H | C(CH$_3$)$_2$CH=CH$_2$ |
| H | NO$_2$ | NR$^7$ | H | CH(CH$_3$)cyclo-C$_3$H$_5$ |
| H | NO$_2$ | NR$^7$ | H | Cyclopropyl |
| H | NO$_2$ | NR$^7$ | H | Cyclopentyl |
| H | NO$_2$ | NR$^7$ | H | Cyclohexyl |
| H | NO$_2$ | NR$^7$ | H | 1-Methylcyclopentyl |
| H | NO$_2$ | NR$^7$ | H | 1-Methylcyclohexyl |
| H | Cl | NR$^7$ | H | CH$_2$C$_6$H$_5$ |
| H | Cl | NR$^7$ | CH$_3$ | CH$_2$C$_6$H$_5$ |
| H | Br | NR$^7$ | H | CH$_2$C$_6$H$_5$ |
| H | Br | NR$^7$ | CH$_3$ | CH$_2$C$_6$H$_5$ |
| H | Cl | NR$^7$ | CH$_3$ | CH$_2$(2-CH$_3$—C$_6$H$_4$) |
| H | Cl | NR$^7$ | H | CH(CH$_3$)C$_6$H$_5$ |
| H | Cl | NR$^7$ | H | CH(CH$_3$)(4-F—C$_6$H$_4$) |
| H | Cl | NR$^7$ | H | CH(CH$_3$)(4-CH$_3$—C$_6$H$_4$) |
| H | Cl | NR$^7$ | H | CH(CH$_3$)(3-Cl—C$_6$H$_4$) |
| H | Cl | NR$^7$ | H | CH(CH$_3$)(4-CH$_3$O—C$_6$H$_4$) |
| H | Cl | NR$^7$ | H | CH(CH$_3$)(3-CF$_3$—C$_6$H$_4$) |
| H | Cl | NR$^7$ | H | CH$_2$CH$_2$C$_6$H$_5$ |
| H | Cl | NR$^7$ | | —CH$_2$CH$_2$OCH$_2$CH$_2$— |
| H | Br | NR$^7$ | | —CH$_2$CH$_2$OCH$_2$CH$_2$— |
| H | Cl | NR$^7$ | | —CH$_2$CH$_2$CH$_2$CH$_2$CH$_2$— |
| H | Br | NR$^7$ | | —CH$_2$CH$_2$CH$_2$CH$_2$CH$_2$— |
| H | Cl | NR$^7$ | | —CH$_2$CH$_2$—N(C$_2$H$_5$)—CH$_2$CH$_2$— |
| H | Br | NR$^7$ | | —CH$_2$CH$_2$—N(C$_2$H$_5$)—CH$_2$CH$_2$— |
| 4-Cl | Cl | NR$^7$ | | —CH$_2$CH$_2$—O—CH$_2$CH$_2$— |
| 4-OCH$_3$ | Cl | NR$^7$ | | —CH$_2$CH$_2$—O—CH$_2$CH$_2$— |
| 6-Cl | Cl | NR$^7$ | | —CH$_2$CH$_2$—O—CH$_2$CH$_2$— |
| 6-C$_6$H$_5$ | Cl | NR$^7$ | | —CH$_2$CH$_2$—O—CH$_2$CH$_2$— |
| H | Cl | NR$^7$ | | —CN=N—CH=CH— |
| H | Br | NR$^7$ | | —CH=N—CH=CH— |
| H | Cl | NR$^7$ | H | 2-Pyrimidinyl |
| H | Cl | NR$^7$ | H | 5-C$_6$H$_5$-Thiazol-2-yl |
| H | Cl | NR$^7$ | H | 4-[C—(=NOCH$_3$)—CO$_2$CH$_3$]—Thiazol-2-yl |
| H | Cl | NR$^7$ | H | Thiazol-2-yl |
| H | Cl | NR$^7$ | H | Tetrahydrothiophen-3-yl-1,1-dioxide |
| H | Cl | NR$^7$ | H | Isoxazol-5-yl |
| H | Cl | NR$^7$ | H | 2-CF$_3$-1,3,5-Thiadiazol-5-yl |
| H | Cl | NR$^7$ | H | CH(CH$_3$)—CO$_2$CH$_3$ |
| H | Cl | NR$^7$ | H | CH[CH(CH$_3$)$_2$]—CO$_2$C(CH$_3$)$_3$ |
| H | Br | NR$^7$ | H | CH[CH(CH$_3$)$_2$]—CO$_2$CH$_3$ |
| H | Cl | NR$^7$ | H | CH[CH(CH$_3$)$_2$]—CO$_2$CH$_3$ |
| H | Cl | NR$^7$ | H | CH(CH$_3$)—CO$_2$C(CH$_3$)$_3$ |
| H | Cl | NR$^7$ | H | CH(C$_6$H$_5$)—CO$_2$CH$_3$ |
| H | Cl | NR$^7$ | H | CH(CO$_2$CH$_3$)—CH$_2$CO$_2$CH$_3$ |
| H | Cl | —NR$^7$O— | H | CH$_3$ |
| H | Cl | —NR$^7$O— | H | CH$_2$CH$_3$ |
| H | Cl | —NR$^7$O— | H | CH$_2$CH$_2$CH$_3$ |
| H | Cl | —NR$^7$O— | H | CH(CH$_3$)$_2$ |

TABLE A.1.3-continued

| | | | | |
|---|---|---|---|---|
| H | Cl | $-NR^7O-$ | H | $C(CH_3)_2$ |
| H | Br | $-NR^7O-$ | H | $C(CH_3)_2$ |
| H | Cl | $-NR^7O-$ | H | $CH_2CH=CH_2$ |
| H | Cl | $-NR^7O-$ | H | $CH_2CH=CH-Cl$ (trans) |
| H | Cl | $-NR^7O-$ | H | $CH_2$-(3-Cl—$C_6H_5$) |
| H | Cl | $-NR^7O-$ | H | $CH_2$-(4-$CO_2CH_3$—$C_6H_4$) |
| H | Cl | $-NR^7O-$ | H | $CH_2-C_6H_5$ |
| H | Cl | $-NR^7O-$ | H | $CH_2$-(3-Thienyl) |
| H | Cl | $-NR^7O-$ | H | $CH_2-C(Cl)=CH_2$ |
| H | Cl | $-NR^7O-$ | H | $CH_2-CH=CHCH_3$(trans) |
| H | Cl | $-NR^7O-$ | H | $C(CH_3)$-Cyclopropyl |
| H | Cl | $-NR^7O-$ | H | Cyclopentyl |
| H | Cl | $-NR^7O-$ | H | Cyclohexyl |
| H | Cl | $-NR^7O-$ | $CH_3$ | $CH_3$ |
| H | Cl | $-NR^7O-$ | $CH_3$ | $CH_2CH_3$ |
| H | Cl | $-NR^7O-$ | $CH_3CH_3$ | $CH_3$ |
| H | Cl | $-NR^7O-$ | $CH_3$ | $CH(CH_3)_2$ |
| H | Cl | $-NR^7O-$ | $CH_3$ | $CH_2-CH\equiv CH_2$ |
| H | Br | $-NR^7O-$ | H | $CH_2CH_3$ |
| H | Br | $-NR^7O-$ | H | $CH_2C_6H_5$ |
| H | Br | $-NR^7O-$ | $CH_3$ | $CH(CH_3)_2$ |
| H | Br | $-NR^7O-$ | H | Cyclohexyl |
| H | Cl | $-NR^7-$ | H | $C_6H_5$ |
| H | Cl | $-NR^7-$ | H | 2-$CH_3-C_6H_4$ |
| H | Cl | $-NR^7-$ | H | 4-$CH_2CH_3-C_6H_4$ |
| H | Cl | $-NR^7-$ | H | 3,4-$(CH_3)_2-C_6H_3$ |
| H | Cl | $-NR^7-$ | H | 3,4-$(CH_3)_2-C_6H_3$ |
| H | Cl | $-NR^7-$ | H | 4-$Cl-C_6H_4$ |
| H | Cl | $-NR^7-$ | H | 3-$F-C_6H_4$ |
| H | Cl | $-NR^7-$ | H | 2,6-$Cl_2-C_6H_3$ |
| H | Cl | $-NR^7-$ | H | 2-$Br-C_6H_4$ |
| H | Cl | $-NR^7-$ | H | 4-$OCH_3-C_6H_4$ |
| H | Cl | $-NR^7-$ | H | 3-$OCH_2CH_3-C_6H_4$ |
| H | Cl | $-NR^7-$ | H | 3,4-$(OCH_3)_2-C_6H_3$ |
| H | Cl | $-NR^7-$ | H | 4-$CN-C_6H_4$ |
| H | Cl | $-NR^7-$ | H | 3-$NO_2-C_6H_4$ |
| H | Cl | $-NR^7-$ | H | 3-$CO_2CH_3-C_6H_4$ |
| H | Cl | $-NR^7-$ | H | 3-$CS-NH_2-C_6H_4$ |
| H | Cl | $-NR^7-$ | H | 3,4-$(OCH_3)_2-C_6H_3$ |
| H | Cl | $-NR^7-$ | H | 4-$CO_2CH_2CH_3-C_6H_4$ |
| H | Cl | $-NR^7-$ | H | 4-$SCN-C_6H_4$ |
| H | Cl | $-NR^7-$ | H | 4-$SCH_3-C_6H_4$ |
| H | Cl | $-NR^7-$ | H | 3-$NO_2-C_6H_4$ |
| H | Cl | $-NR^7-$ | H | 3-$CF_3-C_6H_4$ |
| H | Cl | $-NR^7-$ | $CH_3$ | $C_6H_5$ |
| H | Cl | $-NR^7-$ | $CH_3$ | 2-$CH_3-C_6H_4$ |
| H | Cl | $-NR^7-$ | $CH_3$ | 4-$CH_2CH_3-C_6H_4$ |
| H | Cl | $-NR^7-$ | $CH_3$ | 3,4-$(CH_3)_2-C_6H_3$ |
| H | Cl | $-NR^7-$ | $CH_3$ | 3,4-$(CH_3)_2-C_6H_3$ |
| H | Cl | $-NR^7-$ | $CH_3$ | 4-$Cl-C_6H_4$ |
| H | Cl | $-NR^7-$ | $CH_3$ | 3-$F-C_6H_4$ |
| H | Cl | $-NR^7-$ | $CH_3$ | 2,6-$Cl_2-C_6H_3$ |
| H | Cl | $-NR^7-$ | $CH_3$ | 2-$Br-C_6H_4$ |
| H | Cl | $-NR^7-$ | $CH_3$ | 4-$OCH_3-C_6H_4$ |
| H | Cl | $-NR^7-$ | $CH_3$ | 3-$OCH_2CH_3-C_6H_4$ |
| H | Cl | $-NR^7-$ | $CH_3$ | 3,4-$(OCH_3)_2-C_6H_3$ |
| H | Cl | $-NR^7-$ | $CH_3$ | 4-$CN-C_6H_4$ |
| H | Cl | $-NR^7-$ | $CH_3$ | 3-$NO_2-C_6H_4$ |
| H | Cl | $-NR^7-$ | $CH_3$ | 3-$CO_2CH_3-C_6H_4$ |
| H | Cl | $-NR^7-$ | $CH_3$ | 3-$CS-NH_2-C_6H_4$ |
| H | Cl | $-NR^7-$ | $CH_3$ | 4-$CO_2CH_2CH_3-C_6H_4$ |
| H | Cl | $-NR^7-$ | $CH_3$ | 4-$SCN-C_6H_4$ |
| H | Cl | $-NR^7-$ | $CH_3$ | 4-$SCH_3-C_6H_4$ |
| H | Cl | $-NR^7-$ | $CH_3$ | 3-$NO_2-C_6H_4$ |
| H | Cl | $-NR^7-$ | $CH_3$ | 3-$CF_3-C_6H_4$ |
| H | Br | $-NR^7-$ | H | $C_6H_5$ |
| H | Br | $-NR^7-$ | H | 2-$CH_3-C_6H_4$ |
| H | Br | $-NR^7-$ | H | 4-$CH_2CH_3-C_6H_4$ |
| H | Br | $-NR^7-$ | H | 3,4-$(CH_3)_2-C_6H_3$ |
| H | Br | $-NR^7-$ | H | 3,4-$(CH_3)_2-C_5H_3$ |
| H | Br | $-NR^7-$ | H | 4-$Cl-C_6H_4$ |
| H | Br | $-NR^7-$ | H | 3-$F-C_6H_4$ |
| H | Br | $-NR^7-$ | H | 2,6-$Cl_2-C_6H_3$ |
| H | Br | $-NR^7-$ | H | 2-$Br-C_6H_4$ |
| H | Br | $-NR^7-$ | H | 4-$OCH_3-C_6H_4$ |
| H | Br | $-NR^7-$ | H | 3-$OCH_2CH_3-C_6H_4$ |
| H | Br | $-NR^7-$ | H | 3,4-$(OCH_3)_2-C_6H_3$ |
| H | Br | $-NR^7-$ | H | 4-$CN-C_6H_4$ |

TABLE A.1.3-continued

| | | | | |
|---|---|---|---|---|
| H | Br | —NR[7]— | H | 3-NO$_2$—C$_6$H$_4$ |
| H | Br | —NR[7]— | H | 3—CO$_2$CH$_3$—C$_6$H$_4$ |
| H | Br | —NR[7]— | H | 3-CS—NH$_2$—C$_6$H$_4$ |
| H | Br | —NR[7]— | H | 3,4-(OCH$_3$)$_2$—C$_6$H$_3$ |
| H | Br | —NR[7]— | H | 4-CO$_2$CH$_2$CH$_3$—C$_6$H$_4$ |
| H | Br | —NR[7]— | H | 4-SCN—C$_6$H$_4$ |
| H | Br | —NR[7] | H | 4-SCH$_3$—C$_6$H$_4$ |
| H | Br | —NR[7]— | H | 3-NO$_2$—C$_6$H$_4$ |
| H | Br | —NR[7]— | H | 3-CF$_3$—C$_6$H$_4$ |
| H | Br | NR[7] | CH$_3$ | C$_6$H$_5$ |
| H | CN | —NR[7]— | H | C$_6$H$_5$ |
| H | CN | —NR[7]— | H | 2-CH$_3$—C$_6$H$_4$ |
| H | CN | —NR[7]— | H | 4-CH$_2$CH$_3$—C$_6$H$_4$ |
| H | CN | —NR[7]— | H | 3,4-(CH$_3$)$_2$—C$_6$H$_3$ |
| H | CN | —NR[7]— | H | 3,4-(CH$_3$)$_2$—C$_6$H$_3$ |
| H | CN | —NR[7]— | H | 4-Cl—C$_6$H$_4$ |
| H | CN | —NR[7]— | H | 3-F—C$_6$H$_4$ |
| H | CN | —NR[7]— | H | 2,6-Cl$_2$—C$_6$H$_3$ |
| H | CN | —NR[7]— | H | 2-Br—C$_6$H$_4$ |
| H | CN | —NR[7]— | H | 4-OCH$_3$—C$_6$H$_4$ |
| H | CN | —NR[7]— | H | 3-OCH$_2$CH$_3$—C$_6$H$_4$ |
| H | CN | —NR[7]— | H | 3,4-(OCH$_3$)$_2$—C$_6$H$_3$ |
| H | CN | —NR[7]— | H | 4-CN—C$_6$H$_4$ |
| H | CN | —NR[7]— | H | 3-NO$_2$—C$_6$H$_4$ |
| H | CN | —NR[7]— | H | 3—CO$_2$CH$_3$—C$_6$H$_4$ |
| H | CN | —NR[7]— | H | 3-CS—NH$_2$—C$_6$H$_4$ |
| H | CN | —NR[7]— | H | 3,4-(OCH$_3$)$_2$—C$_6$H$_3$ |
| H | CN | —NR[7]— | H | 4-CO$_2$CH$_2$CH$_3$—C$_6$H$_4$ |
| H | CN | —NR[7]— | H | 4-SCN—C$_6$H$_4$ |
| H | CN | —NR[7]— | H | 4-SCH$_3$—C$_6$H$_4$ |
| H | CN | —NR[7]— | H | 3-NO$_2$—C$_6$H$_4$ |
| H | CN | —NR[7]— | H | 3-CF$_3$—C$_6$H$_4$ |
| H | Br | NR[7] | CH$_3$ | C$_6$H$_5$ |
| H | Br | NR[7] | CH$_3$ | 4-CH$_2$CH$_3$—C$_6$H$_4$ |
| H | Br | NR[7] | CH$_3$ | 4-Cl—C$_6$H$_4$ |
| H | Br | NR[7] | CH$_3$ | 3-F—C$_6$H$_4$ |
| H | Br | NR[7] | CH$_3$ | 4-OCH$_3$—C$_6$H$_4$ |
| H | Br | NR[7] | CH$_3$ | 3-OCF$_3$—C$_6$H$_4$ |
| H | Br | NR[7] | CH$_3$ | 4-CN—C$_6$H$_4$ |
| H | Br | NR[7] | CH$_3$ | 3-CO$_2$CH$_3$—C$_6$H$_4$ |
| H | Br | NR[7] | CH$_3$ | 3-CF$_3$—C$_6$H$_4$ |
| H | Br | NR[7] | CH$_3$ | 4-NO$_2$—C$_6$H$_4$ |
| 4-OCH$_3$ | Cl | NR[7] | H | C$_6$H$_5$ |
| 4-Cl | Cl | NR[7] | H | C6F5 |
| 6-Cl | Cl | NR[7] | H | C$_6$H$_5$ |
| 6-CH$_3$ | Cl | NR[7] | H | C$_6$H$_5$ |
| 4-OCH$_3$ | Cl | NR[7] | CH$_3$ | C$_6$H$_5$ |
| 4-OCH$_3$ | Cl | NR[7] | H | 2-CH$_3$—C$_6$H$_4$ |
| 6-Cl | Cl | NR[7] | H | 4-OCH$_3$—C$_6$H$_4$ |
| 3-Cl | Cl | NR[7] | H | 3—CO$_2$CH$_3$—C$_6$H$_4$ |
| 4-OCH$_3$ | Cl | NR[7] | H | 4-CF$_3$—C$_6$H$_4$ |
| H | Cl | NR[7] | H | 3-C$_6$H$_5$—C$_6$H$_4$ |

TABLE A.1.4

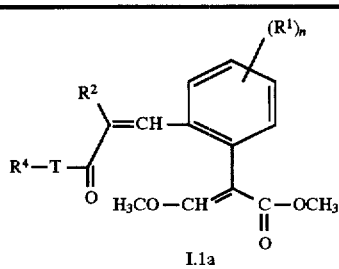
I.1a

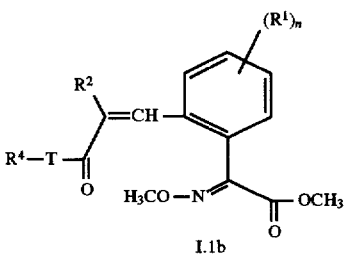
I.1b

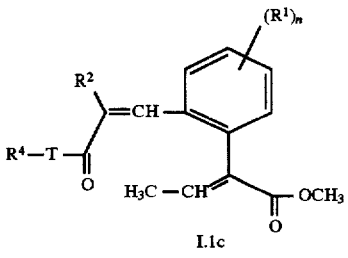
I.1c

| $R^1_n$ | $R^2$ | T | $R^4$ |
|---|---|---|---|
| H | OCH$_3$ | O | CH$_3$ |
| H | OCH$_3$ | O | C$_2$H$_5$ |
| H | OCH$_3$ | O | C(CH$_3$)$_3$ |
| H | OC$_2$H$_5$ | O | CH$_3$ |
| H | OC$_2$H$_5$ | O | C$_2$H$_5$ |
| H | OC$_2$H$_5$ | O | C(CH$_3$)$_3$ |
| H | OCH$_3$ | NH | C$_2$H$_5$ |
| H | OCH$_3$ | NH | CH(CH$_3$)$_2$ |
| H | OCH$_3$ | NH | C(CH$_3$)$_3$ |
| H | OCH$_3$ | NH | C(CH$_3$)$_2$(C≡CH) |
| H | OC$_2$H$_5$ | NH | C$_2$H$_5$ |
| H | OC$_2$H$_5$ | NH | CH(CH$_3$)$_2$ |
| H | OC$_2$H$_5$ | NH | C(CH$_3$)$_3$ |
| H | OC$_2$H$_5$ | NH | C(CH$_3$)$_2$(C≡CH) |
| 4-OCH$_3$ | OCH$_3$ | O | C$_2$H$_5$ |
| 4-OCH$_3$ | OC$_2$H$_5$ | NH | CH(CH$_3$)$_2$ |
| 6-Cl | OCH$_3$ | O | C(CH$_3$)$_3$ |
| H | NH(COCH$_3$) | O | CH$_3$ |
| H | NH(COCH$_3$) | O | C$_2$H$_5$ |
| H | NH(COCH$_3$) | O | C(CH$_3$)$_3$ |
| H | NH(COCH$_3$) | NH | CH(CH$_3$)$_2$ |
| H | NH(COCH$_3$) | NH | C(CH$_3$)$_3$ |
| H | NH(COCH$_3$) | NH | CH$_2$CO$_2$CH$_3$ |
| 4-OCH$_3$ | NH(COCH$_3$) | O | C$_2$H$_5$ |
| 6-Cl | NH(COCH$_3$) | O | C$_2$H$_5$ |
| 6-Cl | NH(COCH$_3$) | NH | C(CH$_3$)$_3$ |
| H | NH(CO$_2$tBu) | O | CH$_3$ |
| H | NH(CO$_2$tBu) | O | C$_2$H$_5$ |
| H | NH(CO$_2$tBu) | O | C(CH$_3$)$_3$ |
| H | NH(CO$_2$tBu) | NH | CH(CH$_3$)$_2$ |
| H | NH(CO$_2$tBu) | NH | C(CH$_3$)$_3$ |
| H | NH(CO$_2$tBu) | NH | CH$_3$CO$_2$CH$_3$ |
| 4-OCH$_3$ | NH(CO$_2$tBu) | O | C$_2$H$_5$ |
| 6-Cl | NH(CO$_2$tBu) | O | C$_2$H$_5$ |
| 6-Cl | NH(CO$_2$tBu) | NH | C(CH$_3$)$_3$ |
| H | NH(CO$_2$Bzl) | O | CH$_3$ |
| H | NH(CO$_2$Bzl) | O | C$_2$H$_5$ |

TABLE A.1.4-continued

| H | NH(CO$_2$BZl) | O | C(CH$_3$)$_3$ |
|---|---|---|---|
| H | NH(CO$_2$Bzl) | NH | CH(CH$_3$)$_2$ |
| H | NH(CO$_2$Bzl) | NH | C(CH$_3$)$_2$ |
| H | NH(CO$_2$Bzl) | NH | CH$_2$CO$_2$CH$_3$ |
| 4-OCH$_3$ | NH(CO$_2$Bzl) | O | C$_2$H$_5$ |
| 6-Cl | NH(CO$_2$Bzl) | O | C$_2$H$_5$ |
| 6-Cl | NH(CO$_2$Bzl) | NH | C(CH$_3$)$_2$ |

TABLE A.2

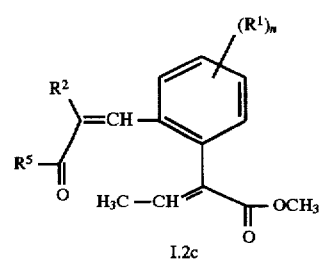
I.2a

I.2b

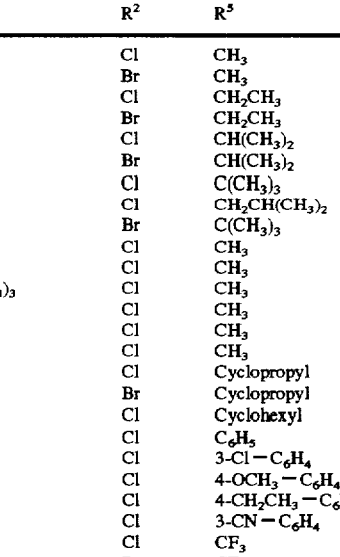
I.2c

| $R^1_n$ | $R^2$ | $R^5$ |
|---|---|---|
| H | Cl | CH$_3$ |
| H | Br | CH$_3$ |
| H | Cl | CH$_2$CH$_3$ |
| H | Br | CH$_2$CH$_3$ |
| H | Cl | CH(CH$_3$)$_2$ |
| H | Br | CH(CH$_3$)$_2$ |
| H | Cl | C(CH$_3$)$_3$ |
| H | Cl | CH$_2$CH(CH$_3$)$_2$ |
| H | Br | C(CH$_3$)$_3$ |
| 4-Cl | Cl | CH$_3$ |
| 4-OCH$_3$ | Cl | CH$_3$ |
| 5-C(CH$_3$)$_3$ | Cl | CH$_3$ |
| 6-CH$_3$ | Cl | CH$_3$ |
| 6-Cl | Cl | CH$_3$ |
| 6-C$_6$H$_5$ | Cl | CH$_3$ |
| H | Cl | Cyclopropyl |
| H | Br | Cyclopropyl |
| H | Cl | Cyclohexyl |
| H | Cl | C$_6$H$_5$ |
| H | Cl | 3-Cl—C$_6$H$_4$ |
| H | Cl | 4-OCH$_3$—C$_6$H$_4$ |
| H | Cl | 4-CH$_2$CH$_3$—C$_6$H$_4$ |
| H | Cl | 3-CN—C$_6$H$_4$ |
| H | Cl | CF$_3$ |
| H | Br | CF$_3$ |

TABLE A.3.1

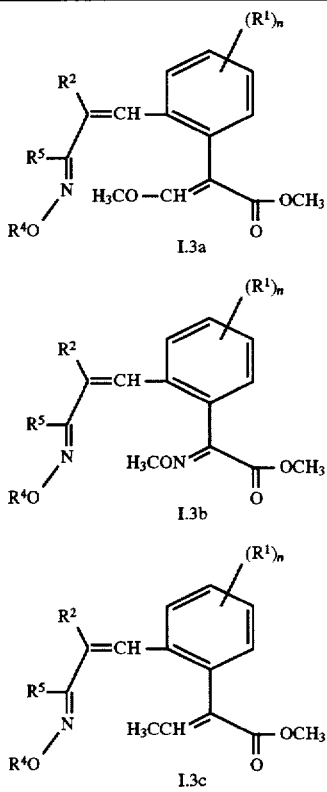

I.3a

I.3b

I.3c

| $R^1_n$ | $R^2$ | $R^5$ | $R^4$ |
|---|---|---|---|
| H | Cl | CH₃ | H |
| H | Cl | CH₃ | Methyl |
| H | Cl | CH₃ | Ethyl |
| H | Cl | CH₃ | n-Propyl |
| H | Cl | CH₃ | i-Propyl |
| H | Cl | CH₃ | n-Butyl |
| H | Cl | CH₃ | s-Butyl |
| H | Cl | CH₃ | i-Butyl |
| H | Cl | CH₃ | t-Butyl |
| H | Cl | CH₃ | Allyl |
| H | Cl | CH₃ | (E)-3-Chloro-2-propenyl |
| H | Cl | CH₃ | 2-Chloro-2-propenyl |
| H | Cl | CH₃ | (E)-2-Butenyl |
| H | Cl | CH₃ | 2-Methyl-2-propenyl |
| H | Cl | CH₃ | 2-Propynyl |
| H | Cl | CH₃ | 2-Butynyl |
| H | Cl | CH₃ | Cyanomethyl |
| H | Cl | CH₃ | tert-Butoxycarbonylmethyl |
| H | Cl | CH₃ | 1-Methoxypropan-2-yl |
| H | Cl | CH₃ | Benzyl |
| H | Cl | CH₃ | 3-Methylbenzyl |
| H | Cl | CH₃ | 4-Methoxycarbonylbenzyl |
| H | Cl | CH₃ | 3-Fluorobenzyl |
| H | Cl | CH₃ | 3-Bromobenzyl |
| H | Cl | CH₃ | 2-Chlorobenzyl |
| H | Cl | CH₃ | 3,4-Dichlorobenzyl |
| H | Cl | CH₃ | 3-Fluorobenzyl |
| H | Cl | CH₃ | 2,6-Difluorobenzyl |
| H | Cl | CH₃ | 3-Phenylbenzyl |
| H | Cl | CH₃ | 3-Phenylbenzyl |
| H | Cl | CH₃ | 3-Cyanobenzyl |
| H | Cl | CH₃ | 2-Phenylethyl |
| H | Cl | CH₃ | 3-Phenylpropan-1-yl |
| H | Cl | CH₃ | 4-Phenylbutan-1-yi |
| H | Cl | CH₃ | 4-(4-Chlorophenyl)-3-buten-1-yl |
| H | Cl | CH₃ | 4-Phenyl-2-buten-1-yl |
| H | Cl | CH₃ | 2-(1-Naphtyl)ethyl [sic] |
| H | Cl | CH₃ | 4-(5-Chloro-2-thienyl)-3-buten-1-yl |
| H | Cl | CH₃ | 2-(4-Methylphenyl)-4-oxazolylmethyl |
| H | Cl | CH₃ | 2-(4-Chlorophenoxy)propan-2-yl) [sic] |
| H | Cl | CH₃ | 6-Methoxy-2-methyl-4-pyrimidoxymethyl |
| H | Cl | CH₃ | 1-Phenylethyl |
| H | Cl | OCH₃ | Methyl |
| H | Cl | OCH₃ | Ethyl |
| H | Cl | OCH₃ | n-Propyl |
| H | Cl | OCH₃ | i-Propyl |
| H | Cl | OCH₃ | n-Butyl |
| H | Cl | OCH₃ | s-Butyl |
| H | Cl | OCH₃ | i-Butyl |
| H | Cl | OCH₃ | t-Butyl |
| H | Cl | OCH₃ | Allyl |
| H | Cl | OCH₃ | (E)-3-Chloro-2-propenyl |
| H | Cl | OCH₃ | 2-Chloro-2-propenyl |
| H | Cl | OCH₃ | (E)-2-Butenyl |
| H | Cl | OCH₃ | 2-Methyl-2-propenyl |
| H | Cl | OCH₃ | 2-Propynyl |
| H | Cl | OCH₃ | 2-Butynyl |
| H | Cl | OCH₃ | Cyanomethyl |
| H | Cl | OCH₃ | tert-Butoxycarbonylmethyl |
| H | Cl | OCH₃ | 1-Methoxypropan-2-yl |
| H | Cl | OCH₃ | Benzyl |
| H | Cl | OCH₃ | 3-Methylbenzyl |
| H | Cl | OCH₃ | 4-Methoxycarbonylbenzyl |
| H | Cl | OCH₃ | 3-Fluorobenzyl |
| H | Cl | OCH₃ | 3-Bromobenzyl |
| H | Cl | OCH₃ | 2-Chlorobenzyl |
| H | Cl | OCH₃ | 3,4-Dichlorobenzyl |
| H | Cl | OCH₃ | 3-Fluorobenzyl |
| H | Cl | OCH₃ | 2,6-Difluorobenzyl |
| H | Cl | OCH₃ | 3-Phenylbenzyl |
| H | Cl | OCH₃ | 3-Phenylbenzyl |
| H | Cl | OCH₃ | 3-Cyanobenzyl |
| H | Cl | OCH₃ | 2-phenylethyl |
| H | Cl | OCH₃ | 3-Phenylpropan-1-yl |
| H | Cl | OCH₃ | 4-Phenylbutan-1-yl |
| H | Cl | OCH₃ | 4-(4-Chlorophenyl)-2-buten-1-yl |
| H | Cl | OCH₃ | 2-(1-Naphtyl)ethyl [sic] |
| H | Cl | OCH₃ | 4-(5-Chloro-2-thienyl)-3-buten-1-yl |
| H | Cl | OCH₃ | 2-(4-Methylphenyl)-4-oxazolylmethyl |
| H | Cl | OCH₃ | 2-(4-Chlorophenoxy)propan-1-yl |
| H | Cl | OCH₃ | 6-Methoxy-2-methyl-4-pyrimidoxymethyl |
| H | Cl | OCH₃ | 1-Phenylethyl |
| H | Cl | OC₂H₅ | Methyl |
| H | Cl | OC₂H₅ | Ethyl |
| H | Cl | OC₂H₅ | n-Propyl |
| H | Cl | OC₂H₅ | i-Propyl |
| H | Cl | OC₂H₅ | i-Butyl |
| H | Cl | OC₂H₅ | t-Butyl |
| H | Cl | OC₂H₅ | Allyl |
| H | Cl | OC₂H₅ | (E)-3-Chloro-2-propenyl |
| H | Cl | OC₂H₅ | 2-Chloro-2-propenyl |
| H | Cl | OC₂H₅ | 2-Propynyl |
| H | Cl | OC₂H₅ | Benzyl |
| H | Cl | OC₂H₅ | 4-Methylbenzyl |
| H | Cl | OC₂H₅ | 3-Fluorobenzyl |
| H | Cl | OC₂H₅ | 3,4-Dichlorobenzyl |
| H | Cl | OC₂H₅ | 3-Cyanobenzyl |
| H | Cl | OC₂H₅ | 2-Phenylethyl |
| H | Cl | OC₂H₅ | 4-(4-Chlorophenyl)-2-buten-1-yl |
| H | Cl | OC₂H₅ | 2-(4-Chlorophenoxy)propan-1-yl |
| H | Cl | 4-Chloro-benzyloxy | Methyl |
| H | Cl | 4-Chloro-benzyloxy | Allyl |
| H | Cl | 4-Chloro-benzyloxy | 2-Chloro-2-propenyl |
| H | Cl | 4-Chloro-benzyloxy | 2-Propynyl |
| H | Br | CH₃ | Methyl |
| H | Br | CH₃ | Ethyl |
| H | Br | CH₃ | n-Propyl |
| H | Br | CH₃ | i-Propyl |
| H | Br | CH₃ | n-Butyl |
| H | Br | CH₃ | s-Butyl |
| H | Br | CH₃ | i-Butyl |
| H | Br | CH₃ | t-Butyl |

TABLE A.3.1-continued

| | | | |
|---|---|---|---|
| H | Br | CH$_3$ | Allyl |
| H | Br | CH$_3$ | (E)-3-Chloro-2-propenyl |
| H | Br | CH$_3$ | 2-Chloro-2-propenyl |
| H | Br | CH$_3$ | (E)-2-Butenyl |
| H | Br | CH$_3$ | 2-Methyl-2-propenyl |
| H | Br | CH$_3$ | 2-Propynyl |
| H | Br | CH$_3$ | 2-Butynyl |
| H | Br | CH$_3$ | Cyanomethyl |
| H | Br | CH$_3$ | tert-Butoxycarbonylmethyl |
| H | Br | CH$_3$ | 1-Methoxypropan-2-yl |
| H | Br | CH$_3$ | Benzyl |
| H | Br | CH$_3$ | 3-Methylbenzyl |
| H | Br | CH$_3$ | 4-Methoxycarbonylbenzyl |
| H | Br | CH$_3$ | 3-Fluorobenzyl |
| H | Br | CH$_3$ | 3-Bromobenzyl |
| H | Br | CH$_3$ | 2-Chlorobenzyl |
| H | Br | CH$_3$ | 3,4-Dichlorobenzyl |
| H | Br | CH$_3$ | 3-Fluorobenzyl |
| H | Br | CH$_3$ | 2,6-Difluorobenzyl |
| H | Br | CH$_3$ | 3-Phenylbenzyl |
| H | Br | CH$_3$ | 3-Phenylbenzyl |
| H | Br | CH$_3$ | 2-Phenylethyl |
| H | Br | CH$_3$ | 3-Phenylpropan-1-yl |
| H | Br | CH$_3$ | 4-Phenylbutan-1-yl |
| H | Br | CH$_3$ | 4-(4-Chlorophenyl)-3-buten-1-yl |
| H | Br | CH$_3$ | 4-Phenyl-2-buten-1-yl |
| H | Br | CH$_3$ | 2-(1-Naphtyl)ethyl [sic] |
| H | Br | CH$_3$ | 4-(5-Chloro-2-thienyl)-3-buten-1-yl |
| H | Br | CH$_3$ | 2-(4-Methylphenyl)-4-oxazolylmethyl |
| H | Br | CH$_3$ | 6-Methoxymethyl-4-pyrimidoxymethyl |
| H | Br | CH$_3$ | 1-Phenylethyl |
| H | Br | CH$_3$ | 2-(4-Chlorophenoxy)propan-1-yl |
| H | Br | OCH$_3$ | Methyl |
| H | Br | OCH$_3$ | n-Propyl |
| H | Br | OCH$_3$ | i-Butyl |
| H | Br | OCH$_3$ | t-Butyl |
| H | Br | OCH$_3$ | Allyl |
| H | Br | OCH$_3$ | (E)-3-Chloro-2-propenyl |
| H | Br | OCH$_3$ | 2-Propynyl |
| H | Br | OCH$_3$ | Benzyl |
| H | Br | OCH$_3$ | 4-Methylbenzyl |
| H | Br | OCH$_3$ | 3-Fluorobenzyl |
| H | Br | OCH$_3$ | 3,4-Dichlorobenzyl |
| H | Br | OCH$_3$ | 3-Cyanobenzyl |
| H | Br | OCH$_3$ | 2-Phenylethyl |
| H | Br | OC$_2$H$_5$ | Methyl |
| H | Br | OC$_2$H$_5$ | Ethyl |
| H | Br | OC$_2$H$_5$ | i-Propyl |
| H | Br | OC$_2$H$_5$ | Allyl |
| H | Br | OC$_2$H$_5$ | (E)-2-Butenyl |
| H | Br | OC$_2$H$_5$ | 2-Propynyl |
| H | Br | OC$_2$H$_5$ | 3-Methylbenzyl |
| H | Br | OC$_2$H$_5$ | 3-Cyanobenzyl |
| H | Br | 4-Chlorobenzyloxy | Methyl |
| H | Br | 4-Chlorobenzyloxy | Ethyl |
| H | Br | 4-Chlorobenzyloxy | 2-Propynyl |
| H | Cl | C$_2$H$_5$ | Methyl |
| H | Cl | C$_2$H$_5$ | i-Propyl |
| H | Cl | C$_2$H$_5$ | Allyl |
| H | Cl | C$_2$H$_5$ | (E)-3-Chloro-2-propenyl |
| H | Cl | C$_2$H$_5$ | (E)-2-Butenyl |
| H | Cl | C$_2$H$_5$ | Cyanomethyl |
| H | Cl | C$_2$H$_5$ | Benzyl |
| H | Cl | C$_2$H$_5$ | 4-Phenylbutan-1-yl |
| H | Cl | C$_2$H$_5$ | 2-Propynyl |
| H | Cl | C$_2$H$_5$ | 1-Methoxypropan-2-yl |
| H | Cl | i-C$_3$H$_7$ | Methyl |
| H | Cl | i-C$_3$H$_7$ | Ethyl |
| H | Cl | i-C$_3$H$_7$ | (E)-3-Chloro-2-propenyl |
| H | Cl | i-C$_3$H$_7$ | (E)-2-Butenyl |
| H | Cl | i-C$_3$H$_7$ | Cyanomethyl |
| H | Cl | i-C$_3$H$_7$ | Benzyl |
| H | Cl | i-C$_3$H$_7$ | 1-Methoxypropan-2-yl |
| H | Cl | C$_6$H$_5$ | Methyl |
| H | Cl | C$_6$H$_5$ | Ethyl |
| H | Cl | C$_6$H$_5$ | Allyl |
| H | Cl | C$_6$H$_5$ | (E)-3-Chloro-2-propenyl |
| H | Cl | C$_6$H$_5$ | (E)-2-Butenyl |
| H | Cl | C$_6$H$_5$ | Cyanomethyl |
| H | Cl | C$_6$H$_5$ | Benzyl |
| H | Cl | C$_6$H$_5$ | 1-Methoxypropan-2-yl |
| H | Cl | H$_3$COCH$_2$ | Methyl |
| H | Cl | H$_3$COCH$_2$ | i-Propyl |
| H | Cl | H$_3$COCH$_2$ | (E)-3-Chloro-2-propenyl |
| H | Cl | H$_3$COCH$_2$ | (E)-2-Butenyl |
| H | Cl | H$_3$COCH$_2$ | Cyanomethyl |
| H | Cl | H$_3$COCH$_2$ | Benzyl |
| H | Cl | H$_3$COCH$_2$ | tert-Butoxycarbonylmethyl |
| H | Cl | H$_3$COCH$_2$ | 2-(4-Methylphenyl)-4-oxazolylmethyl |
| H | Cl | H$_3$COCH$_2$ | 1-Methoxypropan-2-yl |
| H | Cl | CF$_3$ | Methyl |
| H | Cl | CF$_3$ | Ethyl |
| H | Cl | CF$_3$ | s-Butyl |
| H | Cl | CF$_3$ | Allyl |
| H | Cl | CF$_3$ | (E)-3-Chloro-2-propenyl |
| H | Cl | CF$_3$ | (E)-2-Butenyl |
| H | Cl | CF$_3$ | Cyanomethyl |
| H | Cl | CF$_3$ | Benzyl |
| H | Cl | CF$_3$ | 4-(5-Chloro-2-thienyl)-3-buten-1-yl |
| H | Cl | CF$_3$ | 2-Propynyl |
| H | Cl | CF$_3$ | tert-Butoxycarbonylmethyl |
| H | Cl | CF$_3$ | 2-(4-Chlorophenoxy)propan-1-yl |
| 4-OMe | Cl | CH$_3$ | (E)-3-Chloro-2-propen-1-yl |
| 3-Cl | Cl | CH$_3$ | (E)-3-Chloro-2-propenyl |
| 6-Cl | Cl | CH$_3$ | (E)-3-Chloro-2-propenyl |
| 4-OMe | Cl | C$_6$H$_5$ | Methyl |
| 6-Cl | Cl | C$_6$H$_5$ | Methyl |
| H | Br | C$_2$H$_5$ | Methyl |
| H | Br | C$_2$H$_5$ | i-Propyl |
| H | Br | C$_2$H$_5$ | Allyl |
| H | Br | C$_2$H$_5$ | (E)-3-Chloro-2-propenyl |
| H | Br | C$_2$H$_5$ | (E)-2-Butenyl |
| H | Br | C$_2$H$_5$ | Cyanomethyl |
| H | Br | C$_2$H$_5$ | Benzyl |
| H | Br | C$_2$H$_5$ | 4-Phenylbutan-1-yl |
| H | Br | C$_2$H$_5$ | 2-Propynyl |
| H | Br | C$_2$H$_5$ | 2-Methoxypropan-2-yl |
| H | Br | i-C$_3$H$_7$ | Methyl |
| H | Br | i-C$_3$H$_7$ | Ethyl |
| H | Br | i-C$_3$H$_7$ | (E)-3-Chloro-2-propenyl |
| H | Br | i-C$_3$H$_7$ | Cyanomethyl |
| H | Br | i-C$_3$H$_7$ | Benzyl |
| H | Br | i-C$_3$H$_7$ | 2-Methoxypropan-2-yl |
| H | Br | C$_6$H$_5$ | Methyl |
| H | Br | C$_6$H$_5$ | Ethyl |
| H | Br | C$_6$H$_5$ | Allyl |
| H | Br | C$_6$H$_5$ | (E)-3-Chloro-2-propenyl |
| H | Br | C$_6$H$_5$ | (E)-2-Butenyl |
| H | Br | C$_6$H$_5$ | Cyanomethyl |
| H | Br | C$_6$H$_5$ | Benzyl |
| H | Br | C$_6$H$_5$ | 2-Methoxypropan-2-yl |
| H | Br | H$_3$COCH$_2$ | Methyl |
| H | Br | H$_3$COCH$_2$ | i-Propyl |
| H | Br | H$_3$COCH$_2$ | (E)-3-Chloro-2-propenyl |
| H | Br | H$_3$COCH$_2$ | Cyanomethyl |
| H | Br | H$_3$COCH$_2$ | Benzyl |
| H | Br | H$_3$COCH$_2$ | tert-Butoxycarbonylmethyl |
| H | Br | H$_3$COCH$_2$ | 2-(4-Methylphenyl)-4-oxazolylmethyl |
| H | Br | H$_3$COCH$_2$ | 1-Methoxypropan-2-yl |
| H | Br | CF$_3$ | Methyl |
| H | Br | CF$_3$ | Ethyl |
| H | Br | CF$_3$ | a-Butyl |
| H | Br | CF$_3$ | Allyl |
| H | Br | CF$_3$ | (E)-3-Chloro-2-propenyl |
| H | Br | CF$_3$ | (E)-2-Butenyl |
| H | Br | CF$_3$ | Cyanomethyl |
| H | Br | CF$_3$ | Benzyl |
| H | Br | CF$_3$ | 4-(5-Chloro-2-thienyl)-3-buten-1-yl |
| H | Br | CF$_3$ | 2-Propynyl |
| H | Br | CF$_3$ | tert-Butoxycarbonylmethyl |
| H | Br | CF$_3$ | 2-(4-Chlorophenoxy)propan-1-yl |
| 4-OMe | Br | CH$_3$ | (E)-3-Chloro-2-propenyl |
| 3-Cl | Br | CH$_3$ | (E)-3-Chloro-2-propenyl |
| 6-Cl | Br | CH$_3$ | (E)-3-Chloro-2-propenyl |

TABLE A.3.1-continued

| | | | |
|---|---|---|---|
| 4-OMe | Br | C<sub>6</sub>H<sub>5</sub> | Methyl |
| 6-Cl | Br | C<sub>6</sub>H<sub>5</sub> | Methyl |

TABLE A.3.2

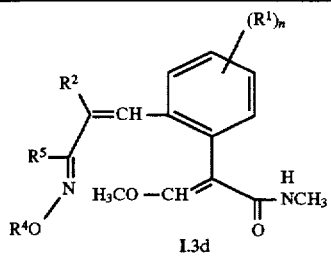
I.3d

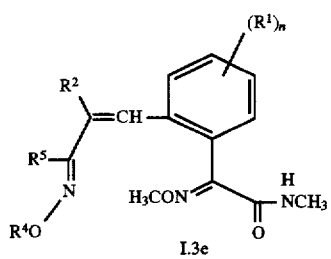
I.3e

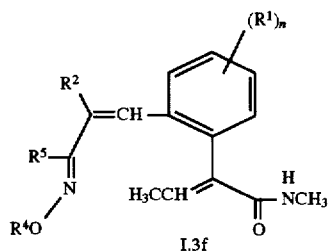
I.3f

| $R^1_n$ | $R^2$ | $R^5$ | $R^4$ |
|---|---|---|---|
| H | Cl | CH$_3$ | H |
| H | Cl | CH$_3$ | Methyl |
| H | Cl | CH$_3$ | Ethyl |
| H | Cl | CH$_3$ | n-Propyl |
| H | Cl | CH$_3$ | i-Propyl |
| H | Cl | CH$_3$ | n-Butyl |
| H | Cl | CH$_3$ | s-Butyl |
| H | Cl | CH$_3$ | i-Butyl |
| H | Cl | CH$_3$ | t-Butyl |
| H | Cl | CH$_3$ | Allyl |
| H | Cl | CH$_3$ | (E)-3-Chloro-2-propenyl |
| H | Cl | CH$_3$ | 2-Chloro-2-propenyl |
| H | Cl | CH$_3$ | (E)-2-Butenyl |
| H | Cl | CH$_3$ | 2-Methyl-2-propenyl |
| H | Cl | CH$_3$ | 2-Propynyl |
| H | Cl | CH$_3$ | 2-Butynyl |
| H | Cl | CH$_3$ | Cyanomethyl |
| H | Cl | CH$_3$ | tert-Butoxycarbonylmethyl |
| H | Cl | CH$_3$ | 1-Methoxypropan-2-yl |
| H | Cl | CH$_3$ | Benzyl |
| H | Cl | CH$_3$ | 3-Methylbenzyl |
| H | Cl | CH$_3$ | 4-Methoxycarbonylbenzyl |
| H | Cl | CH$_3$ | 3-Fluorobenzyl |
| H | Cl | CH$_3$ | 3-Bromobenzyl |
| H | Cl | CH$_3$ | 2-Chlorobenzyl |
| H | Cl | CH$_3$ | 3,4-Dichlorobenzyl |
| H | Cl | CH$_3$ | 3-Fluorobenzyl |
| H | Cl | CH$_3$ | 2,6-Difluorobenzyl |
| H | Cl | CH$_3$ | 3-Phenylbenzyl |

TABLE A.3.2-continued

| | | | |
|---|---|---|---|
| H | Cl | CH$_3$ | 3-Phenylbenzyl |
| H | Cl | CH$_3$ | 3-Cyanobenzyl |
| H | Cl | CH$_3$ | 2-Phenylethyl |
| H | Cl | CH$_3$ | 3-Phenylpropan-1-yl |
| H | Cl | CH$_3$ | 4-Phenylbutan-1-yl |
| H | Cl | CH$_3$ | 4-(4-Chlorophenyl)-3-buten-1-yl |
| H | Cl | CH$_3$ | 4-Phenyl-2-buten-1-yl |
| H | Cl | CH$_3$ | 2-(1-Naphtyl)ethyl [sic] |
| H | Cl | CH$_3$ | 4-(5-Chloro-2-thienyl)-3-buten-1-yl |
| H | Cl | CH$_3$ | 2-(4-Methylphenyl)-4-oxazolylmethyl |
| H | Cl | CH$_3$ | 2-(4-Chlorophenoxy)propan-2-yl |
| H | Cl | CH$_3$ | 6-Methoxy-2-methyl-4-pyrimidoxymethyl |
| H | Cl | CH$_3$ | 1-Phenylethyl |
| H | Cl | OCH$_3$ | Methyl |
| H | Cl | OCH$_3$ | Ethyl |
| H | Cl | OCH$_3$ | n-Propyl |
| H | Cl | OCH$_3$ | i-Propyl |
| H | Cl | OCH$_3$ | n-Butyl |
| H | Cl | OCH$_3$ | s-Butyl |
| H | Cl | OCH$_3$ | i-Butyl |
| H | Cl | OCH$_3$ | t-Butyl |
| H | Cl | OCH$_3$ | Allyl |
| H | Cl | OCH$_3$ | (E)-3-Chloro-2-propenyl |
| H | Cl | OCH$_3$ | 2-Chloro-2-propenyl |
| H | Cl | OCH$_3$ | (E)-2-Butenyl |
| H | Cl | OCH$_3$ | 2-Methyl-2-propenyl |
| H | Cl | OCH$_3$ | 2-Propynyl |
| H | Cl | OCH$_3$ | 2-Butynyl |
| H | Cl | OCH$_3$ | Cyanomethyl |
| H | Cl | OCH$_3$ | tert-Butoxycarbonylmethyl |
| H | Cl | OCH$_3$ | 1-Methoxypropan-2-yl |
| H | Cl | OCH$_3$ | Benzyl |
| H | Cl | OCH$_3$ | 3-Methylbenzyl |
| H | Cl | OCH$_3$ | 4-Methoxycarbonylbenzyl |
| H | Cl | OCH$_3$ | 3-Fluorobenzyl |
| H | Cl | OCH$_3$ | 3-Bromobenzyl |
| H | Cl | OCH$_3$ | 2-Chlorobenzyl |
| H | Cl | OCH$_3$ | 3,4-Dichlorobenzyl |
| H | Cl | OCH$_3$ | 3-Fluorobenzyl |
| H | Cl | OCH$_3$ | 2,6-Difluorobenzyl |
| H | Cl | OCH$_3$ | 3-Phenylbenzyl |
| H | Cl | OCH$_3$ | 3-Phenylbenzyl |
| H | Cl | OCH$_3$ | 3-Cyanobenzyl |
| H | Cl | OCH$_3$ | 2-Phenylethyl |
| H | Cl | OCH$_3$ | 3-Phenylpropan-1-yl |
| H | Cl | OCH$_3$ | 4-Phenylbutan-1-yl |
| H | Cl | OCH$_3$ | 4-(4-Chlorophenyl)-2-buten-1-yl |
| H | Cl | OCH$_3$ | 2-(1-Naphtyl)ethyl [sic] |
| H | Cl | OCH$_3$ | 4-(5-Chloro-2-thienyl)-3-buten-1-yl |
| H | Cl | OCH$_3$ | 2-(4-Methylphenyl)-4-oxazolylmethyl |
| H | Cl | OCH$_3$ | 2-(4-Chlorophenoxy)propan-1-yl |
| H | Cl | OCH$_3$ | 6-Methoxy-2-methyl-4-pyrimidoxmethyl |
| H | Cl | OCH$_3$ | 1-Phenylethyl |
| H | Cl | OC$_2$H$_5$ | Methyl |
| H | Cl | OC$_2$H$_5$ | Ethyl |
| H | Cl | OC$_2$H$_5$ | n-Propyl |
| H | Cl | OC$_2$H$_5$ | i-Propyl |
| H | Cl | OC$_2$H$_5$ | i-Butyl |
| H | Cl | OC$_2$H$_5$ | t-Butyl |
| H | Cl | OC$_2$H$_5$ | Allyl |
| H | Cl | OC$_2$H$_5$ | (E)-3-Chloro-2-propenyl |
| H | Cl | OC$_2$H$_5$ | 2-Chloro-2-propenyl |
| H | Cl | OC$_2$H$_5$ | 2-Propynyl |
| H | Cl | OC$_2$H$_5$ | Benzyl |
| H | Cl | OC$_2$H$_5$ | 4-Methylbenzyl |
| H | Cl | OC$_2$H$_5$ | 3-Fluorobenzyl |
| H | Cl | OC$_2$H$_5$ | 3,4-Dichlorobenzyl |
| H | Cl | OC$_2$H$_5$ | 3-Cyanobenzyl |
| H | Cl | OC$_2$H$_5$ | 2-Phenylethyl |
| H | Cl | OC$_2$H$_5$ | 4-(4-Chlorophenyl)-2-buten-1-yl |
| H | Cl | OC$_2$H$_5$ | 2-(4-Chlorophenoxy)propan-1-yl |
| H | Cl | 4-Chlorobenzyloxy | Methyl |
| H | Cl | 4-Chlorobenzyloxy | Allyl |
| H | Cl | 4-Chlorobenzyloxy | 2-chloro-2-propenyl |
| H | Cl | 4-Chlorobenzyloxy | 2-Propynyl |
| H | Br | CH$_3$ | Methyl |
| H | Br | CH$_3$ | Ethyl |
| H | Br | CH$_3$ | n-Propyl |
| H | Br | CH$_3$ | i-Propyl |

TABLE A.3.2-continued

| | | | |
|---|---|---|---|
| H | Br | CH₃ | n-Butyl |
| H | Br | CH₃ | s-Butyl |
| H | Br | CH₃ | i-Butyl |
| H | Br | CH₃ | t-Butyl |
| H | Br | CH₃ | Allyl |
| H | Br | CH₃ | (E)-3-Chloro-2-propenyl |
| H | Br | CH₃ | 2-Chloro-2-propenyl |
| H | Br | CH₃ | (E)-2-Butenyl |
| H | Br | CH₃ | 2-Methyl-2-propenyl |
| H | Br | CH₃ | 2-Propynyl |
| H | Br | CH₃ | 2-Butynyl |
| H | Br | CH₃ | Cyanomethyl |
| H | Br | CH₃ | tert-Butoxycarbonylmethyl |
| H | Br | CH₃ | 1-Methoxypropan-2-yl |
| H | Br | CH₃ | Benzyl |
| H | Br | CH₃ | 3-Methylbenzyl |
| H | Br | CH₃ | 4-Methoxycarbonylbenzyl |
| H | Br | CH₃ | 3-Fluorobenzyl |
| H | Br | CH₃ | 3-Bromobenzyl |
| H | Br | CH₃ | 2-Chlorobenzyl |
| H | Br | CH₃ | 3,4-Dichlorobenzyl |
| H | Br | CH₃ | 3-Fluorobenzyl |
| H | Br | CH₃ | 2,6-Difluorobenzyl |
| H | Br | CH₃ | 3-Phenylbenzyl |
| H | Br | CH₃ | 3-Phenylbenzyl |
| H | Br | CH₃ | 2-Phenylethyl |
| H | Br | CH₃ | 3-Phenylpropan-1-yl |
| H | Br | CH₃ | 4-Phenylbutan-1-yl |
| H | Br | CH₃ | 4-(4-Chlorophenyl)-3-buten-1-yl |
| H | Br | CH₃ | 4-Phenyl-2-buten-1-yl |
| H | Br | CH₃ | 2-(1-Naphtyl)ethyl [sic] |
| H | Br | CH₃ | 4-(5-Chloro-2-thienyl)-3-buten-1-yl |
| H | Br | CH₃ | 2-(4-Methylphenyl)-4-oxazolylmethyl |
| H | Br | CH₃ | 6-Methoxymethyl-4-pyrimidoxymethyl |
| H | Br | CH₃ | 1-Phenylethyl |
| H | Br | CH₃ | 2-(4-Chlorophenoxy)propan-1-yl |
| H | Br | OCH₃ | Methyl |
| H | Br | OCH₃ | n-Propyl |
| H | Br | OCH₃ | i-Butyl |
| H | Br | OCH₃ | t-Butyl |
| H | Br | OCH₃ | Allyl |
| H | Br | OCH₃ | (E)-3-Chloro-2-propenyl |
| H | Br | OCH₃ | 2-Propynyl |
| H | Br | OCH₃ | Benzyl |
| H | Br | OCH₃ | 4-Methylbenzyl |
| H | Br | OCH₃ | 3-Fluorobenzyl |
| H | Br | OCH₃ | 3,4-Dichlorobenzyl |
| H | Br | OCH₃ | 3-Cyanobenzyl |
| H | Br | OCH₃ | 2-Phenylethyl |
| H | Br | OC₂H₅ | Methyl |
| H | Br | OC₂H₅ | Ethyl |
| H | Br | OC₂H₅ | i-Propyl |
| H | Br | OC₂H₅ | Allyl |
| H | Br | OC₂H₅ | (E)-2-Butenyl |
| H | Br | OC₂H₅ | 2-Propynyl |
| H | Br | OC₂H₅ | 3-Methylbenzyl |
| H | Br | OC₂H₅ | 3-Cyanobenzyl |
| H | Br | 4-Chlorobenzyloxy | Methyl |
| H | Br | 4-Chlorobenzyloxy | Ethyl |
| H | Br | 4-Chlorobenzyloxy | 2-Propynyl |
| H | Cl | C₂H₅ | Methyl |
| H | Cl | C₂H₅ | i-Propyl |
| H | Cl | C₂H₅ | Allyl |
| H | Cl | C₂H₅ | (E)-3-Chloro-2-propenyl |
| H | Cl | C₂H₅ | (E)-2-Butenyl |
| H | Cl | C₂H₅ | Cyanomethyl |
| H | Cl | C₂H₅ | Benzyl |
| H | Cl | C₂H₅ | 4-Phenylbutan-1-yl |
| H | Cl | C₂H₅ | 2-Propynyl |
| H | Cl | C₂H₅ | 1-Methoxypropan-2-yl |
| H | Cl | i-C₃H₇ | Methyl |
| H | Cl | i-C₃H₇ | Ethyl |
| H | Cl | i-C₃H₇ | (E)-3-Chloro-2-propenyl |
| H | Cl | i-C₃H₇ | (E)-2-Butenyl |
| H | Cl | i-C₃H₇ | Cyanomethyl |
| H | Cl | i-C₃H₇ | Benzyl |
| H | Cl | i-C₃H₇ | 1-Methoxypropan-2-yl |
| H | Cl | C₆H₅ | Methyl |
| H | Cl | C₆H₅ | Ethyl |

TABLE A.3.2-continued

| | | | |
|---|---|---|---|
| H | Cl | $C_6H_5$ | Allyl |
| H | Cl | $C_6H_5$ | (E)-3-Chloro-2-propenyl |
| H | Cl | $C_6H_5$ | (E)-2-Butenyl |
| H | Cl | $C_6H_5$ | Cyanomethyl |
| H | Cl | $C_6H_5$ | Benzyl |
| H | Cl | $C_6H_5$ | 1-Methoxypropan-2-yl |
| H | Cl | $H_3COCH_2$ | Methyl |
| H | Cl | $H_3COCH_2$ | i-Propyl |
| H | Cl | $H_3COCH_2$ | (E)-3-Chloro-2-propenyl |
| H | Cl | $H_3COCH_2$ | (E)-2-Butenyl |
| H | Cl | $H_3COCH_2$ | Cyanomethyl |
| H | Cl | $H_3COCH_2$ | Benzyl |
| H | Cl | $H_3COCH_2$ | tert-Butoxycarbonylmethyl |
| H | Cl | $H_3COCH_2$ | 2-(4-Methylphenyl)-4-oxazolylmethyl |
| H | Cl | $H_3COCH_2$ | 1-Methoxypropan-2-yl |
| H | Cl | $CF_3$ | Methyl |
| H | Cl | $CF_3$ | Ethyl |
| H | Cl | $CF_3$ | s-Butyl |
| H | Cl | $CF_3$ | Allyl |
| H | Cl | $CF_3$ | (E)-3-Chloro-2-propenyl |
| H | Cl | $CF_3$ | (E)-2-Butenyl |
| H | Cl | $CF_3$ | Cyanomethyl |
| H | Cl | $CF_3$ | Benzyl |
| H | Cl | $CF_3$ | 4-(5-Chloro-2-thienyl)-3-buten-1-yl |
| H | Cl | $CF_3$ | 2-Propynyl |
| H | Cl | $CF_3$ | tert-Butoxycarbonylmethyl |
| H | Cl | $CF_3$ | 2-(4-Chlorophenoxy)propan-1-yl |
| 4-OMe | Cl | $CH_3$ | (E)-3-Chloro-2-propenyl |
| 3-Cl | Cl | $CH_3$ | (E)-3-Chloro-2-propenyl |
| 6-Cl | Cl | $CH_3$ | (E)-3-Chloro-2-propenyl |
| 4-OMe | Cl | $C_6H_5$ | Methyl |
| 6-Cl | Cl | $C_6H_5$ | Methyl |
| H | Br | $C_2H_5$ | Methyl |
| H | Br | $C_2H_5$ | i-Propyl |
| H | Br | $C_2H_5$ | Allyl |
| H | Br | $C_2H_5$ | (E)-3-Chloro-2-propenyl |
| H | Br | $C_2H_5$ | (E)-2-Butenyl |
| H | Br | $C_2H_5$ | Cyanomethyl |
| H | Br | $C_2H_5$ | Benzyl |
| H | Br | $C_2H_5$ | 4-Phenylbutan-1-yl |
| H | Br | $C_2H_5$ | 2-Propynyl |
| H | Br | $C_2H_5$ | 2-Methoxypropan-2-yl |
| H | Br | i-$C_3H_7$ | Methyl |
| H | Br | i-$C_3H_7$ | Ethyl |
| H | Br | i-$C_3H_7$ | (E)-3-Chloro-2-propenyl |
| H | Br | i-$C_3H_7$ | Cyanomethyl |
| H | Br | i-$C_3H_7$ | Benzyl |
| H | Br | i-$C_3H_7$ | 2-Methoxypropan-2-yl |
| H | Br | $C_6H_5$ | Methyl |
| H | Br | $C_6H_5$ | Ethyl |
| H | Br | $C_6H_5$ | Allyl |
| H | Br | $C_6H_5$ | (E)-3-Chloro-2-propenyl |
| H | Br | $C_6H_5$ | (E)-2-Butenyl |
| H | Br | $C_6H_5$ | Cyanomethyl |
| H | Br | $C_6H_5$ | Benzyl |
| H | Br | $C_6H_5$ | 2-Methoxypropan-2-yl |
| H | Br | $H_3COCH_2$ | Methyl |
| H | Br | $H_3COCH_2$ | i-Propyl |
| H | Br | $H_3COCH_2$ | (E)-3-Chloro-2-propenyl |
| H | Br | $H_3COCH_2$ | Cyanomethyl |
| H | Br | $H_3COCH_2$ | Benzyl |
| H | Br | $H_3COCH_2$ | tert-Butoxycarbonylmethyl |
| H | Br | $H_3COCH_2$ | 2-(4-Methylphenyl)-4-oxazolylmethyl |
| H | Br | $H_3COCH_2$ | 1-Methoxypropan-2-yl |
| H | Br | $CF_3$ | Methyl |
| H | Br | $CF_3$ | Ethyl |
| H | Br | $CF_3$ | s-Butyl |
| H | Br | $CF_3$ | Allyl |
| H | Bz | $CF_3$ | (E)-3-Chloro-2-propenyl |
| H | Br | $CF_3$ | (E)-2-Butenyl |
| H | Br | $CF_3$ | Cyanomethyl |
| H | Br | $CF_3$ | Benzyl |
| H | Br | $CF_3$ | 4-(5-Chloro-2-thienyl)-3-buten-1-yl |
| H | Br | $CF_3$ | 2-Propynyl |
| H | Br | $CF_3$ | tert-Butoxycarbonylmethyl |
| H | Br | $CF_3$ | 2-(4-Chlorophenoxy)propan-1-yl |
| 4-OMe | Br | $CH_3$ | (E)-3-Chloro-2-propenyl |
| 3-Cl | Br | $CH_3$ | (E)-3-Chloro-2-propenyl |
| 6-Cl | Br | $CH_3$ | (E)-3-Chloro-2-propenyl |

TABLE A.3.2-continued

| | | | |
|---|---|---|---|
| 4-OMe | Br | C$_6$H$_5$ | Methyl |
| 6-Cl | Br | C$_6$H$_5$ | Methyl |

TABLE A.4

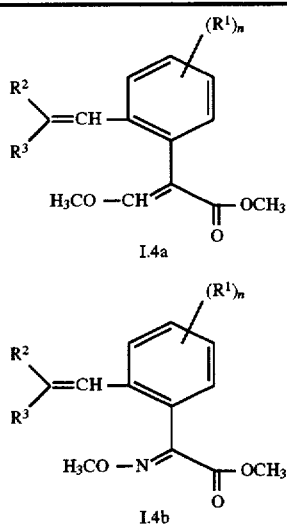

I.4a

I.4b

| R$^1_n$ | R$^2$ | R$^3$ |
|---|---|---|
| H | Cl | Phenyl |
| H | Cl | 4-Cl-Phenyl |
| H | Cl | 3,5-di-F-phenyl |
| H | Cl | 3-H$_3$CO-Phenyl |
| H | Cl | 4-CN-Phenyl |
| H | Cl | 4-NO$_2$-Phenyl |
| H | Cl | 3-H$_3$CO$_2$C-Phenyl |
| H | Cl | 4-CF$_3$-Phenyl |
| H | Cl | 2-Cl, 4-CH$_3$-Phenyl |
| H | Cl | 3-Phenoxyphenyl |
| H | Cl | m-Biphenyl |
| 3-Cl | Cl | 4-Cl-Phenyl |
| 4-Cl | Cl | 2,4-di-CH$_3$-phenyl |
| 6-Cl | Cl | 4-CF$_3$-Phenyl |
| 4-OCH$_3$ | Cl | 4-Cl-Phenyl |
| 6-OCH$_3$ | Cl | 2-Cl, 4-CH$_3$-Phenyl |
| 6-CH$_3$ | Cl | Phenyl |
| H | Br | Phenyl |
| H | Br | 4-Cl-Phenyl |
| H | Br | 2,4-di-CH$_3$-phenyl |
| H | Cl | 3-Phenyl-5-isoxazolyl |
| H | Cl | 3-(4-Chlorophenyl)-5-isoxazolyl |
| H | Cl | 3-(3-Methylphenyl)-5-isoxazolyl |
| H | Cl | 3-(3',5'-Dichlorophenyl)-5-isoxazolyl |
| 4-OCH$_3$ | Cl | 3-(4'-Chlorophenyl)-5-isoxazolyl |
| 6-Cl | Cl | 3-(4'-Chlorophenyl)-5-isoxazolyl |
| 4-tBu | Cl | 3-(4'-Chlorophenyl)-5-isoxazolyl |
| H | Br | 3-(4'-Chlorophenyl)-5-isoxazolyl |
| H | Cl | 3-(2'-Tetrahydrofuranyl)-5-isoxazolyl |
| H | Cl | 3-Isopropyl-5-isoxazolyl |
| H | Cl | 4-Chloro-3-phenyl-5-isoxazolyl |
| H | Cl | 3-(3'-Chlorophenyl)-4-chloro-5-isoxazolyl |
| H | Cl | 4-Chloro-3-isopropyl-5-isoxazolyl |
| H | Cl | 3-(3'-Isopropyl-5'-isoxazolyl)-5-isoxazolyl |
| H | Br | 4-Chloro-3-(3'-chlorophenyl)-5-isoxazolyl |
| H | Cl | 5-(4'-Methylphenyl)-1,3 4-oxadiazol-2-yl |
| 4-OCH$_3$ | Cl | 5-(4'-Methylphenyl)-1,3,4-oxadiazol-2-yl |
| H | Cl | 5-(4'-Chlorophenyl)-1,3,4-thiadiazol-2-yl |
| H | Br | 5-(4'-Chlorophenyl)-1,3,4-thiadiazol-2-yl |
| H | Cl | 3-(4'-Fluorophenyl)-1,2,4-oxadiazol-5-yl |
| H | Cl | 3-(3'-Chlorophenyl)-1,2,4-oxadiazol-5 yl |
| H | Cl | 5-Phenyl-3-isoxazolyl |
| H | Cl | 4-Methyl-5-(4'-chlorophenyl)-3-isoxazolyl |

TABLE A.4-continued

| | | |
|---|---|---|
| 6-Cl | Cl | 5-Phenyl-3-isoxazolyl |
| 6-Me | Cl | 3-(3'-Chlorophenyl)-1,2,4-oxadiazol-5-yl |
| 4-OMe | Br | 5-(4'-Chlorophenyl)-1,3,4-thiadiazol-2-yl |

TABLE A.5

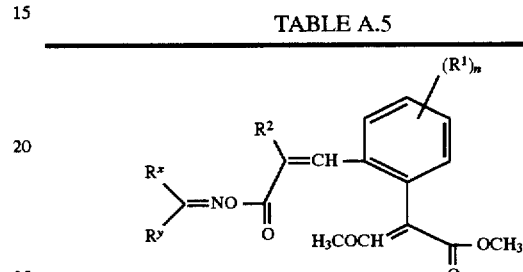

I.5a

I.5b

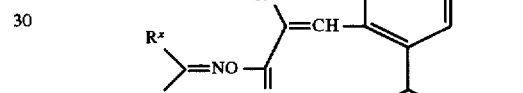

I.5c

| R$^1_n$ | R$^2$ | R$^x$ | R$^y$ |
|---|---|---|---|
| H | Cl | Cl | Phenyl |
| H | Cl | Cl | Cyclopropyl |
| H | Cl | CF$_3$ | Trifluoromethyl |
| H | Cl | CF$_3$ | Phenyl |
| H | Br | CF$_3$ | Phenyl |
| 4-OCH$_3$ | Cl | CF$_3$ | Phenyl |
| 6-Cl | Cl | CF$_3$ | Phenyl |
| H | Cl | Cyclopropyl | Cyclopropyl |
| H | Cl | Cyclopropyl | Phenyl |
| 3-Cl | Cl | Cyclopropyl | Phenyl |
| 4-OCH$_3$ | Cl | Cyclopropyl | Phenyl |
| H | Br | Cyclopropyl | Phenyl |
| H | Cl | Cyclopropyl | 4-Chlorophenyl |
| H | Cl | Cyclopropyl | 3-Fluorophenyl |
| H | Cl | Cyclopropyl | 4-Ethoxyphenyl |
| H | Cl | Cyclopropyl | Trifluoromethyl [sic] |
| H | Cl | CN | Methoxymethyl |
| H | Br | CN | i-Propoxymethyl |
| H | Cl | CN | t-Butoxymethyl |
| H | Cl | CN | Methylthiomethyl |
| H | Cl | CN | Methyl |
| H | Br | CN | Ethenyl |
| H | Br | CN | i-Propyl |
| H | Cl | CN | t-Butyl |

TABLE A.5-continued

| | | | |
|---|---|---|---|
| 5-C(CH₃)₃ | Cl | CN | t-Butyl |
| 4-Cl | Cl | CN | t-Butyl |
| 4-OCH₃ | Cl | CN | t-Butyl |
| H | Cl | CN | n-Pentyl |
| H | Cl | CN | Cyclopropyl |
| H | Cl | CN | Cyclohexyl |
| H | Cl | CN | 2-Propenyl |
| H | Cl | CN | Ethenyl |
| H | Cl | CN | Phenyl |
| H | Br | CN | Phenyl |
| 4-OCH₃ | Cl | CN | Phenyl |
| 4-OCH₃ | Cl | CN | 3-F-Phenyl |
| 4-Cl | Cl | CN | 4-Cl-Phenyl |
| 6-CH₃ | Cl | CN | 4-CH₃O-Phenyl |
| 6-Cl | Cl | CN | 2,6-di-F-phenyl |
| H | Cl | CN | 2,6-di-F-phenyl |
| H | Cl | CN | 3-Cl-Phenyl |
| H | Cl | CN | 4-CN-Phenyl |
| H | Cl | CN | 3-CH₃O-Phenyl |
| H | Cl | CN | 4-CH₃-Phenyl |
| H | Cl | CN | 2-F, 4-CH₃-Phenyl |
| H | Cl | CN | 3-CF₃-Phenyl |
| H | Cl | CN | 4-(CH₃)₂HCO-Phenyl |
| H | Cl | CN | 3-Phenylphenyl |
| H | Cl | CN | 4-Phenoxyphenyl |
| H | Br | CN | 4-F-Phenyl |
| H | Br | CN | 3-Phenylphenyl |
| 4-OCH₃ | Br | CN | 4-CF₃-Phenyl |
| H | Cl | CN | Benzyl |
| H | Cl | CN | 2-Pyridyl |
| H | Cl | CH₃ | Phenyl |
| H | Br | CH₃ | Phenyl |
| H | Cl | CH₃ | 2-Cl-Phenyl |
| H | Cl | CH₃ | 3-Cl-Phenyl |
| H | Br | CH₃ | 3-Cl-Phenyl |
| H | Cl | CH₃ | 4-Cl-Phenyl |
| H | Cl | CH₃ | 3-F-Phenyl |
| H | Br | CH₃ | 3-F-Phenyl |
| H | Cl | CH₃ | 4-Br-Phenyl |
| H | Cl | CH₃ | 4-CH₃O-Phenyl |
| H | Cl | CH₃ | 3-CF₃-Phenyl |
| H | Cl | CH₃ | 2-Cl, 4-NO₂-Phenyl |
| H | Cl | CH₃ | 4-CN-Phenyl |
| H | Cl | CH₃ | 4-CH₃-Phenyl |
| H | Cl | CH₃ | 3-CH₃-Phenyl |
| H | Br | CH₃ | 3-CH₃-Phenyl |
| H | Cl | CH₃ | 3-Phenylphenyl |
| H | Br | CH₃ | 3-Phenylphenyl |
| H | Cl | CH₃ | 4-Phenoxyphenyl |
| 4-OCH₃ | Cl | CH₃ | 3-Cl-Phenyl |
| 6-Cl | Cl | CH₃ | 3-Cl-Phenyl |
| 3-Cl | Cl | CH₃ | 3-Cl-Phenyl |
| 6-CH₃ | Cl | CH₃ | 3-Cl-Phenyl |
| 4-OCH₃ | Br | CH₃ | Phenyl |
| 6-Cl | Br | CH₃ | Phenyl |
| H | Cl | CH₃ | Methoxymethyl |
| H | Cl | CH₃ | Methyl |
| 3-Cl | Cl | CH₃ | Methyl |
| 4-OCH₃ | Cl | CH₃ | Methyl |
| 6-Phenyl | Cl | CH₃ | Methyl |
| H | Br | CH₃ | Methyl |
| H | Br | CH₃ | Ethyl |
| H | Cl | CH₃ | Ethyl |
| H | Br | CH₃ | n-Propyl |
| H | Cl | CH₃ | n-Propyl |
| H | Br | CH₃ | i-Propyl |
| H | Cl | CH₃ | i-Propyl |
| H | Br | CH₃ | n-Butyl |
| H | Cl | CH₃ | n-Butyl |
| H | Br | CH₃ | sec-Butyl |
| H | Cl | CH₃ | sec-Butyl |
| H | Br | CH₃ | i-Butyl |
| H | Cl | CH₃ | i-Butyl |
| H | Br | CH₃ | t-Butyl |
| H | Cl | CH₃ | t-Butyl |
| H | Cl | CH₃ | Cyclopropyl |
| H | Cl | CH₃ | Cyclohexyl |
| H | Br | CH₃ | Cyclopropyl |
| H | Cl | CH₃ | Ethynyl |
| H | Cl | CH₃ | 3-Acetylaminophenyl |
| H | Cl | CH₃ | 3-Ethoxycarbonylaminophenyl |
| H | Cl | Phenyl | Phenyl |
| H | Cl | Phenyl | 3-F-Phenyl |
| H | Cl | Phenyl | 3-CF₃-Phenyl |
| H | Br | Phenyl | Phenyl |
| H | Cl | Phenyl | Methoxymethyl |
| H | Cl | Benzyl | Benzyl |
| H | Cl |  | |
| H | Cl | 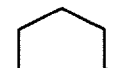 | |
| H | Br | 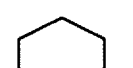 | |
| H | Cl | 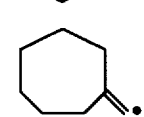 | |
| H | Cl |  | |
| H | Cl | 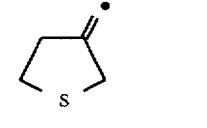 | |
| H | Br | 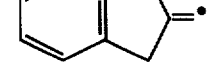 | |
| H | Cl | 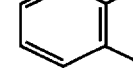 | |
| H | Br |  | |
| H | Cl | Ethyl | Ethyl |
| H | Br | Ethyl | Ethyl |
| H | Cl | Ethyl | i-Propyl |
| H | Cl | Ethyl | n-Butyl |
| H | Cl | Ethyl | t-Butyl |
| H | Cl | i-Propyl | i-Propyl |
| H | Cl | i-Propyl | Trifluoromethyl |
| H | Cl | Methylthio | Phenyl |
| H | Cl | Methylthio | 4-Cl-Phenyl |
| H | Br | Methylthio | Phenyl |
| H | Cl | Methylthio | 3-Pyridyl |
| H | Cl | Methoxy | Phenyl |
| H | Cl | Methoxy | 3-CF₃-Phenyl |
| H | Cl | Dimethyl-amino | Phenyl |
| H | Cl | Methyl-carbonyl | Phenyl |
| H | Cl | Methoxy | Methyl |
| H | Br | Methoxy | Ethyl |

TABLE A.5-continued

| | | | |
|---|---|---|---|
| H | Cl | i-Propoxy | Methyl |
| H | Cl | i-Propoxy | Phenyl |
| H | Cl | Dimethyl-amino | CN |
| H | Cl | Methylthio | Ethyl |
| H | CN | Methyl | Phenyl |
| H | CN | Methyl | i-Propyl |
| H | CN | CN | 4-Chlorophenyl |
| H | CN | CN | t-Butoxymethyl |
| H | CN | Methylthio | Phenyl |
| H | CN | Methoxy | 3-Fluorophenyl |
| H | CN | Cyclopropyl | Phenyl |

TABLE A.6

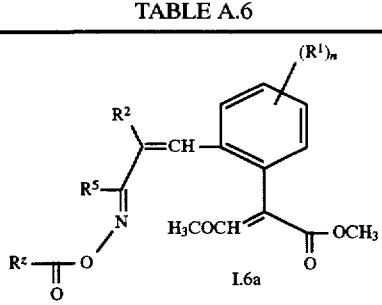

I.6a

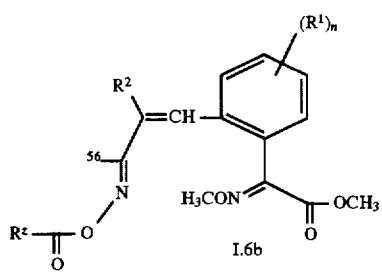

I.6b

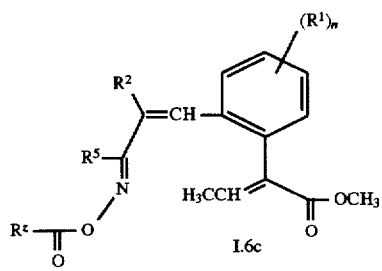

I.6c

| $R^1_n$ | $R^2$ | $R^5$ | $R^z$ |
|---|---|---|---|
| H | Cl | $CH_3$ | $CH_3$ |
| H | Cl | $CH_3$ | $CH_2CH_3$ |
| H | Cl | $CH_3$ | $CH_2CH_2CH_3$ |
| H | Cl | $CH_3$ | $CH(CH_3)_2$ |
| H | Cl | $CH_3$ | $C(CH_3)_3$ |
| H | Cl | $CH_3$ | $C_6H_5$ |
| H | Cl | $CH_3$ | $4\text{-}Cl-C_6H_4$ |
| H | Cl | $CH_3$ | $3\text{-}OCH_3-C_6H_4$ |
| H | Cl | $CH_3$ | Pyridin-3-yl |
| H | Cl | $CH_3$ | $CH_2C_6H_5$ |
| H | Br | $CH_3$ | $CH_2CH_3$ |
| H | Br | $CH_3$ | $C_6H_5$ |
| H | Br | $CH_3$ | $C(CH_3)_3$ |
| H | Cl | $C_6H_5$ | $CH_3$ |
| H | Cl | $C_6H_5$ | $C(CH_3)_3$ |
| H | Cl | $C_6H_5$ | $4\text{-}Cl-C_6H_4$ |
| H | Br | $CF_3$ | $CH_2CH_3$ |
| H | Br | $CF_3$ | $C_6H_5$ |
| H | Cl | $CH_2OCH_3$ | $CH_3$ |
| H | Cl | $CH_2OCH_3$ | $C(CH_3)_3$ |

TABLE A.6-continued

| | | | |
|---|---|---|---|
| H | Cl | $CH_2OCH_3$ | $4\text{-}Cl-C_6H_4$ |
| 4-$OCH_3$ | Cl | $CH_3$ | $CH_3$ |
| 6-Cl | Cl | $CH_3$ | $CH_3$ |
| H | Cl | $CH_3$ | $N(CH_3)_2$ |
| H | Cl | $CH_3$ | $N(CH_2CH_3)_2$ |
| H | Cl | $CH_3$ | 1-Piperidinyl |
| H | Cl | $CH_3$ | 1-Pyrolidinyl [sic] |
| H | Cl | $CH_3$ | 4-Morpholinyl |
| H | Cl | $CH_3$ | $N(CH_3)-CH_2CH_2Cl$ |
| H | Cl | $CH_3$ | $N(CH_3)-CH_2CH=CH_2$ |
| H | Cl | $CH_3$ | $N(CH_3)-C_6H_5$ |
| H | Cl | $CH_3$ | $NH-(4\text{-}Cl-C_6H_4)$ |
| H | Cl | $CH_3$ | $N(CH_3)-OCH_2CH_3$ |
| H | Cl | $CH_3$ | $NHCH_2CH_3$ |
| H | Cl | $CH_3$ | $N(CH_3)-CH(CH_3)_2$ |
| 4-$OCH_3$ | Cl | $CH_3$ | $N(CH_3)_2$ |
| H | Br | $CH_3$ | $N(CH_3)_2$ |
| H | Br | $CH_3$ | $N(CH_3)-C_6H_5$ |
| H | Br | $CH_3$ | $NH-CH_2CH_3$ |
| H | Cl | $C_6H_5$ | $N(CH_3)_2$ |
| H | Cl | $CF_3$ | $N(CH_3)_2$ |
| H | Cl | $CH_3$ | $NHCH_3$ |
| H | Br | $CH_3$ | $NHCH_3$ |
| H | CN | $CH_3$ | $NHCH_3$ |
| H | CN | $CH_3$ | $CH_3$ |
| H | CN | $CH_3$ | $4\text{-}Cl-C_6H_4$ |
| H | CN | $CH_3$ | $N(CH_3)_2$ |
| H | CN | $CH_3$ | $NH-(4\text{-}Cl-C_6H_4)$ |

The compounds I are suitable as fungicides.

The compounds I are extremely effective against a broad spectrum of phytopathogenic fungi, in particular those from the class of the Ascomycetes and Basidiomycetes. Some of them have a systemic action and can be used as foliar and soil fungicides.

They are of particular importance for controlling a large number of fungi in various crops or their seeds, such as wheat, rye, barley, oats, rice, Indian corn, grass, cotton, soybeans, coffee, sugar cane, fruit end ornamentals and vegetable crops such as cucumbers, beans and cucurbits.

In particular they are useful for controlling the following plant diseases:

Erysiphe graminis (powdery mildew) in cereals,

Erysiphe cichoracearum and Sphaerotheca fuliginea in curcurbits,

Podosphaera Leucotricha in apples,

Uncinula necator in grapevines,

Puccinia species in cereals,

Rhizoctonia species in cotton and lawns,

Ustilago species in cereals and sugar cane,

Venturia inaequalis (scab) in apples,

Helminthosporium species in cereals,

Septoria nodorum in wheat,

Botrytis cinerea (gray mold) in strawberries and grapevines,

Cercospora arachidicola in groundnuts,

Pseudocercosporella Herpotrichoides in wheat and barley,

Pyricularia oryzae in rice,

Phytophthora infestans in potatoes and tomatoes,

Fusarium and Verticillium species in various plants,

Plasmopara viticola in grapevines,

Alternaria species in fruit and vegetables.

The compounds I are applied by treating the fungi or the plants, seeds, materials or soil to be protected against fungal attack with a fungicidally effective amount of the active ingredients. They may be applied before or after infection of the materials, plants or seeds by the fungi.

They can be converted into the conventional formulations such as solutions, emulsions, suspensions, dusts, powders, pastes and granules. The application form depends on the intended use in each case; it should at all events ensure a fine and uniform distribution of the ortho-substituted benzyl ester of a cyclopropanecarboxylic acid. The formulations are prepared in a known manner, for example by extending the active ingredient with solvents and/or carriers, with or without the use of emulsifiers and dispersants; if water is used as diluent, it is also possible to employ other organic solvents as auxiliary solvents. Suitable auxiliaries for this purpose are essentially: solvents such as aromatics (e.g. xylene), chlorinated aromatics (e.g. chlorobenzenes), paraffins (e.g. crude oil fractions), alcohols (e.g. methanol, butanol), ketones (e.g. cyclohexanone), amines (e.g. ethanolamine, dimethylformamide), and water; carriers such as ground natural minerals (e.g. kaolins, aluminas, talc and chalk) and ground synthetic minerals (e.g. highly disperse silica and silicates); emulsifiers such as nonionic and anionic emulsifiers (e.g. polyoxyethylene fatty alcohol ethers, alkylsulfonates and arylsulfonates); and dispersants such as lignin-sulfite waste liquors and methylcellulose.

The fungidical compositions generally contain from 0.1 to 95, preferably from 0.5 to 90, % by weight of active ingredient.

The application rates are from 0.02 to 3 kg of active ingredient per ha, depending on the type of effect desired.

In the case of seed treatment, active ingredient rates of from 0.001 to 50 g, preferably from 0.01 to 10 g, per kilogram of seed are generally required.

When used as fungicites, the compositions according to the invention may also be present together with other active ingredients, for example herbicides, insecticides, growth regulators, fungicides or fertilizers.

Admixture with other fungicides frequently results in a greater fungicidal action spectrum.

The following list of fungicides with which the novel compounds may be combined is intended to illustrate possible combinations but not to impose any restrictions:

sulfur, dithiocarbamates and their derivatives, such as ferric dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfides [sic], ammonia complex of zinc N,N'-ethylenebisdithiocarbamate, ammonia complex of zinc N,N'-propylenebisdithiocarbamate, zinc N,N'-propylenebisdithiocarbamate and N,N'-polypropylenebis (thiocarbamyl) disulfide;

nitro derivatives, such as dinitro(1-methylheptyl)phenyl crotonate, 2-sec-butyl-4,6-dinitrophenyl 3,3-dimethylacrylate, 2-sec-butyl-4,6-dinitrophenyl isopropylcarbonate and diisopropyl 5-nitroisophthalate;

heterocyclic substances, such as 2-heptadecyl-2-imidazoline acetate, 2,4-dichloro-6-(o-chloroanilino)-s-triazine, O,O-diethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithio[4,5-b]quinoxaline, methyl 1-(butylcarbamoyl)-2-benzimidazolecarbamate, 2-methoxycarbonylaminobenzimidazole, 2-(fur-2-yl) benzimidazole, 2-(thiazol-4-yl)benzimidazole, N-(1,1,2,2-tetrachloroethylthio)tetrahydrophthalimide, N-trichloromethylthiotetrahydrophthalimide, N-trichloromethylthiophthalimide,
N-dichlorofluoromethylthio-N',N'-dimethyl-N-phenylsulfuric acid diamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thio-1-oxide, 8-hydroxyquinoline or its copper salt, 2,3-dihydro-5-carboxanilido-6-methyl-1,4-oxathiin, 2,3-dihydro-5-carboxanilido-6-methyl-1,4-oxathiin-4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, 2,5-dimethyl-N-cyclohexylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethylacetal, piperazine-1,4-diylbis(1-(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxyethyl)-N'-imidazolylurea, 1-(4-chlorophenoxy)-3,3-dimethyl-1-(1H-1,2,4-triazol-1-yl)butan-2-one, 1-(4-chlorophenoxy)-3,3-dimethyl-1-(1H-1,2,4-triazol-1-yl)butan-2-ol, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, and various fungicides, such as dodecylguanidine acetate, 3-[3-(3,5-dimethyl-2-oxycyclohexyl)-2-hydroxyethyl] glutaramide, hexachlorobenzene, DL-methyl-N-(2,6-dimethylphenyl)-N-fur-2-yl alaninate, methyl DL-N-(2,6-dimethylphenyl)-N-(2'-methoxyacetyl)alaninate, N-(2,6-dimethylphenyl)-N-chloroacetyl-D,L-2-aminobutyrolactone, methyl DL-N-(2,6-dimethylphenyl)-N-phenylacetyl)alaninate, 5-methyl-5-vinyl-3-(3,5-dichlorophenyl)-2,4-dioxo-1,3-oxazolidine, 3-[3,5-dichlorophenyl-5-methyl-5-methoxymethyl]-1,3-oxazolidine-2,4-dione [sic], 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximinio]acetamide, 1-[2-(2,4-dichlorophenyl)pentyl]-1H-1,2,4-triazole, 2,4-difluoro-α-(1H-1,2,4-triazol-1-ylmethyl)benzhydryl alcohol, N-(3-chloro-2,6-dinitro-4-trifluoromethylphenyl)-5-trifluoromethyl-3-chloro-2-aminopyridine, and 1-((bis(4-fluorophenyl)methylsilyl)methyl)-1H-1,2,4-triazole.

The compounds of the formula I are also suitable for effectively controlling pests from the class of the insects, arachnids and nematodes. They may be used as pesticides in crop protection and in the hygiene, stores protection and veterinary sector.

Examples of insect pests belonging to the Lepidoptera order are Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grndiosella [sic], Earias insulana, Elasmopalpus lignosellus, Eupoecilia amgibuella, Eretria bouliana, Feltia subterranea, Galleria mellonella, Grapholita funebrana, Grapholita molesta, Heliothis armigera, Heliothis virescens, Heliothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni and Zeiraphera canadensis.

Examples from the Coleoptera order are Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Ortiorrhynchus sulcatus, Ortiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus and Sitophilus granaria.

Examples from the Diptera order are Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antigua, Phorbia brassicae, Phorbia coarctata, Rhagoletis cerasi, Rhagoletis pomonella, Tabanus bovinus, Tipula oleracea and Tipula paludosa.

Examples from the Thysanoptera order are Frankliniella fusca, Frankliniella occidentalis, Frankliniella tritici, Scirtothrips citri, Thrips oryzae, Thrips palmi and Thrips tabaci.

Examples from the Hymenoptera order are Athalia rosae, Atta cephalotes, Atta sexdens, Atta texana, Hoplocampa minuta, Hoplocampa testudinea, Monomorium pharaonis, Solenopsis geminata and Solenopsis invicta.

Examples from the Heteroptera order are Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis and Thyanta perditor.

Examples from the Homoptera order are Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Drefusia nordmannianae, Dreyfusia piceae, Dyasphis radicola, Dysaulacorthum pseudosolani, Empoasca fabae, Macrosiphum avenae, Macrosiphum euphorbiae, Macrosiphon rosae, Megoura viciae, Metopolphium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum and Viteus vitifolii.

Examples from the Isoptera order are Calotermes flavicollis, Leucotermes flavipes, Reticulitermes lucifugus and Termes natalensis.

Examples from the Orthoptera order are Acheta domestica, Blatta orientalis, Blattella germanica, Forficula auricularia, Gryllotalpa gryllotalpa, Locusta migratoria, Melanoplus birittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus and Tachycines asynamorus.

Examples from the Acarina order are Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Orhithodorus moubata, Otobins megnini, Paratetranychus pilosus, Permanyssus gallinae, Phyllocaptrata oleivora, Polyphagotarsonemus latus, Bsoroptes ovis, Rhipicephalus appendiculatus, Rhipicephalus evertsi, Saccoptes scabiei, Tetranychus cinnabarinus, Tetranychus kanzawai, Tetranychus pacificus, Tetranychus telarius and Tetranychus urticae.

Examples from the nematodes class are root-knot nematodes, e.g. Meloidogyne hapla, Meloidogyne incognita and Meloidogyne javanica, cyst-forming nematodes, e.g. Globodera rostochiensis, Heterodera avenae, Heterodera glycinae, Heterodera schatii [sic] and Heterodera trifolii, and stem and leaf eelworms, e.g. Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus and Pratylenchus goodeyi.

The active ingredients may be applied as such, in the form of their formulations or the application forms prepared therefrom, for example in the form of directly sprayable solutions, powders, suspensions or dispersions, emulsions, oil dispersions, pastes, dusting compositions, broadcasting compositions or granules, by spraying, atomizing, dusting, broadcasting or watering. The forms of application depend entirely on the intended uses; they should at all events ensure as fine a distribution of the active ingredients according to the invention as possible.

The active ingredient concentrations in the ready-to-use formulations may vary widely.

In general, they are from 0.0001 to 10, preferably from 0.01 to 1, %.

The active ingredients may also be successfully used in the ultra-low-volume method (ULV), in which it is possible to apply formulations containing more than 95% by weight of active ingredient, or even the active ingredient without any additives.

The active ingredient application rate for controlling pests in the open is from 0.1 to 2.0, preferably from 0.2 to 1.0, kg/ha.

The following are suitable for the preparation of directly sprayable solutions, emulsions, pastes or oil dispersions: mineral oil fractions of medium to high boiling point, such as kerosene or diesel oil, and also coal-tar oils and oils of vegetable or animal origin, aliphatic, cyclic and aromatic hydrocarbons, e.g. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, e.g. dimethylformamide, dimethyl sulfoxide, N-methylpyrrolidone and water.

Aqueous application forms may be prepared from emulsion concentrates, pastes or wettable powders (spray powders, oil dispersions) by adding water. To prepare emulsions, pastes or oil dispersions, the substances as such or dissolved in an oil or solvent may be homogenized in water by means of wetting agents, adherents, dispersants or emulsifiers. Furthermore, however, concentrates which are suitable for dilution with water may be prepared from active substance, wetting agent, adherent, dispersant or emulsifier and possibly solvent or oil.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and also alkali metal and alkaline earth metal salts thereof, salts of sulfated fatty alcohol glycol ether, condensation products of sulfonated naphthalene and naphthalene derivatives with formaldehyde, condensation products of naphthalene or naphtalenesulfonic [sic] acid with phenol and formaldehyde, polyoxyethylene octylphenol ethers, ethoxylated isooctylphenol, octylphenol, nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Powder, broadcasting and dusting compositions may be prepared by mixing or grinding the active substances together with a solid carrier.

The formulations generally contain from 0.01 to 95, preferably from 0.1 to 90, % by weight of active ingredient. The active ingredients are used in a purity of from 90 to 100, preferably from 95 to 100, % (according to the NMR spectrum).

Examples of formulations are as follows:

I. 5 parts by weight of compound No. 1.005 are intimately mixed with 95 parts by weight of particulate kaolin. A dust containing 5% by weight of the active ingredient is thereby obtained.

II. 30 parts by weight of compound No. 1.011 are intimately mixed with a mixture consisting of 92 parts by weight of powdered silica gel and 8 parts by weight of paraffin oil which has been sprayed onto the surface of this silica gel. A formulation of the active ingredient having good adherence (active ingredient content: 23% by weight) is thereby obtained.

III. 10 parts by weight of compound No. 1.098 are dissolved in a mixture consisting of 90 parts by weight of xylene, 6 parts by weight of the adduct of 8 to 10 moles of ethylene oxide and 1 mole of oleic acid N-monoethanolamide, 2 parts by weight of the calcium salt of dodecylbenzenesulfonic acid, and 2 parts by weight of the adduct of 40 moles of ethylene oxide and 1 mole of castor oil (active ingredient content: 9% by weight).

IV. 20 parts by weight of compound No. 1.082 are dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil (active ingredient content: 16% by weight).

V. 80 parts by weight of compound No. 1.021 are thoroughly mixed with 3 parts by weight of the sodium salt of diisobutylnaphthalene-alpha-sulfonic acid, 10 parts by weight of the sodium salt of a lignosulfonic acid obtained from a sulfite waste liquor, and 7 parts by weight of powdered silica gel, and the mixture is triturated in a hammer mill (active ingredient content: 80% by weight).

VI. 90 parts by weight of compound No. 1.083 are mixed with 10 parts by weight of N-methyl-α-pyrrolidone, resulting in a solution which is suitable for application in the form of very fine drops (active ingredient content: 90% by weight).

VII. 20 parts by weight of compound No. 1.037 are dissolved in a mixture consisting of 40 parts by weight of cyclohexanone, 30 parts by weight of isobutanol, 20 parts by weight of the adduct of 7 moles of ethylene oxide and 1 mole of isooctylphenol, and 10 parts by weight of the adduct of 40 moles of ethylene oxide and 1 mole of castor oil. By pouring the solution into 100,000 parts by weight of water and finely distributing it therein, an aqueous dispersion containing 0.02% by weight of the active ingredient is obtained.

VIII. 20 parts by weight of active ingredient No. 1.078 are thoroughly mixed with 3 parts by weight of the sodium salt of diisobutylnaphthalene-α-sulfonic acid, 17 parts by weight of the sodium salt of a lignosulfonic acid obtained from a sulfite waste liquor, and 60 parts by weight of powdered silica gel, and the mixture is triturated in a hammer mill. By finely distributing the mixture in 20,000 parts by weight of water, a spray liquor containing 0.1% by weight of the active ingredient is obtained.

Granules, e.g. coated, impregnated or homogeneous granules, may be prepared by binding the active ingredients to solid carriers. Examples of solid carriers are mineral earths such as silica gel, silicic acids, silica gels [sic], silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, ureas and vegetable products such as grain meal, bark meal, wood meal and nutshell meal, cellulose powders and other solid carriers.

Oils of various types, herbicides, fungicides, other pesticides and bactericides may be added to the active ingredients, if desired immediately prior to use (tank mix). These agents can be admixed with the agents according to the invention in a weight ratio of from 1:10 to 10:1.

SYNTHESIS EXAMPLES

The directions given in the synthesis examples below were employed, with appropriate modification of the starting compounds, to obtain further compounds I. The compounds thus obtained are listed, together with physical data, in the tables below.

Example 1

Methyl 2-{2-[2-bromo-2-isopropoxycarbonyl-(Z)-ethenyl]phenyl}3-methoxyprop-(E)-2-enoate (compound 1.020 in Table 1)

10 g of bromoisopropoxycarbonylmethylenetriphenylphosphorane and 5 g of methyl 2-(2- formylphenyl)-3-methoxyprop-(E)-2-enoate are stirred for 4 hours at 40° C. in 60 ml of methanol. The batch is then substantially evaporated down, is absorbed onto silica gel and chromatographed in a short silica gel column using methyl tert-butyl ether as the mobile phase. Further purification is by means of medium-pressure chromatography over silica gel using a 3:1 v/v mixture of n-heptane and ethyl acetate as mobile phase. 1.6 g of the title compound are obtained as a pale oil.

$^1$H-NMR (CDCl$_3$, δ in ppm): 1.3 (d, 6H); 3.7 (s, 3H); 3.85 (s, 3H); 5.1 (sep, 1H); 7.25 (m, 1H); 7.35 (m, 2H); 7.55 (s, 1H); 7.8 (m, 1H); 8.05 (s, 1H)

Example 2 methyl 2-{2-[2-chloro-2-tert-butoxycarbonyl-(Z)-ethenyl]phenyl}-3-methoxyprop-(E)-2-enoate (compound 1.012 in Table 1)

197 g of tert-butyl chlorodiethylphosphonoacetate are added dropwise to a 40° C. suspension of 51.8 g of Ca(OH)$_2$ and 154 g of methyl 2-(2-formylphenyl)-3-methoxyprop-(E)-2-enoate in 1.5 l of ethyl acetate. After the mixture has been stirred for about 8 hours at 60° C., the aldehyde has reacted completely. To work up the mixture, it is poured onto ice-water, extraction is carried out three times with ethyl acetate and the combined organic phases are washed until neutral with saturated NaCl solution. The solvent is removed after drying over NaSO$_4$. The crude product (210 g) still contains about 30% by weight of phosphonate, but can be used in this form in Example 5.

For further purification, the phosphonate from 10 g of crude product is distilled off at 0.1 mm Hg and an oil bath temperature of 165° C. 7 g of the title compound remains as a viscous yellow oil which crystallizes out on being coated with diethyl ether.

Mp. 62°–64° C.

$^1$H-NMR (CDCl$_3$, δ in ppm): 1.55 (s, 9H); 3.7 (s, 3H); 3.85 (s, 3H); 7.3–7.5 (m, 3H); 7.6 (s, 1H); 7.8 (s, 1H); 7.9 (m, 1H)

Example 3

Methyl 2-methoxyimino-2-{2-[2-chloro-2-tert-butoxycarbonyl-(Z)-ethenyl]phenyl}acetate (compound 1.038 in Table 1)

Similarly to the procedure in Example 2, 34.9 g of methyl 2-methoximino-2-(2-formylphenyl)acetate and 11.7 g of Ca(OH)$_2$) are reacted with 45.3 g of tert-butyl chlorodiethylphosphonoacetate. 54.0 g of crude product are obtained which can be employed as such in Example 6.

For further purification, 7.0 g are chromatographed over silica gel (mobile phase: toluene/ethyl acetate 1:1, v/v). 4 g of the title compound are obtained as a yellow oil.

$^1$H-NMR (CDCl$_3$, δ in ppm): 1.55 (s, 9H); 3.8 (s, 3H); 4.0 (s, 3H); 7.2–7.5 (m, 3H); 7.65 (s, 1H); 7.9 (m, 1H)

Example 4

Methyl 2-{2-[2-chloro-2-carboxyl-(Z)-ethenyl]phenyl}-3-methoxyprop-(E)-2-enoate (compound 1.042 in Table 1)

130 g of the methyl 2-{2-[2-chloro-2-tert-butoxycarbonyl-(Z)-ethenyl]phenyl}-3-methoxyprop-(E)-2-enoate from Example 2 are stirred in a mixture of 200 ml of trifluoroacetic acid and 160 ml of dichloromethane for about 30 minutes at room temperature. The deep red solution is carefully evaporated down on a rotary evaporator and poured onto ice-water. The aqueous phase is made alkaline with 2N sodium hydroxide solution, and extracted twice with ethyl acetate. The aqueous phase is then acidified to a pH of ~2 with 2N hydrochloric acid and the product is extracted by shaking three times with ethyl acetate. The combined organic phases are washed twice with water and then with saturated NaCl solution.

The solvent is completely removed after drying over sodium sulfate. The remaining 90 g of oil crystallize.

Mp. 114°–118° C.

$^1$H-NMR (CDCl$_3$, δ in ppm): 3.7 (s, 3H); 3.85 (s, 3H); 7.2–7.4 (m, 3H); 7.65 (s, 1H); 7.9 (s, 1H); 8.0 (m, 1H); 8.9 (broad, OH)

Example 5

Methyl 2-{2-[2-chloro-2-tert-butoxycarbonyl-(Z)-ethenyl]phenyl}but-(E)-2-enoate (compound 1.082 in Table 1)

Similarly to the procedure in Example 3, 5.1 g of methyl 2-(2-formylphenyl)but-(E)-2-enoate and 1.9 g of [lacuna] are reacted with 7.2 g of tert-butyl chlorodiethylphosphonoacetate. 7.6 g of crude product which can be used for further reactions after liberation of the acid as described in Example 4 are obtained.

$^1$H-NMR (CDCl$_3$, δ in ppm): 1.5 (s, 9H); 1.6 (d, 3H); 3.7 (s, 3H); 7.1–7.5 (m, 4H); 7.7 (s, 1H); 7.95 (m, 1H)

Example 6

Methyl 2-methoxyimino-2-{2-[2-chloro-2-carboxy-(Z)-ethenyl]phenyl}acetate (compound 1.145 in Table 1)

29 g of methyl 2-methoxyimino-2-{2-[2-chloro-2-tert-butyloxycarbonyl-(Z)-ethenyl]phenyl}acetate from Example 3 are stirred in a mixture of 40 ml of trifluoroacetic acid and 160 ml of dichloromethane for 2.5 hours at room temperature. The dark solution is then stirred into 500 ml of saturated sodium carbonate solution (pH 9). After the addition of 200 ml of methyl tert-butyl ether, the organic phase is separated off. The aqueous phase is again extracted with methyl tert-butyl ether and the pH is adjusted to 2–3 with 6N hydrochloric acid. The product separates out as an emulsion and is isolated by extracting three times with methyl tert-butyl ether and ethyl acetate. The combined organic phases are washed until neutral with saturated NaCl solution and dried over sodium sulfate. The solvent is removed, leaving 20 g of the title compound as a dark oil.

Mp. 107°–109° C.

$^1$H-NMR (CDCl$_3$, δ in ppm): 3.90 (s, 3H); 4.05 (s, 3H); 7.2–7.6 (m, 3H); 7.85 (s, 1H); 8.05 (m, 1H); 10.4 (OH)

Example 7

4-{1-Chloro-2-[2-(1-methoxycarbonyl-2-methoxy-(E)-ethenyl)phenyl]-(Z)-ethenylcarboxy}-3-oxo-2,5-diphenyl-2,3-dihydrothiophene-1,1-dioxide (compound 1.054 in Table 1)

0.5 g of pyridine is added to a solution of 8.9 g of methyl α-{2-[2-chloro-2-carboxyl-(Z)-ethenyl]phenyl}-β-methoxy-(E)-acrylate from Example 4 and 10 g of 4,6-diphenylthieno-[3,4-d]-1,3-dioxol-2-one-5,5-dioxide in 100 ml of anhydrous dichloromethane. After the batch has been stirred for 2 hours at room temperature, it is extracted three times with 20% strength citric acid, four times with saturated sodium bicarbonate solution and once with water. The organic phase is dried over sodium sulfate and evaporated to dryness in a rotary evaporator. The title compound is obtained as a pale yellow solid.

Mp. 68°–72° C.

Example 8

Methyl 2-{2-[2-chloro-2-dimethylaminocarbonyl-(Z)-ethenyl]phenyl}-3-methoxyprop-(E)-2-enoate (compound 1.048 in Table 1)

5.8 g of the thiophene dioxide ester from Example 7 are dissolved in 50 ml of dichloromethane, and 1.6 ml of 40% strength aqueous dimethylamine solution are added. The initial dark red coloration quickly turns orange-red. After 1 hour the batch is worked up as described in Example 7. 2.0 g of crude product are obtained. After chromatography over silica gel (mobile phase: toluene/ethyl acetate 9:1, v/v), 1.4 g of the title compound are obtained as an oil.

$^1$H-NMR (CDCl$_3$, δ in ppm): 3.1 (broad, 6H); 3.7 (s, 3H); 3.85 (s, 3H); 6.8 (s, 1H); 7.2–7.5 (m, 3H); 7.6 (s, 1H); 7.8 (m, 1H).

Example 9

Methyl 2-{2-[2-chloro-2-phenylaminocarbonyl-(Z)-ethenyl]phenyl}-3-methoxyprop-(E)-2-enoate (compound 1.052 in Table 1)

2.4 g of N,N-carbonyldiimidazole are added to a solution of 4.5 g of methyl 2-{2-[2-chloro-2-carboxyl-(Z)-ethenyl]phenyl}-3-methoxyprop-(E)-2-enoate from Example 4 in 30 ml of anhydrous tetrahydrofuran. After the mixture has been stirred for 2 hours at room temperature, a solution of 1.6 g of aniline in 10 ml of tetrahydrofuran is added dropwise. After 1 hour the batch is evaporated down, taken in 100 ml of methyl tert-butyl ether and washed three times with 20% strength citric acid and twice with saturated sodium carbonate solution and water. After the organic phase has been dried over sodium sulfate, the solvent is removed. The crude product is chromatographed over silica gel (mobile phase: toluene/ethyl acetate 9:1; v/v). 2.6 g of the title compound are obtained as colorless crystals.

Mp. 88°–90° C.

$^1$H-NMR (CDCl$_3$, δ in ppm): 3.7 (s, 3H); 3.8 (s, 3H); 7.1–7.9 (m, 10H); 8.05 (s, 1H); 8.5 (broad, 1H)

Example 10

Methyl 2-{2-[2-chloro-2-chlorocarbonyl)-(Z)-ethenyl]phenyl}-3-methoxyprop-(E)-2-enoate 2 drops of dimethylformamide are added to 13.3 g of methyl 2-{2-[2-chloro-2-carboxy-(Z)-ethenyl]phenyl}-3-methoxyprop-(E)-2-enoate from Example 4 in 100 ml of anhydrous dichloromethane. 5.4 g of thionyl chloride are added dropwise at room temperature, and the mixture is then refluxed for 3 hours. After cooling, the solvent is completely removed. The crude product is used directly for further reactions.

Example 11

Methyl 2-methoxyimino-2-{2-[2-chloro-2-chlorocarbonyl-(Z)-ethenyl]phenyl}acetate The compound is prepared analogously to Example 10 from methyl 2-methoximino-{2-[2-chloro-2-carboxy-(Z)-ethenyl]phenyl}acetate from Example 5 and thionyl chloride. The crude product is used directly for further reactions.

Example 12

Methyl 2-{2-[2-chloro-2-(2-propaniminoxycarbonyl)-(Z)-ethenyl]phenyl}-3-methoxyprop-(E)-2-enoate (compound 1.055 in Table 1)

1.02 g of acetone oxime are dissolved in 15 ml of pyridine. At room temperature, 4.46 g of acyl chloride (from Example 10) dissolved in 5 ml of anhydrous tetrahydrofuran are added dropwise. The batch is stirred overnight and worked up by pouring into ice-water and extracting three times with methyl tert-butyl ether. The combined organic phases are washed twice with 20% strength citric acid solution, twice with saturated sodium carbonate solution and then washed until neutral with water. After drying over sodium sulfate, the solvent is removed. The crude product is chromatographed over silica gel (mobile phase: toluene/ethyl acetate 1:1, v/v). 1.6 g of the title compound are obtained as a pale yellow oil.

$^1$H-NMR (CDCl$_3$, δ in ppm): 2.10 (s, 3H); 2.13 (s, 3H); 3.65 (s, 3H); 3.8 (s, 3H); 7.2–7.5 (m, 3H); 7.6 (s, 1H); 7.9 (s, 1H); 8.0 (m, 1H)

Example 13

Methyl 2-{2-[2-chloro-2-tert-butylthiocarbonyl-(Z)-ethenyl]phenyl}-3-methoxyprop-(E)-2-enoate (compound 1.078 in Table 1)

1.12 g of sodium tert-butylthiolate and a spatula tip of sodium carbonate are introduced at 0° C. into 30 ml of anhydrous acetone. With ice-cooling, 3.15 g of the acyl chloride from Example 10 are slowly added dropwise, the temperature rising to 10° C. The mixture is stirred for 2 hours, 30 ml of methyl tert-butyl ether are added and the precipitate is filtered off with suction. The filtrate is evaporated down in a rotary evaporator and purified by silica gel chromatography (mobile phase: toluene/ethyl acetate 9:1, v/v). 0.7 g of the title compound is obtained as a yellow oil.

$^1$H-NMR (CDCl$_3$, δ in ppm): 1.55 (s, 3H); 3.7 (s, 3H); 3.8 (s, 3H); 7.2–7.45 (m, 3H); 7.6 (s, 1H); 7.7 (s, 1H); 7.9 (m, 1H)

Example 14

Methyl 2-{2-[2-chloro-3-oxobut-(Z)-1-enyl]phenyl}-3-methoxyprop-(E)-2-enoate (compound 1.022 in Table 1)

A suspension of 194 g of 1-chloro-1-triphenylphosphoranylidene acetone and 110 g of methyl 2-(2-formylphenyl)-3-methoxyprop-(Z)-E-enylate in 1000 ml of anhydrous methanol is stirred overnight at room temperature. The solvent is then removed and the residue is stirred with 500 ml of cyclohexane/100 ml of diisopropyl ether/100 ml of acetone. The solid which remains is filtered off, the filtrate is evaporated down in a rotary evaporator and this residue is again treated as described above. The remaining solids (triphenylphosphine oxide) are discarded. The filtrate is absorbed onto about 300 g of silica gel and eluted in a silica gel column using toluene/ethyl acetate (95/5 to 80/20, v/v). The resulting product is triturated with diisopropyl ether. 73 g of the title compound remain as a pale yellow solid.

Mp. 109°–110° C.

121

$^1$H-NMR (CDCl$_3$, δ in ppm): 2.5 (s, 3H); 3.7 (s, 3H); 3.8 (s, 3H); 7.2–7.4 (m, 3H); 7.6 (s, 1H); 7.7 (s, 1H); 7.9 (m, 1H)

Example 15

Methyl 2-methoxyimino-2-{2-[2-chloro-3-oxobut-(Z)-1-enyl]phenyl}acetate (compound 1.031 in Table 1)

53 g of 1-chloro-1-triphenylphosphoranylidene acetone and 24 g of methyl 2-methoxyimino-2-(2-formylphenyl)acetate are reacted in 250 ml of methanol as in Example 15 and worked up.

13.5 g of the title compound are obtained as a solid. Mp. 71°–72° C.

$^1$H-NMR (CDCl$_3$, δ in ppm): 2.6 (s, 3H); 3.9 (s, 3H); 4.1 (s, 3H); 7.2–7.5 (m, 3H); 7.6 (s, 1H); 7.95 (m, 1H)

Example 16

Methyl 2-methoxyimino-2-{2-[2-chloro-3-methoxyimino-but-(Z)-1-enyl]phenyl}acetate (compound 1.032 in Table 1)

2.0 g of methyl 2-methoxyimino-2-{2-[2-chloro-3-oxobut-(Z)-1-enyl]phenyl}acetate (from Example 15) are dissolved in 40 ml of methanol. 0.60 g of O-methylhydroxylamine hydrochloride and 2 drops of concentrated hydrochloric acid are added and the mixture is stirred overnight at room temperature. Any keto compound remaining reacts completely on further addition of 0.12 g of O-methylhydroxylamine hydrochloride. For working up, the batch is evaporated down and partitioned between methyl tert-butyl ether and water. The separated aqueous phase is extracted twice with methyl tert-butyl ether. The combined organic phases are washed until neutral with saturated sodium chloride solution, dried over sodium sulfate and evaporated down in a rotary evaporator. 3 g of the title compound remain as a partially crystllizing oil to which solvent adheres (1:9 syn/anti mixture).

$^1$H-NMR (CDCl$_3$, δ in ppm): 2.1 (s, "3H", anti); 2.5 (s, "3H", syn); 3.85 (s, 3H); 4.0 (s, 3H); 4.05 (s, 3H); 6.85 (s, 1H); 7.2–7.5 (m, 3H); 7.75 (d, 1H)

Example 17

2-Methoxyimino-2-{2-[2-chloro-3-methoxyimino-but-(Z)-1-enyl]phenyl}acetic acid methylamide (compound 1.033 in Table 1)

1 g of methyl 2-methoxyimino-2-{2-[2-chloro-3-methoxyimino-but-(Z)-1-enyl}phenyl}acetate (from Example 16) are [sic] dissolved in 10 ml of tetrahydrofuran; 1 ml of aqueous 40% strength methylamine solution is added and the mixture is stirred at 40° C. After 20 hours and further addition of 1 ml of methylamine solution, the ester has completely reacted. For working up, the solvent is completely removed and the residue is partitioned between methyl tert-butyl ether and water. The organic phase is washed twice with 20% strength citric acid solution and water, dried over sodium sulfate and filtered through a small amount of silica gel. The filtrate is evaporated down in a rotary evaporator. 0.6 g of the title compound remains as a yellow oil.

$^1$H-NMR (CDCl$_3$, δ in ppm): 2.1 (s, 3H); 2.9 (d, 3H); 3.95 (s, 3H); 4.05 (s, 3H); 6.75 (broad, 1H); 6.9 (s, 1H); 7.2–7.5 (m, 3H); 7.8 (dd, 1H)

122

Example 18

Methyl 2-{2-[2-bromo-2-(5-[4-chlorophenyl]-1,3,4-thiazdiazol-2-yl)ethenyl]phenyl}-3-methoxyprop-(E)-2-enoate (compound 1.006 in Table 1)

A solution of dimethyl 5-(4-chlorophenyl)-1,3,4-thiadiazol-2-ylmethanephosphate in 50 ml of anhydrous tetrahydrofuran is cooled to –70° C. and 20.6 ml of a 1.6 molar solution of butyllithium in hexane are added dropwise. After 30 minutes at –70° C., 5 g of bromine are added, the temperature rising to –30° C. The mixture is stirred for 1 hour and then 6.6 g of methyl 2-(2-formylphenyl)-3-methoxyprop-(E)-2-enoate in 20 ml of tetrahydrofuran are added dropwise at this temperature. The batch is slowly allowed to come to room temperature and is then stirred for a further 48 hours. To work up the batch, it is poured into 60 ml of ice-water and extracted three times with methyl tert-butyl ether. The combined organic phases are washed until neutral, dried over sodium sulfate and evaporated down in a rotary evaporator. The crude product is triturated with diisopropyl ether/ethyl acetate (9:1, v/v) and filtered off with suction. The filtrate is purified by medium-pressure chromatography over silica gel (mobile phase: n-heptane/ethyl acetate 75/25, v/v). 1.3 g of the title compound are obtained as a partially crystallizing oil (85:15 Z/E mixture).

Z compound: $^1$H-NMR (CDCl$_3$, δ in ppm): 3.65 (s, 3H); 3.75 (s, 3H); 5.3 (s, 1H); 7.2–7.3 (m, 3H); 7.4 (d, 2H); 7.55 (s, 1H); 7.58 (s, 1H); 7.75 (d, 2H)

Example 19

Methyl 2-{2-[2-chloro-2-(3-[4-chlorophenyl]isoxazol-5-yl)ethenyl]-4-chlorophenyl}-3-methoxyprop-(E)-2-enoate (compound 1.001 and 1.002 in Table 1)

A solution of 4.4 g of diethyl 3-(4-chlorophenyl)isoxazol-5-ylmethanephosphonate in 30 ml of anhydrous tetrahydrofuran is cooled to –70° C. and 9.3 ml of a 1.6 molar solution of n-butyllithium in hexane is added dropwise. After 30 minutes at –70° C., 2.3 g of tetrachloromethane are added. The batch is stirred for 1 hour, is allowed to warm up to –30° C. and 3.5 g of methyl 2-(4-chloro-2-formylphenyl)-3-methylprop-(E)-2-enoate in 30 ml of tetrahydrofuran are then added dropwise at this temperature. The batch is slowly allowed to come to room temperature, and is stirred for a further 16 hours. Working up is as described in Example 18. The title compound is obtained as an E/Z ethenyl mixture. The isomers can be separated by medium-pressure chromatography over silica gel (mobile phase: n-hexane/ethyl acetate 82/18, v/v).

Z isomer: 2.5 g; mp. 141°–147° C. (compound 1.001 in Table 1)

$^1$H-NMR (DMSO, δ in ppm): 3.65 (s, 3H); 3.8 (s, 3H); 7.1–8.0 (m, 10H);

E isomer: 2.6 g; mp. 115°–123° C. (compound 1.002 in Table 1)

$^1$H-NMR (DMSO, δ in ppm): 3.55 (s, 3H); 3.7 (s, 3H); 7.15–8.0 (m, 10H)

Example 20

Methyl 2-{2-[2-chloro-2-hydroximinobut-(Z)-1-enyl]phenyl}-3-methoxyprop-(E)-2-enoate (compound 1.079 in Table 1)

23.6 g of methyl 2-{2-[2-chloro-2-hydroximinobut-(Z)-1-enyl]phenyl-3-methoxyprop-(E)-2-enoate from Example 14 and 5.6 g of hydroxylamine hydrochloride are stirred in 300 ml of anhydrous methanol, initially at room temperature. After 18 hours, 2.8 g of hydroxylamine hydrochloride are again added and the batch is heated to 40° C. After a further 2 hours, the solvent is removed and the residue is partitioned between methyl tert-butyl ether and water. The aqueous phase is extracted twice with methyl tert-butyl ester [sic]. The combined organic phases are washed until neutral, dried and evaporated down. The crude product (25.5; 3/7 syn/anti mixture is prefractionated by column chromatography on silica gel (mobile phase: toluene/ethyl acetate 9:1, v/v). Pure anti isomer is partly obtained by variation with diisopropyl ether. For subsequent reactions, a syn/anti mixture (~1:9, 13.6 g) may be used.

anti isomer Mp.: 57°–60° C.

$^1$H-NMR (CDCl$_3$, δ in ppm): 2.15 (s, 3H); 3.7 (s, 3H); 3.85 (s, 3H); 7.0 (s, 1H); 7.25–7.4 (m, 3H); 7.6 (s, 1H); 7.25 (m, 1H); 9.6 (s, OH)

Example 21

Methyl 2-{2-[2-chloro-3-(O-[4-chlorophenylaminocarbonyl]hydroximino]but-(Z)-1-enyl]phenyl}-3-methoxyprop-(E)-2-enoate (compound 1.081 in Table 1)

1.5 g of methyl 2-{2-[2-chloro-2-hydroximinobut-(Z)-1-enyl]phenyl}-3-methoxyprop-(E)-2-enoate from Example 20 are dissolved in 20 ml of anhydrous diethyl ether. At room temperature, 0.8 [lacuna] of 4-chlorophenyl isocyanate in 5 ml of diethyl ether is added. After a further 2 hours, the batch is stirred into ice-water and the organic phase is separated off. The aqueous phase is extracted twice with diethyl ether. The combined organic phases are washed until neutral, dried over sodium sulfate and filtered off.

Some product already precipitates out from the filtrate. After evaporation and trituration of the residue with diisopropyl ether, 1.4 g of the title compound remain as colorless crystals.

Mp.: 175°–177° C.

$^1$H-NMR (CDCl$_3$, δ in ppm): 2.35 (s, 3H); 3.7 (s, 3H); 3.85 (s, 3H); 7.15–7.8 (m, 10H); 8.5 (broad, NH)

Example 22

Methyl 2-{2-[2-cyano-2-tert-butoxycarbonyl-(E)-ethenyl]phenyl}-3-methoxyprop-(E)-2-enoate (compound 1.112 in Table 1)

At 0° C., a solution of 40.7 g of titanium tetrachloride in 50 ml of tetrachloromethane is added dropwise into an ice-cooled receiver containing 400 ml of anhydrous tetrahydrofuran; in an exothermic reaction, a yellow precipitate is formed. The temperature is kept at 0° C., and in succession a solution of 15.1 g of tert-butyl cyanoacetate and 23.6 g of methyl 2-(2-formylphenyl)-3-methoxyprop-(E)-2-enoate in 75 ml of tetrahydrofuran and then, slowly, 35 ml of pyridine in 75 ml of tetrahydrofuran are added dropwise. The batch is allowed to come to room temperature, and is then stirred for a further 3 hours. To work up the batch, it is stirred into ice-water and extracted three times with methyl tert-butyl ether. The combined organic phases are washed with aqueous sodium bicarbonate and saturated sodium chloride solution, dried over magnesium sulfate and evaporated down in a rotary evaporator. 35.0 g of crude product are obtained as a brown oil. 3.0 g of crude product are purified by medium-pressure chromatography over silica gel (mobile phase: n-heptane/ethyl acetate 4:1, v/v). 0.8 g of the title compound is obtained as a pale oil.

$^1$H-NMR (CDCl$_3$, δ in ppm): 1.55 (s, 9H); 3.7 (s, 3H); 3.85 (s, 3H); 7.2–7.5 (m, 3H); 7.65 (s, 1H); 8.2 (s, 1H); 8.3 (d, 1H)

Example 23

Methyl 2-{2-[2-cyano-2-carboxyl-(E)-ethenyl]phenyl}-3-methoxyprop-(E)-2-enoate (compound 1.122 in Table 1)

28 g of the crude product of the tert-butyl ester from Preparation Example 23 [sic] are split into the free acid, similarly to the process of Example 5, with 40 ml of trifluoroacetic acid in 40 ml of dichloromethane. After crystallizing out with diisopropyl ether/acetone, 5.4 g of the title compound are obtained. The concentrated filtrate (7.4 g) can also be used.

Mp.: 169°–173° C.

$^1$H-NMR (DMSO, δ in ppm): 3.65 (s, 3H); 3.85 (s, 3H); 7.3 (d, 1H); 7.4–7.6 (m, 2H); 7.8 (s, 1H); 8.1–8.2 (m, 2H); 14.0 (broad, COOH)

Example 24

Methyl 2-{2-[2-nitro-2-ethoxycarbonyl-(Z/E)-ethenyl]phenyl}-3-methoxyprop-(E)-2-enoate (isomer mixture of compound 1.111 in Table 1)

At 0° C., a solution of 7.6 g of titanium tetrachloride in 10 ml of tetrachloromethane is added dropwise into an ice-cooled receiver containing 80 [lacuna] of anhydrous tetrahydrofuran; in an exothermic reaction, a yellow precipitate is formed. The temperature is obtained [sic] at 0° C. and in succession a solution of 2.7 g of ethyl nitroacetate in 15 ml of tetrahydrofuran and then, slowly, 8.0 g of N-methylmorpholine in 15 ml of tetrahydrofuran are added dropwise. The batch is allowed to come to room temperature and is then stirred for a further 3 hours. For work-up, the batch is stirred into ice-water and extracted three times with methyl tert-butyl ether. The combined organic phases are washed with aqueous sodium bicarbonate and saturated sodium chloride solution, dried over magnesium sulfate and evaporated down in a rotary evaporator. 5.5 g of crude product are obtained as a brown oil, which is purified by medium-pressure chromatography over silica gel (mobile phase: n-heptane/ethyl acetate 4:1, v/v). 3 g of a 1:1E/Z isomer mixture are obtained as an oil.

$^1$H-NMR (CDCl$_3$, δ in ppm): 1.35 ("Z", q, 3H); or 1.45 ("E", q, 3H); 3.75 (s, 3H); 3.85 ("Z", s, 3H); or 3.90 ("E", s, 3H); 7.2–7.5 (m, 4H); 7.65 (s, 1H); 7.68 ("E", s, 1H); or 8.1 ("Z", s, 1H)

Example 25

Methyl 2-{2-[2-chloro-2-(3-fluorobenzyloxyamino)carbonyl-(Z)-ethenylphenyl}-3-methoxyprop-(E)-2-enoate (compound 1.114 in Table 1)

At room temperature, 3.3 g of N,N-carbonyldiimidazole are added to a solution of 5.93 g of methyl 2-{2-[2-chloro-2-carboxy-(Z)-ethenyl]phenyl}-3-methoxyprop-(E)-2-enoate from Example 5 in 50 ml of anhydrous dichloromethane, and the mixture is stirred for 1 hour. A suspension of 3.7 g of (O-(3-fluorobenzyl)hydroxylamine [sic] hydrochloride and 2.1 g of triethylamine in 20 ml of dichloromethane is added thereto in 4 portions. The batch is stirred overnight at room temperature and filtered off with suction, the filtrate is evaporated down and the residue is taken up in ethyl acetate. The organic phase is washed with 20% strength aqueous citric acid solution, 10% strength sodium carbonate solution and water. After drying over magnesium sulfate, the solvent is removed. 5.4 g of the title compound are obtained as colorless crystals.

Mp.: 171°–173° C.

$^1$H-NMR (CDCl$_3$, δ in ppm): 3.7 (s, 3H); 3.8 (s, 3H); 5.0 (s, 2H); 7.0–7.4 (m, 7H); 7.6 (s, 1H); 7.9 (s, 1H); 9.2 (broad, NH)

Example 26

Methyl 2-{2-[2-chloro-3-(3-fluorobenzyloxyimino)-3-methoxyprop-(Z)-1-enyl]phenyl}-3-methoxyprop-(E)-2-enoate (compound 1.116 in Table 1)

2.3 g of methyl 2-{2-[2-chloro-2-(3-fluorobenzyloxyamino)carbonyl-(Z)-ethenyl]phenyl}-3-methoxyprop-(E)-2-enoate from Example 25, 0.79 g of potassium carbonate and 0.005 g of silver carbonate are stirred in 50 ml of acetone/5 ml of 1,3-dimethyltetrahydro-2(1H)-pyrimidinone for about 1 hour at room temperature. 0.72 g of dimethyl sulfate is then added. The batch is stirred for a further 12 hours and poured onto ice-water for working up. It is extracted three times with ethyl acetate, the organic phase is washed with water and dried over magnesium sulfate, and the solvent is removed. 2.4 g of crude product remain, which is split up by silica gel chromatography (mobile phase: toluene/ethyl acetate 9:1, v/v) into 1.2 g of the title compound and 0.7 g of the N-methylated compound.

$^1$H-NMR (CDCl$_3$, δ in ppm): 3.65 (s, 3H); 3.8 (s, 3H); 3.9 (s, 3H); 5.1 (s, 2H); 7.0–7.4 (m, 8H); 7.6 (s, 1H); 7.8 (m, 1H)

By-product: Methyl 2-{2-[2-chloro-2-(N-3-fluorobenzyloxy-N-methylamino)carbonyl-(Z)-ethenyl]phenyl}-3-methoxyprop-(E)-2-enoate (compound 1.115 in Table 1)

$^1$H-NMR (CDCl$_3$, δ in ppm): 3.3 (s, 3H); 3.65 (s, 3H); 3.8 (s, 3H); 4.9 (s, 2H); 7.05–7.45 (m, 8H); 7.55 (s, 1H); 7.85 (s, 1H)

Example 27

Methyl 2-{2-[2-chloro-3-chloro-3-n-propoxyiminoprop-(Z)-1-enyl]phenyl}-3-methoxyprop-(E)-2-enoate 1.3 g of triphenylphosphine and 1.54 g of tetrachloromethane are added to a solution of 1.2 g of methyl 2-{2-[2-chloro-2-n-propoxyaminocarbonyl-Z-ethenyl]phenyl-3-methoxyprop-(E)-2-enoate in 30 ml of anhydrous acetonitrile. The batch is refluxed for 16 hours and evaporated down, and the residue is absorbed on silica gel. The product can be separated by silica gel chromatography (mobile phase: toluene/ethyl acetate 9:1, v/v). 0.45 g of a pale yellow oil is obtained.

$^1$H-NMR (CDCl$_3$, δ in ppm): 1.0 (t, 3H); 1.9 (q, 2H); 3.7 (s, 3H); 3.8 (s, 3H); 4.3 (t, 2H); 7.2–7.45 (m, 3H); 7.6 (s, 1H); 7.8 (dd, 1H)

Example 28

Methyl 2-{2-[ethoxy-2-ethoxycarbonylethenyl]phenyl}-3-methoxyprop-(E)-2-enoate

First a solution of 2.7 g of ethyl ethoxydiethylphosphate in 10 ml of dimethylformamide and, after 10 minutes, a solution of 2.2 g of methyl 2-(2-formylphenyl)-3-methoxyprop-(E)-2-enoate in 30 ml of dimethylformamide are added dropwise to a suspension of 0.3 g of sodium hydride in 20 ml of anhydrous dimethylformamide. After the mixture has been stirred for about 1 hour at room temperature, the aldehyde has reacted completely. To work up the batch, it is poured into ice-water and extracted three times with methyl tert-butyl ether, the combined organic phases are washed with saturated sodium chloride solution, dried over sodium sulfate and evaporated down. After purification by means of medium-pressure chromatography over silica gel (mobile phase: cyclohexane/ethyl acetate 9/1→8/2, v/v), 2 isomers are obtained:

Z compound, 0.9 g:

$^1$H-NMR (CDCl$_3$, δ in ppm): 1.3 (t, 3H); 1.35 (t, 3H); 3.65 (s, 3H); 3.8.(s, 3H), 3.9 (q, 2H); 4.24 (q, 2H); 7.0 (s, 1H); 7.2–7.35 (m, 3H); 7.6 (s, 1H); 8.2 (dd, 1H)

E compound, 0.4 g:

$^1$H-NMR (CDCl$_3$, δ in ppm): 1.0 (t, 3H); 1.4 (t, 3H); 3.65 (s, 3H); 3.8 (s, 3H); 3.85 (q, 2H); 4.0 (q, 2H); 6.0 (s, 1H); 7.15–7.3 (m, 4H); 7.5 (s, 1H)

TABLE 1

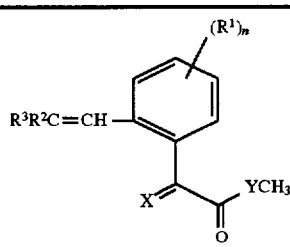

{E configuration with regard to the radical R3 and the phenyl ring}

| No. | Y | X | (R$^1$)$_n$ | R$^2$ | R$^3$ | Mp. [°C.]/IR [cm$^{-1}$] /$^1$H-NMR [ppm] |
|---|---|---|---|---|---|---|
| 1.001 | O | (E)-CHOCH$_3$ | Cl | Cl | 3-(4-Cl—C$_6$H$_4$)isoxazol-5-yl | 141–147 |
| 1.002 | O | (E)-CHOCH$_3$ | Cl | 3-(4-Cl-C$_6$H$_4$)-isoxazol-5-yl | Cl | 115–123 |
| 1.003 | O | (E)-CHOCH$_3$ | H | Cl | 3-(4-Cl-C$_6$H$_4$)isoxazol-5-yl | 119–123 |
| 1.004 | O | (E)-CHOCH$_3$ | 4-tBu | Cl | 3-(4-Cl—C$_6$H$_4$)isoxazol-5-yl | 2961, 1708, 1632, 1426, 1257 |
| 1.005 | O | (E)-CHOCH$_3$ | H | Cl | 4-Cl-3-(4-Cl—C$_6$H$_4$)isoxazol-5-yl | 153–155 |
| 1.006 | O | (E)-CHOCH$_3$ | H | Br | 2-(4-Cl—C$_6$H$_4$)-1,3,4-thiadiazol-5-yl | 2940, 1705, 1628, 1434, 1255, 1128 |
| 1.007 | O | (E)-NOCH$_3$ | H | Br | Br | 59–63 |
| 1.008 | O | (E)-CHOCH$_3$ | H | H | Cl | 3.67 (3H); 3.77 (3H); 6.2 (1H); 6.55(1H); 7.2–7.4 |

TABLE 1-continued

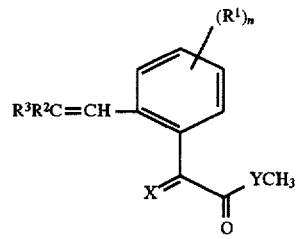

{E configuration with regard to the radical R3 and the phenyl ring}

| No. | Y | X | (R¹)ₙ | R² | R³ | Mp. [°C.]/IR [cm⁻¹] /¹H-NMR [ppm] |
|---|---|---|---|---|---|---|
| | | | | | | (3H); 7.55 (1H); 7.85 (1H) |
| 1.009 | O | (E)-CHOCH₃ | H | Cl | H | 3.70 (3H); 3.80 (3H); 6.53 (1H), 6.78 (1H); 7.1–7.4 (4H); 7.6 (1H) |
| 1.010 | O | (E)-CHOCH₃ | H | Cl | ETO—CO— | 1.35 (3H); 3.6 (3H); 3.85 (3H); 4.3 (2H); 7.2–7.4 (3H); 7.6 (1H); 7.8 (1H); 7.9 (1H) |
| 1.011 | O | (E)-CHOCH₃ | H | Cl | i-PrO—CO— | 2982, 1713, 1630, 1260, 1131, 1105 |
| 1.012 | O | (E)-CHOCH₃ | H | Cl | t-BuO—CO— | 2984, 1713, 1632, 1287, 1250, 1158 |
| 1.013 | O | (E)-CHOCH₃ | H | Cl | 2-Br-BzlO—CO— | 1711, 1630, 1256, 1204, 1130 |
| 1.014 | O | (E)-CHOCH₃ | H | Cl | 4-He-BzlO—CO— | 1712, 1630, 1258, 1204, 1130 |
| 1.015 | O | (E)-CHOCH₃ | H | Cl | 4-Cl-BzlO—CO— | 1711, 1629, 1257, 1203, 1130 |
| 1.016 | O | (E)-CHOCH₃ | H | Cl | 3-Cl-BzlO—CO— | 1711, 1630, 1257, 1204, 1130 |
| 1.017 | O | (E)-CHOCH₃ | H | Cl | 2,6-Cl₂-BzlO—CO— | 1711, 1631, 1255, 1200, 1130 |
| 1.018 | O | (E)-CHOCH₃ | H | Cl | 4-F-BzlO—CO— | 1711, 1630, 1512, 1258, 1226, 1130 |
| 1.019 | O | (E)-CHOCH₃ | H | Br | MeO—CO— | 2950, 1712, 1631, 1435, 1258, 1130 |
| 1.020 | O | (E)-CHOCH₃ | H | Br | i-PrO—CO— | 2980, 1711, 1630, 1258, 1129, 1104 |
| 1.021 | O | (E)-CHOCH₃ | H | Br | t-BUO—CO— | 2980, 1708, 1633, 1257, 1151, 1130 |
| 1.022 | O | (E)-CHOCH₃ | H | Cl | —COCH₃ | 109–110 |
| 1.023 | O | (E)-CHOCH₃ | H | Cl | —C(CH₃)=NOCH₃ | 2945, 1709, 1631, 1435, 1256, 1129, 1052 |
| 1.024 | O | (E)-CHOCH₃ | H | Cl | —C(CH₃)=NO—CH₂C≡CH | 3290, 2945, 2708, 1631, 1435, 1256, 1130 |
| 1.025 | O | (E)-CHOCH₃ | H | Cl | —C(CH₃)=NO—CH₂CN | 2940, 1707, 1631, 1435, 1257, 1130, 1061 |
| 1.026 | O | (E)-CHOCH₃ | H | Cl | —C(CH₃)=NO—CH₂C(Cl)=CH₂ | 2940, 1709, 1631, 1256, 1130 |
| 1.027 | O | (E)-CHOCH₃ | H | Cl | —C(CH₃)=NOCH₂(3-CH₃—C₆H₄) | 2943, 1709, 1631, 1434, 1255, 1129 |
| 1.028 | O | (E)-CHOCH₃ | H | Cl | —C(CH₃)=NOCH₂CH=CH—CH₃ trans | 2940, 1710, 1631, 1435, 1255, 1129 |
| 1.029 | O | (E)-CHOCH₃ | H | Cl | —C(CH₃)=NO—CH₂CH=C(Cl)CH₃ cis | 2945, 1709, 1632, 1434, 1255, 1130 |
| 1.030 | O | (E)-CHOCH₃ | H | Cl | C(CH₃)=NOCH₂-[2-(4-CH₃—C₆H₄)-oxazol-4-yl] | 2945, 1708, 1631 1500, 1255, 1129 |
| 1.031 | O | (E)-NOCH₃ | H | Cl | —COCH₃ | 71 72 |
| 1.032 | O | (E)-NOCH₃ | H | Cl | —C(CH₃)=NOCH₃ | 2939, 1728, 1438, 1221, 1068, 1050 |
| 1.033 | NH | (E)-NOCH₃ | H | Cl | —C(CH₃=NOCH₃ | 3340, 2938, 1668, 1527, 1050 |
| 1.034 | O | (E)-NOCH₃ | H | Cl | —C(CH₃)=NOCH₂C≡CH | 3285, 2940, 1727, 1437, 1221, 1069, 1016 |

TABLE 1-continued

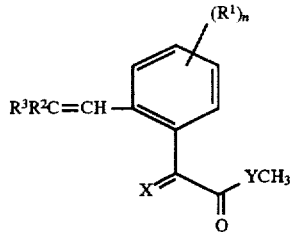

{E configuration with regard to the radical R3 and the phenyl ring}

| No. | Y | X | $(R^1)_n$ | $R^2$ | $R^3$ | Mp. [°C.]/IR [cm$^{-1}$] /$^1$H-NMR [ppm] |
|---|---|---|---|---|---|---|
| 1.035 | O | (E)-NOCH$_3$ | H | Cl | —C(CH$_3$)=NOCH$_2$CN | 108–112 |
| 1.036 | O | (E)-NOCH$_3$ | H | Cl | —C(CH$_3$)=NOCH$_2$CCl=CH$_2$ | 2940, 1727, 1437, 1221, 1068, 1019 |
| 1.037 | O | (E)-NOCH$_3$ | H | Cl | —C(CH$_3$)=NOCH$_2$(3-CH$_3$—C$_6$H$_4$) | 2938, 1727, 1437; 1221, 1069, 1017 |
| 1.038 | O | (E)-NOCH$_3$ | H | Cl | t-BuO—CO— | 2980, 2940, 1725, 1289, 1158, 1069, 1018 |
| 1.039 | O | (E)-NOCH$_3$ | H | Cl | 1-Cyclopropylethoxycarbonyl | 2945, 1725, 1437, 1263, 1221, 1068 1018 |
| 1.040 | O | (E)-NOCH$_3$ | H | Cl | Phenyl-NH—CO— | 130–133 |
| 1.041 | O | (E)-NOCH$_3$ | H | Cl | (H$_3$C)$_2$=NO—CO— | 91–94 |
| 1.042 | O | (E)-CHOCH$_3$ | H | Cl | HO—CO— | 3260, 2949, 1708 1628, 1437, 1259 1195, 1134 |
| 1.043 | O | (E)-CHOCH$_3$ | H | Cl | 1-Cyclopropylethoxycarbonyl | 2940, 1713, 1630, 1435, 1258, 1130 |
| 1.044 | O | (E)-CHOCH$_3$ | H | Cl | s-BuO—CO— | 2970, 2940, 1713 1631, 1435, 1258 1129 |
| 1.045 | O | (E)-CHOCH$_3$ | H | Cl | H$_3$COCH$_2$CH(CH$_3$)O—CO— | 2940, 1713, 1630, 1435, 1258, 1204, 1130 |
| 1.046 | O | (E)-CHOCH$_3$ | H | Cl | H$_5$C$_6$CH(CH$_3$)O—CO— [sic] | 2945, 1712, 1629, 1257, 1204, 1130 |
| 1.047 | O | (E)-CHOCH$_3$ | H | Cl | NCC(CH$_3$)$_2$O—CO— | 2950, 1736, 1709, 1629, 1258, 1144 |
| 1.048 | O | (E)-CHOCH$_3$ | H | Cl | (Me)$_2$N—CO— | 2945, 1707, 1645, 1396, 1258, 1129 |
| 1.049 | O | (E)-CHOCH$_3$ | H | Cl | i-PrNH—CO— | 3294, 2950, 1707, 1643, 1627, 1527, 1259, 1128 |
| 1.050 | O | (E)-CHOCH$_3$ | H | Cl | i-BuNH—CO— | 3245, 2957, 1709, 1665, 1626, 1524, 1257, 1130 |
| 1.051 | O | (E)-CHOCH$_3$ | H | Cl | BzlNH—CO— | 3350, 2945, 1706, 1668, 1629, 1521, 1258, 1130 |
| 1.052 | O | (E)-CHOCH$_3$ | H | Cl | Phenyl-NH—CO— | 88–90 |
| 1.053 | O | (E)-CHOCH$_3$ | H | Cl | Phenyl-NMe—CO— | 139–140 |
| 1.054 | O | (E)-CHOCH$_3$ | H | Cl | —OTDO | 2940, 1776, 1725, 1328, 1230, 1176, 1129 |
| 1.055 | O | (E)-CHOCH$_3$ | H | Cl | (H$_3$C)$_2$C=NO—CO— | 2950–1745, 1708, 1630, 1274, 1257 1194, 1130 |
| 1.056 | O | (E)-CHOCH$_3$ | H | Cl | H$_3$CCH$_2$CH$_2$O—C(CH$_3$)$_2$—C(CN)=NO—CO— | 2945, 1772, 1711, 1632, 1257, 1180, 1130 |
| 1.057 | O | (E)-CHOCH$_3$ | H | Cl | (2-CH$_3$, 3-C$_6$H$_5$—C$_6$H$_3$)HC(CN)O—CO— | 2950, 1737, 1709, 1630, 1257, 1202, 1130 |
| 1.058 | O | (E)-CHOCH$_3$ | H | Cl | (3-C$_6$H$_5$O—C$_6$H$_4$)HC(CN)O—CO— | 3290, 2945, 1728, 1711, 1630, 1585, 1486, 1247 |
| 1.059 | O | (E)-CHOCH$_3$ | H | Cl | i-PrONH—CO— | 3260, 2980, 2950, 1708, 1630, 1484, 1258, 1131 |
| 1.060 | O | (E)-CHOCH$_3$ | H | Cl | t-BuONH—CO— | 3260, 2978, 2945, 1708, 1630, 1484, 1257, 1131 |
| 1.061 | O | (E)-CHOCH$_3$ | H | Cl | 3-F-Phenyl-NH—CO— | 133–135 |

TABLE 1-continued

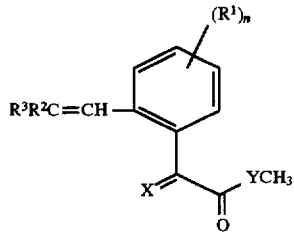

{E configuration with regard to the radical R3 and the phenyl ring}

| No. | Y | X | (R¹)ₙ | R² | R³ | Mp. [°C.]/IR [cm⁻¹] /¹H-NMR [ppm] |
|---|---|---|---|---|---|---|
| 1.062 | O | (E)-CHOCH₃ | H | Br | —C(CH₃)=NOC(CH₃)3 | 2976, 1711, 1632, 1257, 1129 |
| 1.063 | O | (E)-CHOCH₃ | H | Br | —COCH₃ | 2955, 1707, 1690, 1630, 1435, 1258, 1129 |
| 1.064 | O | (E)-CHOCH₃ | H | Br | —C(CH₃)=NOCH₃ | 2950, 1709, 1632, 1255, 1129, 1051 |
| 1.065 | O | (E)-CHOCH₃ | H | Br | —C(CH₃)=NOCH₂CH=CHCH₃ trans | 2950, 1710, 1631, 1255, 1129, 1051 |
| 1.066 | O | (E)-CHOCH₃ | H | Br | —C(CH₃)NOCH₂CH—CH₂ | 2955, 1709, 1631 1435, 1256, 1129 |
| 1.067 | O | (E)-CHOCH₃ | H | Br | —C(CH₃)NOCH₂(3-CH₃—C₆H₄) | 2958, 1709, 1631, 1434, 1255, 1129 |
| 1.068 | O | (E)-CHOCH₃ | H | Br | —C(CH₃)NOCH₂(3-CN—C₆H₄) | 2955, 2240, 1708, 1631, 1434, 1256, 1129 |
| 1.069 | O | (E)-CHOCH₃ | H | Cl | —C(OCH₃)=NOCH₂CH—CH₂ | 2955, 1709, 1631, 1257, 1129 |
| 1.070 | O | (E)-CHOCH₃ | H | Cl | H₂C=CHCH₂ON(CH₃)—CO— | 2958, 1708, 1660, 1634, 1256, 1130 |
| 1.071 | O | (E)-CHOCH₃ | H | Cl | (4-Cl—C₆H₄) H₃CC=NO—CO— | 161–163 |
| 1.072 | O | (E)-CHOCH₃ | H | Cl | (4-Cl—C₆H₄) n-C₃H₇C=NO—CO— | 1756, 1705, 1639, 1264, 1198 |
| 1.073 | O | (E)-CHOCH₃ | H | Cl | (c-Pr)₂C=NO—CO— | 1745, 1708, 1628, 1257, 1193, 1130 |
| 1.074 | O | (E)-CHOCH₃ | H | Cl | (H₃C)₂NO—CO— | 1745, 1709, 1630, 1258, 1197, 1152, 1129 |
| 1.075 | O | (E)-CHOCH₃ | H | Cl | H₃CON(CH₃)—CO— | 1708, 1656, 1634, 1256, 1129 |
| 1.076 | O | (E)-CHOCH₃ | H | Cl | 1-(2,2-Dimethyl-1,3-di-oxlan-5-yl)-propynoxycarbonyl [sic] | 2955, 2130, 1733, 1710, 1629, 1255, 1134 |
| 1.077 | O | (E)-CHOCH₃ | H | Cl | 1-Methylcyclopentyloxycarbonyl | 1712, 1630, 1257, 1190, 1130 |
| 1.078 | O | (E)-CHOCH₃ | H | Cl | t-BuS—CO— | 1.55 (9H); 3.7 (3H); 3.8 (3H); 7.2–7.5 (3H); 7.6 (1H); 7.7 (1H); 7.85 (1H) |
| 1.079 | O | (E)-CHOCH₃ | H | Cl | —C(CH₃)=NOH | 57–60 |
| 1.080 | O | (E)-CHOCH₃ | H | Cl | —C(CH₃)=NO—CO—N(CH₃)₂ | 119–112 |
| 1.081 | O | (E)-CHOCH₃ | H | Cl | —C(CH₃)=NO—CO—NH-(4-Cl—C₆H₄) | 175–177 |
| 1.082 | O | (E)-CHCH₃ | H | Cl | t-BuO—CO— | 1720, 1288, 1252, 1158 |
| 1.083 | O | (E)-CHCH₃ | H | Cl | —C(CH₃)=NOCH₃ | 1717, 1434, 1251, 1051 |
| 1.084 | O | (E)-CHCH₃ | H | Cl | —C(CH₃)=NOCH₂(3-CH₃—C₆H₄) | 1717, 1434, 1251, 1036 |
| 1.085 | O | (E)-CHOCH₃ | H | Cl | —C(CH₃)=NOCH₂CH₃ | 1709, 1632, 1435, 1255, 1129, 1049 |
| 1.086 | O | (E)-CHOCH₃ | H | Cl | —C(CH₃)=NOCH₂CH₂CH₃ | 1710, 1632, 1435, .4 1255, 1129 |
| 1.087 | O | (E)-CHOCH₃ | H | Cl | —C(CH₃)=NOC(CH₃)3 | 1.35 (9H); 2.05 (3H); 3.65 (3H); 6.9 (1H); 7.2–7.4 (3H); 7.55 (1H); 7.25 (1H) |
| 1.088 | O | (E)-CHOCH₃ | H | Cl | —C(CH₃)=NOCH₂CH=CH₂ | 2945, 1705, 1628, 1434, 1252, 1126 |
| 1.089 | O | (E)-CHOCH₃ | H | Cl | —C(CH₃)=NOCH₂C₆H₅ | 2950, 1706, 1629, 1434, 1254, 1127 |
| 1.090 | O | (E)-CHOCH₃ | H | Cl | —C(CH₃)=NOCH₂-(3-CF₃—C₆H₄) | 1710, 1632, 1330, 1127 |

TABLE 1-continued $$R^3R^2C=CH- \underset{\underset{O}{X}}{\overset{(R^1)_n}{\phantom{M}}}-YCH_3$$

I

{E configuration with regard to the radical R3 and the phenyl ring}

| No. | Y | X | $(R^1)_n$ | $R^2$ | $R^3$ | Mp. [°C.]/IR [cm$^{-1}$] /$^1$H-NMR [ppm] |
|---|---|---|---|---|---|---|
| 1.091 | O | (E)-CHOCH$_3$ | H | Cl | $-C(CH_3)=NOCH_2-(3,4-Cl_2-C_6H_3)$ | 1709, 1631, 1256, 1130 |
| 1.092 | O | (E)-NOCH$_3$ | H | Cl | (4-Cl—C$_6$H$_4$)H$_3$CC=NO—CO— | 149–150 |
| 1.093 | O | (E)-CHCH$_3$ | H | Cl | (4-Cl—C$_6$H$_4$)H$_3$CC=NO—CO— | 86–88 |
| 1.094 | O | (E)-CHOCH$_3$ | H | Cl | Cyclo-PrNH—CO— | 3320, 1707, 1859, 1631, 1531, 1258, 1130 |
| 1.095 | O | (E)-NOCH$_3$ | H | Cl | t-BuNH—CO— | 72–75 |
| 1.096 | O | (E)-NOCH$_3$ | H | Cl | t-BuNH—CO— | |
| 1.097 | O | (E)-NOCH$_3$ | H | Cl | 1,1-Dimethylpropynylaminocarbonyl | 109–112 |
| 1.098 | O | (E)-CHOCH$_3$ | H | Cl | 1,1-Dimethylpropynylaminocarbonyl | 95–99 |
| 1.099 | O | (E)-NOCH$_3$ | H | Cl | s-BuNH—CO— | 117–119 |
| 1.100 | O | (E)-CHOCH$_3$ | H | Cl | s-BuNH—CO— | 3330, 1709, 1659, 1630, 1520, 1257, 1130 |
| 1.101 | O | (E)-NOCH$_3$ | H | Cl | L-EtO-ValNH—CO— | 3420, 1730, 1675, 1650, 1513, 1069, 1030 |
| 1.102 | O | (E)-CHOCH$_3$ | H | Cl | L-EtO-Val-NH—CO— | 3420, 1736, 1672, 1630, 1257, 1200, 1130 |
| 1.103 | O | (E)-CHOCH$_3$ | H | Cl | Cyclopentyl-NH(CO) | 115–117 |
| 1.104 | O | (E)-CHOCH$_3$ | H | Cl | 1-Cyclopropylethylaminocarbonyl | 3335, 1708, 1658, 1630, 1517, 1256, 1130 |
| 1.105 | O | (E)-CHOCH$_3$ | H | Cl | Dimethylpropylaminocarbonyl | 90–95 |
| 1.106 | O | (E)-CHOCH$_3$ | H | Cl | —CO—NHNHCO(4-Cl—C$_6$H$_4$) | 157 |
| 1.107 | O | (E)-CHOCH$_3$ | H | Cl | —CO—NHN(CH$_3$)CONHCH(CH$_3$)$_2$ | 140–143 |
| 1.108 | O | (E)-NOCH$_3$ | H | Cl | —CO—N(CH$_3$)OCH$_2$CH=CH$_2$ | 2945, 1726, 1659, 1223, 1069, 1017 |
| 1.109 | O | (E)-NOCH$_3$ | H | Cl | —C(OCH$_3$)=NOCH$_2$CH=CH$_2$ | 2950, 1727, 1311, 1222, 1668, 1019 |
| 1.110 | O | (E)-CHOCH$_3$ | H | Cl | tBuNH—CO— | 3320, 2970, 1710, 1671, 1631, 1517, 1257, 1130 |
| 1.111 | O | (E)-CHOCH$_3$ | H | NO$_2$ | ETO—CO—E/Z homer mixture | 2955, 1732, 1711, 1630, 1538, 1261 |
| 1.112 | O | (E)-CHOCH$_3$ | H | CN | t-BuO—CO— | 2980, 1714, 1630, 1284, 1259, 1158 |
| 1.113 | O | (E)-NOCH$_3$ | H | CN | t-BuO—CO— | 85–87 |
| 1.114 | O | (E)-CHOCH$_3$ | H | Cl | 3-F-BzlONH—CO— | 171–173 |
| 1.115 | O | (E)-CHOCH$_3$ | H | Cl | 3-F-BzlON/CH$_3$)—CO— | 2950, 1707, 1659, 1633, 1257, 1130 |
| 1.116 | O | (E)-CHOCH$_3$ | H | Cl | C(OCH$_3$)=NO(3-F-Bzl) | 2945, 1708, 1630, 1255, 1130 |
| 1.117 | O | (E)-CHOCH$_3$ | H | Cl | H$_2$C=CCl—CH$_2$ONH—CO— | 3300, 2950, 1697, 1670, 1628, 1259 |
| 1.118 | O | (E)-CHOCH$_3$ | H | Cl | C(OCH$_3$)=NOCH$_3$CCl—CH$_2$ | 2945, 1707, 1632, 1256, 1129 |
| 1.119 | O | (E)-CHOCH$_3$ | H | Cl | H$_2$C=CCl—CH$_2$ON(CH$_3$)—CO— | 2950, 1709, 1663, 1634, 1257, 1130 |
| 1.120 | O | (E)-CHOCH$_3$ | H | Cl | HC≡C—CH$_2$ON(CH$_3$)—CO— | 3280, 2945, 2220, 1705, 1653, 1632, 1257, 1129 |
| 1.121 | O | (E)-CHOCH$_3$ | H | Cl | —C(OCH$_3$)=NOCH$_2$—C≡CH | 3290, 2945, 2220, 1707, 1630, 1258, 1130 |
| 1.122 | O | (E)-CHOCH$_3$ | H | Cl | H$_3$CONH—CO— | 3250, 2950, 1707, 1631, 1258, 1131 |

TABLE 1-continued

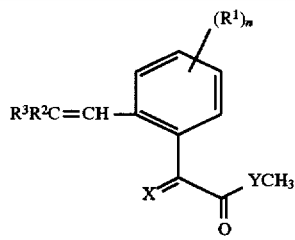

{E configuration with regard to the radical R3 and the phenyl ring}

| No. | Y | X | (R¹)ₙ | R² | R³ | Mp. [°C.]/IR [cm⁻¹]/¹H-NMR [ppm] |
|---|---|---|---|---|---|---|
| 1.123 | O | (E)-CHOCH₃ | H | CN | HO—CO— | 169–173 |
| 1.124 | O | (E)-NOCH₃ | 4-OCH₃ | Cl | t-BuOCO- | 2980, 1726, 1288, 1158, 1019 |
| 1.125 | O | (E)-CHOCH₃ | H | Cl | (H₅C₂)₂NO—CO— | 2980, 1748, 1710, 1630, 1257, 1130 |
| 1.126 | O | (E)-CHOCH₃ | H | Cl | 1-Methylpropynyloxycarbonyl | 3285, 2945, 1712, 1630, 1256, 1131 |
| 1.127 | O | (E)-CHOCH₃ | H | Cl | Propynyloxycarbonyl | 3290, 2950, 1730, 1709, 1630, 1257, 1131 |
| 1.128 | O | (E)-CHOCH₃ | H | Cl | 3-Iodopropynyloxycarbonyl | 2945, 2220, 1729, 1711, 1629, 1257, 1131 |
| 1.129 | O | (E)-CHOCH₃ | H | Cl | 1-Adamantylaminocarbonyl | 160–162 |
| 1.130 | O | (E)-CHOCH₃ | H | Cl | 2,6-Dimethylcyclohexylaminocarbonyl | 3445, 2954, 2928, 1711, 1672, 1630, 1516, 1256, 1130 |
| 1.131 | O | (E)-CHOCH₃ | H | Cl | 2,6-Dimethylpiperidinyl-N-aminocarbonyl | 3232, 2932, 1713, 1657, 1635, 1256 |
| 1.132 | O | (E)-CHOCH₃ | H | Cl | N-Phenyl-N-Me-hydroazinocarbonyl | 3300, 2955, 1707, 1633, 1496, 1257, 1130 |
| 1.133 | O | (E)-CHOCH₃ | H | Cl | (4-CH₃—C₆H₄)(H₃C)CHNH—CO— | 3340, 2950, 1709, 1660, 1631, 1514, 1256, 1130 |
| 1.134 | O | (E)-CHOCH₃ | H | Cl | (4-F—C₆H₄)(H₃C)CHNH—CO— | 3340, 1707, 1659, 1631, 1510, 1257, 1130 |
| 1.135 | O | (E)-CHOCH₃ | H | Cl | 3-Methylbut-2-ylaminocarbonyl | 100–104 |
| 1.136 | O | (E)-CHOCH₃ | H | Cl | MeO-ValNH—CO— | 3420, 2970, 1742, 1709, 1671, 1630, 1258 |
| 1.137 | O | (E)-CHOCH₃ | H | Cl | tBuO-ValNH—CO— | 3410, 2970, 1712, 1672, 1631, 1511, 1257 |
| 1.138 | O | (E)-CHOCH₃ | H | Cl | EtO-AlaNH—CO— | 3360, 2990, 2970, 1739, 1709, 1666, 1632, 1515, 1257, 1130 |
| 1.139 | O | (E)-CHOCH₃ | H | Cl | EtO-GlyNH—CO— | 114–116 |
| 1.140 | O | (E)-CHOCH₃ | H | Cl | —C(4-Cl-BzlO)=NOCH₃ | 2945, 1708, 1631, 1257, 1130, 1058 |
| 1.141 | O | (E)-CHOCH₃ | H | Cl | 3,4-diCl-BzlONH—CO— | 3260, 2950, 1707, 1629, 1473, 1258, 1131 |
| 1.142 | O | (E)-CHOCH₃ | H | Cl | 3,4-diCl-BzlON(CH₃)—CO— | 2950, 1707, 1659, 1633, 1257, 1130 |
| 1.143 | O | (E)-CHOCH₃ | H | Cl | —C(OCH₃)=NO(3,4-diCl-Bzl) | 2945, 1708, 1631, 1257, 1130 |
| 1.144 | O | (E)-CHOCH₃ | H | Cl | tBuO-AlNH—CO— | 3410, 2980, 1731, 1711, 1667, 1630, 1513, 1257, 1149 |
| 1.145 | O | (E)-NOCH₃ | H | Cl | HO—CO— | 107–109 |
| 1.146 | O | (E)-CHOCH₃ | H | CN | (H₃C)₃CNH—CO— | 3460, 2980, 2220, 1709, 1685, 1631, 1258, 1132 |
| 1.147 | O | (E)-CHOCH₃ | H | CN | 1,1-Dimethylpropynylaminocarbonyl | 3395, 2950, 1707, 1630, 1260, 1132 |
| 1.148 | NH | (E)-NOCH₃ | H | Cl | —C(4-Cl-BzlO)=NOCH₃ | 161–165 |
| 1.149 | O | (E)-NOCH₃ | H | Cl | H₃CON(4-Cl-BzlO)=NOCH₃ | 2945, 1741, 1723, 1225, 1057 |
| 1.150 | O | (E)-NOCH₃ | H | Cl | H₃CON(4-Cl-Bzl)—CO— | 2960, 1726, 1658, |

TABLE 1-continued $$\text{R}^3\text{R}^2\text{C}=\text{CH} - \text{[phenyl with }(R^1)_n\text{]} - \text{C}(=X) - \text{C}(=O)\text{YCH}_3$$

{E configuration with regard to the radical R3 and the phenyl ring}

| No. | Y | X | (R¹)ₙ | R² | R³ | Mp. [°C.]/IR [cm⁻¹] /¹H-NMR [ppm] |
|---|---|---|---|---|---|---|
| 1.151 | NH | (E)-NOCH₃ | H | Cl | —C(4-Cl-BzlO)=NOCH₃ | 1222, 1069 3420, 2935, 1663 1063, 1037 |
| 1.152 | NH | (E)-NOCH₃ | H | Cl | —C(CH₃)=NOCH₂C≡CH | 3288, 1667, 1527, 1038 |
| 1.153 | O | (E)-NOCH₃ | H | Cl | C(OCH₃)NOCH₂C≡CH [sic] | 2.5 (1H); 3.85 (3H); 4.05 (3H); 4.7 (2H); 7.1 (1H); 7.25 (1H); 7.4 (2H); 7.85 (1H) |
| 1.154 | O | (E)-NOCH₃ | H | Cl | HC≡CCH₂ON(CH₃)—CO— | 2.6 (1H); 3.4 (3H); 3.85 (3H); 4.0 (3H); 4.6 (2H); 6.95 (1H); 7.2 (1H); 7.4 (2H); 7.85 (1H) |
| 1.155 | O | (E)-NOCH₃ | H | Cl | —C(OCH₃)=NO(3,4-diCl-Bzl) | 3.85 (3H); 3.95 (3H); 4.0 (3H); 7.1 (s, 1H); 7.15–7.5 (6H), 7.8 (d, 1H) |
| 1.156 | O | (E)-NOCH₃ | H | Cl | 3,4-diCl-BzlON(CH₃)—CO— | 3.25 (3H); 3.8 (3H); 4.0 (3H); 4.85 (2H); 6.9 (1H); 7.1–7.5 (6H); 7.9 (1H) |
| 1.157 | O | (E)-NOCH₃ | H | Cl | —C(OCH₃)=NOCH₂CCl=CH₂ | 3.8 (3H); 3.95 (3H); 4.05 (3H); 4.6 (2H); 5.5 (2H); 7.1 (1H); 7.3 (1H); 7.4 (2H); 7.9 (1H) |
| 1.158 | O | (E)-NOCH₃ | H | Cl | H₂C=CClCH₂ON(CH₃)—CO— | 3.3 (3H); 3.9 (3H); 4.05 (3H); 4,5. (2H); 5.55 (2H), 6.9 (1H); 7.25 (1H), 7.4 (2H); 7.9 (1H) |
| 1.159 | O | (E)-NOCH₃ | H | Cl | —C(CH₃)=NOCH₂C≡CH | 3390, 2940, 2220, 1728, 1222, 1069 1015 |
| 1.160 | O | (E)-NOCH₃ | H | Cl | —C(CH₃)=NO(3,4-diCl-Bzl) | 2945, 1727, 1221, 1069, 1018 |
| 1.161 | NH | (E)-NOCH₃ | H | Cl | —C(CH₃)=NO(3,4-diCl-Bzl) | 3340, 2936, 1670 1524, 1035 |
| 1.162 | O | (E)-CHOCH₃ | H | CN | —C(OCH₃)=NOCH₂CH=CH₂ | 2945, 2220, 1709, 1629, 1258, 1131 |
| 1.163 | O | (E)-NOCH₃ | H | Cl | [3-Methyloxetan-3-yl]methyl-oxycarbonyl | 2940, 2870, 1728, 1241, 1224, 1068 |
| 1.164 | NH | (E)-NOCH₃ | H | Cl | —C(OCH₃)=NOCH₂C≡CH | 2.5 (1H); 2.9 (3H); 3.95 (6H); 4.7 (2H); 6.8 (1H); 7.15 (1H); 7.25 (1H); 7.4 (2H); 7.8 (1H) |
| 1.165 | NH | (E)-NOCH₃ | H | Cl | —C(OCH₃)=NO(3,4-di-Cl-Bzl) | 2.85 (3H); 3.85 (3H); 3.9 (3H); 5.1 (2H); 6.8 (1H); 7.1 (1H); 7.2–7.5 (6H); 7.85 (1H) |
| 1.166 | O | (E)-NOCH₃ | H | Cl | Bicycl | 122–125 |
| 1.167 | O | (E)-CHOCH₃ | H | Cl | —CO—(2-Thiazolyl) | 103–105 |
| 1.168 | O | (E)-CHOCH₃ | H | Cl | —C(2-Thiazolyl)=NOCH₃ | 2945, 1707, 1631, 1256, 1130 |
| 1.169 | O | (E)-NOCH₃ | H | Cl | H₃CCH₂CH₂ON(CH₃)—CO— | 2966, 2941, 1727, |

TABLE 1-continued

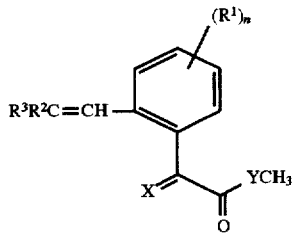

I

{E configuration with regard to the radical R3 and the phenyl ring}

| No. | Y | X | (R¹)ₙ | R² | R³ | Mp. [°C.]/IR [cm⁻¹] /¹H-NMR [ppm] |
|---|---|---|---|---|---|---|
| 1.170 | O | (E)-NOCH₃ | H | Cl | —C(OCH₃)=NOCH₂CH₂CH₃ | 1659, 1223, 1068 74–75 |
| 1.171 | NH | (E)-NOCH₃ | H | Cl | —C(OCH₃)=NOCH₂CH₂CH₃ | 1.0 (3H); 1.8 (2H); 2.9 (3H); 3.9 (6H); 4.1 (2H); 6.8 (1H); 7.15 (1H); 7.2–7.6 (3H); 7.8 (1H) |
| 1.172 | O | (E)-CHOCH₃ | 3-Cl | Cl | tBuO—CO— | 1.55 (9H); 3.7 (3H); 3.85 (3H); 7.2–7.45 (3H); 7.5 (1H); 7.65 (1H) |
| 1.173 | O | (E)-CHOCH₃ | 6-Cl | Cl | tBuO—CO— | 1.55 (9H); 3.7 (3H); 3.85 (3H); 7.3 (1H); 7.4 (1H); 7.6 (1H); 7.7 (1H); 7.8 (1H) |
| 1.174 | O | (E)-CHOCH₃ | H | Cl | C(OCH₃)=NO(3-CH₃-Bzl) | 2945, 1709, 1632, 1258, 1130 |
| 1.175 | O | (E)-CHOCH₃ | H | Cl | 3-CH₃-BzlON(CH₃)—CO— | 2945, 1708, 1661, 1633, 1258, 1130 |
| 1.176 | O | (E)-CHOCH₃ | H | Cl | C(OCH₃)=NOtBu | 2980, 2945, 1710, 1632, 1258, 1129 |
| 1.177 | O | (E)-CHOCH₃ | H | Cl | tBuON(CH₃)—CO— | 100–102 |
| 1.178 | O | (E)-CHOCH₃ | H | Cl | 1-(4-Cl—C₆H₄)ethylaminocarbonyl | 3340, 2950, 1708, 1660, 1631, 1514, 1257, 1131 |
| 1.179 | O | (E)-CHOCH₃ | H | Cl | 1-(3-CH₃—C₆H₄)ethylaminocarbonyl | 3330, 2955, 1708, 1660, 1630, 1515, 1256, 1130 |
| 1.180 | O | (E)-CHOCH₃ | H | Cl | 1-[2,4-(CH₃)₂—C₆H₃]ethylamino-carbonyl | 3340, 2950, 1709, 1661, 1630, 1509, 1256, 1130 |
| 1.181 | O | (E)-CHOCH₃ | H | Cl | 1-[4-iPr-C₆H₄]ethylaminocarbonyl | 3330, 2959, 1709, 1662, 1631, 1513, 1256, 1130 |
| 1.182 | O | (E)-CHOCH₃ | H | Cl | 1-[4-tBu-C₆H₄]ethylaminocarbonyl | 3320, 2951, 1709, 1649, 1631, 1513, 1256, 1130 |
| 1.183 | O | (E)-CHOCH₃ | H | Cl | 1-Phenyl-2-methylpropylamino-carbonyl | 3340, 2965, 1709, 1662, 1630, 1515, 1257, 1130 |
| 1.184 | O | (E)-CHOCH₃ | H | Cl | —CCl=NO(3-CH₃-Bzl) | 2945, 1710, 1632, 1435, 1256, 1130 |
| 1.185 | O | (E)-CHOCH₃ | H | Cl | H₃CC(CH₂CH₂OH)₂CH₂O—CO— | 3442, 2950, 1710, 1630, 1258, 1130 |
| 1.186 | O | (E)-CHOCH₃ | H | Cl | [3-Methyloxetan-3-yl]methyloxy-carbonyl | 2948, 1711, 1630, 1256, 1130 |
| 1.187 | O | (E)-CHOCH₃ | H | Cl | s-BuNH—CS— | 1.0 (3H); 1.3. (3H); 1.7 (2H); 3.7 (3H); 3.85 (3H); 4.7 (3H); 7.1–7,8 (4H); 8.1 (1H) |
| 1.188 | O | (E)-CHOCH₃ | H | Cl | —CBr=NOCH₃ | 2940, 1709, 1631, 1256, 1130, 1034 |
| 1.189 | O | (E)-CHOCH₃ | H | Cl | —CCl=NOCH₃ | 2945, 1709, 1632, 1257, 1130, 1039 |
| 1.190 | O | (E)-CHOCH₃ | H | Cl | 1-iPr-Propynyloxycarbonyl | 2960, 2220, 1727, 1713, 1630, 1255 |
| 1.191 | NH | (E)-NOCH₃ | 4-OCH₃ | Cl | 1,1-Dimethylpropynylamino-carbonyl | 152–155 |
| 1.192 | NH | (E)-NOCH₃ | 4-OCH₃ | Cl | tBuNH—CO— | 3340, 2967, 1734, 1663, 1523, 1034 |
| 1.193 | O | (E)-NOCH₃ | 4-OCH₃ | Cl | tBuNH—CO— | 3420, 2970, 1726, 1674, 1604, 1518 |

TABLE 1-continued

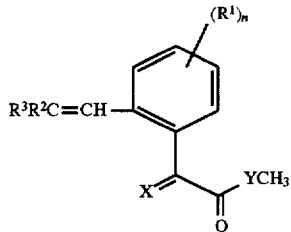

{E configuration with regard to the radical R3 and the phenyl ring}

| No. | Y | X | $(R^1)_n$ | $R^2$ | $R^3$ | Mp. [°C.]/IR [cm$^{-1}$] /$^1$H-NMR [ppm] |
|---|---|---|---|---|---|---|
| 1.194 | O | (E)-NOCH$_3$ | 4-OCH$_3$ | Cl | 1,1-Dimethylpropynylamino-carbonyl | 1236, 1069 112–115 |
| 1.195 | O | (E)-CHOCH$_3$ | H | Cl | (4-Chlorophenyl)cyclopropyl-methyloxycarbonyl | 2950, 1712, 1629, 1492, 1259, 1130 |
| 1.196 | O | (E)-CHOCH$_3$ | H | Cl | (4-Cyano-3-phenylisothiazol-5-yl)aminocarbonyl | 235–236 |
| 1.197 | O | (E)-CHOCH$_3$ | H | Cl | 3-Pentylaminocarbonyl | 102–105 |
| 1.198 | O | (E)-CHOCH$_3$ | H | Cl | 3-Pentyloxycarbonyl | 2969, 1713, 1631, 1259, 1130 |
| 1.199 | O | (E)-CHOCH$_3$ | H | Cl | 3-Methyl-2-pentylaminocarbonyl | 3330, 2965, 1710, 1632, 1520, 1256, 1130 |
| 1.200 | O | (E)-CHOCH$_3$ | H | Cl | 3-Methyl-2-pentyloxycarbonyl | 2964, 1713, 1631, 1258, 1130 |
| 1.201 | O | (E)-CHOCH$_3$ | H | Cl | 2-Pentylaminocarbonyl | 3340, 2960, 1709, 1655, 1631, 1521, 1257, 1130 |
| 1.202 | O | (E)-CHOCH$_3$ | H | Cl | 2-Pentyloxycarbonyl | 2957, 1713, 1631, 1258, 1130 |
| 1.203 | O | (E)-CHOCH$_3$ | H | Cl | 1,1-Dimethylpropenylamino-carbonyl | 3420, 2980, 2960 1709 1675, 1631, 1514, 1258, 1130 |
| 1.204 | O | (E)-CHOCH$_3$ | H | Cl | 1-Methoxy-2-propylaminocarbonyl | 3340, 2940, 1709, 1665, 1631, 1519, 1257, 1130 |
| 1.205 | O | (E)-CHOCH$_3$ | H | Cl | 1-n-Pentoxy-2-propyloxycarbonyl | 2955, 1713, 1631, 1258, 1130 |
| 1.206 | O | (E)-CHOCH$_3$ | H | Cl | 4-Methoxy-2-butyloxycarbonyl | 2950, 1713, 1630, 1258, 1130 |
| 1.207 | O | (E)-CHOCH$_3$ | H | Cl | 2-Isopropyl-1,3-dioxan-5-yl-oxycarbonyl | 2970, 1713, 1631, 1257, 1131 |
| 1.208 | O | (E)-CHOCH$_3$ | H | Cl | 1-(Isopropyloxycarbonyl)ethoxy-carbonyl | 2995, 2945, 1731, 1714, 1629, 1258 |
| 1.209 | O | (E)-CHOCH$_3$ | H | Cl | Cycl-NH—CO— | 160–162 |
| 1.210 | O | (E)-CHOCH$_3$ | H | Cl | 1-Isopropylideneaminoxy-2-propyloxycarbonyl | 2950, 1713, 1631, 1258, 1130 |
| 1.211 | O | (E)-CHOCH$_3$ | H | Cl | 3-Methyl-2-butyloxycarbonyl | 2950, 1713, 1631, 1258, 1130 |
| 1.212 | O | (E)-CHOCH$_3$ | H | Cl | 3,3-Dimethyl-2-butyloxycarbonyl | 2966, 1713, 1631, 1259, 1130 |
| 1.213 | O | (E)-CHOCH$_3$ | H | Cl | 5,9-Dimethyl-2-decyloxycarbonyl | 2951, 2928 1714, 1632, 1259, 1130 |
| 1.214 | O | (E)-CHOCH$_3$ | H | Cl | —C(CH$_3$)=NOCH$_2$CH=CHCl | 2945, 1708, 1632, 1255, 1129 |
| 1.215 | O | (E)-CHOCH$_3$ | H | Cl | —C(CH$_3$)=NOCH$_2$C(CH$_3$)=CH$_2$ | 2950, 1710, 1631, 1935, 1255, 1129 |
| 1.216 | O | (E)-CHOCH$_3$ | H | Cl | —C(CH$_3$)=NO-iC$_3$H$_7$ | 2980, 1710, 1632, 1256, 1129 |
| 1.217 | O | (E)-CHOCH$_3$ | H | Cl | —C(CH$_3$)=NO-[1-methylcyclopentyl] | 2963, 1711, 1632, 1255, 1129 |
| 1.218 | O | (E)-CHOCH$_3$ | H | Cl | —C(CH$_3$)=NO—CH(CH$_3$)C≡CH | 2120, 1708, 1631, 1256, 1130 |
| 1.219 | O | (E)-CHOCH$_3$ | H | Cl | —C(CH$_3$)=NOCH$_2$-(5-Cl-3-thienyl) | 2950, 1708, 1631, 1435, 1256, 1129 |
| 1.220 | O | (E)-CHOCH$_3$ | H | Cl | —C(CH$_3$)=NOCH$_2$-(2,5-diCl-3-thienyl) | 2980, 1709, 1631, 1435, 1256, 1129 |
| 1.221 | O | (E)-CHOCH$_3$ | H | Cl | —C(CH$_3$)=NO(1-(C$_6$H$_5$)ethyl) | 2980, 1709, 1631, 1255, 1129 |
| 1.222 | O | (E)-CHOCH$_3$ | H | Cl | —C(CH$_3$)=[1-(4-Cl—C$_6$H$_4$)ethyl] | 2980, 2360, 1709, 1631, 1255, 1129 |
| 1.223 | O | (E)-CHOCH$_3$ | H | Cl | —C(CH$_3$)=NO[1-(4-CH$_3$—C$_6$H$_4$)ethyl] | 2985, 2960, 1709, |

TABLE 1-continued

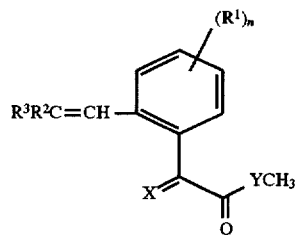

{E configuration with regard to the radical R3 and the phenyl ring}

| No. | Y | X | (R¹)ₙ | R² | R³ | Mp. [°C.]/IR [cm⁻¹] /¹H-NMR [ppm] |
|---|---|---|---|---|---|---|
| 1.224 | O | (E)-CHOCH₃ | H | Cl | —C(CH₃)=NO[1-(2,5(CH₃)₂—C₆H₃)—ethyl] | 1631, 1255, 1129 2975, 1708, 1628, 1251, 1128 |
| 1.225 | O | (E)-CHOCH₃ | H | Cl | —C(CH₃)=NO[1-(3-CF₃—C₆H₄)ethyl] | 2960, 1710, 1632, 1329, 1127 |
| 1.226 | O | (E)-CHOCH₃ | H | Cl | —C(OCH₃)=NO(3-CF3-Bzl) | 2950, 1709, 1632, 1330, 1127 |
| 1.227 | O | (E)-CHOCH₃ | H | Cl | —C(OCH₃)=NO[1-(3-CF₃—C₆H₃)ethyl] | 2955, 1710, 1632, 1329, 1127 |
| 1.228 | O | (E)-CHOCH₃ | H | Cl | —C(OCH₃)=NO[1-(4-Cl—C₆H₄)ethyl] | 2945, 1709, 1631, 1256, 1130 |
| 1.229 | O | (E)-CHOCH₃ | H | Cl | —C(OCH₃)=NOCH₃ | 2950, 1708, 1632, 1257, 1130 |
| 1.230 | O | (E)-CHOCH₃ | H | Cl | —C(OCH₃)=NOCH₂CH₃ | 2950, 1709, 1632, 1256, 1129 |
| 1.231 | O | (E)-CHOCH₃ | H | Cl | —CCl=NOCH₂CH₂CH₃ | 2950, 1710, 1632, 1256, 1129 |
| 1.232 | O | (E)-CHOCH₃ | H | Cl | —CCl=NOCH₂C(CH₃)=CH₂ | 2950, 1710, 1632, 1256, 1129 |
| 1.233 | O | (E)-CHOCH₃ | H | Cl | 3-CF₃-BzlONH—CO— | 104–106 |
| 1.234 | O | (E)-CHOCH₃ | H | Cl | 1-(3-CF₃—C₆H₄)ethylONH—CO— | 3350, 2945, 1708, 1630, 1329, 1128 |
| 1.235 | O | (E)-CHOCH₃ | H | Cl | 3-CF₃-BzlON(CH₃)—CO— | 2955, 1708, 1661, 1634, 1330, 1127 |
| 1.236 | O | (E)-CHOCH₃ | H | Cl | 1-(3-CF₃—C₆H₄)ethylON(CH₃)—CO— | 2960, 1709, 1663, 1634, 1329, 1127 |
| 1.237 | O | (E)-CHOCH₃ | H | Cl | 1-(4-Cl—C₆H₄)ethylON(CH₃)—CO— | 2950, 1708, 1660, 1634, 1256, 1130 |
| 1.238 | O | (E)-CHOCH₃ | H | Cl | H₃CCH₂ON(CH₃)—CO— | 2950, 1708, 1653, 1635, 1256, 1129 |
| 1.239 | O | (E)-CHOCH₃ | H | Cl | (5-Cl-3-Thienyl)CH₂ONH—CO— | 3.7 (3H); 3.8 (3H); 4.9 (2H); 6.9–7.4 (5H); 7.6 (1H); 7.8–(1H); 7.9 (1H); 9.2 (NH) |
| 1.240 | NH | N-NOCH₃ | H | Cl | 3-n-Pentylaminocarbonyl | 109–113 |
| 1.241 | O | N-NOCH₃ | H | Cl | 2-n-Pentylaminocarbonyl | 3330, 2958, 1728, 1659, 1619, 1522, 1069 |
| 1.242 | NH | N-NOCH₃ | H | Cl | 2-n-Pentylaminocarbonyl | 126–179 |
| 1.243 | O | N-NOCH₃ | H | Cl | 1,1-Dimethylpropenylaminocarbonyl | 3350, 2945, 1727, 1676, 1514, 1069 |
| 1.244 | NH | N-NOCH₃ | H | Cl | 1,1-Dimethylpropenylaminocarbonyl | 135–138 |
| 1.245 | O | (E)-CHOCH₃ | H | Cl | 1,1,1-Trifluoro-2-methyl-2-propylaminocarbonyl | 80–82 |
| 1.246 | O | (E)-CHOCH₃ | H | Cl | —C(CH₃)=NOCH₂CO₂CH₃ | 2955, 1761, 1714 1631, 1256, 1130 |
| 1.247 | O | (E) CHOCH₃ | H | Cl | —C(CH₃)=NOCH₂CO₂C(CH₃)₃ | 2980, 1751, 1710 1631, 1256, 1130 |
| 1.248 | O | (E)-CHOCH₃ | H | Cl | —C(CH₃)=NOCHCH₃CO₂C(CH₃)₃ | 2985, 1745, 1711, 1631, 1256, 1130 |
| 1.249 | O | (E)-CHOCH₃ | H | Cl | —CCl=NO[1-(4-Cl—C₆H₄)ethyl] | 1.7 (3H); 3.65 (3H); 3.8 (3H); 5.4 (1H); 7.1–7.4 (8H); 7.6 (1H); 7.75 (1H) |
| 1.250 | O | (E)-CHOCH₃ | H | Cl | —CCl=NO[1-(3-CF₃—C₆H₄)ethyl] | 2965, 1710, 1632, 1329, 1128 |
| 1.251 | O | (E)-CHOCH₃ | H | OEt | ETO—CO— | 1.3 (3H); 1.35 (3H); 3.65 (3H); 3.8 (3H); 3.9 (2H); 4.3 (2H); 6.95 (1H); 7.2–7.4 (3H); 7.6 (1H); 8.2 |

TABLE 1-continued

{E configuration with regard to the radical R3 and the phenyl ring}

| No. | Y | X | (R¹)ₙ | R² | R³ | Mp. [°C.]/IR [cm⁻¹] /¹H-NMR [ppm] |
|---|---|---|---|---|---|---|
| 1.252 | O | (E)-CHOCH₃ | H | ETO—CO— | OEt | (1H) 1.0 (3H); 1.4 (3H); 3.65 (3H); 3:8 (3H); 3.85 (2H); 4.0 (2H); 6.0 (1H); 7.1–7.3 (4H); 7.5 (1H) |
| 1.253 | O | (E)-CHOCH₃ | H | tBuO—CO— | F | 1.3 (9H); 3.7 (3H); 3.8 (3H); 6.75 (1H, d); 7.15–7.35 (4H); 7.5 (1H) |
| 1.254 | O | (E)-CHOCH₃ | F | tBuO—CO— | F | 1.55 (9H); 3.7 (3H) 3.8 (3H); 6.8 (14, d, 50Hz); 7.1–7.3 (3H); 7.6 (1H); 7.95 (1H) |

Remarks:
Me = CH₃
Et = CH₂CH₃
Pr = CH₂CH₂CH₃
i-Pr = CH(CH₃)₂
c-Pr = Cyclopropyl
t-Bu = C(CH₃)₃
i-Bu = CH₂CH(CH₃)₂
s-Bu = CH(CH₃)CH₂CH₃
Bzl = Benzyl
Val = L-Valine{ —CO—CH[CH(CH₃)₂] — }
Ph = Phenyl

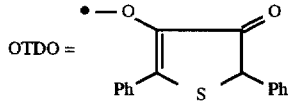

OTDO =

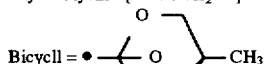

Ala = L-Alanine { —COCHCH₃ — }
Gly = Glycine { —COCH₂ — }

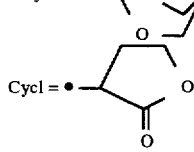

Bicycll =

Cycl =

Use examples

The insecticidal action of the compounds of the general formula I can be illustrated by the following experiment sic]:
The active ingredients were formulated
a) as a 0.1% strength solution in acetone or
b) as a 10% strength emulsion in a mixture of 70% by weight of cyclohexanol, 20% by weight of Nekanil® LN (Lutensol® AP6, wetting agent having an emulsifying and dispersing action based on ethoxylated alkylphenols) and 10% by weight of Emulphor® EL, (Emulan®, emulsifier based on ethoxylated fatty alcohols)

and diluted to the desired concentration with acetone in the case of a) and with water in the case of b).

Upon conclusion of the experiments, the lowest concentration in each case was determined at which the compounds still caused 80–100% inhibition or mortality (host [sic] threshold or minimum concentration) compared with untreated control experiments.

A. Aphis fabae (black louse), contact action

Bush beans (Vicia faba) under heavy aphid attack were treated with aqueous formulations of the active ingredients. The kill rate was determined after 24 hours.

147

In this test, compounds 1.005, 1.006, 1.012, 1.039, 1.058, 1.067, 1.078, 1.086, 1.090, 1.091, 1.094, 1.095, 1.098, 1.100 and 1.102, applied at a rate of 400 ppm, exhibited at least 80% action.

B. Nephotettix cincticeps (green rice cicada), contact action

Circular filter papers were treated with aqueous formulations of the active ingredients. Subsequently, 5 adult cicadas were placed on each paper.

The kill rate was assessed after 24 hours.

In this test, compounds 1.008, 1.009, 1.010, 1.011, 1.012, 1.019, 1.020, 1.021, 1.038, 1.043, 1.044, 1.045, 1.049, 1.050, 1.051, 1.064, 1.069, 1.077, 1.078, 1.082, 1.085, 1.098, 1.110, 1.118, 1.119 and 1.121, applied at rates of 0.4 mg, exhibited at least 80% action.

C. Nephotettix cincticeps (green rice cicada), contact action (spray experiment)

Rice plants about 8 cm high were treated with aqueous formulations of the active ingredients. After drying, 10 adult cicadas were placed on the plants.

The kill rate was assessed after 48 hours.

In this test, compounds 1.008, 1.009, 1.011, 1.012 and 1.021, employed at a rate of 200 ppm, exhibited at least 80% action.

D. Prodenia litura (Egyptian cotton worm), contact action 5 caterpillars were placed on filter papers treated with aqueous formulations of the active ingredients. The first assessment took place after 4 hours. If at least one caterpillar was still alive, a feed mixture was proffered.

The kill rate was determined after 24 hours.

In this test, compounds 1.021 and 1.04, applied at a rate of 0.4 mg, exhibited at least 80% action.

E. Tetranychus telarius (red mite), contact action

Potted bush beans exhibiting the second pair of true leaves and under heavy mite attack were treated with aqueous formulations of the active ingredients.

After 5 days in the greenhouse, the degree of success was assessed by means of a binocular microscope.

In this test, compounds 1.011, 1.012, 1.020, 1.021, 1.024, 1.026, 1.027, 1.028, 1.034, 1.036, 1.037, 1.038, 1.039, 1.043, 1.044, 1.046, 1.062, 1.064, 1.065, 1.067, 1.069, 1.077, 1.078, 1.081, 1.082, 1.084, 1.085, 1.086, 1.087, 1.088, 1.089, 1.090, 1.091, 1.098, 1.100, 1.102, 1.103, 1.105, 1.109, 1.112, 1.116, 1.118, 1.121, 1.130, 1.146 and 1.160, applied at a rate of 400 ppm, exhibited at least 80% action.

We claim:

1. A compound of the formula I

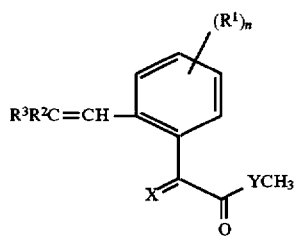

where the index and the substituents have the following meanings:

n is 0, 1, 2, 3 or 4, where the radicals $R^1$ can be different if n>1;

X is $CHOCH_3$, $CHCH_3$ or $NOCH_3$;

Y is O or NH;

$R^1$ is halogen; $C_1-C_4$-alkyl; $C_1-C_4$-haloalkyl; $C_1-C_4$-alkoxy; $C_1-C_4$-haloalkoxy; $C_1$-or, if n>1, R is a 1,3-

148 butadiene-1,4-diyl group bonded to two adjacent C atoms of the parent structure, which group can carry one to four halogen and/or one or two of the following radicals: $C_1-C_4$-alkyl, $C_1-C_4$-haloalkyl, $C_1-C_4$-alkoxy, $C_1-C_4$-haloalkoxy and $C_1-C_4$-alkylthio;

$R^2$ is nitro, cyano, halogen, $C_1-C_4$-alkoxy, $C_1-C_4$-alkylcarbonylamino, $C_1-C_4$-alkoxycarbonylamino or benzylcarbonylamino;

$R^3$ if X is $CHOCH_3$ or $NOCH_3$ and $R^2$ is halogen, is phenyl, 1-naphthyl, 2-naphthyl, 5-isoxazolyl, 4-oxazolyl, 1,2,4-oxadiazol-5-yl, 1,3,4-thiadiazol-2-yl, 3-pyridinyl or 4-pyridinyl, where the aromatic rings may be unsubstituted or substituted;

or is a group $R^4$—T—C(=$Z^1$)— or $R^5$—C(=$Z^2$)—, where

=$Z^1$ is =O, =S or =$NOR^4$;

=$Z^2$ is =O, =$NOR^4$, =N—$NR^7R^8$, =NO—C(=O)—$R^4$, =NO—C(=O)—$NR^7R^8$ or =N—$NR^7$—C(=O)—$R^4$;

—T— is —O—, —S—, —$NR^7$—, —$NR^7$—$NR^8$—, —$NOR^7$— or —$NR^7O$—;

$R^4$ is hydrogen; unsubstituted or substituted alkyl, alkenyl or alkynyl; cyclopropyl, cyclopentyl, cyclohexyl, cyclopent-2-enyl, cyclohex-2-enyl, 2-tetrahydrofuranyl, 2-tetrahydrothienyl, 2-pyrrolidinyl, 3-isoxazolidinyl, 3-isothiazolidinyl, 1,3,4-oxazolidin-2-yl, 2,3-dihydrothien-2-yl, 4,5-isoxazolin-3-yl, 3-piperidinyl, 1,3-dioxan-5-yl, 4-piperidinyl, 2-tetrahydropyranyl or 4-tetrahydropyranyl, where the cyclic radicals may be unsubstituted or substituted; phenyl, 1-naphthyl, 2-naphthyl, 2-imidazolyl, 2-furyl, 3-furyl, 2-thienyl, 3-thienyl, 3-isoxazolyl, 2-oxazolyl, 1,2,4-oxadiazol-3-yl, 1,2,4-triazol-3-yl, 3-pyridinyl, 2-pyridinyl, 2-pyrimidinyl, 4-pyrimidinyl or 1,3,5-triazin-2-yl, where the aromatic radicals may be unsubstituted or substituted;

$R^5$ is hydrogen; cyano; halogen; unsubstituted or substituted alkyl or alkoxy; cyclopropyl, cyclopentyl, cyclohexyl, 2-tetrahydrofuranyl, 3-tetrahydrofuranyl, 2-tetrahydrothienyl, 2-oxazolidinyl or 2-thiazolidinyl, where the cyclic radicals may be unsubstituted or substituted; phenyl, 1-naphthyl, 2-naphthyl, 2-furyl, 2-thienyl, 2-oxazolyl, 2-thiazolyl, 1-imidazolyl, 1-pyrrolyl, 1-pyrazolyl, 3-pyridinyl or 4-pyridinyl, where the aromatic radicals may be unsubstituted or substituted;

$R^6$ is hydrogen or $C_1-C_4$ alkyl;

$R^7$ is hydrogen;

$R^8$ is hydrogen, $C_1-C_4$-alkyl or $COR^7$.

2. A compound of the formula I as defined in claim 1, where n is 0 or 1,

X is $CHOCH_3$, $CHCH_3$ or $NOCH_3$;

$R^1$ is halogen, $C_1-C_4$-alkyl, $C_1-C_2$-haloalkyl, $C_1-C_4$-alkoxy, $C_1-C_2$-haloalkoxy or $C_1-C_2$-alkylthio; and $R^2$ is halogen or cyano.

3. A compound of the formula I as defined in claim 1, where $R^3$ is a group —CO—T—$R^4$ and T is —O—, —S—, —$NR^7$— or —$ONR^7$—, and $R^7$ is hydrogen.

4. A compound of the formula I as defined in claim 1, where $R^3$ is —CO—$R^5$, where $R^5$ is one of the following radicals:

unsubstituted or substituted alkyl; cyclopropyl, cyclopentyl, cyclohexyl, 2-tetrahydrofuranyl, 3-tetrahydrofuranyl, 2-tetrahydrothienyl, 2-oxazolidinyl or 2-thiazolidinyl, where the cyclic radicals may be unsubstituted or substituted; phenyl, 1-naphthyl, 2-naphthyl, 2-furyl, 2-thienyl, 2-oxazolyl, 2-thiazolyl, 1-imidazolyl, 1-pyrrolyl, 1-pyrazolyl, 3-pyridinyl or 4-pyridinyl, where the aromatic radicals may be unsubstituted or substituted.

5. A compound of the formula I as defined in claim 1, where $R^3$ is —$CR^5$=NO—$R^4$, where $R^4$ is unsubstituted or substituted alkyl, alkenyl or alkynyl;

$R^5$ is unsubstituted or substituted alkyl or alkoxy; cyclopropyl, cyclopentyl, cyclohexyl, 2-tetrahydrofuranyl, 3-tetrahydrofuranyl, 2-tetrahydrothienyl, 2-oxazolidinyl or 2-thiazolidinyl, where the cyclic radicals may be unsubstituted or substituted; phenyl, 1-naphthyl, 2-naphthyl, 2-furyl, 2-thienyl, 2-oxazolyl, 2-thiazolyl, 1-imidazolyl, 1-pyrrolyl, 1-pyrazolyl, 3-pyridinyl or 4-pyridinyl, where the aromatic radicals may be unsubstituted or substituted.

6. A compound of the formula I as defined in claim 1, where $R^3$ is one of the following aromatic radicals: phenyl, 1-naphthyl, 2-naphthyl, 2-furyl, 2-thienyl, 2-oxazolyl, 2-thiazolyl, 1-imidazolyl, 1-pyrrolyl, 1-pyrazolyl, 3-pyridinyl or 4-pyridinyl, where the aromatic radicals may be unsubstituted or substituted.

7. A compound of the formula I as defined in claim 1, wherein X denotes $CHOCH_3$.

8. A compound of the formula I as defined in claim 1, wherein X denotes $CHCH_3$.

9. A compound of the formula I as defined in claim 1, wherein X denotes $NOCH_3$.

10. A method of controlling harmful fungal diseases in plants which comprises applying a disease-controlling effective amount of the compound I as defined in claim 1 to the plants or to their habitat.

11. A method of controlling diseases in plants caused by pests from the classes of insects, arachnids or nematodes which comprises applying a disease-controlling effective amount of compound I as defined in claim 1 to the insects or to their habitat.

12. A compound of the formula I as defined in claim 1, where $R^2$ is nitro, cyano or halogen and $R^3$ is a group $R^4$—T—C(=$Z^1$)—.

13. A compound of the formula I as defined in claim 1, where $R^2$ is $C_1$-$C_4$-alkoxy and $R^3$ is a group $R^4$—T—C(=$Z^1$)—.

14. A compound of the formula I as defined in claim 1, where $R^2$ is nitro, cyano or halogen and $R^3$ is a group $R^5$—C(=$Z^2$)—.

15. A process for preparing a compound of the formula I as defined in claim 1, X denoting CH—$OCH_3$, wherein a phenylacetic acid derivative of the formula II

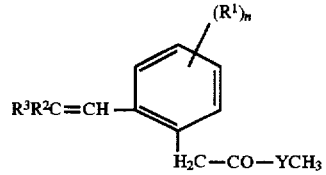

is reacted in a conventional manner in the presence of a base with methyl formate to give the beta-hydroxyacrylate III

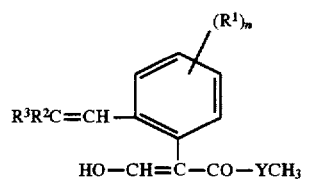

and III is then methylated in a conventional manner.

16. A composition for controlling harmful fungi, containing a fungicidal amount of a compound of the formula I as defined in claim 1 and inert additives.

17. A pesticide containing an effective amount of a compound of the formula I as defined in claim 1 and inert additives.

18. A method of controlling harmful fungi, wherein the harmful fungi, their habitat and/or the plants or materials to be kept free from harmful fungi are treated with a fungicidally effective amount of a compound of the formula I as defined in claim 1.

19. A method of controlling pests, wherein the pests, their habitat and/or the plants or materials to be kept free from pests are treated with an effective amount of a compound of the formula I as defined in claim 1.

* * * * *

UNITED STATES PATENT AND TRADEMARK OFFICE
CERTIFICATE OF CORRECTION

PATENT NO.: 5,633,268

DATED: May 27, 1997

INVENTOR(S): KIRSTGEN et al.

It is certified that error appears in the above-identified patent and that said Letters Patent is hereby corrected as shown below:

Column 147, claim 1, line 67, "$C_1$-or," should be --$C_1$-$C_4$-alkylthio; or,--.

Column 148, claim 1, line 50, "$COR^7$" should be --$COR^6$--.

Signed and Sealed this

Twenty-sixth Day of August, 1997

Attest:

BRUCE LEHMAN

Attesting Officer

Commissioner of Patents and Trademarks